US010221426B2

(12) United States Patent
Cutler

(10) Patent No.: US 10,221,426 B2
(45) Date of Patent: Mar. 5, 2019

(54) CONSTITUTIVELY ACTIVE PYR/PYL RECEPTOR PROTEINS FOR IMPROVING PLANT STRESS TOLERANCE

(71) Applicant: The Regents of the University of California, Oakland, CA (US)

(72) Inventor: Sean R. Cutler, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 969 days.

(21) Appl. No.: 14/254,762

(22) Filed: Apr. 16, 2014

(65) Prior Publication Data

US 2014/0325701 A1 Oct. 30, 2014

Related U.S. Application Data

(62) Division of application No. 12/705,413, filed on Feb. 12, 2010, now Pat. No. 9,315,821.

(Continued)

(51) Int. Cl.

| | |
|---|---|
| ***C12N 9/16*** | (2006.01) |
| ***A01N 37/06*** | (2006.01) |
| ***A01N 37/08*** | (2006.01) |
| ***A01N 37/10*** | (2006.01) |
| ***A01N 37/28*** | (2006.01) |
| ***A01N 37/34*** | (2006.01) |
| ***A01N 37/42*** | (2006.01) |
| ***A01N 41/06*** | (2006.01) |
| ***A01N 43/10*** | (2006.01) |

(Continued)

(52) U.S. Cl.

CPC ......... *C12N 15/8271* (2013.01); *A01N 37/08* (2013.01); *A01N 37/10* (2013.01); *A01N 37/42* (2013.01); *A01N 41/06* (2013.01); *A01N 43/10* (2013.01); *A01N 43/40* (2013.01); *A01N 43/42* (2013.01); *A01N 43/50* (2013.01); *A01N 43/54* (2013.01); *A01N 43/82* (2013.01); *A01N 47/30* (2013.01); *C07K 14/415* (2013.01); *C12N 9/16* (2013.01); *C12N 15/8273* (2013.01); *C12Y 301/03016* (2013.01); *A01N 37/06* (2013.01); *A01N 37/28* (2013.01); *A01N 37/34* (2013.01); *A01N 43/713* (2013.01)

(58) Field of Classification Search

CPC .................................................. C12N 15/8273

See application file for complete search history.

(56) References Cited

U.S. PATENT DOCUMENTS

| | | | |
|---|---|---|---|
| 3,256,148 | A | 6/1966 | Speziale et al. |
| 3,498,780 | A | 3/1970 | Kline et al. |

(Continued)

FOREIGN PATENT DOCUMENTS

| | | | |
|---|---|---|---|
| CN | 101173287 | A | 5/2008 |
| JP | 2007 222129 | A | 9/2007 |

(Continued)

OTHER PUBLICATIONS

Zhang et al (Frontiers in Plant Science (2015) vol. 6, Article 88).*

(Continued)

*Primary Examiner* — Lee A Visone

(74) *Attorney, Agent, or Firm* — Kilpatrick Townsend & Stockton LLP

(57) ABSTRACT

The present invention provides methods of regulating plant stress tolerance.

22 Claims, 24 Drawing Sheets

Specification includes a Sequence Listing.

(-)-Abscisic Acid 1

(+)-Abscisic Acid 2

Pyrabactin 3

Apyrabactin 4

Related U.S. Application Data

(60) Provisional application No. 61/207,684, filed on Feb. 13, 2009.

(51) Int. Cl.

| | |
|---|---|
| ***A01N 43/40*** | (2006.01) |
| ***A01N 43/42*** | (2006.01) |
| ***A01N 43/50*** | (2006.01) |
| ***A01N 43/54*** | (2006.01) |
| ***A01N 43/82*** | (2006.01) |
| ***A01N 47/30*** | (2006.01) |
| ***C12N 15/82*** | (2006.01) |
| ***A01N 43/713*** | (2006.01) |
| ***C07K 14/415*** | (2006.01) |

(56) References Cited

U.S. PATENT DOCUMENTS

| | | | | |
|---|---|---|---|---|
| 4,071,350 | A | 1/1978 | Arneklev et al. | |
| 4,209,530 | A | 6/1980 | Visscher | |
| 5,173,106 | A | 12/1992 | Kamuro et al. | |
| 5,625,130 | A | 4/1997 | Grant et al. | |
| 7,214,786 | B2 | 5/2007 | Kovalic et al. | |
| 7,569,389 | B2 | 8/2009 | Feldmann et al. | |
| 7,847,156 | B2 | 2/2010 | Inze et al. | |
| 9,315,821 | B2 * | 4/2016 | Cutler | C12N 15/8271 |
| 2004/0148654 | A1 | 7/2004 | Helentjaris | |
| 2004/0214272 | A1 | 10/2004 | La Rosa et al. | |
| 2005/0244971 | A1 | 11/2005 | Kim | |
| 2006/0150283 | A1 | 7/2006 | Alexandrov | |
| 2006/0179518 | A1 | 8/2006 | Hill et al. | |
| 2007/0039067 | A1 | 2/2007 | Feldmann et al. | |
| 2009/0105238 | A1 | 4/2009 | Filippini et al. | |
| 2009/0163545 | A1 | 6/2009 | Goldfarb | |
| 2009/0320152 | A1 | 12/2009 | Steber et al. | |
| 2010/0216643 | A1 | 8/2010 | Cutler et al. | |
| 2011/0271408 | A1 | 11/2011 | Cutler et al. | |
| 2013/0324409 | A1 | 12/2013 | Cutler et al. | |

FOREIGN PATENT DOCUMENTS

| | | | |
|---|---|---|---|
| WO | 2003/008540 | A2 | 1/2003 |
| WO | 2004/035798 | A2 | 4/2004 |
| WO | 2010/093954 | A2 | 8/2010 |

OTHER PUBLICATIONS

Gonzalez-Guzman et al (The Plant Cell, vol. 24: 2483-2496, Jun. 2012).*
Mosqunaa et al (PNAS, (2011) vol. 108 (51) pp. 20838-20843).*
Kline et al (Plant Physiology , Oct. 2010, vol. 154, pp. 479-482).*
GenBank Accession 4JDL_A (2013).*
GenBank Accession NP_5636261_May 26, 2011.*
GenBank Accession NP_5636261_2002.*
GenBank Accession 3OQU_A (2002_.*
Chen, Inẽs, "ABA Receptor Diversity," SBKB, Nov. 2010 Featured Articles, Retrieved Jun. 2, 2014, 3 Pages [DOI:10.1038/SBKB. 2010.49].
Cutler et al., *Annual Review of Plant Biology* 61:651-679 (2010).
EMBL accession No. AY042890, Feb. 26, 2010.
Fujii et al., "In vitro reconstitution of an abscisic acid signaling pathway," *Nature*, vol. 462, Dec. 2009, p. 660.
GenBank as accession No. NP_563626, Available online Jan. 28, 2002.
GenBank as accession No. NP_565887, Available online Jan. 28, 2002.
Gonzalez-Guzman M. et al. (2002) *Plant Cell* 14(8):1833-1846.
Gonzalez-Guzman et al., "Arabidopsis PYR-PYL/RCAR receptors play a major role in quantitative regulation of stomatal aperture and transcriptional response to abscisic acid," *The Plant Cell*, 2012, vol. 24, pp. 2483-2496.
Hao Q, et al., "The molecular basis of ABA-independent inhibition of PP2Cs by a subclass of PYL proteins," *Mol Cell* 42 (5):662-672 (2011).
Hauser, Felix et al., "Evolution of abscisic acid synthesis and signaling mechanisms," *Current Biology*, vol. 21, No. 9, May 2011, pp. R346-R355.
International Search Report dated Dec. 15, 2010, for International Application No. PCT/US2010/024139, 5pp.
Kline et al., "Abscisic Acid Receptors," *Plant Physiology*, Oct. 2010, vol. 154, No. 2, pp. 479-482.
Lee, Sung Chul et al., "Functional roles of the pepper antimicrobial protein gene, CaAMP1, in abscisic acid signaling, and salt and drought tolerance in *Arabidopsis*," *Planta* (2009) 229:383-391.
Li et al., (*Science in China Ser. C Life Sciences* 2005 vol. 48, No. 2, 181-186.).
Masgrau, Carles et al.; "Inducible overexpression of oat arginine decarboxylase in transgenic tobacco plants"; 1997, *The Plant Journal*, vol. 11, No. 3, pp. 465-473.
Melcher et al., *Nature* 462: 602-608, 2009.
Melcher K, et al. (2010) *Nature Stuctural and Molecular Biology* 17(9):1102-1108.
Mosquna et al., "Potent and selective activation of abscisic acid receptors in vivo by mutational stabilization of their agonist-bound conformation," *Proc Nat Acad Sci ePub*, Dec. 20, 2011, vol. 108, No. 51, pp. 20838-20843.
Nishimura et al., "Structural Mechanism of Abscisic Acid Binding and Signaling by Dimeric PYRI," *Science*, Dec. 2009, 326(5958):1373-1379.
Park, Sang-Youl et al., "Abscisic acid inhibits type 2C protein phosphatases via the PYR/PYL family of Start proteins," *Science*, vol. 324, No. 5930, May 2009, pp. 1068-1071, XP002676971.
Peterson FC, et al. "Structural basis for selective activation of ABA receptors," *Nature Stuctural and Molecular Biology* 17(9):1109-1113 (2010).
Santiago et al., *The Plant Journal*, 60:575-588, 2009.
Santiago, Julia et al., "The Abscisic acid receptor PYR1 complex with abscisic acid," *Nature*, vol. 462, No. 7273, Nov. 8, 2009, pp. 665-668.
Spencer et al., "Segregation of Transgenes in Maize," Plant Mol. Biol., 1992, vol. 18, pp. 201-210.
Supplementary European Search Report, dated Jul. 2, 2012, for European Application No. EP 10741826.1, 13 Pages.
Uniprotkp Accession No. 049686, Mar. 2, 2010.
Wang et al., Plant J., 2005, vol. 43, pp. 413-424.
Weiner et al., Curr Opin Plant Biol 13:495-502 (2010).
Williams, Robert W. et al.; "A Possible Role for Kinase-Associated Protein Phosphatase in the *Arabidopsis* Clavata1 Signaling Pathway"; 1997, Proc. Natl. Acad. Sci., vol. 94, pp. 10467-10472.
Xie, Chunzheng et al., "Cloning, sequence analysis and prokaryotic expression of pathogenesis-induced protein (PIP) gene from peanut," Crops Research Institute, Guangdong Academy of Agricultural Sciences, China, Jan. 2009, XP002676969, Database accession No. 153:424228, abstract.
Q84MC7 , "Recommended name: Abscisic acid receptor PYL9; Alternative name(s): ABI1-binding protein 4, PYR1—like protein 9, Regulatory components of ABA receptor 1", http://www.uniprot.org/uniprot/Q84MC7, Jun. 1, 2003.

* cited by examiner

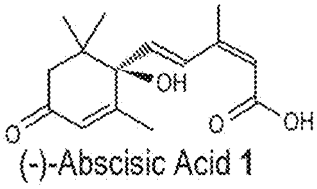
(-)-Abscisic Acid 1
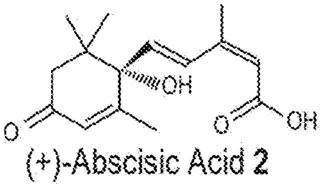
(+)-Abscisic Acid 2
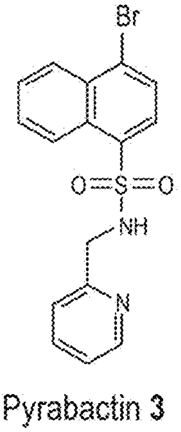
Pyrabactin 3
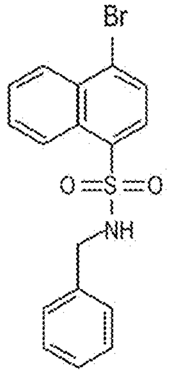
Apyrabactin 4
FIG. 1A
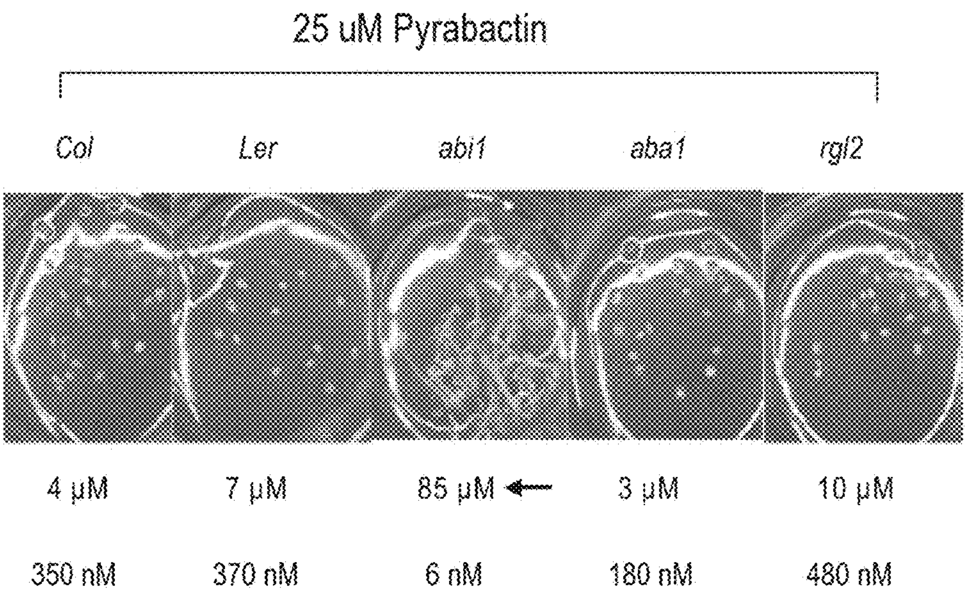
FIG. 1B Pyrabactin vs.
Abscisic Acid Seedling treatments

35S::GFP-PYR1

| | | Strong Receptor Responde to Compound | | | | |
|---|---|---|---|---|---|---|
| Entry | Compound | *PYR1* | *PYRL1* | *PYL2* | *PYL3* | *PYL4* |
| 1 | (+)-Abscisic Acid | + | + | + | + | + |
| 2 | Pyrabactin | + | + | − | + | − |
| 3 | 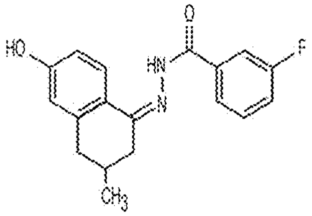 | − | − | − | + | + |
| 4 | 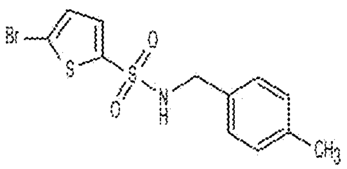 | − | + | − | + | + |
| 5 | 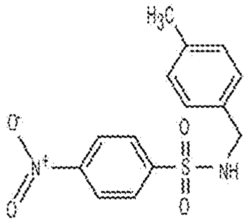 | − | + | − | − | − |
| 6 | 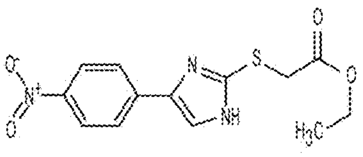 #6655097 | + | + | − | − | + |
FIG. 8

| | | Strong Receptor Responde to Compound | | | | |
|---|---|---|---|---|---|---|
| Entry | Compound | PYR1 | PYRL1 | PYL2 | PYL3 | PYL4 |
| 7 | 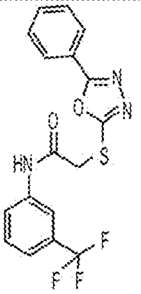 #7563159 | + | + | — | — | — |
| 8 | 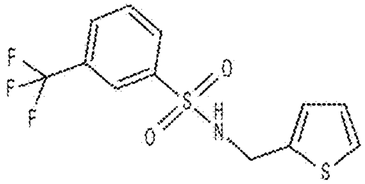 | — | — | — | + | — |
| 9 | 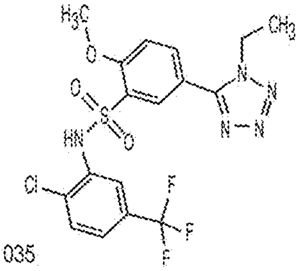 #7561035 | — | — | — | + | — |
| 10 | 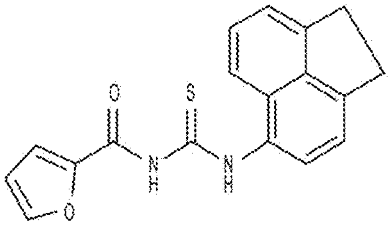 | — | — | — | + | — |
FIG. 8 (cont.)

| | | Strong Receptor Responde to Compound | | | | |
|---|---|---|---|---|---|---|
| Entry | Compound | PYR1 | PYRL1 | PYL2 | PYL3 | PYL4 |
| 11 | 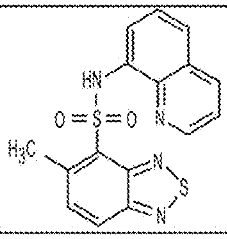 | — | — | — | + | — |
| 12 | 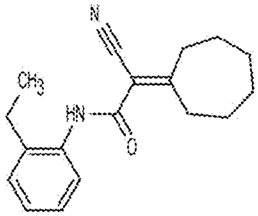 | — | — | — | + | + |
| 13 | 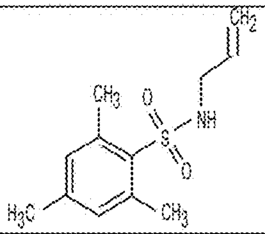 | — | — | — | + | + |
| 14 | 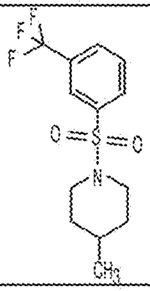 | — | — | — | + | + |
| 15 | 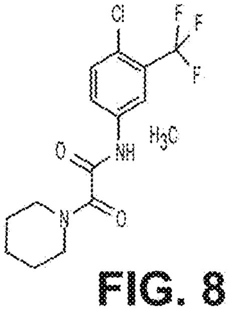 | — | — | — | + | + |
FIG. 8 (cont.)

| Entry | Compound | Strong Receptor Responde to Compound | | | | |
|---|---|---|---|---|---|---|
| | | PYR1 | PYRL1 | PYL2 | PYL3 | PYL4 |
| 16 | 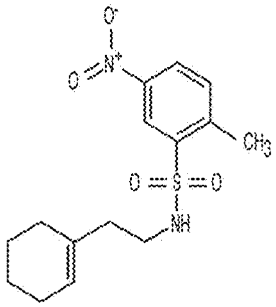 | — | — | — | + | — |
| 17 | 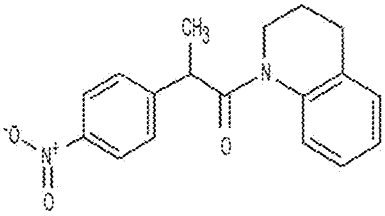 | — | — | — | + | — |
| 18 | 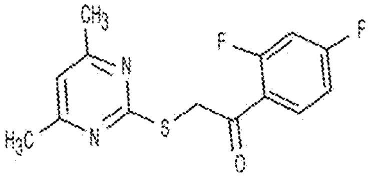 | — | — | + | + | + |
| 19 | 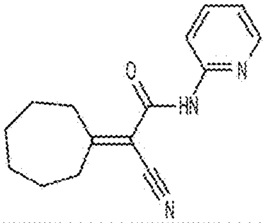 | — | — | + | + | + |
FIG. 8 (cont.)

| | Receptor | | | |
|---|---|---|---|---|
| Compound | PYR1 | PYL1 | PYL2 | PYL3 |
| (+)-ABA | 0.2 | 0.2 | 0.1 | 0.1 |
| Pyrabactin | 0.4 | 0.6 | >50 | >50 |
| 7653159 | 0.5 | 0.55 | >50 | >50 |
| 6655097 | 0.4 | 0.5 | >50 | >50 |
| 7561035 | >50 | >50 | 4 | 5 |

$IC_{50}$ values are shown in μM

Measured using PYR/PYL protein indicated (i.e. receptor) and the PP2C HAB1 with the phophatase substrate pNPP

FIG. 9

| Trait | *Control* | *PYL4-OE* | *Quadruple lof* |
|---|---|---|---|
| Flowering time | ++ | + | +++ |
| Stature | +++ | ++ | + |
| Chlorophyll content | + | ++ | + |
| Wiltiness | ++ | + | ++++ |
| | | flowers late, dark green, less wilty | Flowers early, small plant, very wilty |

Quadruple = pyr1/pyl1/pyl2/pyl quadruple mutant

PYL4-OE = transgenic Arabidopsis plants with Rbcs promotor driving GFP-PYL4, Rbcs = subisco small subunit (high expression promoter).

```
Alignment

PYR1        ---------------------------MPSELTPEERSE----------LKNSIAEFHTY 23
PYL1        MANSESSSSPVNEEENSQRISTLHHQTMPSDLTQDEFTQ----------LSQSIAEFHTY 50
PYL2        ----------------------MSSSPAVKGLTDEEQKT----------LEPVIKTYHQF 28
PYL3        -------MNLAPIHDPSSSSTTTTSSSTPYGLTKDEFST----------LDSIIRTHHTF 43
PYL4        ---------MLAVHRPSSAVSDG-DSVQIPMMIASFQKRFPSLSR-----DSTAARFHTH 45
PYL5        ------MRSPVQLQHGSDATNGF-HTLQPHDQTDGPIKRV-CLTRGMH-VPEHVAMHHTH 51
PYL6        ------MPTSIQFQRSSTAAEAANATVRNYPHHHQKQVQKVSLTRGMADVPEHVELSHTH 54
PYL7        ----------MEMIGGDDTDTEMYGALVT---------------------AQSLRLRHLH 29
PYL9        ------------MMDGVEGGTAMYGGLET---------------------VQYVRTHHQH 27
PYL10       -------------MNGDE------TKKVE---------------------SEYIKKHHRH 20
PYL8        -----------MEANGIEN---LTNPNQE---------------------REFIRRHHKH 25
PYL11       ---------------------------------------------------------MET 3
PYL12       ---------------------------------------------------------MKT 3
PYL13       ---------------------------------------------------------MES 3

  ALL_Con
 1_12_Con
 1_6_ Con                                                            Hxx
 7_10_Con                                                            HxH
11_13_Con
```

FIG. 11B

```
PYR1        QLDPGSCSSLHAQRIHAPPELVWSIVRRFDKPQTYKHFIKSCSVEQNFEM-----RVGCT 78
PYL1        QLGNGRCSSLLAQRIHAPPETVWSVVRRFDRPQIYKHFIKSCNVSEDFEM-----RVGCT 105
PYL2        EPDPTTCTSLITQRIHAPASVVWPLIRRFDNPERYKHFVKRCRL-ISGDG-----DVGSV 82
PYL3        PRSPNTCTSLIAHRVDAPAHAIWRFVRDFANPNKYKHFIKSCTIRVNGNGIKE-IKVGTI 102
PYL4        EVGPNQCCSAVIQEISAPISTVWSVVRRFDNPQAYKHFLKSCSVIGGDGDN-----VGSL 100
PYL5        DVGPDQCCSSVVQMIHAPPESVWALVRRFDNPKVYKNFIRQCRIVQGDGLH-----VGDL 106
PYL6        VVGPSQCFSVVVQDVEAPVSTVWSILSRFEHPQAYKHFVKSCHVVIGDGRE-----VGSV 109
PYL7        HCRENQCTSVLVKYIQAPVHLVWSLVRRFDQPQKYKPFISRCTVNG-DP------EIGCL 82
PYL9        LCRENQCTSALVKHIKAPLHLVWSLVRRFDQPQKYKPFVSRCTVIG-DP------EIGSL 80
PYL10       ELVESQCSSTLVKHIKAPLHLVWSIVRRFDEPQKYKPFISRCVVQGKKL------EVGSV 74
PYL8        ELVDNQCSSTLVKHINAPVHIVWSLVRRFDQPQKYKPFISRCVVKG-NM------EIGTV 78
PYL11       SQKYHTCGSTLVQTIDAPLSLVWSILRRFDNPQAYKQFVKTCNLSSGDGG------EGSV 57
PYL12       SQEQHVCGSTVVQTINAPLPLVWSILRRFDNPKTFKHFVKTCKLRSGDGG------EGSV 57
PYL13       S-KQKRCRSSVVETIEAPLPLVWSILRSFDKPQAYQRFVKSCTMRSGGGGGKGGEGKGSV 62
                     *  *    .  : **    :*  .:   *  .*:  ::  *:   *  :         G::

ALL_Con              CxSxxxxxxxAPxxxxWxxxxxFxxPxxxxxFxxxC                  Gxx
1_12_Con             CxSxxxxxxxAPxxxxWxxxxxFxxPxxxKxFxxxC                  Gxx
1_6_ Con        xxxxxxCxSxxxxxxxAPxxxxWxxxxxFxxPxxYKxFxxxC                VGxx
7_10_Con        xxxxxQCxSxLVKxIxAPxHxVWSxVRRFDxPQKYKPFxSRCxVxGx          ExGxx
11_13_Con            CxSxxVxTIxAPLxLVWSILRxFDxPxxxxxFVKxCxxxSGxGG          GSV
```

FIG. 11C

```
PYR1    RDVTVISGLPANTSTERLDILDDERRVTGFSIIGGEHRLTNYKSVTTVHRFEKEN----- : 133
PYL1    RDVNVISGLPANTSRERLDLLDDDRRVTGFSITGGEHRLRNYKSVTTVHRFEKEEEEE--- : 163
PYL2    REVTVISGLPASTSTERLEFVDDDHRVLSFRVVGGEHRLKNYKSVTSVNEFLNQDSGK--- : 140
PYL3    REVSVVSGLPASTSVEILEVLDEEKRILSFRVLGGEHRLGGEHRLNNYRSVTSVNEFVLEKDKKK : 162
PYL4    RQVHVVSGLPAASSTERLDILDDERHVISFSVVGGDHRLSNYRSVTTLHPSPISG------ : 155
PYL5    REVMVVSGLPAVSSTERLEILDERRHVISFSVVGGDHRLKNYRSVTTLHASDDEG------ : 161
PYL6    RERVVVSGLPAAFSLERLERLBIMDDDRHVISFSVVGGDHRLMNYKSVTTVHESEEDSDGK--- : 167
PYL7    REVNVKSGLPATTSTERLEQLDDEEHILGINIIGGDHRLKNYSSILTVHPEMIDGR----- : 138
PYL9    REVNVKSGLPATTSTERLELILDDDEEHILGIKIIGGDHRLKNYSSILTVHPEIIEGR---- : 136
PYL10   REVDLKSGLPATKSTEVLEILDDNEHILGIRIVGGDHRLKNYSSTISLHSETIDGK----- : 130
PYL8    REVDVKSGLPATRSTERLELLDDNEHILSIRIVGGDHRLKNYSSIISLHPETIEGR----- : 134
PYL11   REVTVVSGLPAEFSRERLDELDDESHVMMISIIGGDHRLVNYRSKTMAFVAADTEE----- : 113
PYL12   REVTVVSDLPASFSLERLDELDDDESHVMVTSIIGGDHRLVNYQSKTTVFVAAE-EE---- : 112
PYL13   RDVTLVSGFPADFSTERLEELDDESHVMVVSIIGGNHRLVNYKSKTKVVASPE-------- : 115
        *.;  *  .:**  *    *   *:  **.; ::    .  :**;*** ** *

ALL_Con     RxVxxxSxxxPAxxSxxExLxxxD                 GGxHRLxNYxS
1_12_Con    RxVxxxSxLPAxxSxExLxxxD                   GGxHRLxNYxS
1_6_Con     RxVxVxSGLPAxxSxExLxxxDxxxxxxxxFxxxGGxHRLxNYxSVT
7_10_Con    REVxxKSGLPATxSTExLExLDDxEHILxIxIxGGDHRLKNYSSxxxxHxExIxGx
11_13_Con   RxVTxVSxxPAxFSxERLxELDDESHVMxxSIIGGxHRLVNYxSKT
```

FIG. 11D

```
PYR1        RIWTVVLESYVVDMPEGNSEDDTRMFADTVVKLNLQKLATVAEAMARNSGDGSGSQVT-- 191
PYL1        RIWTVVLESYVVDVPEGNSEEDTRLFADTVIRLNLQKLASITEAMNRNNNNNNSSQVR-- 221
PYL2        -VYTVVLESYTVDIPEGNTEEDTKMFVDTVVKLNLQKLGVAATSAPMHDDE--------- 190
PYL3        RVYSVVLESYIVDIPQGNTEEDTRMFVDTVVKSNLQNLAVISTASPT------------- 209
PYL4        ---TVVVESYVVDVPPGNTKEETCDFVDVIVRCNLQSLAKIAENTAAESKKKMSL----- 207
PYL5        ---TVVVESYIVDVPPGNTEEETLSFVDTIVRCNLQSLARSTNRQ--------------- 203
PYL6        -KRTRVVESYVVDVPAGNDKEETCSFADTIVRCNLQSLAKLAENTSKFS----------- 215
PYL7        -SGTMVMESFVVDVPQGNTKDDTCYFVESLIKCNLKSLACVSERLAAQDITNSIATFCNA 197
PYL9        -AGTMVIESFVVDVPQGNTKDETCYFVEALIRCNLKSLADVSERLASQDITQ-------- 187
PYL10       -TGTLAIESFVVDVPEGNTKEETCFFVEALIQCNLNSLADVTERLQAES-MEKKI----- 183
PYL8        -IGTLVIESFVVDVPEGNTKDETCYFVEALIKCNLKSLADISERLAVQDTTESRV----- 188
PYL11       --KTVVVESYVVDVPEGNSEEETTSFADTIVGFNLKSLAKLSERVAHLKL---------- 161
PYL12       --KTVVVESYVVDVPEGNTEEETTLFADTIVGCNLRSLAKLSEKMMELT----------- 159
PYL13       ------------------------------------DMAK-------------------- 119
                                                .:.

 ALL_Con
1_12_Con          ESxxVDxPxGNxxxxTxxFxxxxxxxNLxxL
1_6_ Con        VxESYxVDxPxGNxxxxTxxFxDxxxxxNLQxL
7_10_Con     xGTxxxESFVVDVPxGNTKxxTCxFVExLIxCNLxSLAxxxERL
11_13_Con
```

FIG. 11E

```
PYR1     --------------
PYL1     --------------
PYL2     --------------
PYL3     --------------
PYL4     --------------
PYL5     --------------
PYL6     --------------
PYL11    --------------
PYL12    --------------
PYL13    --------------
PYL7     SNGYREKNHTETNL 211
PYL9     --------------
PYL10    --------------
PYL8     --------------
```

| COMPOUND | PYR1 | PYL2 | PYL3 | PYL4 |
|---|---|---|---|---|
| 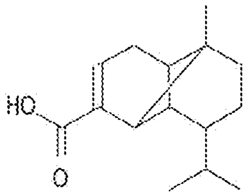 | ND | + | +++ | +++ |
| 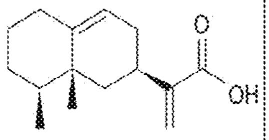 | - | - | ++ | ++ |
| 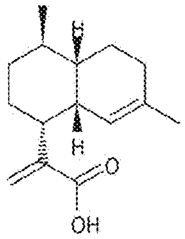 | - | - | ++ | ++ |
| 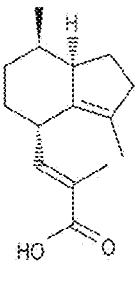 | - | - | + | + |
FIG. 12

| | | | | |
|---|---|---|---|---|
| 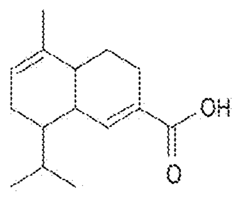 | - | - | + | + |
| 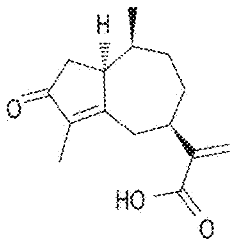 | - | - | + | + |
| 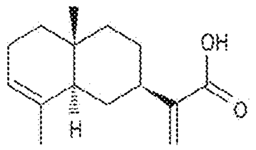 | - | - | + | + |
| 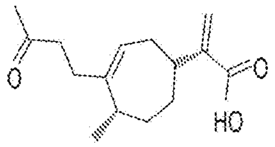 | - | - | + | + |
FIG. 12 (cont.)

CONSTITUTIVELY ACTIVE PYR/PYL RECEPTOR PROTEINS FOR IMPROVING PLANT STRESS TOLERANCE

CROSS-REFERENCE TO RELATED PATENT APPLICATIONS

This application is a divisional of application Ser. No. 12/705,413, filed Feb. 12, 2010, which claims the benefit of U.S. Provisional Patent Application No. 61/207,684, filed Feb. 13, 2009, each of which is incorporated by reference for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file-1954-3.TXT, created on Jun. 3, 2014, 233,472 bytes, machine format IBM-PC, MS-Windows operating system, is hereby incorporated by reference in its entirety for all purposes.

BACKGROUND OF THE INVENTION

Abscisic acid (ABA) has been the focus of intense investigation since it was identified in the 1960s as an endogenous small molecule growth inhibitor and regulator of plant stress physiology (K. Ohkuma, J. L. Lyon, F. T. Addicott, O. E. Smith, *Science* 142, 1592 (1963); C. F. Eagles, P. E. Wareing, *Physiologia Plantarum* 17, 697 (1964); J. W. Cornforth, B. V. Milborrow, G. Ryback, *Nature* 206, 715 (1965); J. W. Cornforth, B. V. Milborrow, G. Ryback, P. F. Wareing, *Nature* 205, 1269 (1965); D. Imber, M. Tal, *Science* 169 592 (1970)). Indeed, when one increases plant ABA sensitivity, improved drought and other stress tolerance results. See, e.g. Wang et al., *Plant J.* 43:413-424 (2005); Pei et al. *Science* 282:287-290 (1998); US Patent Publication No 2004/0010821. Genetic analyses have identified many factors involved in ABA signaling, including the type 2 C protein phosphatases (PP2Cs) ABI1, ABI2 and relatives that form the closely related ABI1/AHG1 clades that function as redundant negative regulators of ABA signaling (R. R. Finkelstein, S. S. L. Gampala, C. D. Rock, *The Plant Cell* 14, S15 (2002); P. McCourt, *Annual Review of Plant Physiology and Plant Molecular Biology* 50, 219 (1999); A. Schweighofer, H. Hirt, I. Meskiene, *Trends in Plant Science* 9, 236 (2004)). Several ABA binding proteins have been reported, however it is not clear how they regulate the myriad effects of ABA, because they do not appear to act through known regulators of its signaling pathway (X. Liu et al., *Science* 315, 1712 (Mar. 23, 2007); F. A. Razem, A. El-Kereamy, S. R. Abrams, R. D. Hill, *Nature* 439, 290 (2006); Y. Y. Shen et al., *Nature* 443, 823 (Oct. 19, 2006)). Additionally, the characterized receptors show negligible binding to the non-natural stereoisomer (−)-ABA 1 at concentrations ~1000-fold higher than their $K_d$s for (+)-ABA 2. (−)-ABA is bioactive in most ABA assays (B.-L. Lin, H.-J. Wang, J.-S. Wang, L. I. Zaharia, S. R. Abrams, *Journal of Experimental Botany* 56, 2935 (2005); D. Huang et al., *The Plant Journal* 50, 414 (2007)) and acts through the same signaling pathway as (+)-ABA (E. Nambara et al., *Genetics* 161, 1247 (July, 2002)), suggesting that receptors that recognize both (−) and (+)-ABA remain to be discovered.

BRIEF SUMMARY OF THE INVENTION

The present invention provides for plants (or a plant cell, seed, flower, leaf, fruit, or other plant part from such plants) comprising a heterologous expression cassette, the expression cassette comprising a promoter operably linked to a polynucleotide encoding a PYR/PYL receptor polypeptide, wherein the plant has improved stress tolerance compared to a plant lacking the expression cassette.

In some embodiments, the PYR/PYL receptor polypeptide comprises one or more of SEQ ID NOs:1, 91, 92, 93, 94, 95, 96, 97, 98, 99, 100, 101, 102, 103, 104, 105, 106, 107 and/or 138.

In some embodiments, the PYR/PYL receptor polypeptide is at least 70% (e.g., at least 70%, 80%, 90%, 95%) identical to any of SEQ ID NOs:2-90 or 108-137.

In some embodiments, the PYR/PYL receptor polypeptide is a constitutively-active form such that the receptor will bind a type 2 protein phosphatase (PP2C) in a yeast two-hybrid assay in the absence of abscisic acid or an ABA agonist.

In some embodiments, the PYR/PYL receptor polypeptide bind a type 2 protein phosphatase (PP2C) in a yeast two-hybrid assay in the presence, but not in the absence, of abscisic acid or an ABA agonist.

In some embodiments, the plant has improved drought tolerance compared to a plant lacking the expression cassette.

In some embodiments, the promoter is a root-specific promoter.

In some embodiments, the promoter is specific for an aerial portion of the plant.

In some embodiments, the promoter is inducible.

The present invention also provides for methods of increasing stress tolerance in a plant as described above. In some embodiments, the method comprises contacting the plant with a sufficient amount of a compound to increase stress tolerance compared to not contacting the plant with the compound, wherein the compound is selected from the following formulas:

(I)

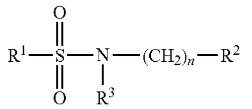

(II)

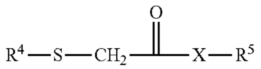

(III)

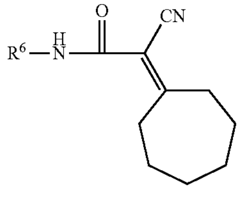

(IV)

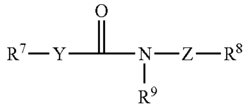

(V)

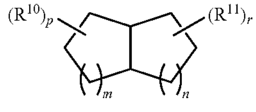

-continued (VI)

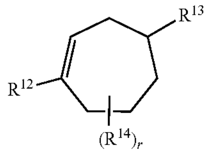

wherein $R^1$ is selected from the group consisting of aryl and heteroaryl, optionally substituted with 1-3 $R^{1a}$ groups;

each $R^{1a}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ hydroxyalkyl, —NR'R", —SR', —OH, —CN, —$NO_2$, —C(O)R', —C(O)OR', —C(O)NR'R", —N(R')C(O)R", —N(R')C(O)OR", —N(R')C(O)NR'R", —OP(O)(OR')$_2$, —S(O)$_2$OR', —S(O)$_2$NR'R", cycloalkyl, heterocycloalkyl, aryl and heteroaryl, wherein the aryl group is optionally substituted with —$NO_2$ and the heteroaryl group is optionally substituted with $C_{1-6}$ alkyl;

alternatively, adjacent $R^{1a}$ groups can combine to form a member selected from the group consisting of cycloalkyl, heterocycloalkyl, aryl and heteroaryl, wherein the aryl group is optionally substituted with —OH;

R' and R" are each independently selected from the group consisting of H and $C_{1-6}$ alkyl;

$R^2$ is selected from the group consisting of $C_{2-6}$ alkenyl, cycloalkenyl, aryl and heteroaryl;

$R^3$ is H or is optionally combined with $R^2$ and the atoms to which each is attached to form a heterocycloalkyl optionally substituted with 1-3 $R^{1a}$ groups;

$R^4$ is a heteroaryl, optionally substituted with 1-3 $R^{1a}$ groups;

$R^5$ is selected from the group consisting of $C_{1-6}$ alkyl and aryl, wherein the aryl is optionally substituted with 1-3 $R^{1a}$ groups;

each of $R^6$ and $R^7$ are independently selected from the group consisting of aryl and heteroaryl, each optionally substituted with 1-3 $R^{1a}$ groups;

$R^8$ is selected from the group consisting of cycloalkyl and aryl, each optionally substituted with 1-3 $R^{1a}$ groups;

$R^9$ is H or is optionally combined with a $R^{1a}$ group of $R^8$ and the atoms to which each is attached to form a heterocycloalkyl; subscript n is 0-2;

X is absent or is selected from the group consisting of —O—, and —N(R')—;

Y is absent or is selected from the group consisting of —C(O)— and —C(R',R")—;

Z is absent or is selected from the group consisting of —N═, and —C(S)—N(R')—, such that one of Y and Z is absent;

each of $R^{10}$ and $R^{11}$ are independently selected from the group consisting of H, $C_{1-6}$ alkyl, —C(O)OR', and $C_{1-6}$ alkenyl-C(O)OH, wherein at least two of the $R^{10}$ and $R^{11}$ groups are $C_{1-6}$ alkyl and at least one of the $R^{10}$ and $R^{11}$ groups is $C_{1-6}$ alkenyl-C(O)OH;

alternatively, two $R^{10}$ or $R^{11}$ groups attached to the same carbon are combined to form ═O;

alternatively, one $R^{10}$ group and one $R^{11}$ group are combined to form a cycloalkyl having from 3 to 6 ring members;

each of subscripts k and m is an integer from 1 to 3, such that the sum of k and m is from 3 to 4;

each of subscripts p and r is an integer from 1 to 10;

wherein two of the $R^{10}$ and $R^{11}$ groups on adjacent carbons are combined to form a bond;

$R^{12}$ is a $C_{1-6}$ alkyl, substituted with a ═O;

$R^{13}$ is $C_{1-6}$ alkenyl-C(O)OH;

$R^{14}$ is selected from the group consisting of H and $C_{1-6}$ alkyl; and subscript r is an integer from 1 to 10;

with the proviso that when $R^1$ is 4-bromo-naphthalen-1-yl, and n is 1, $R^2$ is other than unsubstituted pyrid-2-yl The present invention also provides an expression cassette comprising a promoter operably linked to a polynucleotide encoding a PYR/PYL receptor polypeptide, wherein introduction of the expression cassette into a plant results in the plant having improved stress tolerance compared to a plant lacking the expression cassette.

In some embodiments, the PYR/PYL receptor polypeptide comprises one or more of SEQ ID NOs:1, 91, 92, 93, 94, 95, 96, 97, 98, 99, 100, 101, 102, 103, 104, 105, 106, 107 and/or 138.

In some embodiments, the PYR/PYL receptor polypeptide is at least 70% (e.g., at least 70%, 80%, 90%, 95%) identical to any of SEQ ID NOs:2-90 or 108-137.

In some embodiments, the PYR/PYL receptor polypeptide is a constitutively-active form such that the receptor will bind a type 2 protein phosphatase (PP2C) in a yeast two-hybrid assay in the absence of abscisic acid or an ABA agonist.

In some embodiments, the PYR/PYL receptor polypeptide bind a type 2 protein phosphatase (PP2C) in a yeast two-hybrid assay in the presence, but not in the absence, of abscisic acid or an ABA agonist.

In some embodiments, the plant has improved drought tolerance compared to a plant lacking the expression cassette.

In some embodiments, the promoter is a root-specific promoter. In some embodiments, the promoter is specific for an aerial portion of the plant. In some embodiments, the promoter is inducible.

The present invention also provides for expression vectors comprising an expression cassette of the invention (e.g., as described above).

The present invention also provides for methods of making a plant with increased stress tolerance. In some embodiments, the method comprises:

introducing the an expression cassette of the invention (e.g., as described above) into a plurality of plants; and selecting a plant comprising the expression cassette having increased stress tolerance compared to a plant lacking the expression cassette.

The present invention also provides an agricultural chemical formulation formulated for contacting to plants, the formulation comprising a compound selected from the following formulas:

(I)

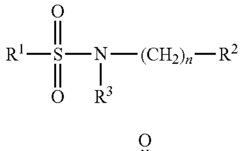

(II)

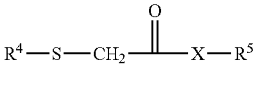

-continued (III)

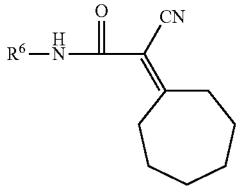

(IV)

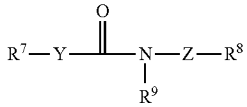

(V)

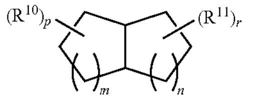

(VI)

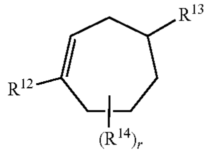

wherein $R^1$ is selected from the group consisting of aryl and heteroaryl, optionally substituted with 1-3 $R^{1a}$ groups;

each $R^{1a}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ hydroxyalkyl, —NR'R", —SR', —OH, —CN, —$NO_2$, —C(O)R', —C(O)OR', —C(O)NR'R", —N(R')C(O)R", —N(R')C(O)OR", —N(R')C(O)NR'R", —OP(O)$(OR')_2$, —$S(O)_2OR'$, —$S(O)_2NR'R"$, cycloalkyl, heterocycloalkyl, aryl and heteroaryl, wherein the aryl group is optionally substituted with —$NO_2$ and the heteroaryl group is optionally substituted with $C_{1-6}$ alkyl;

alternatively, adjacent $R^{1a}$ groups can combine to form a member selected from the group consisting of cycloalkyl, heterocycloalkyl, aryl and heteroaryl, wherein the aryl group is optionally substituted with —OH;

R' and R" are each independently selected from the group consisting of H and $C_{1-6}$ alkyl;

$R^2$ is selected from the group consisting of $C_{2-6}$ alkenyl, cycloalkenyl, aryl and heteroaryl;

$R^3$ is H or is optionally combined with $R^2$ and the atoms to which each is attached to form a heterocycloalkyl optionally substituted with 1-3 $R^{1a}$ groups;

$R^4$ is a heteroaryl, optionally substituted with 1-3 $R^{1a}$ groups;

$R^5$ is selected from the group consisting of $C_{1-6}$ alkyl and aryl, wherein the aryl is optionally substituted with 1-3 $R^{1a}$ groups;

each of $R^6$ and $R^7$ are independently selected from the group consisting of aryl and heteroaryl, each optionally substituted with 1-3 $R^{1a}$ groups;

$R^8$ is selected from the group consisting of cycloalkyl and aryl, each optionally substituted with 1-3 $R^{1a}$ groups;

$R^9$ is H or is optionally combined with a $R^{1a}$ group of $R^8$ and the atoms to which each is attached to form a heterocycloalkyl; subscript n is 0-2;

X is absent or is selected from the group consisting of —O—, and —N(R')—;

Y is absent or is selected from the group consisting of —C(O)— and —C(R',R")—;

Z is absent or is selected from the group consisting of —N=, and —C(S)—N(R')—, such that one of Y and Z is absent;

each of $R^{10}$ and $R^{11}$ are independently selected from the group consisting of H, $C_{1-6}$ alkyl, —C(O)OR', and $C_{1-6}$ alkenyl-C(O)OH, wherein at least two of the $R^{10}$ and $R^{11}$ groups are $C_{1-6}$ alkyl and at least one of the $R^{10}$ and $R^{11}$ groups is $C_{1-6}$ alkenyl-C(O)OH;

alternatively, two $R^{10}$ or $R^{11}$ groups attached to the same carbon are combined to form =O;

alternatively, one $R^{10}$ group and one $R^{11}$ group are combined to form a cycloalkyl having from 3 to 6 ring members;

each of subscripts k and m is an integer from 1 to 3, such that the sum of k and m is from 3 to 4;

each of subscripts p and r is an integer from 1 to 10;

wherein two of the $R^{10}$ and $R^{11}$ groups on adjacent carbons are combined to form a bond;

$R^{12}$ is a $C_{1-6}$ alkyl, substituted with a =O;

$R^{13}$ is $C_{1-6}$ alkenyl-C(O)OH;

$R^{14}$ is selected from the group consisting of H and $C_{1-6}$ alkyl; and subscript r is an integer from 1 to 10;

with the proviso that when $R^1$ is 4-bromo-naphthalen-1-yl, and n is 1, $R^2$ is other than unsubstituted pyrid-2-yl In some embodiments, the formulation further comprises at least one of an herbicide, fungicide, pesticide, or fertilizer. In some embodiments, the formulation further comprises a surfactant.

The present invention also provides for a method of increasing stress tolerance in a plant, the method comprising contacting a plant with a sufficient amount of a formulation as described above to increase stress tolerance in the plant compared to not contacting the plant with the compound.

In some embodiments, the contacting step comprises delivering the formulation to the plant by aircraft or irrigation.

The present invention also provides for a method of identifying an agent that agonizes a PYR/PYL polypeptide. In some embodiments, the method comprises contacting one or more agents to a PYR/PYL polypeptide; and determining whether the one or more agents bind to and/or or activate the PYR/PYL receptor polypeptide, wherein binding or activation identifies the agent as an agonist of the PYR/PYL polypeptide.

In some embodiments, the determining step comprises contacting the agent to a cell comprising a two-hybrid system, wherein the two-hybrid systems detects interaction of the PYR/PYL polypeptide to a type 2 protein phosphatase (PP2C), wherein agent-dependent interaction of the PYR/PYL polypeptide to the PP2C identifies the agent as an agonist of the PYR/PYL polypeptide.

BRIEF DESCRIPTION OF THE DRAWINGS

FIG. 8. Activity of small molecule ABA agonists. This figure summarizes data from screening small molecules for receptor activity of PYR1, PYL1, PYL2, PYL3, and PYL4.

FIG. 9. IC50 values for some compounds identified in the PP2C yeast two-hybrid assay. Compound numbers listed in left column correspond to compounds identified in the assay summarized in FIG. 9. Compound 7653159 corresponds to compound 7 in FIG. 9; compound 6655097 corresponds to compound 6 in FIG. 9; and compound 7561035 corresponds to compound 9 in FIG. 9. For each compound, the ability of the compound to agonize PYR/PYL inhibition of the PP2C HAB1 was assessed using a phosphatase assay with the phosphatase substrate pNPP.

FIG. 10. Table of ABA-related phenotypes in the PYL4 overexpression line. PYL4-overexpressing and pyr1; pyl1; pyl2; pyl4 quadruple mutant *Arabidopsis* plants were examined for changes in stress response associated traits including flowering time, stature, chlorophyll content, and wiltiness relative to control *Arabidopsis* plants. Full details for the construction of the mutant plants are provided in the Examples section.

Figure 11E:
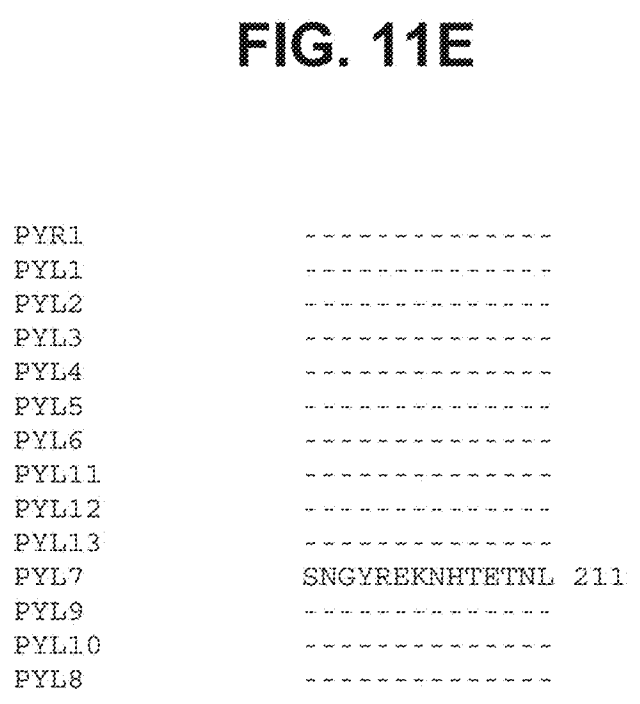

FIG. 11. Alignment of PYR1 and homologs from *Arabidopsis*. (A)-(E) An alignment of *Arabidopsis* PYR/PYL protein sequences is provided. The alignment displays, for example, absolutely conserved amino acids as well as amino acids at positions that are typically conserved. Sequences in the figure include the following PYR/PYL polypeptides: PYL12 (SEQ ID NO:77), PYL8 (SEQ ID NO:78), PYL7 (SEQ ID NO:79), PYL9 (SEQ ID NO:80), PYL11 (SEQ ID NO:81) PYL10 (SEQ ID NO:82), PYL13 (SEQ ID NO:83), PYL5 (SEQ ID NO:84), PYL4 (SEQ ID NO:85), PYL6 (SEQ ID NO:86), PYL2 (SEQ ID NO:87), PYL3 (SEQ ID NO:88), PYR1 (SEQ ID NO:89), and PYL1 (SEQ ID NO:90). Consensus sequences derived from specified members are set forth below the alignment. ALL_Con=SEQ ID NOS:93-95; 1_12_Con=SEQ ID NOS:96-99; 1_6_Con=SEQ ID NOS:100, 139 and 102; 7_10_Con=SEQ ID NOS:103 and 140; 11_13_Con=SEQ ID NOS:106 and 107.

FIG. 12. Activity of additional ABA agonists. The listed compounds include the naturally-occurring plant compound artemisinic acid, as well as analogs thereof.

DEFINITIONS

Figure 1C:
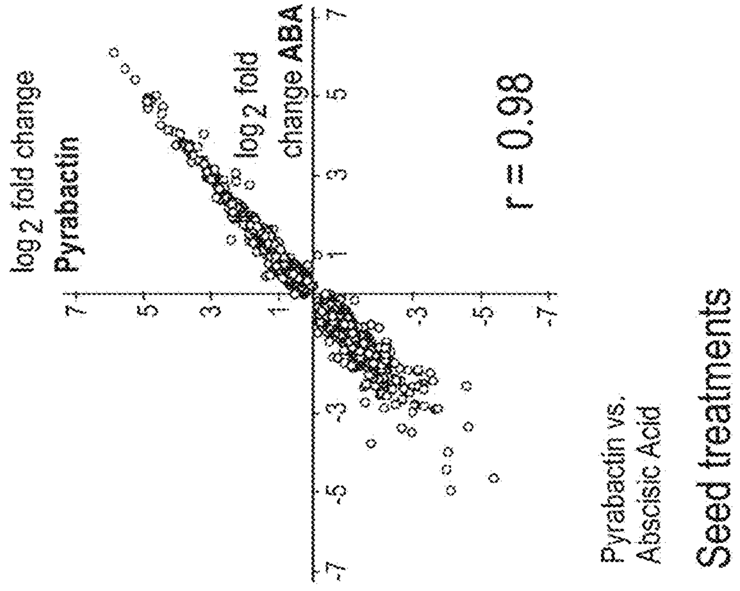
FIG. 1. Pyrabactin is a seed selective ABA agonist. (A) Structures of molecules described in this study. (B) Pyrabactin activity is suppressed by abi1-1. Seeds of the genotype shown at top were imbibed on media containing 25 μM pyrabactin and scored for germination 4 days after stratification. Shown at bottom are $IC_{50}$ values for pyrabactin's germination effect on the genotypes characterized. (C) Microarray comparison of pyrabactin and ABA treatments in seeds. The Y-axis plots the $\log_2$ transformed value for a probe's response to 25 μM pyrabactin (relative to untreated control) and the X-axis a probe's response to 1 μM ABA. Plotted are data for probe sets that showed significant responsiveness to ABA or pyrabactin, after removing germination responsive transcripts. (D) Microarray comparison of cycloheximide and ABA responses in seeds. This plot shows the response of the same probe sets analyzed in panel C, but the comparisons are to mRNAs from cycloheximide treated seeds (y-axis). (E) Microarray comparison of pyrabactin and ABA responses in seedlings. Seven-day old seedlings were transferred to 10 μM ABA or 50 μM pyrabactin containing plates for 24 hours and then mRNA samples profiled. Inset in each scatter plot is the Pearson correlation coefficient for each comparison. Detailed microarray methods are described in the Examples section.

The term "promoter," as used herein, refers to a polynucleotide sequence capable of driving transcription of a coding sequence in a cell. Thus, promoters used in the polynucleotide constructs of the invention include cis-acting transcriptional control elements and regulatory sequences that are involved in regulating or modulating the timing and/or rate of transcription of a gene. For example, a promoter can be a cis-acting transcriptional control element, including an enhancer, a promoter, a transcription terminator, an origin of replication, a chromosomal integration sequence, 5' and 3' untranslated regions, or an intronic sequence, which are involved in transcriptional regulation. These cis-acting sequences typically interact with proteins or other biomolecules to carry out (turn on/off, regulate, modulate, etc.) gene transcription. A "plant promoter" is a promoter capable of initiating transcription in plant cells. A "constitutive promoter" is one that is capable of initiating transcription in nearly all tissue types, whereas a "tissue-specific promoter" initiates transcription only in one or a few particular tissue types.

The term "plant" includes whole plants, shoot vegetative organs and/or structures (e.g., leaves, stems and tubers), roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, plant tissue (e.g., vascular tissue, ground tissue, and the like), cells (e.g., guard cells, egg cells, trichomes and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, and multicellular algae. It includes plants of a variety of ploidy levels, including aneuploid, polyploid, diploid, haploid, and hemizygous.

A polynucleotide sequence is "heterologous" to an organism or a second polynucleotide sequence if it originates from a foreign species, or, if from the same species, is modified from its original form. For example, when a promoter is said to be operably linked to a heterologous coding sequence, it means that the coding sequence is derived from one species whereas the promoter sequence is derived another, different species; or, if both are derived from the same species, the coding sequence is not naturally associated with the promoter (e.g., is a genetically engineered coding sequence, e.g., from a different gene in the same species, or an allele from a different ecotype or variety).

A polynucleotide "exogenous" to an individual plant is a polynucleotide which is introduced into the plant by any means other than by a sexual cross. Examples of means by which this can be accomplished are described below, and include *Agrobacterium*-mediated transformation, biolistic methods, electroporation, and the like. Such a plant containing the exogenous nucleic acid is referred to here as a $T_1$ (e.g., in *Arabidopsis* by vacuum infiltration) or $R_0$ (for plants regenerated from transformed cells in vitro) generation transgenic plant.

As used herein, the term "transgenic" describes a non-naturally occurring plant that contains a genome modified by man, wherein the plant includes in its genome an exogenous nucleic acid molecule, which can be derived from the same or a different plant species. The exogenous nucleic acid molecule can be a gene regulatory element such as a promoter, enhancer, or other regulatory element, or can contain a coding sequence, which can be linked to a heterologous gene regulatory element. Transgenic plants that arise from sexual cross or by selfing are descendants of such a plant and are also considered "transgenic.".

An "expression cassette" refers to a nucleic acid construct that, when introduced into a host cell, results in transcription and/or translation of an RNA or polypeptide, respectively. Antisense or sense constructs that are not or cannot be translated are expressly included by this definition. In the case of both expression of transgenes and suppression of endogenous genes (e.g., by antisense, or sense suppression) one of skill will recognize that the inserted polynucleotide sequence need not be identical, but may be only "substantially identical" to a sequence of the gene from which it was derived. As explained below, these substantially identical variants are specifically covered by reference to a specific nucleic acid sequence.

"Increased" or "enhanced" PYR/PYL expression or activity refers to an augmented change in the protein's expression or activity. Examples of such increased activity or expression include, e.g., where PYR/PYL expression is increased above control levels and/or where it is ectopically expressed, e.g., in a place or time where it is not expressed in a control. In some embodiments, PYR/PYL expression or activity is increased above the level of that in wild-type, non-transgenic control plants (i.e., the quantity of PYR/PYL activity or expression of the PYR/PYL gene is increased). In some embodiments, PYR/PYL expression or activity can be present, for example, in an organ, tissue, or cell where it is not normally detected in wild-type, non-transgenic control plants (i.e., PYR/PYL expression or activity is increased within certain tissue types). In some embodiments, PYR/PYL expression or activity is increased when its expression or activity is present in an organ, tissue or cell for a longer period than in a wild-type, non-transgenic controls (i.e., duration of PYR/PYL expression or activity is increased).

Two nucleic acid sequences or polypeptides are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

The phrase "substantially identical," used in the context of two nucleic acids or polypeptides, refers to a sequence that has at least 25% sequence identity with a reference sequence. Alternatively, percent identity can be any integer from 25% to 100%. Some embodiments include at least: 25%, 30%, 35%, 40%, 45%, 50%, 55%, 60%, 65%, 70%, 75%, 80%, 85%, 90%, 95%, or 99%, compared to a reference sequence using the programs described herein; preferably BLAST using standard parameters, as described below. The present invention provides for nucleic acids encoding polypeptides that are substantially identical to any of SEQ ID NO:2-90 or 108-137.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

(see, e.g., Creighton, *Proteins* (1984)).

As used herein, the term "drought-resistance" or "drought-tolerance," including any of their variations, refers to the ability of a plant to recover from periods of drought stress (i.e., little or no water for a period of days). Typically, the drought stress will be at least 5 days and can be as long as, for example, 18 to 20 days or more (e.g., at least 6, 7, 8, 9, 10, 11, 12, 13, 14, 15, 16, 17, 18, 19, 20 days), depending on, for example, the plant species.

DETAILED DESCRIPTION OF THE INVENTION

I. Introduction

The present invention is based, in part, on the discovery of selective abscisic acid (ABA) agonist small organic molecules as well as a protein, PYR1, which is required for the ABA agonist activity. It has further been discovered that PYR1 is a member of the PYR/PYL receptor protein family. Plants examined to date express more than one PYR/PYL receptor protein family members and have at least somewhat redundant activity. Increasing expression or activity of one or more PYR/PYL protein in a plant therefore will result in increased ABA sensitivity and accordingly improved stress (e.g. cold, heat, salinity, or drought) response and tolerance as well as other desirable ABA-mediated phenotypes.

Abscisic acid is a multifunctional phytohormone involved in a variety of phyto-protective functions including bud dormancy, seed dormancy and/or maturation, abscission of leaves and fruits, and response to a wide variety of biological stresses (e.g. cold, heat, salinity, and drought). ABA is also responsible for regulating stomatal closure by a mechanism independent of $CO_2$ concentration. Thus, because PYR/PYL ABA receptor proteins mediate ABA signalling, these phenotypes can be modulated by modulating expression of PYR/PYL. Phenotypes that are induced by ABA can be increased or speeded in plants with increased expression of PYR/PYL whereas such phenotypes can be reduced or slowed in plants with decreased expression of PYR/PYL. PYR/PYL mediates ABA signaling as a positive regulator in, for example, seed germination, post-germination growth, stomatal movement and plant tolerance to stress including, but not limited to, drought. Accordingly, when abscisic acid sensitivity is increased by overexpressing PYR/PYL, desirable characteristics in plants such as increased stress (e.g., drought) tolerance and delayed seed germination is achieved. Other desirable characteristics that can be generated in the plants of the invention include, e.g., a change in flowering time and/or increased chlorophyll content.

II. ABA Agonists

The present invention provides for small molecule ABA agonists, i.e., compounds that activate PYR/PYL proteins. Exemplary ABA agonists include, e.g., a compound selected from the following formulas:

(I)

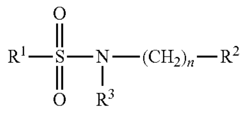

(II)

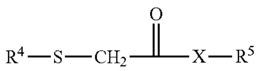

(III)

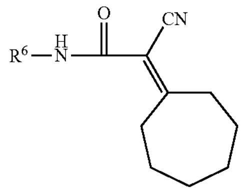

(IV)

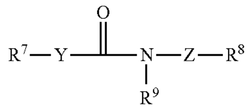

(V)

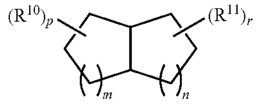

(VI)

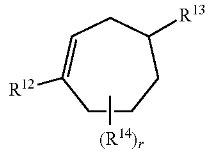

wherein $R^1$ is selected from the group consisting of aryl and heteroaryl, optionally substituted with 1-3 $R^{1a}$ groups;

each $R^{1a}$ is independently selected from the group consisting of H, halogen, $C_{1-6}$ alkyl, $C_{1-6}$ haloalkyl, $C_{2-6}$ alkenyl, $C_{2-6}$ alkynyl, $C_{1-6}$ alkoxy, $C_{1-6}$ haloalkoxy, $C_{1-6}$ hydroxyalkyl, —NR'R", —SR', —OH, —CN, —$NO_2$, —C(O)R', —C(O)OR', —C(O)NR'R", —N(R')C(O)R", —N(R')C(O)OR", —N(R')C(O)NR'R", —OP(O)(OR')$_2$, —$S(O)_2$OR', —$S(O)_2$NR'R", cycloalkyl, heterocycloalkyl, aryl and heteroaryl, wherein the aryl group is optionally substituted with —$NO_2$ and the heteroaryl group is optionally substituted with $C_{1-6}$ alkyl;

alternatively, adjacent $R^{1a}$ groups can combine to form a member selected from the group consisting of cycloalkyl, heterocycloalkyl, aryl and heteroaryl, wherein the aryl group is optionally substituted with —OH;

R' and R" are each independently selected from the group consisting of H and $C_{1-6}$ alkyl;

$R^2$ is selected from the group consisting of $C_{2-6}$ alkenyl, cycloalkenyl, aryl and heteroaryl;

$R^3$ is H or is optionally combined with $R^2$ and the atoms to which each is attached to form a heterocycloalkyl optionally substituted with 1-3 $R^{1a}$ groups;

$R^4$ is a heteroaryl, optionally substituted with 1-3 $R^{1a}$ groups;

$R^5$ is selected from the group consisting of $C_{1-6}$ alkyl and aryl, wherein the aryl is optionally substituted with 1-3 $R^{1a}$ groups;

each of $R^6$ and $R^7$ are independently selected from the group consisting of aryl and heteroaryl, each optionally substituted with 1-3 $R^{1a}$ groups;

$R^8$ is selected from the group consisting of cycloalkyl and aryl, each optionally substituted with 1-3 $R^{1a}$ groups;

$R^9$ is H or is optionally combined with a $R^{1a}$ group of $R^8$ and the atoms to which each is attached to form a heterocycloalkyl; subscript n is 0-2;

X is absent or is selected from the group consisting of —O—, and —N(R')—;

Y is absent or is selected from the group consisting of —C(O)— and —C(R',R")—;

Z is absent or is selected from the group consisting of —N═, and —C(S)—N(R')—, such that one of Y and Z is absent;

each of $R^{10}$ and $R^{11}$ are independently selected from the group consisting of H, $C_{1-6}$ alkyl, —C(O)OR', and $C_{1-6}$ alkenyl-C(O)OH, wherein at least two of the $R^{10}$ and $R^{11}$ groups are $C_{1-6}$ alkyl and at least one of the $R^{10}$ and $R^{11}$ groups is $C_{1-6}$ alkenyl-C(O)OH;

alternatively, two $R^{10}$ or $R^{11}$ groups attached to the same carbon are combined to form ═O;

alternatively, one $R^{10}$ group and one $R^{11}$ group are combined to form a cycloalkyl having from 3 to 6 ring members;

each of subscripts k and m is an integer from 1 to 3, such that the sum of k and m is from 3 to 4;

each of subscripts p and r is an integer from 1 to 10;

wherein two of the $R^{10}$ and $R^{11}$ groups on adjacent carbons are combined to form a bond;

$R^{12}$ is a $C_{1-6}$ alkyl, substituted with a ═O;

$R^{13}$ is $C_{1-6}$ alkenyl-C(O)OH;

$R^{14}$ is selected from the group consisting of H and $C_{1-6}$ alkyl; and subscript r is an integer from 1 to 10;

with the proviso that when $R^1$ is 4-bromo-naphthalen-1-yl, and n is 1, $R^2$ is other than unsubstituted pyrid-2-yl Exemplary compounds are further depicted in the Examples and Figures. See, e.g., FIGS. 9, 10, and 13.

The ABA agonist compounds of the present invention can be prepared by a variety of methods known to one of skill in the art. For example, the sulphonamide compounds can be prepared by reaction of a sulfonyl chloride and an amine to provide the sulphonamide. Amide compounds of the present invention can be prepared in a similar fashion using an acid chloride in place of the sulfonyl chloride, or carbodiimide coupling reagents known to one of skill in the art. Additional methods of making the compounds of the present invention are known to one of skill in the art, for example, those described in Comprehensive Organic Transformations, 2d ed., Richard C. Larock, 1999. The starting materials for the methods described above are commercially available (Sigma-Aldrich) or can be prepared by methods known to one of skill in the art.

Phenotypes that are induced by ABA can be increased or speeded in plants (or plant parts such as seeds) by contacting the plants with a sufficient amount of an ABA agonist of the invention to induce the ABA-inducible phenotypes. ABA agonists of the invention are useful as, e.g., positive enhancers of, for example, delayed seed germination, post-germination growth, stomatal movement and plant tolerance to stress including, but not limited to, drought.

III. ABA Agonist Formulations

The present invention provides for agricultural chemical formulation formulated for contacting to plants, wherein the formulation comprises an ABA agonist of the present invention. In some embodiments, the plants that are contacted with the agonists do not comprise or express a heterologous PYR/PYL polypeptide (e.g., the plants are not transgenic or are transgenic but express heterologous proteins other than heterologous PYR/PYL proteins). In some embodiments, the plants that are contacted with the agonists do comprise or express a heterologous PYR/PYL polypeptide as described herein.

The formulations can be suitable for treating plants or plant propagation material, such as seeds, in accordance with the present invention, e.g., in a carrier. Suitable additives include buffering agents, wetting agents, coating agents, polysaccharides, and abrading agents. Exemplary carriers include water, aqueous solutions, slurries, solids and dry powders (e.g., peat, wheat, bran, vermiculite, clay, pasteurized soil, many forms of calcium carbonate, dolomite, various grades of gypsum, bentonite and other clay minerals, rock phosphates and other phosphorous compounds, titanium dioxide, humus, talc, alginate and activated charcoal. Any agriculturally suitable carrier known to one skilled in the art would be acceptable and is contemplated for use in the present invention. Optionally, the formulations can also include at least one surfactant, herbicide, fungicide, pesticide, or fertilizer.

Treatment can be performed using a variety of known methods, e.g., by spraying, atomizing, dusting or scattering the compositions over the propagation material or brushing or pouring or otherwise contacting the compositions over the plant or, in the event of seed, by coating, encapsulating, or otherwise treating the seed. In an alternative to directly treating a plant or seed before planting, the formulations of the invention can also be introduced into the soil or other media into which the seed is to be planted. In some embodiments, a carrier is also used in this embodiment. The carrier can be solid or liquid, as noted above. In some embodiments peat is suspended in water as a carrier of the ABA agonist, and this mixture is sprayed into the soil or planting media and/or over the seed as it is planted.

IV. Screening for New ABA Agonists and Antagonists

The present invention also provides methods of screening for ABA agonists and antagonists by screening for a molecule's ability to induce PYR/PYL-PP2C binding in the case of agonists, or to disrupt the ability of ABA and other agonists to promote PYR/PYL-PP2C binding in the case of antagonists. A number of different screening protocols can be utilized to identify agents that agonize or antagonize a PYR/PYL polypeptide.

Screening can take place using isolated, purified or partially purified reagents. In some embodiments, purified or partially purified PYR/PYL polypeptide can be used.

Alternatively, cell-based methods of screening can be used. For example, cells that naturally-express a PYR/PYL polypeptide or that recombinantly express a PYR/PYL polypeptide can be used. In some embodiments, the cells used are plant cells, animal cells, bacterial cells, fungal cells, including but not limited to yeast cells, insect cells, or mammalian cells. In general terms, the screening methods involve screening a plurality of agents to identify an agent that modulates the activity of a PYR/PYL polypeptide by, e.g., binding to PYR/PYL polypeptide, or activating a PYR/PYL polypeptide or increasing expression of a PYR/PYL polypeptide, or a transcript encoding a PYR/PYL polypeptide.

1. PYR/PYL Polypeptide Binding Assays

Optionally, preliminary screens can be conducted by screening for agents capable of binding to a PYR/PRL polypeptide, as at least some of the agents so identified are likely PYR/PYL polypeptide modulators.

Binding assays can involve contacting a PYR/PYL polypeptide with one or more test agents and allowing sufficient time for the protein and test agents to form a binding complex. Any binding complexes formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. Other binding assays involve the use of mass spectrometry or NMR techniques to identify molecules bound to PYR/PYL polypeptide or displacement of labeled substrates (e.g., labeled ABA). The PYR/PYL polypeptide protein utilized in such assays can be naturally expressed, cloned or synthesized.

2. Activity

PYR/PYL polypeptide agonists can be identified by screening for agents that activate or increase activity of a PYR/PYL polypeptide. Antagonists can be identified by reducing activity.

One activity assay involves testing whether a candidate agonist can induce binding of a PYR/PYL protein to a type 2 protein phosphatase (PP2C) polypeptide in an agonist-specific fashion. Mammalian or yeast two-hybrid approaches (see, e.g., artel, P. L. et. al. *Methods Enzymol,* 254:241 (1995)) can be used to identify polypeptides or other molecules that interact or bind when expressed together in a cell. In some embodiments, agents that agonize a PYR/PYL polypeptide are identified in a two-hybrid assay between a PYR/PYL polypeptide and a type 2 protein phosphatase (PP2C) polypeptide, wherein an ABA agonist is identified as an agent that activates or enables binding of the PYR/PYL polypeptide and the PP2C polypeptide. Thus, the two polypeptides bind in the presence, but not in the absence of the agent.

In some embodiments, agents that antagonize a PYR/PYL polypeptide are identified in a two-hybrid assay between a PYR/PYL polypeptide and a type 2 protein phosphatase (PP2C) polypeptide, wherein an ABA antagonist is identified as an agent that decreases binding of the PYR/PYL polypeptide and the PP2C polypeptide, optionally in the presence of ABA or a PYR/PYL ABA agonist. Thus, the antagonist blocks the normal binding of the two polypeptides that is normally promoted by ABA or other agonists, or alternatively, that is observed in constitutively interacting PYR/PYL proteins.

3. Expression Assays

Screening for a compound that increases the expression of a PYR/PYL polypeptide is also provided. Screening methods generally involve conducting cell-based or plant-based assays in which test compounds are contacted with one or more cells expressing PYR/PYL polypeptide, and then detecting an increase in PYR/PYL expression (either transcript or translation product). Assays can be performed with cells that naturally express PYR/PYL or in cells recombinantly altered to express PYR/PYL, or in cells recombinantly altered to express a reporter gene under the control of the PYR/PYL promoter.

Various controls can be conducted to ensure that an observed activity is authentic including running parallel reactions with cells that lack the reporter construct or by not contacting a cell harboring the reporter construct with test compound.

4. Validation

Agents that are initially identified by any of the foregoing screening methods can be further tested to validate the apparent activity and/or determine other biological effects of the agent. In some cases, the identified agent is tested for the ability to effect plant stress (e.g., drought tolerance), seed germination, or another phenotype affected by ABA. A number of such assays and phenotypes are known in the art and can be employed according to the methods of the invention.

5. Solid Phase and Soluble High Throughput Assays

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 or more different compounds are possible using the integrated systems of the invention. In addition, microfluidic approaches to reagent manipulation can be used.

The molecule of interest (e.g., PYR/PYL or a cell expressing a PYR/PYL polypeptide) can be bound to the solid state component, directly or indirectly, via covalent or non covalent linkage.

The invention provides in vitro assays for identifying, in a high throughput format, compounds that can modulate the expression or activity of PYR/PYL.

V. PYR/PYL Receptor Polypeptides

Polypeptides of the invention, when expressed in plants, mediate ABA and ABA analog signaling. In some embodiments, the PYR/PYL polypeptides interact (e.g., in a yeast two-hybrid assay) with a PP2C polypeptide (e.g., ABI1 or 2 or orthologs thereof, e.g., from the group A subfamily of PP2Cs) in an ABA, pyrabactin, or other ABA agonist—dependent manner as described herein.

A wide variety of PYR/PYL polypeptide sequences are known in the art and can be used according to the methods and compositions of the invention. As noted herein, while PYR1 was originally identified as an ABA receptor in *Arabidopsis*, in fact PYR1 is a member of a group of at least 14 proteins (PYR/PYL proteins) in the same protein family in *Arabidopsis* and that also mediate ABA signaling. This protein family is also present in other plants (see, e.g., SEQUENCE LISTING) is characterized in part by the presence of one or more or all of a polyketide cyclase domain 2 (PF10604), a polyketide cyclase domain 1 (PF03364), and a Bet V I domain (PF03364). START/Bet v 1 superfamily domain are described in, for example, Radauer, *BMC Evol. Biol.* 8:286 (2008).

In situations where variants or orthologs of the above sequences are desired, it can be useful to generate sequence alignments to identify conserved amino acid or motifs (i.e., where alteration in sequences may alter protein function) and regions where variation occurs in alignment of sequences (i.e., where variation of sequence is not likely to significantly affect protein activity). SEQ ID NO:1, 91, and 92 provide consensus sequences useful for identifying PYR/PYL polypeptides. Other useful consensus sequences include, e.g., EXLXXXDXXXXXXXXXXXGGXHXL (SEQ ID NO:138); CxSxxxxxxxAPxxxxWxxxxxFxx-PxxxxxFxxxC (SEQ ID NO:93), GxxRxVxxxSxxPAxxSx-ExLxxxD (SEQ ID NO:94), and/or GGxHRLxNYxS (SEQ ID NO:95). In addition, more specific consensus sequences can be represented by aligning subsets of the 14 members of the *Arabidopsis* PYR/PYL proteins. Examples of such consensus sequences include, e.g.,

```
PYR1 to PYL12
                                        (SEQ ID NO: 96)
CxSxxxxxxxAPxxxxWxxxxxFxxPxxxKxFxxxC

                                        (SEQ ID NO: 97)
GxxRxVxxxSxLPAxxSxExLxxxD

                                        (SEQ ID NO: 98)
GGxHRLxNYxS

                                        (SEQ ID NO: 99)
ESxxVDxPxGNxxxxTxxFxxxxxxxNLxxL

PYR1-PYL6
                                       (SEQ ID NO: 100)
HxxxxxxxxCxSxxxxxxxAPxxxxWxxxxxFxxPxxYKxFxxxC

                                       (SEQ ID NO: 101)
VGRxVxVxSGLPAxxSxExLxxxDxxxxxxxFxxxGGxHRLxNYxSVT

                                       (SEQ ID NO: 102)
VxESYxVDxPxGNxxxxTxxFxDxxxxxNLQxL

PYL7-PYL10
                                       (SEQ ID NO: 103)
HxHxxxxxQCxSxLVKxIxAPxHxVWSxVRRFDxPQKYKPFxSRCxVxGx

                                       (SEQ ID NO: 104)
ExGxxREVxxKSGLPATxSTExLExLDDxEHILxIxIxGGDHRLKNYSSxxxxHxExIxGxxGTx

                                       (SEQ ID NO: 105)
xxESFVVDVPxGNTKxxTCxFVExLIxCNLxSLAxxxERL

PYL11-PYL13
                                       (SEQ ID NO: 106)
CxSxxVxTIxAPLxLVWSILRxFDxPxxxxxFVKxCxxxSGxGG

                                       (SEQ ID NO: 107)
GSVRxVTxVSxxPAxFSxERLxELDDESHVMxxSIIGGxHRLVNYxSKT
```

Accordingly, in some embodiments, the PYR/PYL polypeptides of the invention comprise one or more of the above-described consensus sequences or conservative variants thereof.

Those of skill in the art will recognize that the variable positions within the above consensus sequences can be selected based on what amino acids occur at their corresponding positions in specific PYR1 polypeptides (e.g., as occur in any of SEQ ID NOs:2-90) or alternatively can be conservative substitutions thereof. In some embodiments, the PYR/PYL polypeptides of the invention are substantially identical to (e.g., at least 70%, 75%, 80%, 85%, 90%, 95% identical to) any of SEQ ID NO:2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 108, 109, 110, 111, 112, 113, 114, 115, 116, 117, 118, 119, 120, 121, 122, 123, 124, 125, 126, 127, 128, 129, 130, 131, 132, 133, 134, 135, 136, or 137.

The present invention provides for use of the above proteins and/or nucleic acid sequences, encoding such polypeptides, in the methods and compositions (e.g., expression cassettes, plants, etc.) of the present invention. The isolation of a polynucleotide sequence encoding a plant PYR/PYL (e.g., from plants where PYR/PYL sequences have not yet been identified) may be accomplished by a number of techniques. For instance, oligonucleotide probes based on the PYR/PYL coding sequences disclosed (e.g., as listed in the SEQUENCE LISTING) here can be used to identify the desired PYR/PYL gene in a cDNA or genomic DNA library.

To construct genomic libraries, large segments of genomic DNA are generated by random fragmentation, e.g., using restriction endonucleases, and are ligated with vector DNA to form concatemers that can be packaged into the appropriate vector. To prepare a cDNA library, mRNA is isolated from the desired tissue, such as a leaf from a particular plant species, and a cDNA library containing the gene transcript of interest is prepared from the mRNA. Alternatively, cDNA may be prepared from mRNA extracted from other tissues in which PYR/PYL gene is expressed.

The cDNA or genomic library can then be screened using a probe based upon the sequence of a PYR/PYL gene disclosed here. Probes may be used to hybridize with genomic DNA or cDNA sequences to isolate homologous genes in the same or different plant species. Alternatively, antibodies raised against a polypeptide can be used to screen an mRNA expression library.

Alternatively, the nucleic acids encoding PYR/PYL can be amplified from nucleic acid samples using amplification techniques. For instance, polymerase chain reaction (PCR) technology can be used to amplify the coding sequences of PYR/PYL directly from genomic DNA, from cDNA, from genomic libraries or cDNA libraries. PCR and other in vitro amplification methods may also be useful, for example, to clone polynucleotide sequences encoding PYR/PYL to be expressed, to make nucleic acids to use as probes for detecting the presence of the desired mRNA in samples, for nucleic acid sequencing, or for other purposes. For a general overview of PCR see *PCR Protocols: A Guide to Methods and Applications*. (Innis, M, Gelfand, D., Sninsky, J. and White, T., eds.), *Academic Press*, San Diego (1990). Appropriate primers and probes for identifying sequences from plant tissues are generated from comparisons of the sequences provided here with other related genes.

In some embodiments, the partial or entire genome of a number of plants has been sequenced and open reading frames identified. By a BLAST search, one can identify the coding sequence for PYR/PYL in various plants.

Variants from naturally-occurring PYR/PYL polypeptides (or nucleic acids encoding such polypeptides) are contemplated by the term PYR/PYL polypeptide. Variants include, e.g., fusion proteins, deletions or mutations that retain activity.

In some embodiments, the PYR/PYL polypeptide is activated (e.g., as measured in a two-hybrid assay with PP2C or other receptor assays) in the presence of ABA (or ABA agonist) but is not significantly active in the absence of ABA or agonist. Alternatively, in some embodiments, the PYR/PYL polypeptides of the invention are constitutively active, i.e., are active in the absence of ABA or an ABA agonist. As described in the Examples, the inventors have found that the mutations H60P, M158T, M158I, M158S, or M158V in *Arabidopsis* PYR1 changes the protein to a constitutively active protein. As both of these positions (H60 and M158) are present on the dimer interface of the PYR/PYL protein, it is believed that other constitutive mutants can be generated by introducing amino acid changes at other dimer interface positions (e.g., F61, K63, I84, S85, L87, P88, A89, S152, D155, T156, F159, T162, L166, and/or K170). While the positions above are made with reference to the *Arabidopsis* PYR1 protein, it is intended that the corresponding position in other PYR/PYL polypeptides are also included in the above description. The corresponding position in another PYR/PYL polypeptide can be readily determined using standard alignment software such as BLAST. While specific amino acid changes are described above, the invention is intended to encompass mutations to other amino acids aside those specifically described above. In some embodiments, for example, conservative amino acids can be included in place of the mutations set forth above.

Interestingly, the inventors have observed that some naturally occurring PYR/PYL proteins naturally have a P at the position that corresponds to H60. For example, *Arabidopsis* PYL9 has a P at this position. The inventors have found that PYL9 is constitutively active. In some embodiments, a constitutively active PYR/PYL protein is converted to a protein activated by ABA or an ABA agonist by changing a proline at position "H60" (with reference to the position in *Arabidopsis* PYR1) to a Histidine or other non-proline amino acid.

Accordingly, the present invention provides for PYR/PYL polypeptides that are constitutively active and having a mutation as described above. In some embodiments, the constitutive polypeptides will comprise one or more of the above-described consensus sequences and/or will be substantially identical to one of SEQ ID NOs:2-90.

VI. Use of PYR/PYL Nucleic Acids and Polypeptides of the Invention

The invention provides methods of modulating ABA sensitivity in a plant by altering PYR/PYL expression or activity, for example, by introducing into a plant a recombinant expression cassette comprising a regulatory element (e.g., a promoter) operably linked to a PYR/PYL polynucleotide, i.e., a nucleic acid encoding PYR/PYL or a sequence comprising a portion of the sequence of a PYR/PYL mRNA or complement thereof.

In some embodiments, the methods of the invention comprise increasing and/or ectopically expressing one or more PYR/PYL polynucleotide encoding a PYR/PYL polypeptide in a plant. Such embodiments are useful for increasing ABA sensitivity of a plant, and resulting in, for example, improved stress (e.g., drought) tolerance and/or delayed seed germination (to avoid pre-mature germination, for example as can occur in humid environments or due to other exposure to moisture). For stress tolerance, promoters can be selected that are generally constitutive and are expressed in most plant tissues, or can be leaf or root specific. To affect seed germination, promoters are generally used that result in expression in seed or, in some embodiments, floral organs or embryos.

In some embodiments, the methods of the invention comprise decreasing endogenous PYR/PYL expression in plant, thereby decreasing ABA sensitivity in the plant. Such methods can involve, for example, mutagenesis (e.g., chemical, radiation, transposon or other mutagenesis) of PYR/PYL sequences in a plant to reduce PYR/PYL expression or activity, or introduction of a polynucleotide substantially identical to at least a portion of a PYR/PYL cDNA sequence or a complement thereof (e.g., an "RNAi construct") to reduce PYR/PYL expression. Decreased (or increased) PYR/PYL expression can be used to control the development of abscission zones in leaf petioles and thereby control leaf loss, i.e., delay leaf loss if expression is decreased and speed leaf loss if expression is increased in abscission zones in a leaf.

A. Increasing PYR/PYL Expression or Activity

Isolated sequences prepared as described herein can also be used to prepare expression cassettes that enhance or increase PYR/PYL gene expression. Where overexpression of a gene is desired, the desired gene (or at least the polynucleotide encoding a PYR/PYL polypeptide) from the same species or a different species (or substantially identical to the gene or polynucleotide encoding a PYR/PYL polypeptide from another species) may be used. In some embodiments, to decrease potential sense suppression effects, a polynucleotide encoding a PYR/PYL polypeptide from a different species (or substantially identical to the gene or polynucleotide encoding a PYR/PYL polypeptide from another species) may be used.

Any of a number of means well known in the art can be used to increase PYR/PYL activity in plants. Any organ or plant part can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat), fruit, abscission zone, etc. Alternatively, one or several PYR/PYL genes can be expressed constitutively (e.g., using the CaMV 35S promoter or other constitutive promoter).

One of skill will recognize that the polypeptides encoded by the genes of the invention, like other proteins, have different domains which perform different functions. Thus, the overexpressed or ectopically expressed polynucleotide sequences need not be full length, so long as the desired functional domain of the protein is expressed. Alternatively, or in addition, active PYR/PYL proteins can be expressed as fusions, without necessarily significantly altering PYR/PYL activity. Examples of fusion partners include, but are not limited to, poly-His or other tag sequences.

B. Decreasing PYR/PYL Expression or Activity

A number of methods can be used to inhibit gene expression in plants. A variety of methods to inhibit gene expression are known and can be used to inhibit expression of one of more PYR/PYL genes. See, e.g., U.S. Pat. Nos. 5,759,829; 5,107,065; 5,231,020; 5,283,184; 6,506,559; 6,573,099, 6,326,193; 7,109,393. For instance, antisense technology can be conveniently used. To accomplish this, a nucleic acid segment from the desired gene is cloned and operably linked to a promoter such that the antisense strand of RNA will be transcribed. The expression cassette is then transformed into plants and the antisense strand of RNA is produced. In plant cells, it has been suggested that antisense RNA inhibits gene expression by preventing the accumulation of mRNA which encodes the enzyme of interest, see, e.g., Sheehy et al., *Proc. Nat. Acad. Sci. USA,* 85:8805-8809 (1988); Pnueli et al., *The Plant Cell* 6:175-186 (1994); and Hiatt et al., U.S. Pat. No. 4,801,340.

The antisense nucleic acid sequence transformed into plants will be substantially identical to at least a portion of the endogenous gene or genes to be repressed. The sequence, however, does not have to be perfectly identical to inhibit expression. Thus, an antisense or sense nucleic acid molecule encoding only a portion of PYR/PYL polypeptide, or a portion of the PYR/PYL cDNA, can be useful for producing a plant in which PYR/PYL expression is suppressed. The vectors of the present invention can be designed such that the inhibitory effect applies to other proteins within a family of genes exhibiting homology or substantial homology to the target gene. In some embodiments, it may be desirable to inhibit the expression of more than one PYR/PYL polypeptide at the same time using one or more antisense or sense or other siRNA nucleic acid molecules.

For antisense suppression, the introduced sequence also need not be full length relative to either the primary transcription product or fully processed mRNA. Generally, higher homology can be used to compensate for the use of a shorter sequence. Furthermore, the introduced sequence need not have the same intron or exon pattern, and homology of non-coding segments may be equally effective. For example, a sequence of between about 30 or 40 nucleotides can be used, and in some embodiments, about full length nucleotides should be used, though a sequence of at least about 20, 50 100, 200, or 500 nucleotides can be used.

Catalytic RNA molecules or ribozymes can also be used to inhibit expression of PYR/PYL genes. It is possible to design ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum *nodiflorum* mottle virus and subterranean clover mottle virus. The design and use of target RNA-specific ribozymes is described in Haseloff et al. *Nature,* 334:585-591 (1988).

Another method of suppression is sense suppression (also known as co-suppression). Introduction of expression cassettes in which a nucleic acid is configured in the sense orientation with respect to the promoter has been shown to be an effective means by which to block the transcription of target genes. For an example of the use of this method to modulate expression of endogenous genes see, Napoli et al., *The Plant Cell* 2:279-289 (1990); Flavell, *Proc. Natl. Acad. Sci., USA* 91:3490-3496 (1994); Kooter and Mol, *Current Opin. Biol.* 4:166-171 (1993); and U.S. Pat. Nos. 5,034,323, 5,231,020, and 5,283,184.

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity can exert a more effective repression of expression of the endogenous sequences. In some embodiments, sequences with substantially greater identity are used, e.g., at least about 80, at least about 95%, or 100% identity are used. As with antisense regulation, the effect can be designed and tested to apply to any other proteins within a similar family of genes exhibiting homology or substantial homology.

For sense suppression, the introduced sequence in the expression cassette, needing less than absolute identity, also need not be full length, relative to either the primary transcription product or fully processed mRNA. This may be preferred to avoid concurrent production of some plants that are overexpressers. A higher identity in a shorter than full length sequence compensates for a longer, less identical sequence. Furthermore, the introduced sequence need not have the same intron or exon pattern, and identity of non-coding segments will be equally effective. In some embodiments, a sequence of the size ranges noted above for antisense regulation is used, i.e., 30-40, or at least about 20, 50, 100, 200, 500 or more nucleotides.

Endogenous gene expression may also be suppressed by means of RNA interference (RNAi) (and indeed co-suppression can be considered a type of RNAi), which uses a double-stranded RNA having a sequence identical or similar to the sequence of the target gene. RNAi is the phenomenon in which when a double-stranded RNA having a sequence identical or similar to that of the target gene is introduced into a cell, the expressions of both the inserted exogenous gene and target endogenous gene are suppressed. The double-stranded RNA may be formed from two separate complementary RNAs or may be a single RNA with internally complementary sequences that form a double-stranded RNA. Although complete details of the mechanism of RNAi are still unknown, it is considered that the introduced double-stranded RNA is initially cleaved into small fragments, which then serve as indexes of the target gene in some manner, thereby degrading the target gene. RNAi is known to be also effective in plants (see, e.g., Chuang, C. F. & Meyerowitz, E. M., *Proc. Natl. Acad. Sci. USA* 97: 4985 (2000); Waterhouse et al., *Proc. Natl. Acad. Sci. USA* 95:13959-13964 (1998); Tabara et al. *Science* 282:430-431 (1998); Matthew, *Comp Funct Genom* 5: 240-244 (2004); Lu, et al., *Nucleic Acids Research* 32(21):e171 (2004)). For example, to achieve suppression of the expression of a DNA encoding a protein using RNAi, a double-stranded RNA having the sequence of a DNA encoding the protein, or a substantially similar sequence thereof (including those engineered not to translate the protein) or fragment thereof, is introduced into a plant of interest. The resulting plants may then be screened for a phenotype associated with the target protein and/or by monitoring steady-state RNA levels for transcripts encoding the protein. Although the genes used for RNAi need not be completely identical to the target gene, they may be at least 70%, 80%, 90%, 95% or more identical to the target (e.g., PYR/PYL) gene sequence. See, e.g., U.S. Patent Publication No. 2004/0029283. The constructs encoding an RNA molecule with a stem-loop structure that is unrelated to the target gene and that is positioned distally to a sequence specific for the gene of interest may also be used to inhibit target gene expression. See, e.g., U.S. Patent Publication No. 2003/0221211.

The RNAi polynucleotides can encompass the full-length target RNA or may correspond to a fragment of the target RNA. In some cases, the fragment will have fewer than 100, 200, 300, 400, 500 600, 700, 800, 900 or 1,000 nucleotides corresponding to the target sequence. In addition, in some embodiments, these fragments are at least, e.g., 50, 100, 150, 200, or more nucleotides in length. In some cases, fragments for use in RNAi will be at least substantially similar to regions of a target protein that do not occur in other proteins in the organism or may be selected to have as little similarity to other organism transcripts as possible, e.g., selected by comparison to sequences in analyzing publicly-available sequence databases.

Expression vectors that continually express siRNA in transiently- and stably-transfected have been engineered to express small hairpin RNAs, which get processed in vivo into siRNAs molecules capable of carrying out gene-specific silencing (Brummelkamp et al., *Science* 296:550-553 (2002), and Paddison, et al., *Genes & Dev.* 16:948-958 (2002)). Post-transcriptional gene silencing by double-stranded RNA is discussed in further detail by Hammond et al. *Nature Rev Gen* 2: 110-119 (2001), Fire et al. *Nature* 391: 806-811 (1998) and Timmons and Fire *Nature* 395: 854 (1998).

One of skill in the art will recognize that using technology based on specific nucleotide sequences (e.g., antisense or sense suppression technology), families of homologous genes can be suppressed with a single sense or antisense transcript. For instance, if a sense or antisense transcript is designed to have a sequence that is conserved among a family of genes, then multiple members of a gene family can be suppressed. Conversely, if the goal is to only suppress one member of a homologous gene family, then the sense or antisense transcript should be targeted to sequences with the most variance between family members.

Another means of inhibiting PYR/PYL function in a plant is by creation of dominant negative mutations. In this approach, non-functional, mutant PYR/PYL polypeptides, which retain the ability to interact with wild-type subunits are introduced into a plant. A dominant negative construct also can be used to suppress PYR/PYL expression in a plant. A dominant negative construct useful in the invention generally contains a portion of the complete PYR/PYL coding sequence sufficient, for example, for DNA-binding or for a protein-protein interaction such as a homodimeric or heterodimeric protein-protein interaction but lacking the transcriptional activity of the wild type protein.

VII. Recombinant Expression Vectors

Once the coding or cDNA sequence for PYR/PYL is obtained, it can also be used to prepare an expression cassette for expressing the PYR/PYL protein in a transgenic plant, directed by a heterologous promoter. Increased expression of PYR/PYL polynucleotide is useful, for example, to produce plants with enhanced drought-resistance. Alternatively, as described above, expression vectors can also be used to express PYR/PYL polynucleotides and variants thereof that inhibit endogenous PYR/PYL expression.

Any of a number of means well known in the art can be used to increase or decrease PYR/PYL activity or expression in plants. Any organ can be targeted, such as shoot vegetative organs/structures (e.g. leaves, stems and tubers), roots, flowers and floral organs/structures (e.g. bracts, sepals, petals, stamens, carpels, anthers and ovules), seed (including embryo, endosperm, and seed coat) and fruit. Alternatively, the PYR/PYL gene can be expressed constitutively (e.g., using the CaMV 35S promoter).

To use PYR/PYL coding or cDNA sequences in the above techniques, recombinant DNA vectors suitable for transformation of plant cells are prepared. Techniques for transforming a wide variety of higher plant species are well known and described in the technical and scientific literature. See, e.g., Weising et al. *Ann. Rev. Genet.* 22:421-477 (1988). A DNA sequence coding for the PYR/PYL polypeptide preferably will be combined with transcriptional and translational initiation regulatory sequences which will direct the transcription of the sequence from the gene in the intended tissues of the transformed plant.

For example, a plant promoter fragment may be employed to direct expression of the PYR/PYL gene in all tissues of a regenerated plant. Such promoters are referred to herein as "constitutive" promoters and are active under most environmental conditions and states of development or cell differentiation. Examples of constitutive promoters include the cauliflower mosaic virus (CaMV) 35S transcription initiation region, the 1'- or 2'-promoter derived from T-DNA of *Agrobacterium tumafaciens*, and other transcription initiation regions from various plant genes known to those of skill.

Alternatively, the plant promoter may direct expression of the PYR/PYL protein in a specific tissue (tissue-specific promoters) or may be otherwise under more precise environmental control (inducible promoters). Examples of tissue-specific promoters under developmental control include promoters that initiate transcription only in certain tissues, such as leaves or guard cells (including but not limited to those described in WO/2005/085449; U.S. Pat. No. 6,653,535; Li et al., *Sci China C Life Sci.* 2005 April; 48(2):181-6; Husebye, et al., *Plant Physiol*, April 2002, Vol. 128, pp. 1180-1188; and Plesch, et al., *Gene*, Volume 249, Number 1, 16 May 2000, pp. 83-89(7)). Examples of environmental conditions that may affect transcription by inducible promoters include anaerobic conditions, elevated temperature, or the presence of light.

If proper protein expression is desired, a polyadenylation region at the 3'-end of the coding region should be included. The polyadenylation region can be derived from the natural gene, from a variety of other plant genes, or from T-DNA.

The vector comprising the sequences (e.g., promoters or PYR/PYL coding regions) will typically comprise a marker gene that confers a selectable phenotype on plant cells. For example, the marker may encode biocide resistance, particularly antibiotic resistance, such as resistance to kanamycin, G418, bleomycin, hygromycin, or herbicide resistance, such as resistance to chlorosluforon or Basta.

In some embodiments, the PYR/PYL nucleic acid sequence is expressed recombinantly in plant cells to enhance and increase levels of total PYR/PYL polypeptide. A variety of different expression constructs, such as expression cassettes and vectors suitable for transformation of plant cells can be prepared. Techniques for transforming a wide variety of higher plant species are well known and described in the technical and scientific literature. See, e.g., Weising et al. *Ann. Rev. Genet.* 22:421-477 (1988). A DNA sequence coding for a PYR/PYL protein can be combined with cis-acting (promoter) and trans-acting (enhancer) transcriptional regulatory sequences to direct the timing, tissue type and levels of transcription in the intended tissues of the transformed plant. Translational control elements can also be used.

The invention provides a PYR/PYL nucleic acid operably linked to a promoter which, in some embodiments, is capable of driving the transcription of the PYR/PYL coding sequence in plants. The promoter can be, e.g., derived from plant or viral sources. The promoter can be, e.g., constitutively active, inducible, or tissue specific. In construction of recombinant expression cassettes, vectors, transgenics, of the invention, a different promoters can be chosen and employed to differentially direct gene expression, e.g., in some or all tissues of a plant or animal.

A. Constitutive Promoters

A promoter fragment can be employed to direct expression of a PYR/PYL nucleic acid in all transformed cells or tissues, e.g., as those of a regenerated plant. The term "constitutive regulatory element" means a regulatory element that confers a level of expression upon an operatively linked nucleic molecule that is relatively independent of the cell or tissue type in which the constitutive regulatory element is expressed. A constitutive regulatory element that is expressed in a plant generally is widely expressed in a large number of cell and tissue types. Promoters that drive expression continuously under physiological conditions are referred to as "constitutive" promoters and are active under most environmental conditions and states of development or cell differentiation.

A variety of constitutive regulatory elements useful for ectopic expression in a transgenic plant are well known in the art. The cauliflower mosaic virus 35S (CaMV 35S) promoter, for example, is a well-characterized constitutive regulatory element that produces a high level of expression in all plant tissues (Odell et al., *Nature* 313:810-812 (1985)). The CaMV 35S promoter can be particularly useful due to its activity in numerous diverse plant species (Benfey and Chua, *Science* 250:959-966 (1990); Futterer et al., *Physiol. Plant* 79:154 (1990); Odell et al., supra, 1985). A tandem 35S promoter, in which the intrinsic promoter element has been duplicated, confers higher expression levels in comparison to the unmodified 35S promoter (Kay et al., *Science* 236:1299 (1987)). Other useful constitutive regulatory elements include, for example, the cauliflower mosaic virus 19S promoter; the Figwort mosaic virus promoter; and the nopaline synthase (nos) gene promoter (Singer et al., *Plant Mol. Biol.* 14:433 (1990); An, *Plant Physiol.* 81:86 (1986)).

Additional constitutive regulatory elements including those for efficient expression in monocots also are known in the art, for example, the pEmu promoter and promoters based on the rice Actin-1 5' region (Last et al., *Theor. Appl. Genet.* 81:581 (1991); Mcelroy et al., *Mol. Gen. Genet.* 231:150 (1991); Mcelroy et al., *Plant Cell* 2:163 (1990)). Chimeric regulatory elements, which combine elements from different genes, also can be useful for ectopically expressing a nucleic acid molecule encoding a PYR/PYL protein (Comai et al., *Plant Mol. Biol.* 15:373 (1990)).

Other examples of constitutive promoters include the 1'- or 2'-promoter derived from T-DNA of *Agrobacterium tumafaciens* (see, e.g., Mengiste (1997) supra; O'Grady (1995) *Plant Mol. Biol.* 29:99-108); actin promoters, such as the *Arabidopsis* actin gene promoter (see, e.g., Huang (1997) *Plant Mol. Biol.* 1997 33:125-139); alcohol dehydrogenase (Adh) gene promoters (see, e.g., Millar (1996) *Plant Mol. Biol.* 31:897-904); ACT11 from *Arabidopsis* (Huang et al. *Plant Mol. Biol.* 33:125-139 (1996)), Cat3 from *Arabidopsis* (GenBank No. U43147, Zhong et al., *Mol. Gen. Genet.* 251:196-203 (1996)), the gene encoding stearoyl-acyl carrier protein desaturase from *Brassica napus* (Genbank No. X74782, Solocombe et al. *Plant Physiol.* 104:1167-1176 (1994)), GPc1 from maize (GenBank No. X15596, Martinez et al. *J. Mol. Biol* 208:551-565 (1989)), Gpc2 from maize (GenBank No. U45855, Manjunath et al., *Plant Mol. Biol.* 33:97-112 (1997)), other transcription initiation regions from various plant genes known to those of skill. See also Holtorf *Plant Mol. Biol.* 29:637-646 (1995).

B. Inducible Promoters

Alternatively, a plant promoter may direct expression of the PYR/PYL gene under the influence of changing environmental conditions or developmental conditions. Examples of environmental conditions that may effect transcription by inducible promoters include anaerobic conditions, elevated temperature, drought, or the presence of light. Such promoters are referred to herein as "inducible" promoters. For example, the invention can incorporate drought-specific promoter such as the drought-inducible promoter of maize (Busk (1997) supra); or alternatively the cold, drought, and high salt inducible promoter from potato (Kirch (1997) *Plant Mol. Biol.* 33:897-909).

Alternatively, plant promoters which are inducible upon exposure to plant hormones, such as auxins, are used to express the PYR/PYL gene. For example, the invention can use the auxin-response elements E1 promoter fragment (AuxREs) in the soybean (*Glycine max* L.) (Liu (1997) *Plant Physiol.* 115:397-407); the auxin-responsive *Arabidopsis* GST6 promoter (also responsive to salicylic acid and hydrogen peroxide) (Chen (1996) *Plant J.* 10: 955-966); the auxin-inducible parC promoter from tobacco (Sakai (1996) 37:906-913); a plant biotin response element (Streit (1997) *Mol. Plant Microbe Interact.* 10:933-937); and, the promoter responsive to the stress hormone abscisic acid (Sheen (1996) *Science* 274:1900-1902).

Plant promoters inducible upon exposure to chemicals reagents that may be applied to the plant, such as herbicides or antibiotics, are also useful for expressing the PYR/PYL gene. For example, the maize In2-2 promoter, activated by benzenesulfonamide herbicide safeners, can be used (De Veylder (1997) *Plant Cell Physiol.* 38:568-577); application of different herbicide safeners induces distinct gene expression patterns, including expression in the root, hydathodes, and the shoot apical meristem. A PYR/PYL coding sequence can also be under the control of, e.g., a tetracycline-inducible promoter, e.g., as described with transgenic tobacco plants containing the *Avena sativa* L. (oat) arginine decarboxylase gene (Masgrau (1997) *Plant J.* 11:465-473); or, a salicylic acid-responsive element (Stange (1997) *Plant J.* 11:1315-1324; Uknes et al., *Plant Cell* 5:159-169 (1993); Bi et al., *Plant J.* 8:235-245 (1995)).

Examples of useful inducible regulatory elements include copper-inducible regulatory elements (Mett et al., *Proc. Natl. Acad. Sci. USA* 90:4567-4571 (1993); Furst et al., *Cell* 55:705-717 (1988)); tetracycline and chlor-tetracycline-inducible regulatory elements (Gatz et al., *Plant J.* 2:397-404 (1992); Roder et al., *Mol. Gen. Genet.* 243:32-38 (1994);

Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gen. Genet.* 250: 533-539 (1996)); and lac operon elements, which are used in combination with a constitutively expressed lac repressor to confer, for example, IPTG-inducible expression (Wilde et al., *EMBO J.* 11:1251-1259 (1992)). An inducible regulatory element useful in the transgenic plants of the invention also can be, for example, a nitrate-inducible promoter derived from the spinach nitrite reductase gene (Back et al., *Plant Mol. Biol.* 17:9 (1991)) or a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)).

C. Tissue-Specific Promoters

Alternatively, the plant promoter may direct expression of the PYR/PYL gene in a specific tissue (tissue-specific promoters). Tissue specific promoters are transcriptional control elements that are only active in particular cells or tissues at specific times during plant development, such as in vegetative tissues or reproductive tissues.

Examples of tissue-specific promoters under developmental control include promoters that initiate transcription only (or primarily only) in certain tissues, such as vegetative tissues, e.g., roots or leaves, or reproductive tissues, such as fruit, ovules, seeds, pollen, pistols, flowers, or any embryonic tissue, or epidermis or mesophyll. Reproductive tissue-specific promoters may be, e.g., ovule-specific, embryo-specific, endosperm-specific, integument-specific, seed and seed coat-specific, pollen-specific, petal-specific, sepal-specific, or some combination thereof. In some embodiments, the promoter is cell-type specific, e.g., guard cell-specific.

Other tissue-specific promoters include seed promoters. Suitable seed-specific promoters are derived from the following genes: MAC1 from maize (Sheridan (1996) *Genetics* 142:1009-1020); Cat3 from maize (GenBank No. L05934, Abler (1993) *Plant Mol. Biol.* 22:10131-1038); vivparous-1 from *Arabidopsis* (Genbank No. U93215); atmyc1 from *Arabidopsis* (Urao (1996) *Plant Mol. Biol.* 32:571-57; Conceicao (1994) *Plant* 5:493-505); napA from *Brassica napus* (GenBank No. J02798, Josefsson (1987) JBL 26:12196-1301); and the napin gene family from *Brassica napus* (Sjodahl (1995) *Planta* 197:264-271).

A variety of promoters specifically active in vegetative tissues, such as leaves, stems, roots and tubers, can also be used to express polynucleotides encoding PYR/PYL polypeptides (or RNAi or antisense or sense constructs). For example, promoters controlling patatin, the major storage protein of the potato tuber, can be used, see, e.g., Kim (1994) *Plant Mol. Biol.* 26:603-615; Martin (1997) *Plant J.* 11:53-62. The ORF13 promoter from *Agrobacterium rhizogenes* that exhibits high activity in roots can also be used (Hansen (1997) *Mol. Gen. Genet.* 254:337-343. Other useful vegetative tissue-specific promoters include: the tarin promoter of the gene encoding a globulin from a major taro (*Colocasia esculenta* L. Schott) corm protein family, tarin (Bezerra (1995) *Plant Mol. Biol.* 28:137-144); the curculin promoter active during taro corm development (de Castro (1992) *Plant Cell* 4:1549-1559) and the promoter for the tobacco root-specific gene TobRB7, whose expression is localized to root meristem and immature central cylinder regions (Yamamoto (1991) *Plant Cell* 3:371-382).

Leaf-specific promoters, such as the ribulose biphosphate carboxylase (RBCS) promoters can be used. For example, the tomato RBCS1, RBCS2 and RBCS3A genes are expressed in leaves and light-grown seedlings, only RBCS1 and RBCS2 are expressed in developing tomato fruits (Meier (1997) *FEBS Lett.* 415:91-95). A ribulose bisphosphate carboxylase promoters expressed almost exclusively in mesophyll cells in leaf blades and leaf sheaths at high levels, described by Matsuoka (1994) *Plant J.* 6:311-319, can be used. Another leaf-specific promoter is the light harvesting chlorophyll a/b binding protein gene promoter, see, e.g., Shiina (1997) *Plant Physiol.* 115:477-483; Casal (1998) *Plant Physiol.* 116:1533-1538. The *Arabidopsis thaliana* myb-related gene promoter (Atmyb5) described by Li (1996) *FEBS Lett.* 379:117-121, is leaf-specific. The Atmyb5 promoter is expressed in developing leaf trichomes, stipules, and epidermal cells on the margins of young rosette and cauline leaves, and in immature seeds. Atmyb5 mRNA appears between fertilization and the 16 cell stage of embryo development and persists beyond the heart stage. A leaf promoter identified in maize by Busk (1997) *Plant J.* 11:1285-1295, can also be used.

Another class of useful vegetative tissue-specific promoters are meristematic (root tip and shoot apex) promoters. For example, the "SHOOTMERISTEMLESS" and "SCARECROW" promoters, which are active in the developing shoot or root apical meristems, described by Di Laurenzio (1996) *Cell* 86:423-433; and, Long (1996) *Nature* 379:66-69; can be used. Another useful promoter is that which controls the expression of 3-hydroxy-3-methylglutaryl coenzyme A reductase HMG2 gene, whose expression is restricted to meristematic and floral (secretory zone of the stigma, mature pollen grains, gynoecium vascular tissue, and fertilized ovules) tissues (see, e.g., Enjuto (1995) *Plant Cell.* 7:517-527). Also useful are kn1-related genes from maize and other species which show meristem-specific expression, see, e.g., Granger (1996) *Plant Mol. Biol.* 31:373-378; Kerstetter (1994) *Plant Cell* 6:1877-1887; Hake (1995) *Philos. Trans. R. Soc. Lond. B. Biol. Sci.* 350:45-51. For example, the *Arabidopsis thaliana* KNAT1 promoter (see, e.g., Lincoln (1994) *Plant Cell* 6:1859-1876).

One of skill will recognize that a tissue-specific promoter may drive expression of operably linked sequences in tissues other than the target tissue. Thus, as used herein a tissue-specific promoter is one that drives expression preferentially in the target tissue, but may also lead to some expression in other tissues as well.

In another embodiment, the PYR/PYL polynucleotide is expressed through a transposable element. This allows for constitutive, yet periodic and infrequent expression of the constitutively active polypeptide. The invention also provides for use of tissue-specific promoters derived from viruses including, e.g., the tobamovirus subgenomic promoter (Kumagai (1995) *Proc. Natl. Acad. Sci. USA* 92:1679-1683; the rice tungro bacilliform virus (RTBV), which replicates only in phloem cells in infected rice plants, with its promoter which drives strong phloem-specific reporter gene expression; the cassava vein mosaic virus (CVMV) promoter, with highest activity in vascular elements, in leaf mesophyll cells, and in root tips (Verdaguer (1996) *Plant Mol. Biol.* 31:1129-1139).

VIII. Production of Transgenic Plants

As detailed herein, the present invention provides for transgenic plants comprising recombinant expression cassettes either for expressing PYR/PYL proteins in a plant or for inhibiting or reducing endogenous PYR/PYL expression. Thus, in some embodiments, a transgenic plant is generated that contains a complete or partial sequence of an endogenous PYR/PYL encoding polynucleotide, either for increasing or reducing PYR/PYL expression and activity. In some embodiments, a transgenic plant is generated that contains a complete or partial sequence of a polynucleotide that is substantially identical to an endogenous PYR/PYL encoding polynucleotide, either for increasing or reducing PYR/PYL expression and activity. In some embodiments, a transgenic plant is generated that contains a complete or partial sequence of a polynucleotide that is from a species other than the species of the transgenic plant. It should be recognized that transgenic plants encompass the plant or plant cell in which the expression cassette is introduced as well as progeny of such plants or plant cells that contain the expression cassette, including the progeny that have the expression cassette stably integrated in a chromosome.

A recombinant expression vector comprising a PYR/PYL coding sequence driven by a heterologous promoter may be introduced into the genome of the desired plant host by a variety of conventional techniques. For example, the DNA construct may be introduced directly into the genomic DNA of the plant cell using techniques such as electroporation and microinjection of plant cell protoplasts, or the DNA construct can be introduced directly to plant tissue using ballistic methods, such as DNA particle bombardment. Alternatively, the DNA construct may be combined with suitable T-DNA flanking regions and introduced into a conventional *Agrobacterium tumefaciens* host vector. The virulence functions of the *Agrobacterium tumefaciens* host will direct the insertion of the construct and adjacent marker into the plant cell DNA when the cell is infected by the bacteria. While transient expression of PYR/PYL is encompassed by the invention, generally expression of construction of the invention will be from insertion of expression cassettes into the plant genome, e.g., such that at least some plant offspring also contain the integrated expression cassette.

Microinjection techniques are also useful for this purpose. These techniques are well known in the art and thoroughly described in the literature. The introduction of DNA constructs using polyethylene glycol precipitation is described in Paszkowski et al. *EMBO J.* 3:2717-2722 (1984). Electroporation techniques are described in Fromm et al. *Proc. Natl. Acad. Sci. USA* 82:5824 (1985). Ballistic transformation techniques are described in Klein et al. *Nature* 327:70-73 (1987).

*Agrobacterium tumefaciens*-mediated transformation techniques, including disarming and use of binary vectors, are well described in the scientific literature. See, for example, Horsch et al. *Science* 233:496-498 (1984), and Fraley et al. *Proc. Natl. Acad. Sci. USA* 80:4803 (1983).

Transformed plant cells derived by any of the above transformation techniques can be cultured to regenerate a whole plant that possesses the transformed genotype and thus the desired phenotype such as enhanced drought-resistance. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985. Regeneration can also be obtained from plant callus, explants, organs, or parts thereof. Such regeneration techniques are described generally in Klee et al. *Ann. Rev. of Plant Phys.* 38:467-486 (1987).

One of skill will recognize that after the expression cassette is stably incorporated in transgenic plants and confirmed to be operable, it can be introduced into other plants by sexual crossing. Any of a number of standard breeding techniques can be used, depending upon the species to be crossed.

The expression cassettes of the invention can be used to confer drought resistance on essentially any plant. Thus, the invention has use over a broad range of plants, including species from the genera *Asparagus, Atropa, Avena, Brassica, Citrus, Citrullus, Capsicum, Cucumis, Cucurbita, Daucus, Fragaria, Glycine, Gossypium, Helianthus, Heterocallis, Hordeum, Hyoscyamus, Lactuca, Linum, Lolium, Lycopersicon, Malus, Manihot, Majorana, Medicago, Nicotiana, Oryza, Panieum, Pannesetum, Persea, Pisum, Pyrus, Prunus, Raphanus, Secale, Senecio, Sinapis, Solanum, Sorghum, Trigonella, Triticum, Vitis, Vigna*, and, *Zea*. In some embodiments, the plant is selected from the group consisting of rice, maize, wheat, soybeans, cotton, canola, turfgrass, and alfalfa. In some embodiments, the plant is an ornamental plant. In some embodiment, the plant is a vegetable- or fruit-producing plant.

Those of skill will recognize that a number of plant species can be used as models to predict the phenotypic effects of transgene expression in other plants. For example, it is well recognized that both tobacco (*Nicotiana*) and *Arabidopsis* plants are useful models of transgene expression, particularly in other dicots.

The plants of the invention have either enhanced or reduced abscisic acid sensitivity compared to plants are otherwise identical except for expression of PYR/PYL. Abscisic acid sensitivity can be monitored by observing or measuring any phenotype mediated by ABA. Those of skill in the art will recognize that ABA is a well-studied plant hormone and that ABA mediates many changes in characteristics, any of which can be monitored to determined whether ABA sensitivity has been modulated. In some embodiments, modulated ABA sensitivity is manifested by altered timing of seed germination or altered stress (e.g., drought) tolerance.

Drought resistance can assayed according to any of a number of well-known techniques. For example, plants can be grown under conditions in which less than optimum water is provided to the plant. Drought resistance can be determined by any of a number of standard measures including turgor pressure, growth, yield, and the like. In some embodiments, the methods described in the Example section, below can be conveniently used.

EXAMPLES

The following examples are offered to illustrate, but not to limit the claimed invention.

Example 1: PYR/PYL Modulation of ABA Signaling

Unlike biochemical screens for ABA-binding proteins, genetic analyses focused on ABA perception have not yet identified proteins resembling receptors, suggesting that the receptor(s) may be functionally redundant, have overlapping functions or cannot mutate to yield viable gametes or seedlings (P. McCourt, *Annual Review of Plant Physiology and Plant Molecular Biology* 50, 219 (1999)). As a complementary approach, we have pursued a chemical genetic strategy in plants (Y. Zhao et al., *Nat Chem Biol* 3, 716 (2007)). This approach can be advantageous for organisms with highly redundant genomes, because the variable selectivity of small molecules can cause phenotypes not revealed by single gene mutations (N. Raikhel, M. Pirrung, *PLANT PHYSIOLOGY* 138, 563 (2005); S. Cutler, P. McCourt, *Plant Physiol.* 138, 558 (2005)). For example an antagonist with low selectivity can perturb the function of an entire protein family (as seen with microtubule antagonists), while an agonist with high selectivity may illuminate the function of an individual member of normally redundant receptors, as we describe here with pyrabactin 3 (FIG. 1A).

Pyrabactin is a Seed-Selective ABA Agonist

As part of an earlier effort, we identified a germination inhibitor named pyrabactin (Y. Zhao et al., *Nat Chem Biol* 3, 716 (2007)). By examining the sensitivity of multiple wild accessions to pyrabactin, we found that the Cold Spring Harbor Lab wild type, which is ABA-hypersensitive and hyperdormant, is also hypersensitive to pyrabactin, but not an inactive analog apyrabactin 4 (FIG. 1A). This suggested that pyrabactin might act through the ABA response pathway. To test this hypothesis, we examined the pyrabactin sensitivity of mutant lines with altered ABA signaling, biosynthesis or gibberellic acid (GA) perception. We found that ABA perception, but not biosynthesis, mutants affect pyrabactin sensitivity (FIG. 1B). Additionally an rgl2-1 mutant line, which does not require GA during germination (S. Lee et al., *Genes Dev.* 16, 646 (Mar. 1, 2002, 2002)), has normal pyrabactin sensitivity (FIG. 1B). Together, these observations suggest that pyrabactin inhibits germination by activating the ABA signaling pathway, rather than by modulating ABA or GA biosynthesis.

We next performed microarray experiments to evaluate the similarity of the transcriptional responses induced by ABA and pyrabactin treatments. For microarray, tissue was prepared and RNA extracted from Columbia wild type seeds sown on 0.5×MS media (~2500 seeds per 150 mm plate) containing either 1 μM ABA, 25 μM pyrabactin, 25 μM 2,4-Dinitrophenol (DNP), 1 μM cycloheximide, 2 μM methotrexate or 1% DMSO control plates (all chemicals are dissolved in DMSO). The concentrations utilized for these experiments were normalized for germination inhibition activity by dose curve analyses, i.e. the amount of both compounds required to ensure 100% inhibition of germination when scored 3 days post-imbibition. ABA (±stereoisomers), DNP, cycloheximide and methotrexate were purchased from Sigma Aldrich. Seeds were stratified for 4 days and then incubated in the dark at room temperature for 24 hours. Seeds were collected and frozen in liquid nitrogen, then ground to fine powder form with frozen mortar and pestle, after which total RNA was extracted using the RNAqueous kit (Ambion; Austin, USA) for the first set of replicate samples. Subsequent RNA extractions were performed using the phenol-chloroform extraction protocol, as described by (Y. Suzuki, T. Kawazu, H. Koyama, *Biotechniques,* 37, 542 (October, 2004)). For each sample of total RNA, 1 μl of RNA was quantified in 99 μl 10 mM Tris-Cl (pH 7.4) by the GeneQuant RNA/DNA Calculator (GE Healthcare Bio-Sciences Corp.; New Jersey, USA), where absorbance measurements were taken at 260 nm and 280 nm. Purity of the RNA was assessed by $OD_{260}/OD_{280}$ ratios (only ratios between 1.7 and 2.2 were used), while quality of the RNA was assessed by gel electrophoresis. Total RNA samples were converted to biotin-labeled cRNA using oligo-dT priming as described by the manufacturer (Enzo kit; Affymetrix; Santa Clara, USA) and hybridized to 22K ATH1 Affymetrix microarrays at the CAGEF (University of Toronto). Duplicate biological replicate samples were hybridized for DNP, cycloheximide and methotrexate, triplicate for control and quadruplicate samples were hybridized for, pyrabactin and ABA treatments. Probe sets with expression signals called present or marginal by the statistical algorithms applied to the microarrays as described as described for the GCOS/MAS5.0 algorithm (Affymetrix; Santa Clara, USA). Significance Analysis of Microarrays was used to identify probe sets that are significantly regulated by treatments using unlogged data, with a false discovery rate (FDR) at about 5%. Average transcript levels were compared to control values to compute fold-change, which was in turn $\log_2$ transformed and used to compute Pearson Correlation Coefficients between experiments.

Figure 1D:
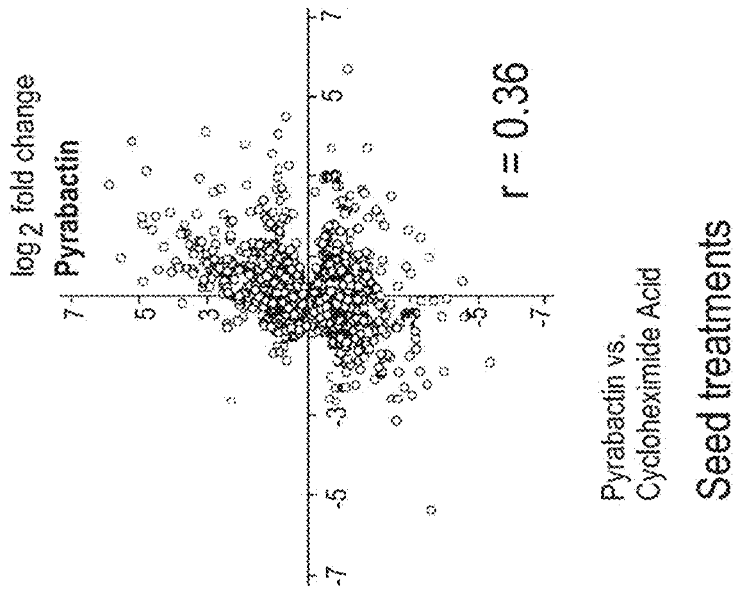

We first examined seeds treated with both compounds for 24 hours. Due to inhibitory effects on seedling development, any two germination inhibitors will share some common responses; we therefore used a previously defined set of germination responsive transcripts (G. W. Bassel et al., *Plant Physiol* 147, 143 (2008)) to minimize developmental effects in our comparisons. 1225 probe sets were identified as responsive to either ABA or pyrabactin using SAM analysis (V. G. Tusher, R. Tibshirani, G. Chu, *Proc. Nat'l. Acad. Sci. USA* 98, 5116 (2001)), after removal of 403 germination-regulated transcripts. Scatter plots comparing a probe's responsiveness to pyrabactin and ABA demonstrate highly correlated responses (r=0.98; FIG. 1C), consistent with the hypothesis that pyrabactin activates ABA signaling. As a control, we also profiled the effects of the three germination inhibitors (G. W. Bassel et al., *Plant Physiol* 147, 143 (2008)) cycloheximide, methotrexate and 2,4-dinitrophenol, and observed much weaker transcript-response correlations when compared to ABA treatments (r=0.36, 0.73 and 0.81 respectively; cycloheximide shown in FIG. 1D). This demonstrates that an indirect developmental effect is not sufficient to account for the ABA-like transcriptional effects of pyrabactin.

Figure 1E:
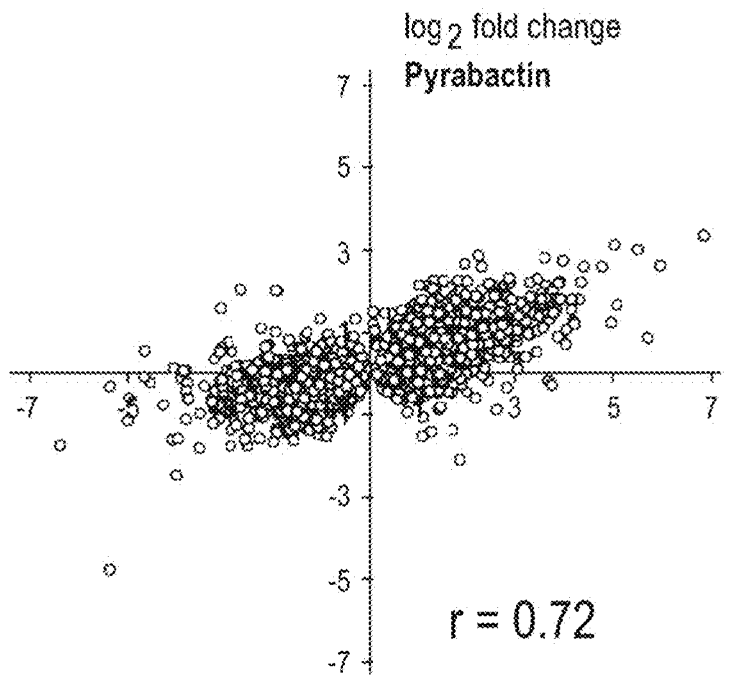

To establish if pyrabactin is a general ABA agonist, we examined its activity in seedlings treated with either compound for 24 hours, which showed that pyrabactin induces a greatly muted ABA response (r=0.72) in seedling tissues (FIG. 1E). For seedling microarray experiments, Columbia wild type seeds were surface sterilized and sown on 0.5× MS, 0.6% (w/v) agar plates (15 mg seeds, 25 ml media per 150 mm plate), followed by stratification for 4 days at 4° C. and grown under 24-h light at room temperature for 9 days. 40 seedlings were then transferred to either DMSO control, 10 μM ABA or 33 μM pyrabactin plates and returned to the growth environment for another 24 hours, after which total RNA was extracted using the method described above. Triplicate samples were hybridized per treatment. The concentrations used for seedling experiments were based on concentrations of ABA or pyrabactin that are required to inhibit primary root growth by equivalent amounts, i.e. they were normalized to a measure of bioactivity. In these experiments, 57 transcripts responded significantly to both pyrabactin and ABA, suggesting that pyrabactin can induce aspects of an ABA response in seedlings. However, since 3021 transcripts in this experiment showed a significant response to ABA, but not pyrabactin, we conclude that pyrabactin acts with greater selectivity for the seed pathway in comparison to ABA. Pyrabactin does agonize ABA responses in vegetative tissues.

PYR1, a START Protein, is Necessary for Pyrabactin Action

Figure 2A:
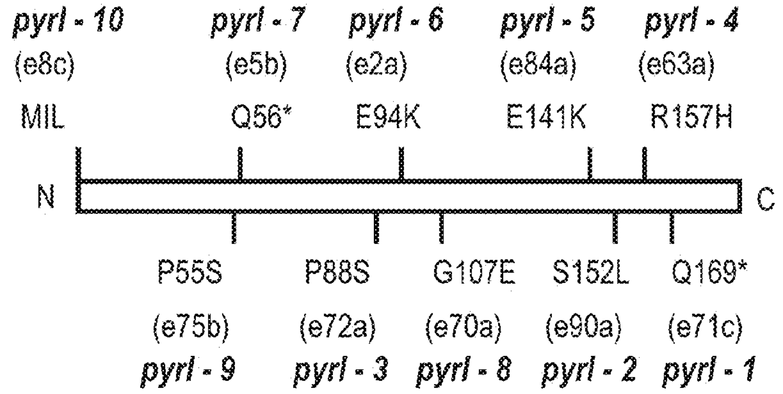
FIG. 2. PYR1 encodes an ABA responsive START-domain protein. (A) Pyr1 alleles. Shown are the allele names, strain names (in parentheses) and amino acid changes caused by the Pyr1 mutant alleles identified by screening for pyrabactin resistant mutations. (B) Pictographic representation of Pyr1 and Pyl1-Pyl4 expression values housed in public microarray databases. The heatmap shown at top right is for the first upper three panels and the bottom heatmap for the guard cell data. Plots were made using the eFP browser (D. Winter et al., *PLoS ONE* 2, e718 (2007)). (C) 35S::GFP-PYR1 complements pyr1-1. Seeds of the genotypes shown were stratified 4 days on 25 μM pyrabactin and then germinated at RT, 90% RH for 3 days in darkness. The Columbia wild type is unable to germinate under these conditions, but pyr1-1 does because it is resistant to pyrabactin. Introduction of a 35S::GFP-PYR1 construct into the pyr1-1 genetic background restores pyrabactin sensitivity, which indicates that the GFP fusion protein is functional. (D) Pyr/Pyls are required for normal ABA-induced gene expression in seedlings. Shown are qRT-PCR results for the ABA-responsive gene RD29. L, Ler; C, Col; and Q, quadruple mutant. (E) Pyr/Pyl genes are required for normal ABA-induced stress-induced gene expression in seedlings. Shown are qRT-PCR results for two ABA-responsive taqman probes, as described in the Examples section. L=Ler, C=Col, Q=quadruple mutant.
Figure 2B:
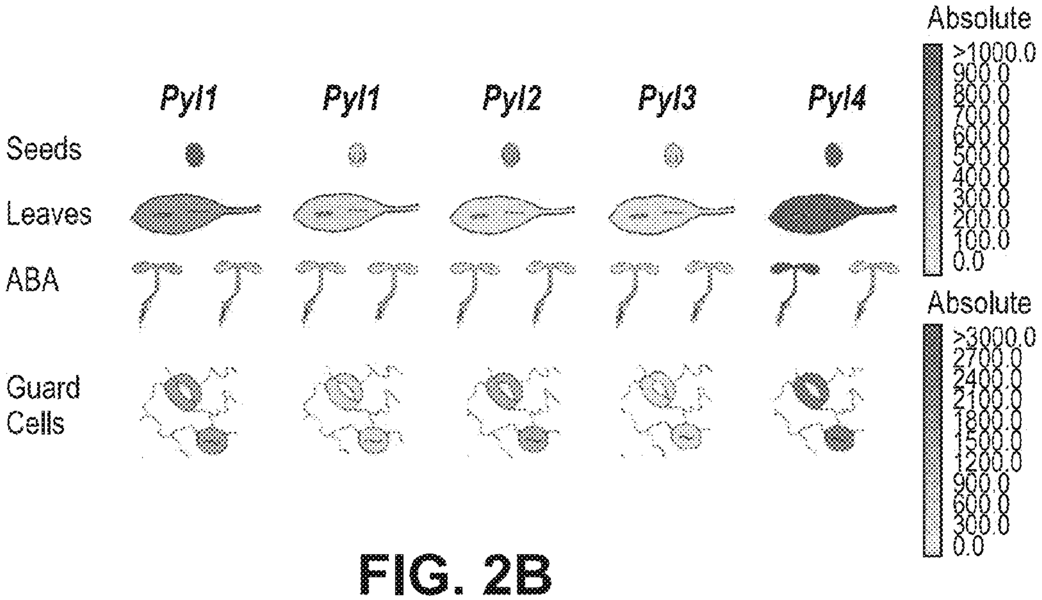
Figure 2C:
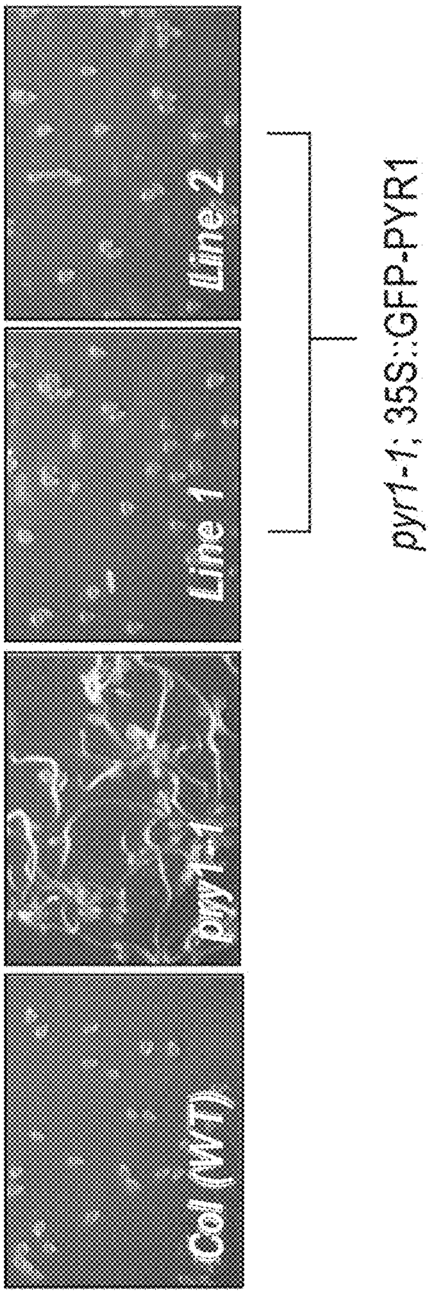

To dissect pyrabactin's mechanism of action, we isolated a collection of 16 pyrabactin insensitive mutant lines from a screen of ~450,000 EMS mutagenized M2 seed. Surface sterilized EMS seeds were sown on 0.33×MS media containing 25 µM pyrabactin (50 mg seeds per 150 mm plate). Seeds were stratified for 4 days at 4° C. and grown under constant light for 4 days at room temperature, after which plates were scored for mutants resistant to the germination inhibition effect of pyrabactin. Seedlings with fully expanded cotyledons were considered resistant, and all mutants identified as resistant were then retested in the next generation to identify true mutants. The strong pyr1-7 allele was used to map Pyr1 using a mapping population of ~400 plants (created from progeny of a cross to Ler). This delimited Pyr1 to an ~150 Kb interval containing 12 genes. The identity of Pyr1 was first suggested after sequencing the 12 genes in this interval and identifying a stop codon in At4g17870 (Pyr1). After this, the Pyr1 coding sequence for 14 of the 16 mutations isolated were sequenced and 12 independent strains were determined by map based cloning and sequencing to contain mutations in the same locus, PYRABACTIN RESISTANCE 1 (Pyr1). Pyr1 encodes a protein that is a member of the START/Bet v 1 superfamily whose members share a conserved ligand-binding helix-grip architecture (L. M. Iyer, E. V. Koonin, L. Aravind, *Proteins: Structure, Function, and Genetics* 43, 134 (2001); C. Radauer, P. Lackner, H. Breiteneder, *BMC Evol Biol* 8, 286 (2008)). PYR1 resides in a Bet v 1 subfamily similar to bacterial polyketide synthases/cyclases and other non-enzymatic proteins (C. Radauer, P. Lackner, H. Breiteneder, *BMC Evol Biol* 8, 286 (2008)). There are 13 genes in the *Arabidopsis* genome that show significant similarity to Pyr1 in BLAST searches, which we have named PYL1-PYL13 (for PYR1-Like; their AGIs are listed in Table 1). The pyrabactin insensitive pyr1 alleles we isolated are predicted to produce a variety of defects in PYR1, including truncations and non-conservative amino acid substitutions (FIG. 2A). Transformation of a 35S::GFP-PYR1 expression construct into the strong pyr1-1 mutant line restores seed pyrabactin sensitivity (FIG. 2C), which provides further support that PYR1 is necessary for pyrabactin action. None of the pyr1 alleles isolated show strong ABA insensitivity, which as we describe below, is explained by the action of redundant Pyr1 relatives (including, but not limited to Pyl1, 2, 4). By querying public microarray databases (M. Schmid et al., *Nat Genet* 37, 501 (2005); K. Nakabayashi, M. Okamoto, T. Koshiba, Y. Kamiya, E. Nambara, *Plant J* 41, 697 (March, 2005); H. Goda et al., *Plant J* 55, 526 (August, 2008); D. Winter et al., *PLoS ONE* 2, e718 (2007); Y. Yang, A. Costa, N. Leonhardt, R. S. Siegel, J. I. Schroeder, *Plant Methods* 4, 6 (2008)) it is clear that Pyr1 mRNA is expressed highly in seeds and guard cells and is responsive to ABA (FIG. 2B), consistent with a role for PYR1 in ABA signaling.

TABLE 1

Members of PYR/PYL family and corresponding *Arabidopsis* Genome Initative (AGI) annotations.

| Gene | AGI |
| --- | --- |
| Pyr1 | AT4G17870 |
| Pyl1 | AT5G46790 |
| Pyl2 | AT2G26040 |
| Pyl3 | AT1G73000 |
| Pyl4 | AT2G38310 |
| Pyl5 | AT5G05440 |
| Pyl6 | AT2G40330 |
| Pyl7 | AT4G01026 |
| Pyl8 | AT5G53160 |
| Pyl9 | AT1G01360 |
| Pyl10 | AT4G27920 |
| Pyl11 | AT5G45860 |
| Pyl12 | AT5G45870 |
| Pyl13 | AT4G18620 |

PYR/PYL Proteins Bind PP2Cs in Response to ABA

Figures 3A, 3B, 3C:
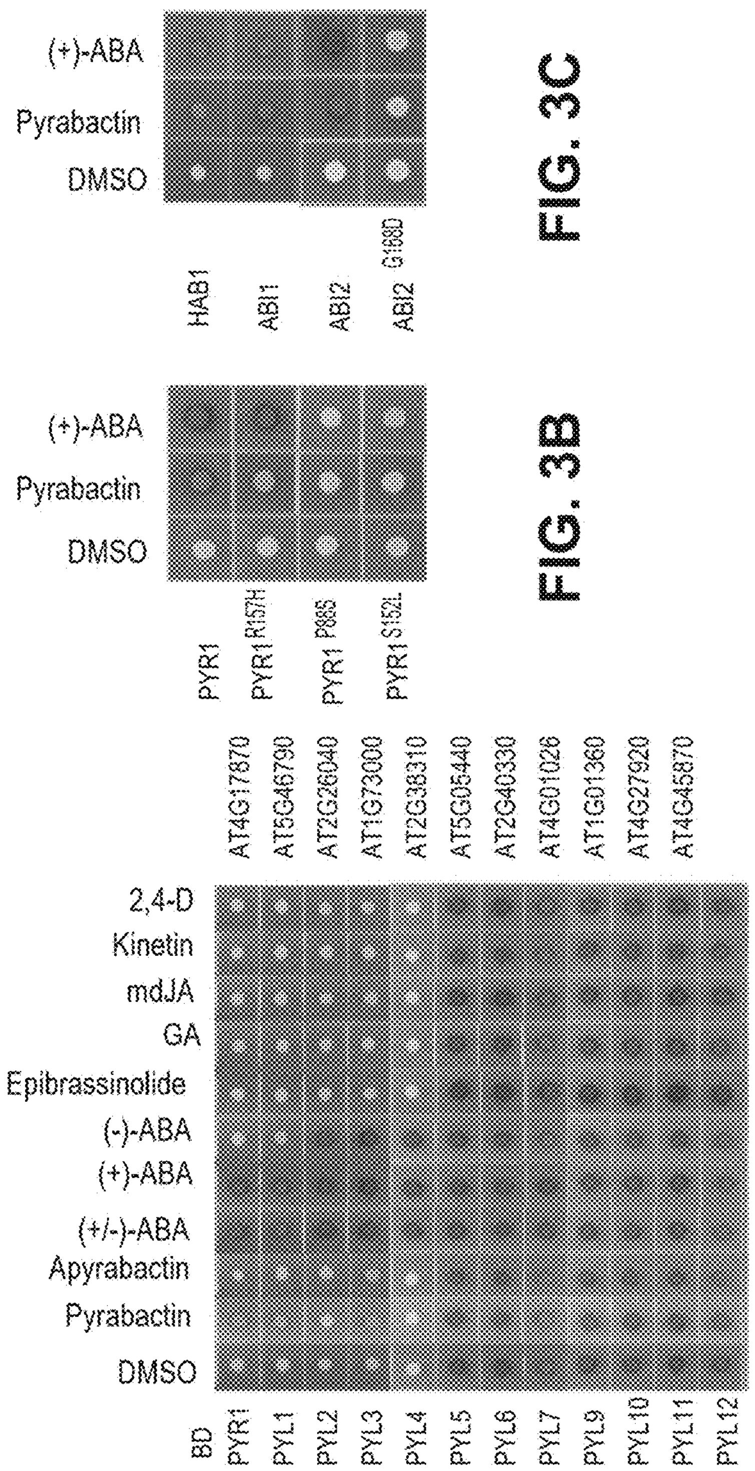
FIG. 3. ABA promotes PYR/PYL binding to PP2Cs. (A) Characterization of the PYR/PYL protein interactions with HAB1. Shown are X-gal stains of yeast colonies grown on plates containing the compounds shown at top. The *Arabidopsis* Genome Initiative (AGI) annotations for each PYR/PYL gene characterized is shown at the right of the panel. Not tested were PYL8 (AT5G53160) and PYL13 (AT4G18620). Each strain tested expresses an AD-HAB1 fusion protein and the BD-fusion shown at left. Chemicals were tested at 10 μM with the exception of epi-brassinolide (50 nM). (B) PYR1 mutant proteins are defective in their interactions with HAB1. 3 PYR1 amino acid substitution mutants that display strong pyrabactin insensitivity in *Arabidopsis* seeds were tested for their interactions with HAB1 in the Y2H. (C) PYR1 interacts with ABI1 and ABI2 but not the mutant protein encoded by abi2-1.

Given that PYR1 is necessary for pyrabactin action and is a predicted ligand-binding protein, we hypothesized that pyrabactin agonizes ABA signaling by inducing a protein-protein interaction between PYR1 and a downstream effector. To test this, ~2 million prey cDNA clones were screened against a PYR1 Y2H bait construct on media containing 10 µM pyrabactin. To create the PYR1 Y2H bait construct, the Pyr1 open reading frame was PCR amplified from genomic DNA and cloned to pGem-T easy vector (Promega). After sequence confirmation, the Pyr1 ORF was then cloned in-frame between EcoRI and SalI sites of the pBD-GAL4 Cam vector (Stratagene) and transformed into yeast strain Y190. For the screen, an etiolated seedling cDNA library (J. Kim, K., Harter, A., *Theologis, Proc Natl Acad Sci USA* 94, 11786 (Oct. 28, 1997)) (ABRC stock CD4-22) was used. The cDNA library was first converted from phage to plasmid DNA, yielding $7.6 \times 10^7$ transformants. Plasmid DNA prepared from library was then used to transform Y190 as described in the GAL4 Two-Hybrid system manual (Stratagene). For each screen, 40 µg of prey plasmid was transformed into 1 ml of competent Y190 cell harboring bait construct and then grown on SD agar plates lacking His, Leu, and Trp, but containing 15 mM 3-AT and 10 µM pyrabactin. After 4 days incubation at 30° C., well-grown colonies were rescued and interactions validated using filter lift assay or chloroform-agarose overlay method and X-Gal staining. This identified two pyrabactin-dependent hits which sequencing determined encoded cDNAs for the PP2C HAB1, a close relative of the well-characterized ABA response factor ABI1 (A. Saez et al., *The Plant Journal* 37, 354 (2004); N. Leonhardt et al., *THE PLANT CELL* 16, 596 (2004)). Next, Y2H strains expressing an AD-HAB1 fusion protein and a BD-PYR1 fusion protein were grown on plates and tested for interactions in response to various compounds, all at 10 µM except for epi-brassinolide (50 nM) and dimethyl sulfoxide (DMSO) (carrier solvent, 1%). When the pyrabactin-responsive PYR1-HAB1 Y2H strains were tested on (+)-ABA, strong interactions were observed by X-gal stain, but neither (−)-ABA, kinetin, 2,4-D, Gibberellic acid (GA), epi-brassinolide (BR), methyl jasmonate (meJA) or apyrabactin showed activity (FIG. 3A). Thus, PYR1 interacts with HAB1 in a (+)-ABA dependent fashion.

To see if ABA and pyrabactin responsiveness is unique to PYR1, we tested 11 of the 13 PYL proteins as described above, using Y2H strains expressing an AD-HAB1 fusion protein and a BD-PYR/PYL fusion protein (listed at the left of FIG. 3A). BD-PYR/PYL fusion proteins were constructed in the same manner as for BD-PYR1 above. This assay showed that PYL1-PYL4 interact with HAB1 in an ABA-stimulated manner (FIG. 3A). Ligand-selective interactions are also observed for pyrabactin, which promotes interactions between HAB1 and PYR1, PYL1, or PYL3 (FIG. 3A). Of these, only Pyr1 is highly transcribed in seeds, which likely explains why mutations in Pyr1 cause the seeds to be insensitive to pyrabactin. PYL2-PYL4 respond to both (+)-

ABA and (−)-ABA (FIG. 3A), suggesting that they could be involved in both (+) and (−)-ABA responses. Notably, the remaining PYLs tested in the yeast two hybrid assay show constitutive interactions with HAB1, suggesting they may have different thresholds for interaction with the PP2Cs from PYR1 and PYLs 1 to 4. However the interactions of PYLs 5-12 with the PP2Cs are indicative that the entire protein family is likely to share a similar mechanism of action involving PP2C modulation, as we describe below. Thus, we conclude that entire family modulates ABA responses via PP2C interactions.

Figure 4:
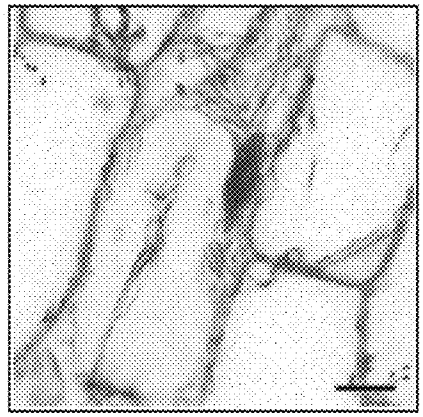
FIG. 4. GFP-PYR1 localizes to the cytoplasm and nucleoplasm. Confocal images are shown of a 35S::GFP-PYR1 construct in the pyr1-1 mutant background. This construct complements the pyrabactin insensitivity phenotype of the pyr1-1 mutant.

To investigate the ABA/pyrabactin responses further, we used the Y2H assay as described above to examine three substitution mutant proteins that cause strong pyrabactin insensitive phenotypes in plants. Two of the mutants tested, PYR1$^{S152L}$ and PYR1$^{P88S}$, greatly reduce ABA induced PYR1-HAB1 interactions, while the PYR1$^{R157H}$ mutation does not affect the interaction (FIG. 3B). HAB1 possesses genetic redundancy with ABI1, ABI2 and other related PP2Cs (T. Yoshida et al., *PLANT PHYSIOLOGY* 140, 115 (2006)). We therefore tested ABI1 and ABI2 in the Y2H assay, using publicly available sequence validated cDNAs for ABI1 and ABI2 (C104649, and U24491 respectively). We observed that PYR1 interacts with wild type ABI1 and ABI2, but not the ABA insensitive protein ABI2$^{G168D}$ encoded by abi2-1 (FIG. 3C). Thus, residues important to PYR1 and PP2C function in planta are important for the ABA response reconstituted in yeast. These in vivo interactions between PYR1 and PP2C likely occur in the cytoplasm and nucleoplasm, as suggested by the localization pattern observed for GFP-PYR1 (FIG. 4).

PYR/PYL Proteins Act Redundantly in ABA Signaling

Figure 2D:
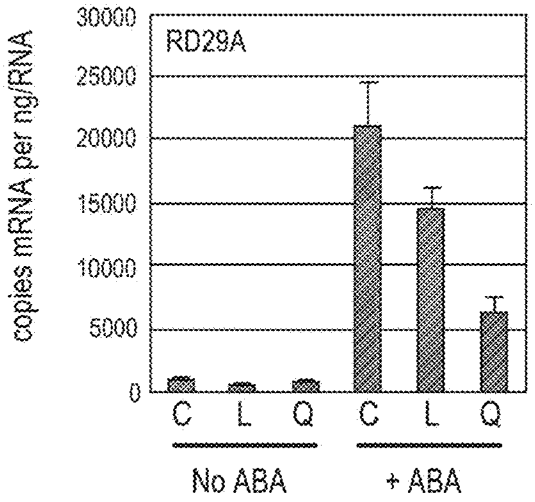
Figure 2E:
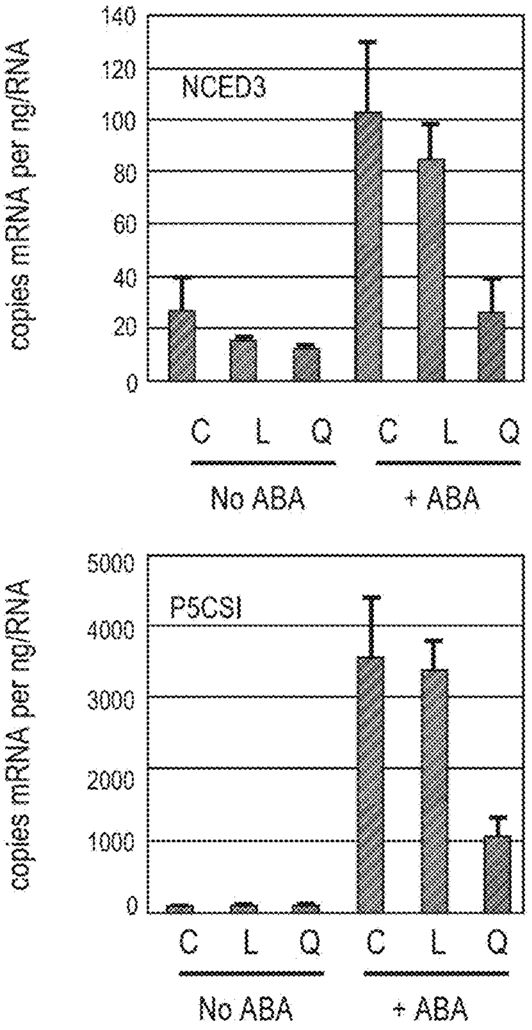
Figure 5A:
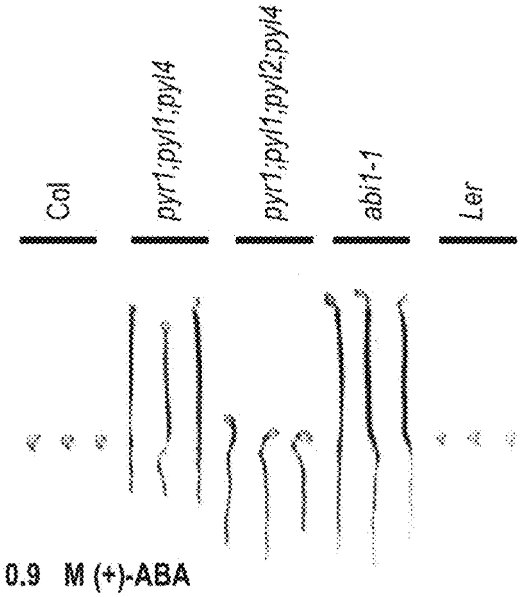
FIG. 5. Pyr1 and Pyl1, 2 and 4 function redundantly in ABA perception. (A) ABA responses in the triple and quadruple mutant lines are altered during germination. Seeds of the genotypes shown at top were stratified 4 days on media containing 0.9 μM (+)-ABA and then photographed 3 days after germination in darkness. The short hypocotyl observed in the quadruple mutant when germinated on (+)-ABA is due to the presence of the *erecta* mutation that is tightly linked to the pyl2-1 insertion allele. (B) ABA responses in the triple and quadruple mutant lines are altered during root growth. Seeds of the genotypes shown at top were stratified 4 days and then transferred to darkness (RT, 90% RH). After 30 hours, seeds with radicle emergence were transferred to plates contain 10 μM (+)-ABA and their roots photographed after an additional 3 days growth in the dark.
Figure 5B:
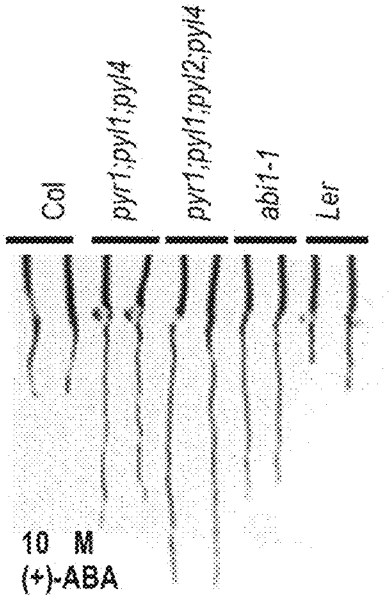

To examine whether the ABA-responsive PYL proteins act redundantly with PYR1 in ABA signaling, we isolated homozygous insertion alleles for PYL1, 2 and 4 from public insertion-allele collections (seed strains=Salk_054640, GT_2864, Sail_517_C08 respectively) (J. M. Alonso et al., *Science* 301, 653 (2003); A. Sessions et al., *THE PLANT CELL* 14, 2985 (2002); V. Sundaresan et al., *Genes and Development* 9, 1797 (1995)). The homozygous insertion lines and pyr1-1 were crossed to create pyr1-1:pyl2-1 and pyl1-1:pyl4-1 heterozygous lines, which were then crossed to one another. ~70 progeny from this cross were genotyped by PCR to identify lines heterozygous for all 4 mutations, and 2 plants were identified. To assess if these lines segregated ABA insensitive plants, the F2 seed from a quadruple heterozygous plant were germinated on 0.7 μM (+)-ABA. Extensive variation in germination and growth was observed, and the most ABA-resistant seedlings were selected from ~1000 seed and genotyped by PCR and sequencing. None of the homozygous single mutant parents showed marked ABA insensitivity, but both a triple (pyr1-1, pyl1-1, pyl4-1) and quadruple (pyr1-1, pyl1-1, pyl2-1, pyl4-1) mutant line showed ABA insensitivity. The root and germination responses of the quadruple and triple mutants lines were examined in comparison to abi1-1, the strongest ABA-insensitive mutant isolated to date. For germination assays, seeds were stratified on plates containing (+)-ABA on 0.33×MS for 4 days at 4° C. and then germinated at 23° C. in the dark for 3 days at 90% RH. Seeds showing radicals ½ seed length or longer were scored as positive for germination. To investigate root growth, seeds were allowed to first germinate on MS plates after 4 days of stratification and then transferred to germinate at 23° C. in darkness at 90% RH. 48 hours post imbibition, seedlings showing radical emergence were transferred to (+)-ABA containing or control plates, grown vertically for 4 additional days in the dark and then new root growth measured. In germination assays, the quadruple mutant was more insensitive than the triple, but both exhibited a weaker phenotype than abi1-1 (FIG. 5A). In root growth assays, the quadruple and triple mutant lines both showed greater ABA insensitivity than abi1-1 (FIG. 5B). The quadruple mutant line also exhibits defects in ABA-induced gene expression. Quantitative RT-PCR experiments were conducted as described previously (H. Fujii, et al., *Plant Cell,* 19, 485 (2007)) using taqman probes identical to those described by Fujii et al. Briefly, 7 day old seedlings grown under continuous illumination on 0.3×MS plates were transferred to 0.3×MS media containing carrier solvent (0.1% DMSO) or 100 μM (+)-ABA for 5 hours, after which total RNA was isolated using Qiagen plant RNeasy isolation kit. 5 μg total RNA was used per 20 μL first strand cDNA synthesis reaction using SuperScript Reverse Transcriptase. The reactions were diluted to 100 μl with TE and 1.5 μl of this was used in 15 μL qRT-PCR reactions using taqman probes described previously (6). Values shown are the average of triplicate measurements. Quadruple mutants exhibit decreased transcription of the ABA-responsive genes RD29 (FIG. 2D), NCED3 (FIG. 2E), and P5CS1 (FIG. 2E) in the presence of (+)-ABA. These experiments show that PYL1, PYL2 and PYL4 function redundantly with PYR1 in the control of ABA-induced gene expression and germination and root responses to ABA.

In Vitro Reconstitution of ABA Perception: ABA and PYR1 Inhibit PP2C Activity

Figure 6A:
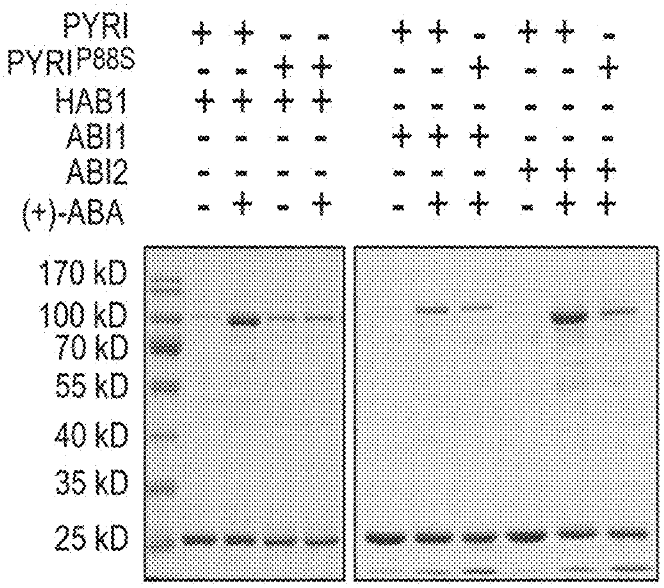
FIG. 6. PYR1 is an ABA receptor that regulates PP2C activity. (A) Reconstitution of ABA perception in vitro. Pull-down assays using GST-HAB1 and 6×His-PYR1 (or mutants) were conducted using purified recombinant proteins (left panel). GST-ABI1 and ABI2 were additionally tested in pull-downs using purified 6×His-PYR1 (or mutants) and crude lysates containing the PP2Cs shown. 10 μM (+)-ABA was used. (B) PYR1 inhibits PP2C activity in the presence of ABA. The PP2C activity of GST-HAB1 was tested in the presence or PYR1 or PYR1$^{P88S}$ at different concentrations of ABA using the substrate pNPP. (C) ABA/PYL4-dependent inhibition of HAR1 PP2C activity. Recombinant PYL4 (refolded from inclusion bodies) and HAB1 were used in PP2C assays as described. Activity was measured for GST-HAB1 using the phosphatase substrate pNPP. Phosphatase initial reaction velocities were calculated in triplicate by monitoring reactions over time using a plate reader in triplicate and used to calculate activities. The top panel shows the full concentration ranged studied; bottom panel a zoomed region of the lower concentrations tested. The specific activity of the GST-HAB1 used in these experiments was 452.4±12.3 μmol/min/mg. Points plotted use ±SD as error bars.

To explore the functional implications of the PYR1-PP2C interaction, we examined if an ABA response could be reconstituted in vitro. Recombinant GST-HAB1, GST-ABI1 and GST-ABI2 were expressed in *E. coli* and tested for ligand-dependent interactions with 6×His-PYR1 in pull-down assays. Purified 6×His-PYR1 and GST-HAB1 (20 and 100 μg respectively, 8 μM PYR1 final concentration), were combined in 100 μl TBS containing 10 μM (+)-ABA or 1% DMSO for negative control. The reaction was incubated for 90 minutes at RT and 5 μl of PrepEase (USB) His-tagged protein purification resin was added. The resin and reaction mixture was incubated 30 min at RT with gentle shaking at 5 min intervals. The resin was washed five times with TBS containing 10 μM (+)-ABA. After the final wash, the bound protein was eluted in 20 μl SDS-PAGE buffer, boiled for 5 minutes and centrifuged. 5 μl of eluate was analyzed on SDS-PAGE. For pull-downs with ABI1 and ABI2, crude lysates were used in a similar method, except purified PP2C was replaced with cleared *E. coli* lysates. The amount of lysate added was determined by SDS-page analysis to yield ~100 μg PP2C, such that the same stoichiometry was used as in assays using purified proteins. We found that both (+)-ABA and pyrabactin promote PP2C interactions with PYR1; however PYR1$^{P88S}$ is insensitive in this assay (FIG. 6A).

Figure 6B:
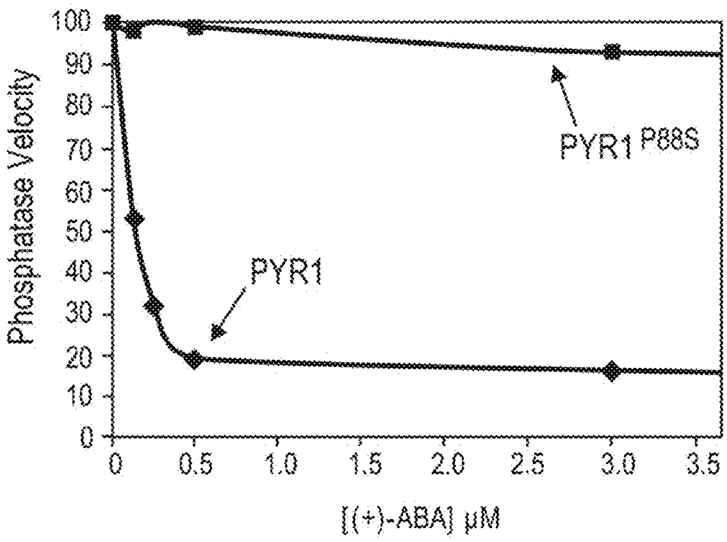

Since ABI1 and relatives are negative regulators of the ABA signaling pathway, we hypothesized that the function of the ABA-promoted PYR1-PP2C interaction was to inhibit phosphatase activity and remove a negative input into the pathway, which would then promote signaling. To test this hypothesis, we examined the effects of (+)-ABA on PP2C enzyme kinetics using recombinant GST-HAB1, 6×His-PYR1 or 6×His-PYR1$^{P88S}$ using the phosphatase substrate pNPP. The ORF of *Arabidopsis* HAB1 was amplified by PCR from a pUni clone obtained from the ABRC and cloned into pGex-2T to create a GST-HAB1 fusion protein. Both constructs were transformed into BL21[DE3]pLysS. For expression, cells harboring pGex-GST-HAB1 were grown overnight in 20 ml LB and then inoculated to 700 ml media containing 1 mM $MnCl_2$ and continued incubation with shaking at RT for 8 hr. Protein expression was then induced by addition of IPTG to final concentration of 0.5 mM, and cells were cultured overnight at RT. Cells were then harvested by centrifugation at 4500 rpm for 20 min, resuspended in 10 ml TBS containing 10 mM $MnCl_2$. Cells were stored at −80° C. To prepare cleared lysates, cells were freeze-thawed twice and the lysate's viscosity reduced by shearing. The lysate was then spun at 12000×g for 10 min to yield the final cleared lysates. This was applied to 1 ml of immobilized glutathione column, washed with 20 ml of TBS and bound protein then eluted with 20 mM reduced glutathione. The eluate was dialyzed against TBS containing 10 mM $MnCl_2$. $MnCl_2$ was used through purification steps and found to be critical for recovery of highly active HAB1 protein, as described previously for other PP2Cs (C. C. Fjeld, J. M. Denu, *J Biol Chem,* 274, 20336 (Jul. 16, 1999)). The PYR1 and $PYR1^{P88S}$ coding sequences were amplified by PCR from genomic DNA of wild type or the pyr1-3 mutant respectively and cloned into pET28 to produce various 6×His-PYR1 proteins, which were validated by sequencing. For 6×His-PYR1 and 6×His-$PYR1^{P88S}$ protein expressions, 20 ml of an overnight culture was inoculated to 700 ml LB and was grown for additional 3 hours at 37° C. with shaking Protein expression was induced by addition of IPTG to 1 mM. Cells were harvested 5 hr later by centrifugation for 15 min at 5000×g and the pellet was resuspended in 5 ml of the Buffer A (50 mM $NaH_2PO_4$, 300 mM NaCl) containing 10 mM imidazole, pH 8.0). Cells were stored at −80° C. before purification. After thawing, cells were sonicated on ice five times for 30 sec with 30 sec resting intervals. A cleared lysate was obtained after centrifugation at 12,000×g for 10 min and applied to 1 ml of Ni-NTA column (Qiagen) and washed with 20 column volumes of Buffer A containing 30 mM imidazole. Bound protein was eluted with 10 ml of Buffer A with 100 mM imidazole. The elutate was dialyzed against TBS. For the pNPP assay, initial reaction velocities for GST-HAB1 were conducted using the synthetic phosphatase substrate pNPP. Reactions contained 1 μM GST-HAB1, 1.5 μM 6×His-PYR1 or 6×His-$PYR1^{P88S}$ and a reaction buffer consisting of 33 mM Tris-OAc, pH 7.9, 66 mM KOAc, 0.1% BSA, 25 mM $Mg(OAc)_2$, 50 mM pNPP and varying (+)-ABA concentrations. Reactions were initiated by the addition of assay buffer to protein/ABA mixes. Immediately after mixing, reactions were monitored for hydrolysis of pNPP at A405 t~10 second intervals over 20 minutes using a Wallac plate reader. Reaction progressions were plotted, initial velocities calculated and converted to specific activities using a standard curve for 4-nitrophenol made in the same buffer system volumes/plate reader used for enzymatic reaction measurements. These experiments show that (+)-ABA acts as a potent inhibitor of HAB1 phosphatase activity ($IC_{50}$=0.18 μM) in the presence of PYR1, but not $PYR1^{P88S}$ (FIG. 6B).

Figure 6C:
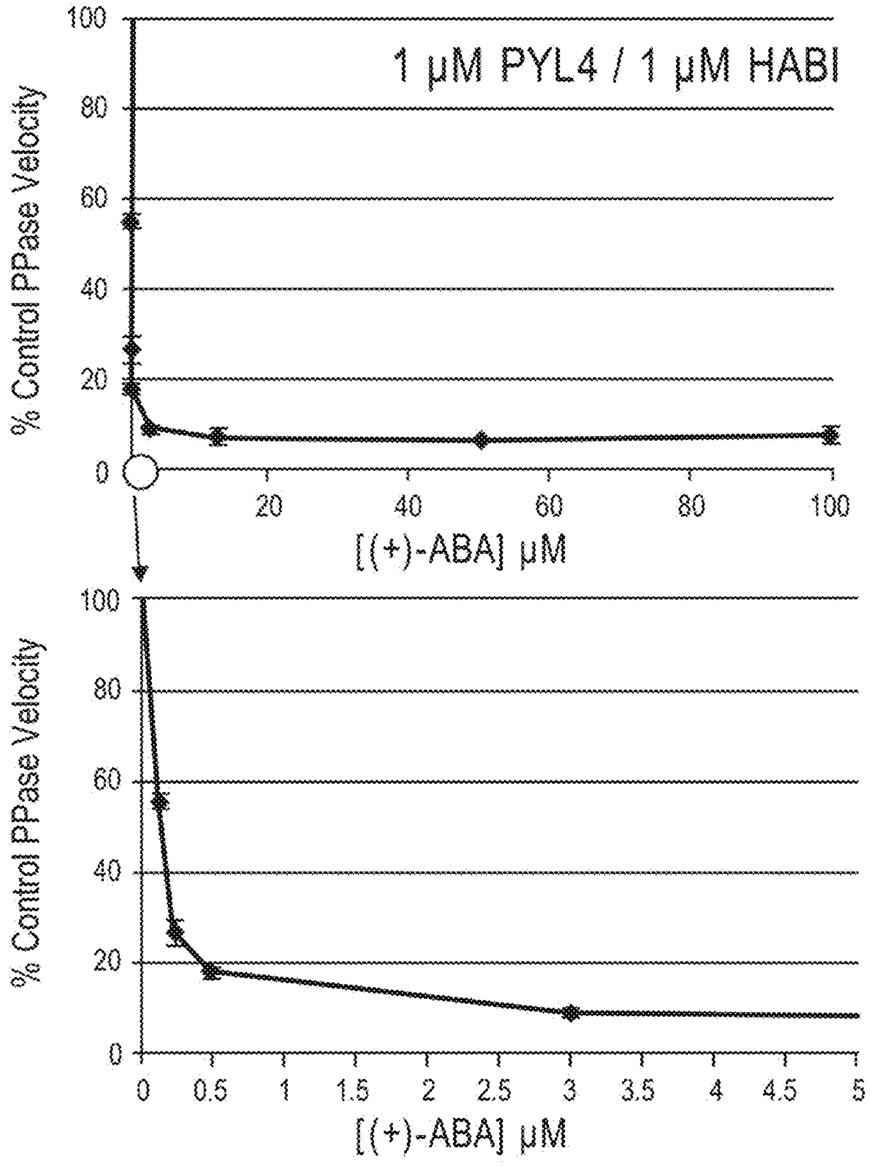

Similarly, ABA displays saturable inhibition of HAB1 PP2C activity in the presence of recombinant PYL4. A PYL4 6×His-tagged (SEQ ID NO:141) protein was constructed using a public pUni clone. This was recombined into the His-tagged expression vector pHB3. The construct was expressed in BL21[DE3] pLysS as described above for PYR1, but the protein formed inclusion bodies, which were solubilized in Buffer B+8 M urea, prior to purification. The protein was purified under denaturing conditions using Ni-NTA resin according to manufacturer's instructions. After binding of protein to resin, the column was washed with 20 volume of Buffer B (pH6.3) and protein eluted using Buffer A (pH4.5). The eluted protein was dialyzed slowly from TBS containing 2 M urea, 10 mM DTT into TBS containing 1 mM DTT over three days, gradually lowering the urea concentration over time. The activity of refolded PYL4 was validated using in vitro pull down assays developed for PYR1, where it was shown that PYL4 binds HAB1 in response to ABA. For the PP2C assays, recombinant PYL4 (refolded from inclusion bodies) and HAB1 were used. When phosphatase activity was measured for GST-HAB1 using the phosphatase substrate pNPP, we found that (+)-ABA inhibits HAB1 phosphatase activity in the presence of PYL4 (FIG. 6C). Thus, PP2C inhibition is a primary ABA-response that can be reconstituted in vitro with only proteins.

DISCUSSION

Figure 7:
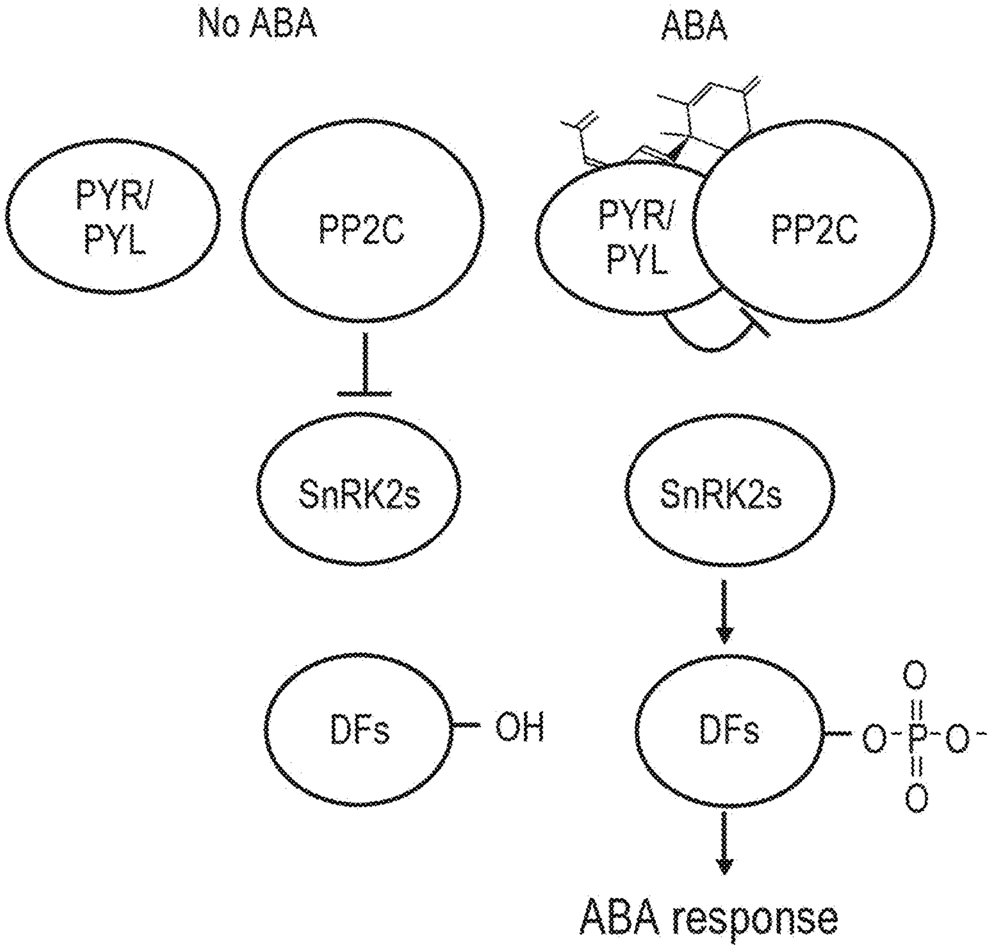
FIG. 7. Proposed model for PYR/PYL control of ABA signaling. Without intending to limit the scope of the invention, we propose the following model: In the absence of ABA (left), PYR/PYL proteins show low binding to PP2Cs, and therefore, PP2C activity is high, which prevents phosphorylation and activation of SnRK2s and downstream factors (DFs). In the presence of ABA, PYR/PYLs bind and inhibit PP2Cs. This allows accumulation of phosphorylated downstream factors and ABA transcriptional responses. The regulation of SnRK2s by PYR/PYLs may be indirect or may involve other factors.

We have shown that PYR1 has the properties expected of an ABA receptor and that it binds to and inhibits PP2C activity when ligand is present. In contrast to previously identified ABA binding proteins (P. McCourt, R. Creelman, *Current Opinion in Plant Biology* 11, 474 (2008)), PYR1 interacts directly with core components of the ABA signaling pathway. ABI1 interacts with at least one positively acting factor in the ABA response pathway (R. Yoshida et al., *Journal of Biological Chemistry* 281, 5310 (2006)). It may therefore be that the role of ABI1/AHG1 class PP2Cs in the absence of a signal is to repress the action of positively acting factors. In this model, ABA functions at the apex of a negative regulatory pathway and the PP2Cs control signal output through their direct targets. This imbues the PP2Cs with a critical role in controlling the selectivity of signal-output, which could explain the extensive diversification of the PP2C gene family in plants relative to animals (A. Schweighofer, H. Hirt, I. Meskiene, *Trends in Plant Science* 9, 236 (2004)). Based on the interaction of PP2Cs with SnRK2 proteins and the critical role of SnRK2s for ABA signaling (FIG. 7) we have proposed the following model for ABA action in which ABA and PYR/PYLs inhibit the PP2Cs, which in turn relieves repression of positive factors, such as the SnRK2s. This in turn allows the positive SnRK2 kinases to modulate activity of downstream factors via phosphorylation.

Our experiments show that at least 12 of the 14-members in the PYR/PYL gene family bind to PP2Cs, and some members such as PYL2s, 3 and 4 enable yeast cells to respond to the unnatural stereoisomer (−)-ABA. We believe the entire family are ABA receptors and that some may also be (−)-ABA receptors. This hypothesis is consistent with earlier conclusions that both stereoisomers act through the same signaling pathway (E. Nambara et al., *Genetics* 161, 1247 (July, 2002)).

PYR1 is unable to bind to the proteins encoded by abi1-1 and abi2-1, which both contain mutations in glycines near one of the two conserved PP2C metal binding sites. These mutations lower, but do not abolish, PP2C activity (F. Gosti et al., *The Plant Cell* 11, 1897 (1999); N. Robert, S. Merlot, V. N'Guyen, A. Boisson-Dernier, J. I. Schroeder, *FEBS Letters* 580, 4691 (2006)) and a second site mutation that completely abolishes abi1-1's catalytic activity suppresses its dominant phenotype (F. Gosti et al., *The Plant Cell* 11, 1897 (1999)). Together with our observations on defective PYR1 interactions, these data suggest a model where the dominance of the abi1-1 and abi2-1 mutations stems from their ability to escape negative regulation by the PYR/PYL proteins. In this model, a major function of ABA is to lower ABI1/AHG1 class PP2C activity via PYR/PYL proteins, but this does not occur properly in the abi1-1 and abi2-1 mutant lines, which retain sufficient PP2C activity after ABA perception to disrupt signal transduction.

The regulation of PP2Cs is poorly understood with respect to other phosphatase classes, which is surprising given their important roles in mammals, worms, flies and yeast (G. Lu, Y. Wang, *Clinical and Experimental Pharmacology and Physiology* 35, 107 (2008)). Our observations provide a new mechanism for receptor-mediated regulation of PP2C activity. Although the precise mechanism of PP2C inhibition by PYR1 is unknown, the PYR1$^{R157H}$ mutation is able to separate ligand perception from downstream functions in vivo. This residue may therefore play a critical role in steps that lead to inhibition of PP2C activity after signal perception. Regardless of the precise details of PP2C inhibition, the novel regulatory mechanism discovered suggests that it may be worth investigating receptor-mediated PP2C regulation in other models, given the dearth of regulatory factors for these vital phosphatases.

The ABA signaling pathway has been the subject of genetic analysis for almost 30 years, but the PYR/PYL proteins never emerged as factors necessary for an ABA response in genetic screens. In hindsight, this is now obvious due to the necessity of a triple mutant to observe an ABA-insensitive phenotype. When using pyrabactin as a synthetic agonist of the pathway however, Pyr1 was identified with ease. The reason for this is due to pyrabactin's selectivity for a subset of the entire receptor family, which enabled us to bypass the genetic redundancy that obscures an ABA phenotype in single mutant lines. Thus, our results demonstrate the power of the chemical genetic approach to reveal phenotypes for normally redundant genes. Because plant genomes are highly redundant, we expect that small molecule approaches will provide a powerful addendum to classical genetic analysis.

Example 2: Screens for Agonists of PYR/PYL

We next investigated whether other compounds besides ABA and pyrabactin could act as agonists of PYR/PYL proteins. Yeast two hybrid strains expressing ABA-receptors and type 2 C protein phosphatases in the appropriate vectors can be used to monitor activation of ABA receptors. These yeast strains therefore create a facile screening system for the identification of cell permeant compounds that act as ABA agonists, i.e. compounds that promote binding of PYR/PYL family members to their protein phosphatase targets. When PYR/PYL proteins are bound to PP2C targets in the yeast two hybrid context, a reporter gene is activated which, depending on strains used, can lead to expression of a reporter construct such as the LacZ/B-galactoisidase marker or to a nutritional reporter gene that enables growth on auxotrophic media.

To conduct these agonist assays, screening compounds are added to microtiter wells and appropriate yeast growth media are added. The wells are then seeded with PYR/PYL-PP2C strains and agonist activity is monitored after growth of the strains on the chemical-containing medium. Numerous approaches can be used to monitor activation including simple growth (via restoration of expression of a nutritional reporter gene) of colorimetric X-gal assays, which are well known in the art. An alternative screening method, called the "Halo Assay," can also be used to identify agonists. In this assay, yeast strains can be embedded in suitable growth medium containing agarose and chemicals can be spotted onto plates using a pin replicator. The growth medium, lacking a nutrient needed for growth, prevents yeast growth unless one of the screening chemicals supplied enters the yeast cell and activates the PYR/PYL receptors, which results in expression of the nutritional marker genes in the yeast two hybrid strain. Activated cells appear as regions of cell growth and can be easily identified by visual inspection.

Using a combination of the conventional and halo assays as described above, 65,000 screening compounds were tested for activation of PYR1, PYL2, PYL3 or PYL4 expressing yeast two hybrid strains. Hit compounds that activated any of the yeast strains were retested on all 4 yeast strains and activity assessed qualitatively using X-gal staining assays. This led to the identification of the compounds shown in FIG. 8. Estimates of the relative activity of each of these compounds on the PYR/PYL receptors PYR1, PYL1, PYL2, PYL3, and PYL4 is depicted in FIG. 8. We note that the PYL3 yeast strain used in these screening assays is exceptionally sensitive to ABA, and therefore the estimate of the relative activity of ABA or other compounds on the PYL3 receptor may be refined by later performing in vitro phosphatase assays, described below.

As a further validation of hit compounds identified in the yeast two-hybrid assay, we utilized in vitro PP2C assays conducted in the presence of recombinant PYR/PYL receptor proteins PYR1, PYL1, PYL2, or PYL3 and the PP2C HAB1. Recombinant proteins were made as described above in Example 1. Phosphatase assays using the phosphatase substrate pNPP were performed as described in Example 1. As demonstrated by the IC50 values, we found that compound 7653159, which is the same compound as compound 7 in FIG. 8, is a potent agonist of PYR1 and PYL1 inhibition of HAB1 but is not an agonist for PYL2 or PYL3 (FIG. 9). Similarly, compound 6655097, which is the same compound as compound 6 in FIG. 8, is a potent agonist of PYR1 and PYL1 inhibition of HAB1 but is not an agonist for PYL2 or PYL3 (FIG. 9). Compound 7561035, which is the same compound as compound 9 in FIG. 8, is a potent agonist of PYL2 and PYL3 inhibition of HAB1 but is not an agonist for PYR1 or PYL1 (FIG. 9).

Example 3: Phenotypic Analysis of PYR/PYL Overexpression and Loss-of-Function Mutant Plants Abscisic acid is a multifunctional phytohormone involved in a variety of phyto-protective functions including bud dormancy, seed dormancy and/or maturation, abscission of leaves and fruits, and response to a wide variety of biological stresses (e.g. cold, heat, salinity, and drought). ABA is also responsible for regulating stomatal closure by a mechanism independent of $CO_2$ concentration. Because PYR/PYL receptor proteins mediate ABA signaling, these phenotypes can be modulated by modulating expression of PYR/PYL. However, as discussed above, experiments with single, triple, and quadruple Pyr/Pyl mutant plants demonstrate that PYL receptors PYL1, 2 and 4 function redundantly with PYR1 in the control of germination and root responses to ABA function. In these experiments, we asked whether other PYR/PYL receptors function redundantly with PYR1 in the control of plant phyto-protective functions such as flowering time, stature, chlorophyll content, and wiltiness. We used the pyr1; pyl1; pyl2; pyl4 quadruple mutants as described above in Example 1 to test the effect of loss of function of multiple PYR/PYL receptors on these phyto-protective functions. We found that pyr1; pyl1; pyl2; pyl4 quadruple mutants exhibit defects in flowering time, stature, and wiltiness (FIG. 10). Relative to a control *Arabidopsis* plant, pyr1; pyl1; pyl2; pyl4 quadruple mutants flower early, are smaller in stature, and are very wilty. We also examined the effect on phyto-protective functions from overexpressing the PYR/PYL receptor PYL4. We generated transgenic *Arabidopsis* plants expressing GFP-PYL4 under the control of the high expression promoter Rbcs, and found that plants that overexpress PYL4 exhibit defects in flowering time, stature, wiltiness, and the chlorophyll content of the plants; relative to control plants, these PYL4-overexpressing plants flower later, are darker green, and less wilty (FIG. 10). These results demonstrate that PYR/PYL receptors modulate a wide variety of ABA-mediated activities in plants.

Example 4: Screens of Plant Extracts for PYR/PYL Agonists

The yeast strains expressing PYR/PYL receptors and type 2 C protein phosphatases were also used to screen HPLC-fractionated plant extracts for the presence of endogenous compounds that activate PYL/PYL receptors PYR1, PYL2, PYL3, and/or PYL4. HPLC fractionation of extracts was used to identify compounds different from abscisic acid (the known agonist). This led to the identification of a PYL3/PYL4 selective agonist in extracts made from *Hypericum perforatum* aerial tissues. Purification of the agonist was achieved via multiple rounds of chromatographic separation coupled to yeast two hybrid assays that informed the fractions to move forward at each step of the purification. The structure of the purified agonist was deduced by X-ray crystallography of crystalline purified agonist. This revealed the compound to be the previously known compound artemisinic acid. This compound has not been reported outside of the genus *Artemisia* (Asteraceae) and our isolation of this compound from *Hypericum* (Clusiaceae) suggests the compound may have widespread occurrence in plants, consistent with a functionally important role to plant physiology. Several related compounds were obtained from commercial sources and also found to possess PYL3/PYL4 selective agonist activity (FIG. 12). Following a similar approach to that described above for artemisinic acid, a second naturally occurring ABA agonist was identified from seeds of *Cola accumulata* and identified by 2D-NMR as a previously undescribed derivative of alpha-copaene, copaenoic acid (FIG. 12).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

INFORMAL SEQUENCE LISTING

SEQ ID NO: 1 xWxxxxxxFxxPxxxxxxFxxxC

SEQ ID NO: 2

*Brassica_oleracea* {89257688}
gb|ABD65175.1|
mpsqltpeerselaqsiaefhtyhlgpgscsslhaqrihappeivwsvvrrfdkpqtykhfikscsvedgfemrvgct ravnvisglpantsterldildderrvtgfsiiggehrltnyksvttvhrfekerriwtvvlesyvvdmpegnseddt rmfadtvvklnlqklatvteamarnagdgsgaqvt

SEQ ID NO: 3

*Brassica_oleracea* {89274227}
gb|ABD65631.1|
mpseltqeerskltqsisefhtyhlgpgscsslhaqrihappeivwsvvrqfdkpqtykhfikscsveegfemrvgct rdvivisglpantsterldmldderrvtgfsiiggehrlknyksyttyhrfererriwtvvlesyvvdmpegnseddt rmfadtvvklnlqklatvteamarnagdgrgsrettcresfhlitafekqrqiteptvyqnppyhtgmtpeprtstvf ieledhrtlpgnltptteehlqrmyqrfwgirqlqrprqsfgerqsi

SEQ ID NO: 4

*Vitis_vinifera* {157341954}
emb|CAO63410.1|
mqmkylegkqnlmeekgekqcipmdlavreaqfkgslldritwleqrlhklslqletrskqqphpsrmqtagetssrh gpkkelscsfpvfstrnhnhghkqtsqfhvprfeyqeggrenpavvitkltpfhhpkiitilfpisnyfiiffltfd tkkqypllfpilpsrflpishlitqeiekyktsshfsspaslfaamnkaetssmaeaesedsetttptthhltippgl tqpefqelahsisefhtyqvgpgqcssllaqrvhaplptvwsvvrrfdkpqtykhfikschvedgfemrvgclrdvnv isglpaetsterldildderhvtgfsiiggehrlrnyrsvttnhggeiwtvvlesyvvdmpegnteedtrlfadtvvk lnlqklasvtevsqscnypcqfhiienediqpeemnlgvlttsieeqrkkkrvvamkdgstss

SEQ ID NO: 5

*Vitis_vinifera* {147789129}
emb|CAN64657.1|
maeaesedsetttptthhltippgltqpefqelahsisefhtyqvgpgqcssllaqrvhaplptvwsvvrrfdkpqty khfikschvedgfemrvgclrdvnvisglpaetsterldildderhvtgfsiiggehrlrnyrsvttvheyqnhggei wtvvlesyvvdmpegnteedtrlfadtvvklnlseaxrr -continued SEQ ID NO: 6
*Medicago_truncatula* {217073334}
gb|ACJ85026.1|
mekaesstastsdqdsdenhrtqhhltlpsglrqhefdslipfinshhtyligpnqcstllaqrihappqtvwsvvrs fdkpqiykhiikscslkegfqmkvgctrdvnvisglpaatsterldvlddervtgfsiiggehrlknyrsvtsvhgf gdgdnggeiwtvvlesyvvdvpegnteedtrlfadtvvklnlqklasvtegknrdgdgksh SEQ ID NO: 7
*Oryza_sativa_Japonica*_Group {115483600}
ref|NP_001065470.1|
meqqeevppppaglgltaeeyaqvratveahhryavgpgqcssllaqrihappaavwavvrrfdcpqvykhfirscvl rpdphhddngndlrpgrlrevsvisglpaststerldllddahrvfgftitggehrtrnyrsvttvsqldeictlvle syivdvpdgnteddtrlfadtvirlnlqklksyseananaaaaaaappppppaaae SEQ ID NO: 8
*Zea_mays* {195641068}
gb|ACG40002.1|
mdqqgaggdaevpaglgltaaeyeqlrstvdahhryavgegqcssllaqrihappeavwavvrrfdcpqvykhfirsc alrpdpeagdalcpgrlrevsvisglpaststerldllddaarvfgfsitggehrlrnyrsvttvselavpaictvvl esyvvdvpdgnteddtrlfadtvirlnlqklksvaeanaaeaaattnsvllprpae SEQ ID NO: 9
*Zea_mays* {195625286}
gb|ACG34473.1|
mdqqgaggdaxvpaglgltaaeyeqlrstvdahhryavgegqcssllaqrihappeavwavvrrfdcpqvykhfirsc alrpdpeagdalcpgrlrevsvisglpaststerldllddaarvfgfsitggehrlrnyrsvttvseladpaictvvl esyvvdvpdgnteddtrlfadtvirlnlqklksvteanaaeaaattnsvllprpae SEQ ID NO: 10
*Vitis_vinifera* {57339249}
emb|CAO43790.1|
mdphhhhglteeefralepiiqnyhtfepspntctslitqkidapaqvvwpfvrsfenpqkykhfikdctmrgdggvg sirevtvvsglpaststerleilddekhilsfrvvggehrinnyrsvtsvndfskegkdytivlesyivdipegntge dtkmfvdtvvklnlqklavvaitslheneeiadnegpsreislqsetesaergderrdgdgpskacnrnewhcttke SEQ ID NO: 11
*Oryza_saliva_Japonica*_Group {49388537}
dbj|BAD25659.1|
mephmeralreavaseaerrelegvvrahhtfpaaeraagpgrrptctslvaqrvdaplaavwpivrgfanpqrykhf ikscelaagdgatvgsvrevavvsglpaststerleildddrhvlsfrvvggdhrlrnyrsvtsvtefsspsspprpy cvvvesyvvdvpegnteedtrmftdtvvklnlqklaavatsssppaagnhh SEQ ID NO: 12
*Oryza_sativa_Indica*_Group {125538682}
gb|EAY85077.1|
mephmeralreavaseaerrelegvvrahhtfpaaeraagpgrrptctslvaqrvdaplaavwpivrgfanpqrykhf ikscelaagdgatvgsvrevavvsglpaststerleildddrhvlsfrvvggdhrlrnyrsvtsvtefsspsspppspp rpycvvvesyvvdvpegnteedtrmftdtvvklnlqklaavatsssppaagnhh SEQ ID NO: 13
*Zea_mays* {194695858}
gb|ACF82013.1|
mpytaprpspqqhsrvlsgggakaashgascaavpaevarhhehaaragqccsavvqaiaapvgavwsvvrrfdrpqa ykhfirscrlvgggdvavgsvrevrvvsglpatssrerleildderrvlsfrvvggehrlanyrsvttvheagagagt gtvvvesyvvdvphgntadetrvfvdtivrcnlqslartaerla SEQ ID NO: 14
*Vitis_vinifera* {157355387}
emb|CAO48777.1|
mpsnppkssl vvhrinspnsittattasaaannhntstmpphkqvpdavsrhhthvvgpnqccsavvqqiaapvstvw svvrrfdnpqaykhfvkschvvvgdgdygtlrevhvisglpaansterleildderhvlsfsviggdhrlsnyrsvtt lhpspsstgtvvlesyvvdippgntkedtcvfvdtivrcnlqslaqiaenaagckrsss -continued

SEQ ID NO: 15

*Nicotiana_tabacum* {62867576}
emb|CA184653.1|
mppsspdssvllqrissnttpdfackqsqqlqrrtmpipcttqvpdsvvrfhthpvgpnqccsaviqrisapvstvws vvrrfdnpqayvkhfvkschvivgdgdygtlrevrvisglpaassterleildderhvisfsvvggdhrlanyrsvttl hpepsgdgttivvesyvvdvppgntrdetcvfvdtivkcnltslsqiavnvnrrkds

SEQ ID NO: 16

*Oryza_sativa_Indica*_Group {125528236}
gb|EAY76350.1|
mpyaavrpspppqlsrpigsgagggkacpavpcevaryhehavgagqccstvvqaiaapadavwsvvrrfdrpqaykk fikscrlvdgdggevgsvrevrvvsglpatssrerlevldddrrvlsfrivggehrlanyrsvttvheaaapamavvv esyvvdvppgntweetrvfvdtivrcnlqslartverlapeaprangsidha

SEQ ID NO: 17

*Oryza_sativa_Japonica*_Group {15624049}
dbj|BAB68102.1|
mpyaavrpspppqlsrpigsgagggkacpavpcevaryhehavgagqcfstvvqaiaapadavwsvvrrfdrpqaykk fikscrlvdgdggevgsvrevrvvsglpatssrerlevldddrrvlsfrivggehrlanyrsvttvheaaapamavvv esyvvdvppgntweetrvfvdtivrcnlqslartverlapeaprangsidha

SEQ ID NO: 18

*Picea_sitchensis* {116783434}
gb|ABK22940.1|
mdiiagfdqlsfrlsgaskqitktgavqylkgeegygewlkevmgryhyhshdgarecrcssvvvqqveapvsvvwsl vafdqpqvykhfvsncfmrgdlkvgclrevrvvsglpaatsterldildeerhilsfsivggdhrlnnyrsittlhet lingkpgtiviesyvldvphgntkeetclfvdtivkcnlqslahvsnhlnsthrcl

SEQ ID NO: 19

*Oryza_sativa_Japonica*_Group {115468550}
ref|NP_001057874.1|
meahveralregltееeraalepavmahhtfppstttattaaatctslvtqrvaapvravwpivrsfgnpqrykhfvr tcalaagdgasvgsvrevtvvsglpaststerlemldddrhiisfrvvggqhrlrnyrsvtsvtefqppaagpgpapp ycvvvesyvvdvpdgntaedtrmftdtvvklnlqmlaavaedsssasrrrd

SEQ ID NO: 20

*Oryza_sativa_Japonica*_Group {115464439}
ref|NP_001055819.1|
mpytaprpsppqhsriggcggggvlkaagaaghaascvavpaevarhhehaagvgqccsavvqaiaapvdavwsvvrr fdrpqaykhfirscrlldgdgdggavavgsvrevrvvsglpatssrerleildderrvlsfrvvggehrlsnyrsvtt vhetaagaaaavvvesyvvdvphgntadetrmfvdtivrcnlqslartaeqlalaapraa

SEQ ID NO: 21

*Vitis_vinifera* {157351249}
emb|CAO41436.1|
mpsslqlhrinnidpttvavaataavnchkqsrtplrcatpvpdavasyhahavgphqccsmvvqttaaalptvwsvv rrfdnpqaykhflkschvifgdgdigtlrevhvvsglpaesssterleildderhylsfsvvggdhrlcnyrsvttlhp sptgtgtvvvesyvvdippgntkedtcvfvdtivkcnlqslaqmsekltnnnrnss

SEQ ID NO: 22

*Zea_mays* {195617008}
gb|ACG30334.1|
mpclqasspgsmpyqhhgrgvgcaaeagaavgasagtgtrcgahdgevpaeaarhhehaapgpgrccsavvqrvaapa eavwsvvrrfdqpqaykrfyrscallagdggvgtlrevrvvsglpaassrerlevlddeshvlsfrvvggehrlqnyl svttvhpspaapdaatvvvesyvvdvppgntpedtrvfvdtivkcnlqslattaeklalaav

SEQ ID NO: 23

*Physcomitrella_patens*_subsp._*patens* {168051209}
ref|XP_001778048.1|
mqtkgrqadfqtllegqqdlicrfhrhelqphqcgsillqlikapvetvwsvarsfdkpqvykrfiqtceiiegdggv gsirevrlvssipatssierleilddeehiisfrvigggbriqnywsvtslhsheidgqmgtivlesyvvdipegntr eethmfvdtvvrcnlkalaqvse -continued

SEQ ID NO: 24

*Oryza_sativa_Indica_*Group {125543492}
gb|EAY89631.1|
mpcipasspgiphqhqhqhhralagvgmavgcaaeaavaaagvagtrcgahdgevpmevarhhehaepgsgrccsavv qhvaapapavwsvvrrfdqpqaykrfvrscallagdggvgtfrevrvvsglpaassrerleilddeshvlsfrvvgge hriknylsvttyhpspsaptaatvvvesyvvdvppgntpedtrvfvdtivkcnlqslaktaeklaagaraags

SEQ ID NO: 25

*Oryza_sativa_Japonica_*Group {115452475}
ref|NP_001049838.1|
mpcipasspgiphqhqhqhhralagvgmavgcaaeaavaaagvagtrcgahdgevpmevarhhehaepgsgrccsavv qhvaapaaavwsvvrrfdqpqaykrfvrscallagdggvgtlrevrvvsglpaassrerleilddeshvlsfrvvgge hrlknylsvttvhpspsaptaatvvvesyvvdvppgntpedtrvfvdtivkcnlqslaktaeklaagaraags

SEQ ID NO: 26

*Medicago_truncatula* {217075076}
gb|ACJ85898.1|
mpspvqfqrfdsntaitngvncpkqiqacryalsslkptvsvpetvvdhhmhvvgqnqcysvviqtinasystvwsvv rrfdypqgykhfvkscnvvasgdgirvgalrevrlvsglpayssterldildeerhvisfsvvggvhrcrnyrsvttl hgdgnggtvviesyvvdvpqgntkeetcsfadtivrcnlqslvqiaekl

SEQ ID NO: 27

*Zea_mays* {195608982}
gb|ACG26321.1|
mpfaasrtsqqqhsrvatngravavcaghagvpdevarhhehavaagqccaamvqsiaapvdavwslvrrfdqpqryk rfirschlvdgdgaevgsvrelllysglpaessrerleirdderrvisfrvlggdhrlanyrsvttvheaapsqdgrp ltmvvesyvvdvppgntveetrifvdtivrcnlqslegtvirqleiaamphddnqn

SEQ ID NO: 28

*Zea_mays* {194705858}
gb|ACF87013.1|
mrernssidqehqrgsssrstmpfaasrtsqqqhsrvatngravavcaghagvpdevarhhehavaagqccaamvqsi aapvdavwslvrrfdqpqrykrfirschlvdgdgaevgsvrelllvsglpaessrerleirdderrvisfrvlggdhr lanyrsvttvheaapsqdgrpltmvvesyvvdvppgntveetrifvdtivrcnlqslegtvirqleiaamphddnqn

SEQ ID NO: 29

*Physcomitrella_patens_subsp._patens* {168019160}
ref|XP_001762113.1|
mmqekqgrpdfqfllegqqdlicrfhkhellphqcgsillqqikapvqtvwlivrrfdepqvykrfiqrcdivegdgv vgsirevqlvssipatssierleilddeehiisfrviggghrlqnywsvtslhrheiqgqmgflylesyvvdipdgnt reethtfvdtvvrcnlkalaqvseqkhllnsnekpaap

SEQ ID NO: 30

*Vitis_vinifera* {157354734}
emb|CAO48052.1|
mkvyspsqilaergpraqamgnlyhthhllpnqcsslvvqttdaplpqvwsmvrrfdrpqsykrfvrgctlrrgkggv gsvrevnivsglpaeislerldkldddlhvmrftviggdhrlanyhstltlhedeedgvrktvvmesyvvdvpggnsa getcyfantiigfnlkalaavtetmalkanipsgf

SEQ ID NO: 31

*Physcomitrella_patens_subsp._patens* {168030621}
ref|XP_001767821.1|
mqqvkgrqdfqrlleaqqdlicryhthelkahqcgsillqqikvplpivwaivrsfdkpqvykrfiqtckitegdggy gsirevhlvssvpatcsierleilddekhiisfrvlggghrlqnyssysslheleveghpctlvlesymydipdgntr eethmfvdtvvrcnlkslaqiseqqynkdclqqkqhdqqqmyqqrhpplppipitdknmer

SEQ ID NO: 32

*Physcomitrella_patens_subsp._patens* {168028995}
ref|XP_001767012.1|
mrfdighndvrgfftceeehayalhsqtvelnqcgsilmqqihapievvwsivrsfgspqiykkfiqaciltvgdggv gsirevflvsgvpatssierleilddekhvfsfrvlkgghrlqnyrsvttlheqevngrqtttvlesyvvdvpdgntr eethmfadtvvmcnlkslaqvaewramqgitqqlstssl -continued SEQ ID NO: 33
*Vitis_vinifera* {147840019}
emb|CAN72620.1|
mgnlyhthhllpnqcsslvvqttdaplpqvwsmvrrfdrpqsykrfvrgct/rrgkggygsvrevnivsglpaeisle rldklddd1hvmrftviggdhrlanyhstltlhedeedgvrktvvmesyvvdvpggnsagetcyfantiigfnlkala avtetmalkanipsgf SEQ ID NO: 34
*Picea_sitchensis* {116785512}
gb|ABK23752.1|
medlsswregramwlgnppseselvcrhhrhelqgnqcssflvkhirapvhlywsivrtfdqpqkykpfvhscsvrgg itygsirnvnvksglpataseerleilddnehvfsikilggdhrlqnyssiitvhpeiidgrpgtlviesyvvdvpeg ntreetrffvealvkcnlksladvserlasqhhtellert SEQ ID NO: 35
*Solanum_tuberosum* {78191398}
gb|ABB29920.1|
mnangfcgvekeyirkhhlhepkenqcssflvkhirapvhlvwslvrrfdqpqkykpfisrcivqgdleigslrevdv ksglpattsterlelelddeehilsvrivggdhrlrnyssvisvhpevidgrpgtvvlesfvvdvpegntkdetcyfve alincnlksladiservavqdrtepidqv SEQ ID NO: 36
*Medicago_truncatula* {217075184}
gb|ACJ85952.1|
mnngceqqqysvietqyirrhhkhdlrdnqcssalvkhikapvhlvwslvrrfdqpqkykpfisrcimqgdlsigsvr evnvksglpattsterleqlddeehilgirivggdhrlrnyssiitvhpgvidgrpgtmviesfvvdvpegntkdetc yfvealirynlssladvsermavqgrtdpininp SEQ ID NO: 37
*Vitis_vinifera* {157358179}
emb|CAO65816.1|
msgygcikmedeyirrhhrheirdnqcssslvkhikapvhlvwslvrsfdqpqkykpfvsrcivqgdleigsvrevnv ksglpattsterlelelddeehifgmrivggdhrlknyssivtvhpeiidgrpgtiviesfvvdvpdgntkdetcyfve alikcnlksladvserlaiqdrtepidrm SEQ ID NO: 38
*Vitis_vinifera* {157360187}
emb|CAO69376.1|
mngnglssmeseyirrhhrhepaenqcssalvkhikapvplvwslvrrfdqpqkykpfisrcvvqgnleigslrevdv ksglpattsterlellddd ehilsmriiggdhrlrnyssiislhpeiidgrpgtmviesyvvdvpegntkdetcyfve alikcnlksladvserlavqdrtepidrm SEQ ID NO: 39
*Oryza_sativa_Japonica*_Group {125597584}
gb|EAZ37364.1|
meahveralregltееeraalepavmahhtfppstttattaaatctslvtqrvaapvravwpivrsfgnpqrykhfvr tcalaagngpsfgsvrevtvvsgpsrlppgterlemlddd rhiisfrvvggqhrlrnyrsvtsvtefqppaagpgpap pycvvvesyvvdvpdgntaedtrmftdtvvklnlqmlaavaedsssasrrrd SEQ ID NO: 40
*Capsicum_annuum* {47558817}
gb|AAT35532.1|
mmnangfsgvekeyirkhhlhqpkenqcssflvkhirapvhlvwslvrrfdqpqkykpfvsrciaqgdleigslrevd vksglpattsterlellddeehilsfriiggdhrlrnyssiislhpevidgrpgtlviesfvvdvpqgntkdetcyfv ealincnlksladvserlavqdrtepidqv SEQ ID NO: 41
*Populus_trichocarpa* {118481075}
gb|ABK92491.1|
mngsdaysateaqyvrrhhkheprenqctsalvkhikapahlvwslvrrfdqpqrykpfvsrcvmngelgigsvrevn vksglpattsterlellddeehilgvqivggdhrlknyssimtvhpefidgrpgtlviesfivdvpdgntkdetcyfv ealircnlksladvsermavqdrvepvnqf -continued SEQ ID NO: 42
*Capsicum_annuum* {104304209}
gb|ABF72432.1|
mnangfsgvekeyirkhhlhqpkenqcssflvkhirapvhlvwslvrrfdqpqkykpfvsrciaqgdleigslrevdv ksglpattsterlellddeehilsfriiggdhrlrnyssiislhpevidgrpgtlviesfvvdvpqgntkdetcyfve alincnlksladvserlavqdrtepidqv SEQ ID NO: 43
*Populus_trichocarpa_x_Populus_deltoides* {118489403}
gb|ABK96505.1|
mngsdaysateaqyvrrhhkheprenqctsalvkhikapahlvwslvrrfdqpqrykpfvsrcvmngelgigsvrevn vksglpattsterlellddeehilgvqivggdhrlknyssimtvhpefidgrpgtlviesfivdvpdgntkdetcyfv kalircnlksladvsermavqdrvepvnqf SEQ ID NO: 44
*Pisum_sativum* {56384584}
gb|AAV85853.1|
mnnggeqysaietqyirrrhkhdlrdnqcssalvkhikapvhlvwslvrrfdqpqkykpfvsrcimqgdlgigsvrev nvksglpattsterleqlddeehilgirivggdhrtrnyssvitvhpevidgrpgtmviesfvvdvpegntrdetcyf vealirgnissladvsermavqgrtdpinvnp SEQ ID NO: 45
*Vitis_vinifera* {157349888}
emb|CAO39744.1|
meaqvicrhhaheprenqcssvlvrhvkapanlvwslvrrfdqpqkykpfvsrcvvqgdlrigsvrevnvktglpatt sterlelfdddehvlgikildgdhrlrnyssvitvhpeiidgrpgtlviesfvvdvpegntkddtcyfvralincnlk claevsermamlgrvepanav SEQ ID NO: 46
*Vitis_vinifera* {147856414}
emb|CAN82501.1|
mmeaqvicrhhaheprenqcssvlvrhvkapanlvwslvrrfdqpqkykpfvsrcvvqgdlrigsvrevnvktglpat tsterlelfdddehvlgikildgdhrlrnyssvitvhpeiidgrpgtiviesfvvdvpegntkddtcyfvralincnl kclaevsermamlgrvepanav SEQ ID NO: 47
*Arachis_hypogaea* {196196276}
gb|ACG76109.1|
mmngscgggggggeaygaieaqyirrhhrheprdnqctsalvkhirapvhlvwslvrrfdqpqkykpfvsrcimqgdlg igsvrevnvksglpattsterleqlddeehilgirivggdhrtrnyssiitvhpeviegrpgtmviesfvvdvpdgnt kdetcxfvealircnlssladvsermavqgrtdpinq SEQ ID NO: 48
*Zea_mays* {195639836}
gb|ACG39386.1|
mvvemdggvgvaagggggaqtpapapprrwrladercdlrametdyvrrfhrheprdhqcssavakhikapvhlvwsl vrrfdqpqlfkpfvsrcemkgnieigsvrevnyksglpatrsterlellddderilsvrfvggdhrlqnyssiltvhp evidgrpgtiviesfvvdvpdgntkdetcyfveallkcnlrslaevsegqvimdqtepldr SEQ ID NO: 49
*Zea_mays* {194691986}
gb|ACF80077.1|
mvvemdggvgvaagggggaqtpappppprrwrladercdlrametdyvrrfhrheprdhqcssavakhikapvhlvwsl vrrfdqpqlfkpfvsrcemkgnieigsvrevnvksglpatrsterlellddderilsvrfvggdhrlqnyssiltvhp evidgrpgtiviesfvvdvpdgntkdetcyfveallkcnlrslaevsegqvimdqtepldr SEQ ID NO: 50
*Oryza_sativa_Japonica*_Group {115468346}
ref|NP_001057772.1|
mngvggaggaaagklpmvshrrvqwrladercelreeemeyirrfhrhepssnqctsfaakhikaplhtvwslvrrfd qpqlfkpfvrncvmreniiatgcirevnvqsglpatrsterlellddnehilkvnfiggdhmlknyssiltvhsevid gqlgtlvvesfivdvpegntkddisyfienvlrcnlrtladvseerlanp -continued

SEQ ID NO: 51

*Oryza_sativa_Indica*_Group {125555582}
gb|EAZ01188.1|
mngaggaggaaagklpmvshrqvqwrladercelreeemeyirqfhrhepssnqctsfvakhikaplqtvwslvrrfd qpqlfkpfvrkcvmreniiatgcvrevnvqsglpatrsterlellddnehilkvkfiggdhmlknyssiltihsevid gqlgtivvesfvvdipegntkddicyfienilrcnlmtladvseerlanp

SEQ ID NO: 52

*Oryza_sativa_Japonica*_Group {125581525}
gb|EAZ22456.1|
mvevgggaaeaaagrrwrladercdlraaeteyvrrfhrheprdhqcssavakhikapvhlvwslvrrfdqpqlfkpf vsrcemkgnieigsvrevnvksglpatrsterlellddnehilsvrfvggdhrlknyssiltvhpevidgrpgtivie sfvvdvpegntkdetcyfveallkcnlkslaevserlvcqgpnrapstr

SEQ ID NO: 53

*Oryza_sativa_Japonica*_Group {115445369}
ref|NP_001046464.1|
mvevgggaaeaaagrrwrladercdlraaeteyvrrfhrheprdhqcssavakhikapvhlvwslvrrfdqpqlfkpf vsrcemkgnieigsvrevnvksglpatrsterlellddnehilsvrfvggdhrlknyssiltvhpevidgrpgtlvie sfvvdvpegntkdetcyfveallkcnlkslaevserlvvkdqtepldr

SEQ ID NO: 54

*Medicago_truncatula* {217075288}
gb|ACJ86004.1|
mekmngtenngvfnstemeyirrhhnqqpgenqcssalvkhirapvplvwslvrrfdqpqkykpfvsrcvvrgnleig slrevdvksglpattsterlevlddnehilsiriiggdhrlrnyssimslhpeiidgrpgtiviesfvvdvpegntkd etcyfvealikcnlkslsdvseghavqdltepldrvhellisg

SEQ ID NO: 55

*Medicago_truncatula* {217071196}
gb|ACJ83958.1|
mekmngtenngvfnstemeyirrhhnqqpgenqcssalvkhirapvplvwslvrrfdqpqkykpfvsrcvvrgnleig slrevdvksglpattsterlevlddnehilsiriiggdhrlrnyssimslhpeiidgrpgtiviesfvvdvpegntkd etcyfvealikcnlkslsdvseghaaqdltepldrmhellisg

SEQ ID NO: 56

*Zea_mays* {195625792}
gb|ACG34726.1|
mvglvggstaraehvvanaggeaeyvrrmhrhaptehqctstivkhikapvhlvwqlvrrfdqpqrykpfvrncvvrg dqlevgslrdvnvktglpattsterleqldddlhilgvkfvggdhrlqnyssiitvhpesidgrpgtiviesfvvdvp dgntkdetcyfveavikcnlnslaevseqlavesptslidq

SEQ ID NO: 57

*Zea_mays* {195608384}
gb|ACG26022.1|
mvglvggstaraehvvanaggeaeyvrrmhrhaptehqctstivkhikapvhlvwelvrrfdqpqrykpfvrncvvrg dqlevgslrdvnyktglpattsterleqldddlhilgvkfvggdhrlqnyssiitvhpesidgrpgtiviesfvvdvp dgntkdetcyfveavikcnlnslaevseqlavesptslidq

SEQ ID NO: 58

*Zea_mays* {194704156}
gb|ACF86162.1|
mvmvemdggvgggggggqtpaprrwrladercdlrametdyvrrfhrheprehqcssavakhikapvhlvwslvrrfd qpqlfkpfvsrcemkgnieigsvrevnvksglpatrsterlellddnehilsvrfvggdhrlqnyssiltvhpevidg rpgtiviesfvvdvpdgntkdetcyfveallkcnlkslaevserqvvkdqtepldr

SEQ ID NO: 59

*Oryza_sativa_Japonica*_Group {115468344}
ref|NP_001057771.1|
mngaggaggaaagklpmvshrrvqcrladkrcelreeemeyirqfhrhepssnqctsfvakhikaplqtvwslvrrfd qpqlfkpfvrkcvmreniivtgcvrevnvqsglpatrsterlellddnehilkvkfiggdhmlknyssiltihsevid gqlgtivvesfvvdipdgntkddicyfienvlrcnlmtladvseerlanp -continued

SEQ ID NO: 60

*Zea_mays* {194701978}
gb|ACF85073.1|
mvglvggstaraehvvanaggeteyvrrlhrhapaehqctstlvkhikapvhlvwelvrsfdqpqrykpfvrncvvrg dqlevgslrdvnvktglpattsterleqldddlhilgvkfvggdhrlqnyssiitvhpesidgrpgtiviesfvvdvp dgntkdetcyfveavikcnlkslaevseqlavesptspidq

SEQ ID NO: 61

*Oryza_sativa_Indica*_Group {125555585}
gb|EAZ01191.1|
mngvggaggaaagklpmvshrrvqwrladercelreeemeyirrfhrhepssnqctsfaakhikaplhtvwslvrrfd qpqlfkpfvrncvmreniiatgcirevnvqsglpatrsterlellddnehilkvkfiggdhmlknyssilivhsevid gqlgtivvesfivdvlegntkddisyfienvlrcnlrtladvseerlanp

SEQ ID NO: 62

*Oryza_sativa_Japonica*_Group {115462647}
ref|NP_001054923.1|
mvglvggggwrvgddaaggggggavaagaaaaaeaehmrrlhshapgehqcssalvkhikapvhlvwslvrsfdqpqr ykpfvsrcvvrggdleigsvrevnvktglpattsterlellddd ehilsvkfvggdhrlrnyssivtvhpesidgrpg tlviesfvvdvpdgntkdetcyfveavikcnltslaevserlavqsptspleq

SEQ ID NO: 63

*Oryza_sativa_Japonica*_Group {50251668}
dbj|BAD29692.1|
mvemdaggrpepsppsgqcssavtmrinapvhlvwsivrrfeephifqpfvrgctmrgstslavgcvrevdfksgfpa kssverleilddkehvfgvriiggdhrlknyssvltakpevidgepatlvsesfvvdvpegntadetrhfveflircn lrslamvsqrlllaqgdlaeppaq

SEQ ID NO: 64

*Vitis_vinifera* {147797548}
emb|CAN64668.1|
mngnglssmeseyirrhhrhepaenqcssalvkhikapvplvwslvrrfdqpqkykpfisrcvvqgnleigslrevdv ksglpattsterlellddd ehilsmriiggdhrlrnyssiislhpeiidgrpgtmviesyvvdvpegntkdetcyfsl advserlavagtvtepidrm

SEQ ID NO: 65

*Oryza_sativa_Indica*_Group {218190432}
gb|EEC72859.1|
mvemdaggrpepsppsgqcssavtmrinapvhlvwsivrrfeephifqpfvrgctmrgstslavgcvrevdfksgfsa kssverleilddkehvfgvriiggdhrlknyssvltakpevidgepatlvsesfvidvpegntadetrhfveflircn lrslamvsqrlllaqgdlaeppaq

SEQ ID NO: 66

*Oryza_sativa_Japonica*_Group {125585934}
gb|EAZ26598.1|
mpcipasspgiphqhqhqhhralagvgmavgcaaeaavaaagvagtrcgahdgevpmevarhhehaepgsgrccsavv qhvaapaaavwsvvrrfdqpqaykrfvrscallagdgglgkvrerleilddeshvlsfrvvggehrlknylsvttvhp spsaptaatvvvesyvvdvppgntpedtrvfvdtivkcnlqslaktaeklaagaraags

SEQ ID NO: 67

*Rheum_australe* {197312913}
gb|ACH63237.1|
mngdgyggseeefvkryhehvladhqcssvlvehinaplhlvwslvrsfdqpqkykpfvsrcvvqggdleigsvrevd vksglpattsmeelellddkehvirvkfvggdhrlknyssivslhpeiiggrsgtmviesfivdiadgntkeetcyfi eslincnlkslscvserlavediaeriaqm -continued SEQ ID NO: 68
*Oryza_sativa*_Japonica_Group {125593228}
gb|EAZ33287.1|
mvglvggggwrvgddaaggggggavaagaaaaaeaehmrrlhsqgprrapvqlrarqahqgscsppriecanfavfla ardpkivwslvrsfdqpqrykpfvsrcvvrggdleigsvrevnyktglpattsterlellddde hilsvkfvggdhrl rnyssivtvhpesidgrpgtlviesfvvdvpdgntkdetcyfveavikcnltslaemvrmislvlpfmlvdrmsgitc eshlettivrcgeyavlahv SEQ ID NO: 69
*Oryza_sativa_Japonica*_Group {125581370}
gb|EAZ22301.1|
mephmeralreavaseaerrelegvvrahhtgwnaplaavwphrarvrptrsgtstsssrassppgdgatvgsvreva vvsglpaststerleilddd rhvlsfrvvggdhrlrnyrsvtsvtefsspsspprpycvvvesyvvdvpegnteedtr mftdtvvklnlqklaavatsssppaagnhh SEQ ID NO: 70
*Oryza_sativa_Japonica*_Group {125581524}
gb|EAZ22455.1|
mevvwsivrrfeephifqpfvrgctmrgstslavgcvrevdfksgfpakssverleilddkehvfgvriiggdhrlkn yssvltakpevidgepatlvsesfvvdvpegntadetrhfveflircnirslamvsqrlllaqgdlaeppgq SEQ ID NO: 71
*Oryza_sativa_Japonica*_Group {125594587}
gb|EAZ34646.1|
mpytaprpsppqhsriggcggggvlkaagaaghaascvavpaevarhhehaagvgqccsavvqaiaapvdavwrtsts sgaaaswtatatagplpvgsvrefrvlsglpgtssrerleildderrvlsfrvvggehrlsnyrsvttvhetaagaaa avvvesyvvdvphgntadetrmfvdtivrcnlqslartaeqlalaapraa SEQ ID NO: 72
*Vitis_vinifera* {147770961}
emb|CAN76441.1|
mpisslpfslytvtpnplklitthahaftphthiftlkfmshtycphihhitsihythllxpiphmplqpplpphpil psmpafqhlystnqhlqvalfsargpnirdfnfqdadllkldilapgsliwaawspngtdeanyvgegsptvamiakr gprhgkymafcxmyrdnvapkgvnxavatvktkrtiqlktsleiachyaginisgingevmpgqweyqvgpgqcssll aqrvhvplsavgsvvhrfdkpqryqhvikscriedgfemrmgxlrdvniisglptatntgrldmqdderhvtrcphqr qseskytennnsdassikspingpsehlktaaspktesiividtskflneedfegkdetsssnqvqiedenwetrfpn tdagiw SEQ ID NO: 73
*Vitis_vinifera* {147828564}
emb|CAN59881.1|
mpsaxksstvplslxqfklglrhghrvipwgdldslamlqrqldvdilvtghthrfftaykheggvvinpgsatgafgs itydvnpsfvlmdidglrvvvcvyelidetaniikelharkisfgtksmixclllkrrstpkfrrkklflfqcrvqmt ltltnlavsgiaqtlqvdqwtvcalifmtrrdihldkarfldfkdmgklladasglrkalsggxvtagmaifdtmrhi rpdvptvcvglaavamiakrgprhgkymafcpmyrdnvapkgvnvavvtvktkrtiqlktsleiachyaginisging evmpgqweyqvgpgqcssllaqrvhvplsavgsvvhrfdkpqryqhvikscriedgfemrmgrlrdvniisglptatn tgrldmqddexhvtrcphqrqseskytennnsdassvkspingpsehlktaax SEQ ID NO: 74
*Oryza_sativa_Indica*_Group {149392053}
gb|ABR25904.1|
eigsvrevnyktglpattsterlellddde hilsvkfvggdhrlrnyssivtvhpesidgrpgtlviesfvvdvpdgn tkdetcyfveavikcnl -continued

SEQ ID NO: 75

*Zea_mays* {194701080}
gb|ACF84624.1|
mvvemdggvgvaaaggggaqtpappppprrwrladercdlrametdyvrrfhrheprdhqcssavakhikapvhlvwsl vrrfdqpqlfkpfvsrcemkgnieigsvrevnvksglpatrsterlelldddderilsvrfvggdhrlqvcsvlhlsif caaharyfahhlkcvleflcqmhldvlpcddaile

SEQ ID NO: 76

*Oryza_sativa_Japonica*_Group {125597418}
gb|EAZ37198.1|
mngctggaggvaagrlpavslqqaqwklvdercelreeemeyvrrfhrheigsnqcnsfiakhvraplqnvwslvrrf dqpqtykpfvrkcvmrgnvetgsvreiivqsglpatrsierlefldd neyilrvkfiggdhmlkkripkktyaissrt csdsaiiavgqsncapeitamnggvsiqpwlillaffsspsnqtnpdslrdmhpgswfqillvlamftcskgsvlpps ekvnv

SEQ ID NO: 91

GxxRxVxxxSGxPAxxSxExLxxxDxxxxxxxxxxxGGxHRLxNYKSxxx

SEQ ID NO: 92 xxxxxxxxxESxxVDxPxGNxxxxTxxFxxxxxxxNLxxLx

SEQ ID NO: 93

CxSxxxxxxxAPxxxxWxxxxxFxxPxxxxxFxxxC

SEQ ID NO: 94

GxxRxVxxxSxxPAxxSxExLxxxD

SEQ ID NO: 95

GGxHRLxNYxS

SEQ ID NO: 96

CxSxxxxxxxAPxxxxWxxxxxFxxPxxxKxFxxxC

SEQ ID NO: 97

GxxRxVxxxSxLPAxxSxExLxxxD

SEQ ID NO: 98

GGxHRLxNYxS

SEQ ID NO: 99

ESxxVDxPxGNxxxxTxxFxxxxxxxNLxxL

SEQ ID NO: 100

HxxxxxxxxCxSxxxxxxxAPxxxxWxxxxxFxxPxxYKxFxxxC

SEQ ID NO: 101

VGRxVxVxSGLPAxxSxExLxxxDxxxxxxxFxxxGGxHRLxNYxSVT

SEQ ID NO: 102

VxESYxVDxPxGNxxxxTxxFxDxxxxxNLQxL

SEQ ID NO: 103

HxHxxxxxQCxSxLVKxIxAPxHxVWSxVRRFDxPQKYKPFxSRCxVxGx

SEQ ID NO: 104

ExGxxREVxxKSGLPATxSTExLExLDDxEHILxIxIxGGDHRLKNYSSxxxxHxExIxGxxGTx

SEQ ID NO: 105 xxESFVVDVPxGNTKxxTCxFVExLIxCNLxSLAxxxERL

SEQ ID NO: 106

CxSxxVxTIxAPLxLVWSILRxFDxPxxxxxFVKxCxxxSGxGG

SEQ ID NO: 107

GSVRxVTxVSxxPAxFSxERLxELDDESHVMxxSIIGGxHRLVNYxSKT

SEQ ID NO: 108

MEPHMESALRQGLSEAEQRELEGVVRAHHTFPGRAPGTCTSLVTQRVDAPLAAVWPI

VRGFGSPQRYKHFIKSCDLKAGDGATVGSVREVTVVSGLPASTSTERLEILDDHRHILS

FRVVGGDHRLRNYRSVTSVTEFQPGPYCVVLESYVVDVPDGNTEEDTRMFTDTVVKL

NLQKLAAIATSSSAN

-continued

SEQ ID NO: 109

MDQQGAGGDVEVPAGLGLTAAEYEQLRPTVDAHHRYAVGEGQCSSLLAQRIHAPPA
AVWAIVRRFDCPQVYKHFIRSCAVRPDPDAGDALRPGRLREVCVISGLPASTSTERLDH
LDDAARVFGFSITGGEHRLRNYRSVTTVSELAGPGICTVVLESYAVDVPDGNTEDDTR
LFADTVIRLNLQKLKSVAEASTSSSAPPPPSE

SEQ ID NO: 110

MPCIQASSPGGMPHQHGRGRVLGGGVGCAAEVAAAVAASAGGMRCGAHDGEVPAE
AARHHEHAAAGPGRCCSAVVQHVAAPAAAVWSVVRRFDQPQVYKRFVRSCALLAG
DGGVGTLREVRVVSGLPAASSRERLEVLDDESHVLSFRVVGGEHRLRNYLSVTTVHPS
PAAPDAATVVVESYVVDVPPGNTPEDTRVFVDTIVKCNLQSLATTAEKLAAV

SEQ ID NO: 111

MEKAESSASTSEPDSDENHHRHPTNHHINPPSGLTPLEFASLIPSVAEHHSYLVGSGQCS
SLLAQRVQAPPDAVWSVVRRFDKPQTYKHFIKSCAVKEPFHMAVGVTRDVNVISGLP
AATSTERLDLLDDIRCVTGFSIIGGEHRLRNYRSVTTVHSFEDDADDGKIYTVVLESYV
VDVPDGNTEEDTRLFADTVVKLNLQKLASVTEGTNRDGDGKSHSR

SEQ ID NO: 112

MEKTHSSSAEEQDPTRRHLDPPPGLTAEEFEDLKPSVLEHHTYSVTPTRQSSSLLAQRIH
APPHAVWSVVRCFDNPQAYKHFIKSCHVKEGFQLAVGSTRDVHVISGLPAATSTERLD
LLDDDRHVIGFTIVGGDHRLRNYRSVTSVHGFECDGKIWTVVLESYVVDVPEGNTEED
TRLFADTVVKLNLQKLASVSEGMCGDGDGDGDGKGNKS

SEQ ID NO: 113

MLQNSSMSSLLLHRINGGGGATTATNCHDTVFMTVPDGVARYHTHAVAPNQCCSSVA
QEIGASVATVWSVLRRFDNPQAYKHFVKSCHVIGGDGDVGTLREVHVISGLPAARSTE
RLEILDDERHVISFSVVGGDHRLANYRSVTTLHPTASSASGGCSGTVVVESYVVDVPPG
NTREDTRVFVDTIVKCNLQSLAQTAENLTLRKNNNNDYKCCS

SEQ ID NO: 114

MTSLQFHRFNPATDTSTAIANGVNCPKPPSTLRLLAKVSLSVPETVARHHAHPVGPNQ
CCSVVIQAIDAPVSAVWPVVRRFDNPQAYKHFVKSCHVVAAAGGGEDGIRVGALREV
RVVSGLPAVSSTERLEILDDERHVMSFSVVGGDHRLRNYRSVTTLHGDGNGGTVVIES
YVVDVPPGNTKEETCVFVDTIVRCNLQSLAQIAET

SEQ ID NO: 115

AYPVLGLTPEEFSELESIINTHHKFEPSPEICSSIIAQRIDAPAHTVWPLVRSFENPQKYKH
FVKSCNMRSGDGGVGSIREVTVVSGLPASTSTERLEILDDDKHLLSFRVVGGEHRLHN
YRSVTSVNEFKNPDNGKVYTIVLESYVVDIPEGNTGVDTKMFVDTVVKLNLQKLGE

SEQ ID NO: 116

EFTELESTINTHHKFEASPEICSSIIAQRIDAPAHTVWPLVRSFENPQKYKHFVKSCNMRS
GDGGVGSIREVTVVSGLPASTSTERLEILDDDNHLLSFRVVGGEHRLHNYRSVTSVNEF
KRPDNGKVYTIVLESYVVDIPEGNTGVDTKMFVDTVVKLNLQKLGEVAMATN

SEQ ID NO: 117

MTELSSREVEYIRRHHSKAAEDNQCASALVKHIRAPLPLVWSLVRRFDEPQKYKPFVS
RCVVRGNLEIGSLREVDVKSGLPATTSTERLEILDDNHHILSVRIIGGDHRLRNYSSIMS
LHPEIVDGRPGTLVIESFVVDIPEGNTKDETCYFVEALIKCNLKSLADVSEGLTLQDHTE
PIDRKYELLITRG

SEQ ID NO: 118

MNGGESYGAIETQYIRRHHKHEPRENQCTSALVKHIRAPVHLVWSLVRRFDQPQKYKP
FVSRCIMQGDLGIGSVREVNVKSGLPATTSTERLEQLDDEEHILGIRIVGGDHRLRNYSS

-continued

IITVHPEVIDGRPGTMVIESFVVDVPDGNTRDETCYFVEALIRCNLSSLADVSERMAVQ
GRTNPINH

SEQ ID NO: 119

MSPNNPSTIVSDAVARHHTHVVSPHQCCSAVVQEIAAPVSTVWSVVRRFDNPQAYKH
FVKSCHVILGDGDVGTLREVRVISGLPAAVSTERLDVLDDERHVIGFSMVGGDHRLSN
YRSVTILHPRSATDTVVVESYVVDVPAGNTTEDTRVFVDTILRCNLQSLAKFAENLTN
KLHQR

SEQ ID NO: 120

MSRSHNKRKPFSFIFKITLLELLSSLLSSSLRFAMDKTHSGEEQDPNPTHPTRNHLDPPPG
LTPEEFEDLKPSVLEHHTYSVTPTRQCSSLLAQRIHAPPHTVWTVVRCFDNPQAYKHFI
KSCHVKEGFQLAVGSTRDVHVISGLPAATSTERLDLLDDDRHVIGFTIVGGDHRLRNY
RSVTSVHGFERDGKIWTVVLESYVVDVPEGNTEEDTRLFADTVVKLNLQKLASVTEG
MCGDSDGKGNN

SEQ ID NO: 121

MEKAESSASTSEPDSDDNHHRHPTNHHLNPPSGLTPLEFASLVPSVAEHHSYLVGPGQC
SSLLAQRVHAPPDAVWSFVRRFDKPQTYKHFIKSCAVKEPFHMAVGVTRDVNVISGLP
AATSTERLDFLDDVRRVTGFSIIGGEHRLRNYRSVTTVHSFDDDNASADGKIYTVVLES
YVVDVPDGNTEEDTRLFADTVVKLNLQKLASVTEGTNGDGDGKPHSR

SEQ ID NO: 122

MPSSLHFDRFNPITHAATTVAIANGVNCPKQPQAPPSSTAARRLVVPSLSSGRGIAAPDT
VALHHAHVVDPNQCCSIVTQHINAPVSAVWAVVRRFDNPQGYKNFVRSCHVITGDGI
RVGAVREVRVVSGLPAETSTERLEILDDERHVISFSMVGGDHRLRNYQSVTTLHANGN
GTLVIESYVVDVPQGNTKEETCVFVDTIVRCNLQSLAQIAENRTNNCEHTAQHC

SEQ ID NO: 123

MNGIGNDGGGGLSNVEMEYIRRHHRHEPGENQCGSALVKHIRAPVPQVWSLVRRFDQ
PQKYKPFVSRCVVRGNLEIGSLREVDVKSGLPATTSTERLELLDDNEHLLSIRIIGGDHR
LRNYSSIMSLHPEIIDGRPGTLVIESFVVDVPEGNTKDETCYFVEALIKCNLKSLADVSE
GIAVQDRTEPIDRI

SEQ ID NO: 124

MVARHHAHAVGPNQCCSFVIQAIDAPVSAVWPVVRRFDNPQAYKHFVKSCHVVAAG
GAGGDGGIHVGALREVRVVSGLPAVSSTERLEILDDERHVMSFSVVGGDHRLRNYRS
VTTLHGDGSNGGTVVIESYVVDIPAGNTKEETCVFVDTIVRCNLQSLAQMAENMGS

SEQ ID NO: 125

MTILPHSNNKSSNHKFIAHQNYMASETHHHVQGLTPEELTKLEPIIKKYHLFEQSPNTCF
SIITYRIEAPAKAVWPFVRSFDNPQKYKHFIKGCNMRGDGGVGSIREVTVVSGLPASTS
TERLEILDDDKHVLSFRVVGGEHRLKNYRSVTSVNEFNKEGKVYTIVLESYIVDIPEGN
TEEDTKMFVDTVVKLNLQKLGVVAMASSMHGQ

SEQ ID NO: 126

MNRIGNGGGGGGGLSNVEMEYIRRHHRHEPGENQCGSALVKHIRAPVPQVWSLVRRF
DQPQKYKPFISRCVVRGNLEIGSLREVDVKSGLPATTSTERLELLDDNEHILSIRIIGGDH
RLRNYSSIMSLHPEIIDGRPGTLVIESFVVDVPEGNTKDETCYFVEALIKCNLKSLADVS
EGLAVQDCTEPIDRI

SEQ ID NO: 127

MASETHHHVQGLTPEELTQLEPIIKKYHLFEASSNKCFSIITHRIEAPASSVWPLVRNFD
NPQKYKHFIKGCNMKGDGSVGSIREVTVVSGLPASTSTERLEILDDDKHVLSFRVVGG

-continued

EHRLQNYRSVTSVNEFHKEGKVYTIVLESYIVDIPEGNTEEDTKMFVDTVVKLNLQKL
GVVAMASSMNGR

SEQ ID NO: 128

MLPNNPSTIVPDAVARHHTHVVSPQQCCSAVVQEIAAPVSTVWSVVRRFDNPQAYKH
FVKSCHVILGDGDVGTLREVHVISGLPAAVSTERLDVLDDERHVIGFSMVGGDHRLFN
YRSVTTLHPRSAAGTVVVESYVVDVPPGNTTEDTRVFVDTILRCNLQSLAKFAENLTK
LHQR

SEQ ID NO: 129

MNGGESYGAIETQYIRRHHKHEPRENQCTSALVKHIRAPVHLVWSLVRRFDQPQKYKP
FVSRCIMQGDLGIGSVREVNVKSGLPATTSTERLEQLDDEEHILGIRIVGGDHRLRNYSS
IITVHPEVIDGRPGTMVIESFVVDVPDGNTRDETCYFVEALIRCNLSSLADVSERMAVQ
GRTNPINH

SEQ ID NO: 130

MGITIGIQCLEIEEISICDGMFCYLVDFVDVKEKMNYCLMWFGYFPSQVWSLVRRFDQP
QKYKPFVSRCIMQGDLGIGSVREVNVKSGLPATTSTERLEQLDDEEHILGIRIVGGDHR
LRNYSSIITVHPEVIDGRPSTMVIESFVVDVPDGNTRDETCYFVEALIRCNLSSLADVSE
RMAVQGRTDPINH

SEQ ID NO: 131

MNGGESYGAIETQYIRRHHKHEPRENQCTSALVKHIRAPVHLVWSLVRRFDQPQKYKP
FVSRCIMQGDLGIGSVREVNVKSGLPATTSTERLEQLDDEEHILGIRIVGGDHRLRNYSS
IITVHPEVIDGRPSTMVIESFVVDVPDGNTRDETCYFVEALIRCNLSSLADVSERMAVQG
RTDPINH

SEQ ID NO: 132

METHVERALRATLTEAEVRALEPAVREHHTFPAGRVAAGTTTPTPTTCTSLVAQRVSA
PVRAVWPIVRSFGNPQRYKHFVRTCALAAGDGASVGSVREVTVVSGLPASSSTERLEV
LDDDRHILSFRVVGGDHRLRNYRSVTSVTEFQPGPYCVVVESYAVDVPEGNTAEDTR
MFTDTVVRLNLQKLAAVAEESAAAAAAGNRR

SEQ ID NO: 133

MEPHMETALRQGGLSELEQRELEPVVRAHHTFPGRSPGTTCTSLVTQRVDAPLSAVWP
IVRGFAAPQRYKHFIKSCDLRSGDGATVGSVREVTVVSGLPASTSTERLEILDDDRHILS
FRVVGGDHRLRNYRSVTSVTEFHHHHQAAAGRPYCVVVESYVVDVPEGNTEEDTRM
FTDTVVKLNLQKLAAIATSSAAAAASNSST

SEQ ID NO: 134

MVESPNPNSPSRPLCIKYTRAPARHFSPPLPFSSLIISANPIEPKAMDKQGAGGDVEVPA
GLGLTAAEYEQLRSTVDAHHRYAVGEGQCSSLLAQRIQAPPAAVWAIVRRFDCPQVY
KHFIRSCALRPDPEAGDALRPGRLREVSVISGLPASTSTERLDLLDDAARVFGFSITGGE
HRLRNYRSVTTVSELADPGICTVVLESYVVDVPDGNTEDDTRLFADTVIRLNLQKLKS
VAEANAAAAASFVSVVPPPEPEE

SEQ ID NO: 135

MPCLQASSSPGSMPHQHHGRVLAGVGCAAEVAAAAVAATSPAAGMRCGAHDGEVP
AEAARHHEHAAPGPGRCCSAVVQHVAAPASAVWSVVRRFDQPQAYKRFVRSCALLA
GDGGVGTLREVRVVSGLPAASSRERLEVLDDESHVLSFRVVGGEHRLQNYLSVTTVHP
SPAAPDAATVVVESYVVDVPPGNTPEDTRVFVDTIVKCNLQSLATTAEKLAAV

-continued

SEQ ID NO: 136
MVEMDGGVGVVGGGQQTPAPRRWRLADELRCDLRAMETDYVRRFHRHEPRDHQCS

SAVAKHIKAPVHLVWSLVRRFDQPQLFKPFVSRCEMKGNIEIGSVREVNVKSGLPATR

STERLELLDDNEHILSVKFVGGDHRLQNYSSILTVHPEVIDGRPGTLVIESFVVDVPDGN

TKDETCYFVEALLKCNLKSLAEVSERQVIKDQTEPLDR

SEQ ID NO: 137
MPYTAPRPSPQQHSRVTGGGAKAAIVAASHGASCAAVPAEVARHHEHAARAGQCCS

AVVQAIAAPVGAVWSVVRRFDRPQAYKHFIRSCRLVDDGGGGAGAGAGATVAVGSV

REVRVVSGLPATSSRERLEILDDERRVLSFRVVGGEHRLANYRSVTTVHEAEAGAGGT

VVVESYVVDVPPGNTADETRVFVDTIVRCNLQSLARTAERLALALA

SEQ ID NO: 138
EXLXXXDXXXXXXXXXXXGGXHXL

---

What is claimed is:

1. An expression cassette comprising a heterologous promoter operably linked to a polynucleotide encoding a mutated PYR/PYL receptor polypeptide, wherein the mutated PYR/PYL receptor polypeptide is at least 90% identical to any of SEQ ID NO:85, SEQ ID NO:87, SEQ ID NO:88, SEQ ID NO:89, or SEQ ID NO:90, and further comprises an amino acid substitution, relative to a naturally-occurring PYR/PYL receptor polypeptide, at position H60 as numbered with reference to SEQ ID NO:89, wherein the naturally-occurring PYR/PYL receptor polypeptide does not inhibit a type 2 protein phosphatase (PP2C) in the absence of abscisic acid (ABA) and wherein the mutated PYR/PYL receptor polypeptide inhibits the PP2C in the absence of ABA or an ABA agonist.

2. The expression cassette of claim 1, wherein the mutated PYR/PYL receptor polypeptide further comprises an amino acid substitution at one or more dimer interface positions selected from positions F61, K63, I84, S85, L87, P88, A89, S152, D155, T156, M158, F159, T162, L166, and K170, wherein the positions are numbered with reference to SEQ ID NO:89.

3. The expression cassette of claim 1, wherein the mutated PYR/PYL receptor polypeptide comprises a H60P substitution.

4. The expression cassette of claim 2, wherein the constitutively active PYR/PYL receptor polypeptide comprises an amino acid substitution at position M158.

5. The expression cassette of claim 4, wherein the constitutively active PYR/PYL receptor polypeptide comprises a M158I, M158T, or M158V substitution.

6. The expression cassette of claim 1, wherein the promoter is tissue-specific or inducible.

7. The expression cassette of claim 1, wherein a plant into which the expression cassette is introduced has improved stress tolerance compared to a plant lacking the expression cassette.

8. The expression cassette of claim 7, wherein a plant into which the expression cassette is introduced has improved drought tolerance compared to a plant lacking the expression cassette.

9. An expression vector comprising the expression cassette of claim 1.

10. A method of making a plant with increased stress tolerance, the method comprising:

introducing the expression cassette of claim 1 into a plurality of plants; and selecting a plant comprising the expression cassette having increased stress tolerance compared to a plant lacking the expression cassette.

11. A plant comprising a heterologous expression cassette, the expression cassette comprising a heterologous promoter operably linked to a polynucleotide encoding a mutated PYR/PYL receptor polypeptide, wherein the mutated PYR/PYL, receptor polypeptide is at least 90% identical to any of SEQ ID NO:85, SEQ ID NO:87, SEQ ID NO:88, SEQ ID NO:89, or SEQ ID NO:90 and further comprises an amino acid substitution, relative to a naturally-occurring PYR/PYL receptor polypeptide, at position H60 as numbered with reference to SEQ ID NO:89, wherein the naturally-occurring PYR/PYL receptor polypeptide does not inhibit a type 2 protein phosphatase (PP2C) in the absence of abscisic acid (ABA) and wherein the mutated PYR/PYL receptor polypeptide inhibits the PP2C in the absence of ABA or an ABA agonist.

12. The plant of claim 11, wherein the mutated PYR/PYL receptor polypeptide further comprises an amino acid substitution at one or more dimer interface positions selected from positions F61, K63, I84, S85, L87, P88, A89, S152, D155, T156, M158, F159, T162, L166, and K170, wherein the positions are numbered with reference to SEQ ID NO:89.

13. The plant of claim 11, wherein the mutated PYR/PYL receptor polypeptide comprises a H60P substitution.

14. The plant of claim 12, wherein the constitutively active PYR/PYL receptor polypeptide comprises an amino acid substitution at position M158.

15. The plant of claim 14, wherein the constitutively active PYR/PYL receptor polypeptide comprises a M158I, M158T, or M158V substitution.

16. The plant of claim 11, wherein the plant has improved stress tolerance compared to a plant lacking the expression cassette.

17. The plant of claim 16, wherein the plant has improved drought tolerance compared to a plant lacking the expression cassette.

18. The plant of claim 11, wherein the promoter is tissue-specific or inducible.

19. A plant cell from the plant of claim 11.

20. A seed, flower, leaf or fruit from the plant of claim 11 comprising the heterologous expression cassette.

21. The expression cassette of claim 1, wherein the mutated PYR/PYL receptor polypeptide is at least 95% identical to any of SEQ ID NO:85, SEQ ID NO:87, SEQ ID NO:88, SEQ ID NO:89, or SEQ ID NO:90.

22. The plant of claim 11, wherein the mutated PYR/PYL receptor polypeptide is at least 95% identical to any of SEQ ID NO:85, SEQ ID NO:87, SEQ ID NO:88, SEQ ID NO:89, or SEQ ID NO:90.

* * * * *

SEQUENCE LISTING

<160> NUMBER OF SEQ ID NOS: 141

<210> SEQ ID NO 1
<211> LENGTH: 21
<212> TYPE: PRT
<213> ORGANISM: Artificial Sequence
<220> FEATURE:
<223> OTHER INFORMATION: synthetic PYR/PYL receptor polypeptide
consensus sequence
<220> FEATURE:
<221> NAME/KEY: VARIANT
<222> LOCATION: (1)...(21)
<223> OTHER INFORMATION: Xaa = any amino acid

<400> SEQUENCE: 1

Xaa Trp Xaa Xaa Xaa Xaa Xaa Phe Xaa Xaa Pro Xaa Xaa Xaa Xaa Xaa
1 5 10 15

Phe Xaa Xaa Xaa Cys
20

<210> SEQ ID NO 2
<211> LENGTH: 191
<212> TYPE: PRT
<213> ORGANISM: Brassica oleracea
<220> FEATURE:
<223> OTHER INFORMATION: kale Streptomyces cyclase/dehydrase family
protein, locus 40.t00062

<400> SEQUENCE: 2

Met Pro Ser Gln Leu Thr Pro Glu Glu Arg Ser Glu Leu Ala Gln Ser
1 5 10 15

Ile Ala Glu Phe His Thr Tyr His Leu Gly Pro Gly Ser Cys Ser Ser
20 25 30

Leu His Ala Gln Arg Ile His Ala Pro Pro Glu Ile Val Trp Ser Val
35 40 45

Val Arg Arg Phe Asp Lys Pro Gln Thr Tyr Lys His Phe Ile Lys Ser
50 55 60

Cys Ser Val Glu Asp Gly Phe Glu Met Arg Val Gly Cys Thr Arg Ala
65 70 75 80

Val Asn Val Ile Ser Gly Leu Pro Ala Asn Thr Ser Thr Glu Arg Leu
85 90 95

Asp Ile Leu Asp Asp Glu Arg Arg Val Thr Gly Phe Ser Ile Ile Gly
100 105 110

```
Gly Glu His Arg Leu Thr Asn Tyr Lys Ser Val Thr Thr Val His Arg
        115                 120                 125

Phe Glu Lys Glu Arg Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Thr Glu
                165                 170                 175

Ala Met Ala Arg Asn Ala Gly Asp Gly Ser Gly Ala Gln Val Thr
            180                 185                 190


<210> SEQ ID NO 3
<211> LENGTH: 281
<212> TYPE: PRT
<213> ORGANISM: Brassica oleracea
<220> FEATURE:
<223> OTHER INFORMATION: kale Streptomyces cyclase/dehydrase family
      protein, locus 23.t00047

<400> SEQUENCE: 3

Met Pro Ser Glu Leu Thr Gln Glu Glu Arg Ser Lys Leu Thr Gln Ser
 1               5                  10                  15

Ile Ser Glu Phe His Thr Tyr His Leu Gly Pro Gly Ser Cys Ser Ser
            20                  25                  30

Leu His Ala Gln Arg Ile His Ala Pro Pro Glu Ile Val Trp Ser Val
        35                  40                  45

Val Arg Gln Phe Asp Lys Pro Gln Thr Tyr Lys His Phe Ile Lys Ser
    50                  55                  60

Cys Ser Val Glu Glu Gly Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Met Leu Asp Asp Glu Arg Arg Val Thr Gly Phe Ser Ile Ile Gly
            100                 105                 110

Gly Glu His Arg Leu Lys Asn Tyr Lys Ser Val Thr Thr Val His Arg
        115                 120                 125

Phe Glu Arg Glu Arg Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Thr Glu
                165                 170                 175

Ala Met Ala Arg Asn Ala Gly Asp Gly Arg Gly Ser Arg Glu Thr Thr
            180                 185                 190

Cys Arg Glu Ser Phe His Leu Ile Thr Ala Phe Glu Lys Gln Arg Gln
        195                 200                 205

Ile Thr Glu Pro Thr Val Tyr Gln Asn Pro Pro Tyr His Thr Gly Met
    210                 215                 220

Thr Pro Glu Pro Arg Thr Ser Thr Val Phe Ile Glu Leu Glu Asp His
225                 230                 235                 240

Arg Thr Leu Pro Gly Asn Leu Thr Pro Thr Thr Glu Glu His Leu Gln
                245                 250                 255

Arg Met Tyr Gln Arg Phe Trp Gly Ile Arg Gln Leu Gln Arg Pro Arg
            260                 265                 270

Gln Ser Phe Gly Glu Arg Gln Ser Ile
```

```
        275                 280


<210> SEQ ID NO 4
<211> LENGTH: 453
<212> TYPE: PRT
<213> ORGANISM: Vitis vinifera
<220> FEATURE:
<223> OTHER INFORMATION: grapevine cultivar PN40024 unnamed protein
      product, locus GSVIVT00015766001

<400> SEQUENCE: 4

Met Gln Met Lys Tyr Leu Glu Gly Lys Gln Asn Leu Met Glu Glu Lys
 1               5                  10                  15

Gly Glu Lys Gln Cys Ile Pro Met Asp Leu Ala Val Arg Glu Ala Gln
            20                  25                  30

Phe Lys Gly Ser Leu Leu Asp Arg Ile Thr Trp Leu Glu Gln Arg Leu
        35                  40                  45

His Lys Leu Ser Leu Gln Leu Glu Thr Arg Ser Lys Gln Gln Pro His
    50                  55                  60

Pro Ser Arg Met Gln Thr Ala Gly Glu Thr Ser Ser Arg His Gly Pro
65                  70                  75                  80

Lys Lys Glu Leu Ser Cys Ser Phe Pro Val Phe Ser Thr Arg Asn His
                85                  90                  95

Asn His Gly His Lys Gln Thr Ser Gln Phe His Val Pro Arg Phe Glu
            100                 105                 110

Tyr Gln Glu Gly Gly Arg Glu Asn Pro Ala Val Val Ile Thr Lys Leu
        115                 120                 125

Thr Pro Phe His His Pro Lys Ile Ile Thr Ile Leu Phe Pro Ile Ser
    130                 135                 140

Asn Tyr Phe Ile Ile Phe Phe Phe Leu Thr Phe Asp Thr Lys Lys Gln
145                 150                 155                 160

Tyr Pro Leu Leu Phe Pro Ile Leu Pro Ser Arg Phe Leu Pro Ile Ser
                165                 170                 175

His Leu Ile Thr Gln Glu Ile Glu Lys Tyr Lys Thr Ser Ser His Phe
            180                 185                 190

Ser Ser Pro Ala Ser Leu Phe Ala Ala Met Asn Lys Ala Glu Thr Ser
        195                 200                 205

Ser Met Ala Glu Ala Glu Ser Glu Asp Ser Glu Thr Thr Thr Pro Thr
    210                 215                 220

Thr His His Leu Thr Ile Pro Pro Gly Leu Thr Gln Pro Glu Phe Gln
225                 230                 235                 240

Glu Leu Ala His Ser Ile Ser Glu Phe His Thr Tyr Gln Val Gly Pro
                245                 250                 255

Gly Gln Cys Ser Ser Leu Leu Ala Gln Arg Val His Ala Pro Leu Pro
            260                 265                 270

Thr Val Trp Ser Val Val Arg Arg Phe Asp Lys Pro Gln Thr Tyr Lys
        275                 280                 285

His Phe Ile Lys Ser Cys His Val Glu Asp Gly Phe Glu Met Arg Val
    290                 295                 300

Gly Cys Leu Arg Asp Val Asn Val Ile Ser Gly Leu Pro Ala Glu Thr
305                 310                 315                 320

Ser Thr Glu Arg Leu Asp Ile Leu Asp Asp Glu Arg His Val Thr Gly
                325                 330                 335

Phe Ser Ile Ile Gly Gly Glu His Arg Leu Arg Asn Tyr Arg Ser Val
            340                 345                 350
```

```
Thr Thr Asn His Gly Gly Glu Ile Trp Thr Val Val Leu Glu Ser Tyr
        355                 360                 365

Val Val Asp Met Pro Glu Gly Asn Thr Glu Glu Asp Thr Arg Leu Phe
    370                 375                 380

Ala Asp Thr Val Val Lys Leu Asn Leu Gln Lys Leu Ala Ser Val Thr
385                 390                 395                 400

Glu Val Ser Gln Ser Cys Asn Tyr Pro Cys Gln Phe His Ile Ile Glu
                405                 410                 415

Asn Glu Asp Ile Gln Pro Glu Glu Met Asn Leu Gly Val Leu Thr Thr
            420                 425                 430

Ser Ile Glu Glu Gln Arg Lys Lys Lys Arg Val Val Ala Met Lys Asp
        435                 440                 445

Gly Ser Thr Ser Ser
    450


<210> SEQ ID NO 5
<211> LENGTH: 195
<212> TYPE: PRT
<213> ORGANISM: Vitis vinifera
<220> FEATURE:
<223> OTHER INFORMATION: grapevine cultivar Pinot Noir, clone ENTAV 115
      hypothetical protein, locus VITISV_033963
<220> FEATURE:
<221> NAME/KEY: VARIANT
<222> LOCATION: (193)...(193)
<223> OTHER INFORMATION: Xaa = Lys or Glu

<400> SEQUENCE: 5

Met Ala Glu Ala Glu Ser Glu Asp Ser Glu Thr Thr Thr Pro Thr Thr
 1               5                  10                  15

His His Leu Thr Ile Pro Pro Gly Leu Thr Gln Pro Glu Phe Gln Glu
            20                  25                  30

Leu Ala His Ser Ile Ser Glu Phe His Thr Tyr Gln Val Gly Pro Gly
        35                  40                  45

Gln Cys Ser Ser Leu Leu Ala Gln Arg Val His Ala Pro Leu Pro Thr
    50                  55                  60

Val Trp Ser Val Val Arg Arg Phe Asp Lys Pro Gln Thr Tyr Lys His
65                  70                  75                  80

Phe Ile Lys Ser Cys His Val Glu Asp Gly Phe Glu Met Arg Val Gly
                85                  90                  95

Cys Leu Arg Asp Val Asn Val Ile Ser Gly Leu Pro Ala Glu Thr Ser
            100                 105                 110

Thr Glu Arg Leu Asp Ile Leu Asp Asp Glu Arg His Val Thr Gly Phe
        115                 120                 125

Ser Ile Ile Gly Gly Glu His Arg Leu Arg Asn Tyr Arg Ser Val Thr
    130                 135                 140

Thr Val His Glu Tyr Gln Asn His Gly Gly Glu Ile Trp Thr Val Val
145                 150                 155                 160

Leu Glu Ser Tyr Val Val Asp Met Pro Glu Gly Asn Thr Glu Glu Asp
                165                 170                 175

Thr Arg Leu Phe Ala Asp Thr Val Val Lys Leu Asn Leu Ser Glu Ala
            180                 185                 190

Xaa Arg Arg
        195


<210> SEQ ID NO 6
<211> LENGTH: 217
<212> TYPE: PRT
```

<213> ORGANISM: Medicago truncatula
<220> FEATURE:
<223> OTHER INFORMATION: barrel medic unkown protein, clone MTYFD_FE_FF_FGIG-N-24

<400> SEQUENCE: 6

Met Glu Lys Ala Glu Ser Ser Thr Ala Ser Thr Ser Asp Gln Asp Ser
1 5 10 15

Asp Glu Asn His Arg Thr Gln His His Leu Thr Leu Pro Ser Gly Leu
20 25 30

Arg Gln His Glu Phe Asp Ser Leu Ile Pro Phe Ile Asn Ser His His
35 40 45

Thr Tyr Leu Ile Gly Pro Asn Gln Cys Ser Thr Leu Leu Ala Gln Arg
50 55 60

Ile His Ala Pro Pro Gln Thr Val Trp Ser Val Val Arg Ser Phe Asp
65 70 75 80

Lys Pro Gln Ile Tyr Lys His Ile Ile Lys Ser Cys Ser Leu Lys Glu
85 90 95

Gly Phe Gln Met Lys Val Gly Cys Thr Arg Asp Val Asn Val Ile Ser
100 105 110

Gly Leu Pro Ala Ala Thr Ser Thr Glu Arg Leu Asp Val Leu Asp Asp
115 120 125

Glu Arg Arg Val Thr Gly Phe Ser Ile Ile Gly Gly Glu His Arg Leu
130 135 140

Lys Asn Tyr Arg Ser Val Thr Ser Val His Gly Phe Gly Asp Gly Asp
145 150 155 160

Asn Gly Gly Glu Ile Trp Thr Val Val Leu Glu Ser Tyr Val Val Asp
165 170 175

Val Pro Glu Gly Asn Thr Glu Glu Asp Thr Arg Leu Phe Ala Asp Thr
180 185 190

Val Val Lys Leu Asn Leu Gln Lys Leu Ala Ser Val Thr Glu Gly Lys
195 200 205

Asn Arg Asp Gly Asp Gly Lys Ser His
210 215

<210> SEQ ID NO 7
<211> LENGTH: 212
<212> TYPE: PRT
<213> ORGANISM: Oryza sativa
<220> FEATURE:
<223> OTHER INFORMATION: rice Japonica cultivar group, cultivar Nipponbare (GA3) conserved hypothetical protein Os10g0573400, putative cyclase/dehydrase family protein

<400> SEQUENCE: 7

Met Glu Gln Gln Glu Glu Val Pro Pro Pro Pro Ala Gly Leu Gly Leu
1 5 10 15

Thr Ala Glu Glu Tyr Ala Gln Val Arg Ala Thr Val Glu Ala His His
20 25 30

Arg Tyr Ala Val Gly Pro Gly Gln Cys Ser Ser Leu Leu Ala Gln Arg
35 40 45

Ile His Ala Pro Pro Ala Ala Val Trp Ala Val Val Arg Arg Phe Asp
50 55 60

Cys Pro Gln Val Tyr Lys His Phe Ile Arg Ser Cys Val Leu Arg Pro
65 70 75 80

Asp Pro His His Asp Asp Asn Gly Asn Asp Leu Arg Pro Gly Arg Leu
85 90 95

```
Arg Glu Val Ser Val Ile Ser Gly Leu Pro Ala Ser Thr Ser Thr Glu
            100                 105                 110

Arg Leu Asp Leu Leu Asp Asp Ala His Arg Val Phe Gly Phe Thr Ile
        115                 120                 125

Thr Gly Gly Glu His Arg Leu Arg Asn Tyr Arg Ser Val Thr Thr Val
    130                 135                 140

Ser Gln Leu Asp Glu Ile Cys Thr Leu Val Leu Glu Ser Tyr Ile Val
145                 150                 155                 160

Asp Val Pro Asp Gly Asn Thr Glu Asp Asp Thr Arg Leu Phe Ala Asp
                165                 170                 175

Thr Val Ile Arg Leu Asn Leu Gln Lys Leu Lys Ser Val Ser Glu Ala
            180                 185                 190

Asn Ala Asn Ala Ala Ala Ala Ala Ala Ala Pro Pro Pro Pro Pro Pro
        195                 200                 205

Ala Ala Ala Glu
    210


<210> SEQ ID NO 8
<211> LENGTH: 212
<212> TYPE: PRT
<213> ORGANISM: Zea mays
<220> FEATURE:
<223> OTHER INFORMATION: corn (maize) clone 306819 cyclase/dehydrase
      family protein

<400> SEQUENCE: 8

Met Asp Gln Gln Gly Ala Gly Gly Asp Ala Glu Val Pro Ala Gly Leu
 1               5                  10                  15

Gly Leu Thr Ala Ala Glu Tyr Glu Gln Leu Arg Ser Thr Val Asp Ala
            20                  25                  30

His His Arg Tyr Ala Val Gly Glu Gly Gln Cys Ser Ser Leu Leu Ala
        35                  40                  45

Gln Arg Ile His Ala Pro Pro Glu Ala Val Trp Ala Val Val Arg Arg
    50                  55                  60

Phe Asp Cys Pro Gln Val Tyr Lys His Phe Ile Arg Ser Cys Ala Leu
65                  70                  75                  80

Arg Pro Asp Pro Glu Ala Gly Asp Ala Leu Cys Pro Gly Arg Leu Arg
                85                  90                  95

Glu Val Ser Val Ile Ser Gly Leu Pro Ala Ser Thr Ser Thr Glu Arg
            100                 105                 110

Leu Asp Leu Leu Asp Asp Ala Ala Arg Val Phe Gly Phe Ser Ile Thr
        115                 120                 125

Gly Gly Glu His Arg Leu Arg Asn Tyr Arg Ser Val Thr Thr Val Ser
    130                 135                 140

Glu Leu Ala Val Pro Ala Ile Cys Thr Val Val Leu Glu Ser Tyr Val
145                 150                 155                 160

Val Asp Val Pro Asp Gly Asn Thr Glu Asp Asp Thr Arg Leu Phe Ala
                165                 170                 175

Asp Thr Val Ile Arg Leu Asn Leu Gln Lys Leu Lys Ser Val Ala Glu
            180                 185                 190

Ala Asn Ala Ala Glu Ala Ala Ala Thr Thr Asn Ser Val Leu Leu Pro
        195                 200                 205

Arg Pro Ala Glu
    210


<210> SEQ ID NO 9
```

<211> LENGTH: 212
<212> TYPE: PRT
<213> ORGANISM: Zea mays
<220> FEATURE:
<223> OTHER INFORMATION: corn (maize) clone 241996 cyclase/dehydrase family protein
<220> FEATURE:
<221> NAME/KEY: VARIANT
<222> LOCATION: (11)...(11)
<223> OTHER INFORMATION: Xaa = Lys or Glu

<400> SEQUENCE: 9

```
Met Asp Gln Gln Gly Ala Gly Gly Asp Ala Xaa Val Pro Ala Gly Leu
 1               5                  10                  15

Gly Leu Thr Ala Ala Glu Tyr Glu Gln Leu Arg Ser Thr Val Asp Ala
            20                  25                  30

His His Arg Tyr Ala Val Gly Glu Gly Gln Cys Ser Ser Leu Leu Ala
        35                  40                  45

Gln Arg Ile His Ala Pro Pro Glu Ala Val Trp Ala Val Val Arg Arg
    50                  55                  60

Phe Asp Cys Pro Gln Val Tyr Lys His Phe Ile Arg Ser Cys Ala Leu
65                  70                  75                  80

Arg Pro Asp Pro Glu Ala Gly Asp Ala Leu Cys Pro Gly Arg Leu Arg
                85                  90                  95

Glu Val Ser Val Ile Ser Gly Leu Pro Ala Ser Thr Ser Thr Glu Arg
            100                 105                 110

Leu Asp Leu Leu Asp Asp Ala Ala Arg Val Phe Gly Phe Ser Ile Thr
        115                 120                 125

Gly Gly Glu His Arg Leu Arg Asn Tyr Arg Ser Val Thr Thr Val Ser
    130                 135                 140

Glu Leu Ala Asp Pro Ala Ile Cys Thr Val Val Leu Glu Ser Tyr Val
145                 150                 155                 160

Val Asp Val Pro Asp Gly Asn Thr Glu Asp Asp Thr Arg Leu Phe Ala
                165                 170                 175

Asp Thr Val Ile Arg Leu Asn Leu Gln Lys Leu Lys Ser Val Thr Glu
            180                 185                 190

Ala Asn Ala Ala Glu Ala Ala Ala Thr Thr Asn Ser Val Leu Leu Pro
        195                 200                 205

Arg Pro Ala Glu
    210
```

<210> SEQ ID NO 10
<211> LENGTH: 233
<212> TYPE: PRT
<213> ORGANISM: Vitis vinifera
<220> FEATURE:
<223> OTHER INFORMATION: grapevine cultivar PN40024 unnamed protein product, locus GSVIVT00032173001

<400> SEQUENCE: 10

```
Met Asp Pro His His His His Gly Leu Thr Glu Glu Glu Phe Arg Ala
 1               5                  10                  15

Leu Glu Pro Ile Ile Gln Asn Tyr His Thr Phe Glu Pro Ser Pro Asn
            20                  25                  30

Thr Cys Thr Ser Leu Ile Thr Gln Lys Ile Asp Ala Pro Ala Gln Val
        35                  40                  45

Val Trp Pro Phe Val Arg Ser Phe Glu Asn Pro Gln Lys Tyr Lys His
    50                  55                  60

Phe Ile Lys Asp Cys Thr Met Arg Gly Asp Gly Gly Val Gly Ser Ile
```

-continued

```
65                  70                  75                  80

Arg Glu Val Thr Val Val Ser Gly Leu Pro Ala Ser Thr Ser Thr Glu
                85                  90                  95

Arg Leu Glu Ile Leu Asp Asp Glu Lys His Ile Leu Ser Phe Arg Val
            100                 105                 110

Val Gly Gly Glu His Arg Leu Asn Asn Tyr Arg Ser Val Thr Ser Val
        115                 120                 125

Asn Asp Phe Ser Lys Glu Gly Lys Asp Tyr Thr Ile Val Leu Glu Ser
    130                 135                 140

Tyr Ile Val Asp Ile Pro Glu Gly Asn Thr Gly Glu Asp Thr Lys Met
145                 150                 155                 160

Phe Val Asp Thr Val Val Lys Leu Asn Leu Gln Lys Leu Ala Val Val
                165                 170                 175

Ala Ile Thr Ser Leu His Glu Asn Glu Glu Ile Ala Asp Asn Glu Gly
            180                 185                 190

Pro Ser Arg Glu Ile Ser Leu Gln Ser Glu Thr Glu Ser Ala Glu Arg
        195                 200                 205

Gly Asp Glu Arg Arg Asp Gly Asp Gly Pro Ser Lys Ala Cys Asn Arg
    210                 215                 220

Asn Glu Trp His Cys Thr Thr Lys Glu
225                 230


<210> SEQ ID NO 11
<211> LENGTH: 207
<212> TYPE: PRT
<213> ORGANISM: Oryza sativa
<220> FEATURE:
<223> OTHER INFORMATION: rice Japonica cultivar group, cultivar
      Nipponbare (GA3) Bet v I allergen-like protein

<400> SEQUENCE: 11

Met Glu Pro His Met Glu Arg Ala Leu Arg Glu Ala Val Ala Ser Glu
 1               5                  10                  15

Ala Glu Arg Arg Glu Leu Glu Gly Val Val Arg Ala His His Thr Phe
            20                  25                  30

Pro Ala Ala Glu Arg Ala Ala Gly Pro Gly Arg Arg Pro Thr Cys Thr
        35                  40                  45

Ser Leu Val Ala Gln Arg Val Asp Ala Pro Leu Ala Ala Val Trp Pro
    50                  55                  60

Ile Val Arg Gly Phe Ala Asn Pro Gln Arg Tyr Lys His Phe Ile Lys
65                  70                  75                  80

Ser Cys Glu Leu Ala Ala Gly Asp Gly Ala Thr Val Gly Ser Val Arg
                85                  90                  95

Glu Val Ala Val Val Ser Gly Leu Pro Ala Ser Thr Ser Thr Glu Arg
            100                 105                 110

Leu Glu Ile Leu Asp Asp Asp Arg His Val Leu Ser Phe Arg Val Val
        115                 120                 125

Gly Gly Asp His Arg Leu Arg Asn Tyr Arg Ser Val Thr Ser Val Thr
    130                 135                 140

Glu Phe Ser Ser Pro Ser Ser Pro Pro Arg Pro Tyr Cys Val Val Val
145                 150                 155                 160

Glu Ser Tyr Val Val Asp Val Pro Glu Gly Asn Thr Glu Glu Asp Thr
                165                 170                 175

Arg Met Phe Thr Asp Thr Val Val Lys Leu Asn Leu Gln Lys Leu Ala
            180                 185                 190
```

Ala Val Ala Thr Ser Ser Ser Pro Pro Ala Ala Gly Asn His His
195 200 205

<210> SEQ ID NO 12
<211> LENGTH: 210
<212> TYPE: PRT
<213> ORGANISM: Oryza sativa
<220> FEATURE:
<223> OTHER INFORMATION: rice Indica cultivar group, cultivar 93-11 hypothetical protein OsI_06433

<400> SEQUENCE: 12

Met Glu Pro His Met Glu Arg Ala Leu Arg Glu Ala Val Ala Ser Glu
1 5 10 15

Ala Glu Arg Arg Glu Leu Glu Gly Val Val Arg Ala His His Thr Phe
20 25 30

Pro Ala Ala Glu Arg Ala Ala Gly Pro Gly Arg Arg Pro Thr Cys Thr
35 40 45

Ser Leu Val Ala Gln Arg Val Asp Ala Pro Leu Ala Ala Val Trp Pro
50 55 60

Ile Val Arg Gly Phe Ala Asn Pro Gln Arg Tyr Lys His Phe Ile Lys
65 70 75 80

Ser Cys Glu Leu Ala Ala Gly Asp Gly Ala Thr Val Gly Ser Val Arg
85 90 95

Glu Val Ala Val Val Ser Gly Leu Pro Ala Ser Thr Ser Thr Glu Arg
100 105 110

Leu Glu Ile Leu Asp Asp Asp Arg His Val Leu Ser Phe Arg Val Val
115 120 125

Gly Gly Asp His Arg Leu Arg Asn Tyr Arg Ser Val Thr Ser Val Thr
130 135 140

Glu Phe Ser Ser Pro Ser Ser Pro Pro Ser Pro Pro Arg Pro Tyr Cys
145 150 155 160

Val Val Val Glu Ser Tyr Val Val Asp Val Pro Glu Gly Asn Thr Glu
165 170 175

Glu Asp Thr Arg Met Phe Thr Asp Thr Val Val Lys Leu Asn Leu Gln
180 185 190

Lys Leu Ala Ala Val Ala Thr Ser Ser Ser Pro Pro Ala Ala Gly Asn
195 200 205

His His
210

<210> SEQ ID NO 13
<211> LENGTH: 200
<212> TYPE: PRT
<213> ORGANISM: Zea mays
<220> FEATURE:
<223> OTHER INFORMATION: corn (maize) strain B73, clone ZM_BFb0151H07 unknown protein

<400> SEQUENCE: 13

Met Pro Tyr Thr Ala Pro Arg Pro Ser Pro Gln Gln His Ser Arg Val
1 5 10 15

Leu Ser Gly Gly Gly Ala Lys Ala Ala Ser His Gly Ala Ser Cys Ala
20 25 30

Ala Val Pro Ala Glu Val Ala Arg His His Glu His Ala Ala Arg Ala
35 40 45

Gly Gln Cys Cys Ser Ala Val Val Gln Ala Ile Ala Ala Pro Val Gly
50 55 60

-continued

```
Ala Val Trp Ser Val Val Arg Arg Phe Asp Arg Pro Gln Ala Tyr Lys
65                  70                  75                  80

His Phe Ile Arg Ser Cys Arg Leu Val Gly Gly Gly Asp Val Ala Val
                85                  90                  95

Gly Ser Val Arg Glu Val Arg Val Val Ser Gly Leu Pro Ala Thr Ser
            100                 105                 110

Ser Arg Glu Arg Leu Glu Ile Leu Asp Asp Glu Arg Arg Val Leu Ser
        115                 120                 125

Phe Arg Val Val Gly Gly Glu His Arg Leu Ala Asn Tyr Arg Ser Val
    130                 135                 140

Thr Thr Val His Glu Ala Gly Ala Gly Ala Gly Thr Gly Thr Val Val
145                 150                 155                 160

Val Glu Ser Tyr Val Val Asp Val Pro His Gly Asn Thr Ala Asp Glu
                165                 170                 175

Thr Arg Val Phe Val Asp Thr Ile Val Arg Cys Asn Leu Gln Ser Leu
            180                 185                 190

Ala Arg Thr Ala Glu Arg Leu Ala
        195                 200


<210> SEQ ID NO 14
<211> LENGTH: 215
<212> TYPE: PRT
<213> ORGANISM: Vitis vinifera
<220> FEATURE:
<223> OTHER INFORMATION: grapevine cultivar PN40024 unnamed protein
      product, locus GSVIVT0003790001

<400> SEQUENCE: 14

Met Pro Ser Asn Pro Pro Lys Ser Ser Leu Val Val His Arg Ile Asn
 1               5                  10                  15

Ser Pro Asn Ser Ile Thr Thr Ala Thr Thr Ala Ser Ala Ala Ala Asn
            20                  25                  30

Asn His Asn Thr Ser Thr Met Pro Pro His Lys Gln Val Pro Asp Ala
        35                  40                  45

Val Ser Arg His His Thr His Val Val Gly Pro Asn Gln Cys Cys Ser
    50                  55                  60

Ala Val Val Gln Gln Ile Ala Ala Pro Val Ser Thr Val Trp Ser Val
65                  70                  75                  80

Val Arg Arg Phe Asp Asn Pro Gln Ala Tyr Lys His Phe Val Lys Ser
                85                  90                  95

Cys His Val Val Val Gly Asp Gly Asp Val Gly Thr Leu Arg Glu Val
            100                 105                 110

His Val Ile Ser Gly Leu Pro Ala Ala Asn Ser Thr Glu Arg Leu Glu
        115                 120                 125

Ile Leu Asp Asp Glu Arg His Val Leu Ser Phe Ser Val Ile Gly Gly
    130                 135                 140

Asp His Arg Leu Ser Asn Tyr Arg Ser Val Thr Thr Leu His Pro Ser
145                 150                 155                 160

Pro Ser Ser Thr Gly Thr Val Val Leu Glu Ser Tyr Val Val Asp Ile
                165                 170                 175

Pro Pro Gly Asn Thr Lys Glu Asp Thr Cys Val Phe Val Asp Thr Ile
            180                 185                 190

Val Arg Cys Asn Leu Gln Ser Leu Ala Gln Ile Ala Glu Asn Ala Ala
        195                 200                 205

Gly Cys Lys Arg Ser Ser Ser
    210                 215
```

```
<210> SEQ ID NO 15
<211> LENGTH: 213
<212> TYPE: PRT
<213> ORGANISM: Nicotiana tabacum
<220> FEATURE:
<223> OTHER INFORMATION: common tobacco cell line BY-2 hypothetical
      protein c17

<400> SEQUENCE: 15

Met Pro Pro Ser Ser Pro Asp Ser Ser Val Leu Leu Gln Arg Ile Ser
 1               5                  10                  15

Ser Asn Thr Thr Pro Asp Phe Ala Cys Lys Gln Ser Gln Gln Leu Gln
            20                  25                  30

Arg Arg Thr Met Pro Ile Pro Cys Thr Thr Gln Val Pro Asp Ser Val
        35                  40                  45

Val Arg Phe His Thr His Pro Val Gly Pro Asn Gln Cys Cys Ser Ala
    50                  55                  60

Val Ile Gln Arg Ile Ser Ala Pro Val Ser Thr Val Trp Ser Val Val
65                  70                  75                  80

Arg Arg Phe Asp Asn Pro Gln Ala Tyr Lys His Phe Val Lys Ser Cys
                85                  90                  95

His Val Ile Val Gly Asp Gly Asp Val Gly Thr Leu Arg Glu Val Arg
            100                 105                 110

Val Ile Ser Gly Leu Pro Ala Ala Ser Ser Thr Glu Arg Leu Glu Ile
        115                 120                 125

Leu Asp Asp Glu Arg His Val Ile Ser Phe Ser Val Val Gly Gly Asp
    130                 135                 140

His Arg Leu Ala Asn Tyr Arg Ser Val Thr Thr Leu His Pro Glu Pro
145                 150                 155                 160

Ser Gly Asp Gly Thr Thr Ile Val Val Glu Ser Tyr Val Val Asp Val
                165                 170                 175

Pro Pro Gly Asn Thr Arg Asp Glu Thr Cys Val Phe Val Asp Thr Ile
            180                 185                 190

Val Lys Cys Asn Leu Thr Ser Leu Ser Gln Ile Ala Val Asn Val Asn
        195                 200                 205

Arg Arg Lys Asp Ser
    210


<210> SEQ ID NO 16
<211> LENGTH: 208
<212> TYPE: PRT
<213> ORGANISM: Oryza sativa
<220> FEATURE:
<223> OTHER INFORMATION: rice Indica cultivar group, cultivar 93-11
      hypothetical protein OsI_04285

<400> SEQUENCE: 16

Met Pro Tyr Ala Ala Val Arg Pro Ser Pro Pro Pro Gln Leu Ser Arg
 1               5                  10                  15

Pro Ile Gly Ser Gly Ala Gly Gly Gly Lys Ala Cys Pro Ala Val Pro
            20                  25                  30

Cys Glu Val Ala Arg Tyr His Glu His Ala Val Gly Ala Gly Gln Cys
        35                  40                  45

Cys Ser Thr Val Val Gln Ala Ile Ala Ala Pro Ala Asp Ala Val Trp
    50                  55                  60

Ser Val Val Arg Arg Phe Asp Arg Pro Gln Ala Tyr Lys Lys Phe Ile
65                  70                  75                  80
```

```
Lys Ser Cys Arg Leu Val Asp Gly Asp Gly Gly Glu Val Gly Ser Val
                85                  90                  95

Arg Glu Val Arg Val Val Ser Gly Leu Pro Ala Thr Ser Ser Arg Glu
            100                 105                 110

Arg Leu Glu Val Leu Asp Asp Asp Arg Arg Val Leu Ser Phe Arg Ile
        115                 120                 125

Val Gly Gly Glu His Arg Leu Ala Asn Tyr Arg Ser Val Thr Thr Val
    130                 135                 140

His Glu Ala Ala Ala Pro Ala Met Ala Val Val Val Glu Ser Tyr Val
145                 150                 155                 160

Val Asp Val Pro Pro Gly Asn Thr Trp Glu Glu Thr Arg Val Phe Val
                165                 170                 175

Asp Thr Ile Val Arg Cys Asn Leu Gln Ser Leu Ala Arg Thr Val Glu
            180                 185                 190

Arg Leu Ala Pro Glu Ala Pro Arg Ala Asn Gly Ser Ile Asp His Ala
        195                 200                 205


<210> SEQ ID NO 17
<211> LENGTH: 208
<212> TYPE: PRT
<213> ORGANISM: Oryza sativa
<220> FEATURE:
<223> OTHER INFORMATION: rice Japonica cultivar group, cultivar
      Nipponbare, clone B1088C09 Bet v I allergen-like protein

<400> SEQUENCE: 17

Met Pro Tyr Ala Ala Val Arg Pro Ser Pro Pro Pro Gln Leu Ser Arg
 1               5                  10                  15

Pro Ile Gly Ser Gly Ala Gly Gly Gly Lys Ala Cys Pro Ala Val Pro
            20                  25                  30

Cys Glu Val Ala Arg Tyr His Glu His Ala Val Gly Ala Gly Gln Cys
        35                  40                  45

Phe Ser Thr Val Val Gln Ala Ile Ala Ala Pro Ala Asp Ala Val Trp
    50                  55                  60

Ser Val Val Arg Arg Phe Asp Arg Pro Gln Ala Tyr Lys Lys Phe Ile
65                  70                  75                  80

Lys Ser Cys Arg Leu Val Asp Gly Asp Gly Gly Glu Val Gly Ser Val
                85                  90                  95

Arg Glu Val Arg Val Val Ser Gly Leu Pro Ala Thr Ser Ser Arg Glu
            100                 105                 110

Arg Leu Glu Val Leu Asp Asp Asp Arg Arg Val Leu Ser Phe Arg Ile
        115                 120                 125

Val Gly Gly Glu His Arg Leu Ala Asn Tyr Arg Ser Val Thr Thr Val
    130                 135                 140

His Glu Ala Ala Ala Pro Ala Met Ala Val Val Val Glu Ser Tyr Val
145                 150                 155                 160

Val Asp Val Pro Pro Gly Asn Thr Trp Glu Glu Thr Arg Val Phe Val
                165                 170                 175

Asp Thr Ile Val Arg Cys Asn Leu Gln Ser Leu Ala Arg Thr Val Glu
            180                 185                 190

Arg Leu Ala Pro Glu Ala Pro Arg Ala Asn Gly Ser Ile Asp His Ala
        195                 200                 205


<210> SEQ ID NO 18
<211> LENGTH: 213
<212> TYPE: PRT
```

<213> ORGANISM: Picea sitchensis
<220> FEATURE:
<223> OTHER INFORMATION: Sitka spruce cultivar FB3-425, clone WS0276_P02
unknown protein

<400> SEQUENCE: 18

```
Met Asp Ile Ile Ala Gly Phe Asp Gln Leu Ser Phe Arg Leu Ser Gly
 1               5                  10                  15

Ala Ser Lys Gln Ile Thr Lys Thr Gly Ala Val Gln Tyr Leu Lys Gly
            20                  25                  30

Glu Glu Gly Tyr Gly Glu Trp Leu Lys Glu Val Met Gly Arg Tyr His
        35                  40                  45

Tyr His Ser His Asp Gly Ala Arg Glu Cys Arg Cys Ser Ser Val Val
    50                  55                  60

Val Gln Gln Val Glu Ala Pro Val Ser Val Val Trp Ser Leu Val Arg
65                  70                  75                  80

Arg Phe Asp Gln Pro Gln Val Tyr Lys His Phe Val Ser Asn Cys Phe
                85                  90                  95

Met Arg Gly Asp Leu Lys Val Gly Cys Leu Arg Glu Val Arg Val Val
            100                 105                 110

Ser Gly Leu Pro Ala Ala Thr Ser Thr Glu Arg Leu Asp Ile Leu Asp
        115                 120                 125

Glu Glu Arg His Ile Leu Ser Phe Ser Ile Val Gly Gly Asp His Arg
    130                 135                 140

Leu Asn Asn Tyr Arg Ser Ile Thr Thr Leu His Glu Thr Leu Ile Asn
145                 150                 155                 160

Gly Lys Pro Gly Thr Ile Val Ile Glu Ser Tyr Val Leu Asp Val Pro
                165                 170                 175

His Gly Asn Thr Lys Glu Glu Thr Cys Leu Phe Val Asp Thr Ile Val
            180                 185                 190

Lys Cys Asn Leu Gln Ser Leu Ala His Val Ser Asn His Leu Asn Ser
        195                 200                 205

Thr His Arg Cys Leu
    210
```

<210> SEQ ID NO 19
<211> LENGTH: 207
<212> TYPE: PRT
<213> ORGANISM: Oryza sativa
<220> FEATURE:
<223> OTHER INFORMATION: rice Japonica cultivar group, cultivar
Nipponbare (GA3) hypothetical protein Os06g0562200, Bet v I
allergen family protein

<400> SEQUENCE: 19

```
Met Glu Ala His Val Glu Arg Ala Leu Arg Glu Gly Leu Thr Glu Glu
 1               5                  10                  15

Glu Arg Ala Ala Leu Glu Pro Ala Val Met Ala His His Thr Phe Pro
            20                  25                  30

Pro Ser Thr Thr Thr Ala Thr Thr Ala Ala Ala Thr Cys Thr Ser Leu
        35                  40                  45

Val Thr Gln Arg Val Ala Ala Pro Val Arg Ala Val Trp Pro Ile Val
    50                  55                  60

Arg Ser Phe Gly Asn Pro Gln Arg Tyr Lys His Phe Val Arg Thr Cys
65                  70                  75                  80

Ala Leu Ala Ala Gly Asp Gly Ala Ser Val Gly Ser Val Arg Glu Val
                85                  90                  95
```

```
Thr Val Val Ser Gly Leu Pro Ala Ser Thr Ser Thr Glu Arg Leu Glu
            100                 105                 110

Met Leu Asp Asp Asp Arg His Ile Ile Ser Phe Arg Val Val Gly Gly
        115                 120                 125

Gln His Arg Leu Arg Asn Tyr Arg Ser Val Thr Ser Val Thr Glu Phe
    130                 135                 140

Gln Pro Pro Ala Ala Gly Pro Gly Pro Ala Pro Pro Tyr Cys Val Val
145                 150                 155                 160

Val Glu Ser Tyr Val Val Asp Val Pro Asp Gly Asn Thr Ala Glu Asp
                165                 170                 175

Thr Arg Met Phe Thr Asp Thr Val Val Lys Leu Asn Leu Gln Met Leu
            180                 185                 190

Ala Ala Val Ala Glu Asp Ser Ser Ser Ala Ser Arg Arg Arg Asp
        195                 200                 205


<210> SEQ ID NO 20
<211> LENGTH: 216
<212> TYPE: PRT
<213> ORGANISM: Oryza sativa
<220> FEATURE:
<223> OTHER INFORMATION: rice Japonica cultivar group, cultivar
      Nipponbare (GA3) hypothetical protein Os05g0473000, Bet v I
      allergen family protein

<400> SEQUENCE: 20

Met Pro Tyr Thr Ala Pro Arg Pro Ser Pro Pro Gln His Ser Arg Ile
 1               5                  10                  15

Gly Gly Cys Gly Gly Gly Gly Val Leu Lys Ala Ala Gly Ala Ala Gly
            20                  25                  30

His Ala Ala Ser Cys Val Ala Val Pro Ala Glu Val Ala Arg His His
        35                  40                  45

Glu His Ala Ala Gly Val Gly Gln Cys Cys Ser Ala Val Val Gln Ala
    50                  55                  60

Ile Ala Ala Pro Val Asp Ala Val Trp Ser Val Val Arg Arg Phe Asp
65                  70                  75                  80

Arg Pro Gln Ala Tyr Lys His Phe Ile Arg Ser Cys Arg Leu Leu Asp
                85                  90                  95

Gly Asp Gly Asp Gly Gly Ala Val Ala Val Gly Ser Val Arg Glu Val
            100                 105                 110

Arg Val Val Ser Gly Leu Pro Ala Thr Ser Ser Arg Glu Arg Leu Glu
        115                 120                 125

Ile Leu Asp Asp Glu Arg Arg Val Leu Ser Phe Arg Val Val Gly Gly
    130                 135                 140

Glu His Arg Leu Ser Asn Tyr Arg Ser Val Thr Thr Val His Glu Thr
145                 150                 155                 160

Ala Ala Gly Ala Ala Ala Ala Val Val Val Glu Ser Tyr Val Val Asp
                165                 170                 175

Val Pro His Gly Asn Thr Ala Asp Glu Thr Arg Met Phe Val Asp Thr
            180                 185                 190

Ile Val Arg Cys Asn Leu Gln Ser Leu Ala Arg Thr Ala Glu Gln Leu
        195                 200                 205

Ala Leu Ala Ala Pro Arg Ala Ala
    210                 215


<210> SEQ ID NO 21
<211> LENGTH: 212
<212> TYPE: PRT
```

<213> ORGANISM: Vitis vinifera
<220> FEATURE:
<223> OTHER INFORMATION: grapevine cultivar PN40024 unnamed protein
product, locus GSVIVT00029635001

<400> SEQUENCE: 21

```
Met Pro Ser Ser Leu Gln Leu His Arg Ile Asn Asn Ile Asp Pro Thr
 1               5                  10                  15

Thr Val Ala Val Ala Ala Thr Ala Ala Val Asn Cys His Lys Gln Ser
            20                  25                  30

Arg Thr Pro Leu Arg Cys Ala Thr Pro Val Pro Asp Ala Val Ala Ser
        35                  40                  45

Tyr His Ala His Ala Val Gly Pro His Gln Cys Cys Ser Met Val Val
    50                  55                  60

Gln Thr Thr Ala Ala Ala Leu Pro Thr Val Trp Ser Val Val Arg Arg
65                  70                  75                  80

Phe Asp Asn Pro Gln Ala Tyr Lys His Phe Leu Lys Ser Cys His Val
                85                  90                  95

Ile Phe Gly Asp Gly Asp Ile Gly Thr Leu Arg Glu Val His Val Val
            100                 105                 110

Ser Gly Leu Pro Ala Glu Ser Ser Thr Glu Arg Leu Glu Ile Leu Asp
        115                 120                 125

Asp Glu Arg His Val Leu Ser Phe Ser Val Val Gly Gly Asp His Arg
    130                 135                 140

Leu Cys Asn Tyr Arg Ser Val Thr Thr Leu His Pro Ser Pro Thr Gly
145                 150                 155                 160

Thr Gly Thr Val Val Val Glu Ser Tyr Val Val Asp Ile Pro Pro Gly
                165                 170                 175

Asn Thr Lys Glu Asp Thr Cys Val Phe Val Asp Thr Ile Val Lys Cys
            180                 185                 190

Asn Leu Gln Ser Leu Ala Gln Met Ser Glu Lys Leu Thr Asn Asn Asn
        195                 200                 205

Arg Asn Ser Ser
    210
```

<210> SEQ ID NO 22
<211> LENGTH: 218
<212> TYPE: PRT
<213> ORGANISM: Zea mays
<220> FEATURE:
<223> OTHER INFORMATION: corn (maize) clone 1678999 cyclase/dehydrase
family protein

<400> SEQUENCE: 22

```
Met Pro Cys Leu Gln Ala Ser Ser Pro Gly Ser Met Pro Tyr Gln His
 1               5                  10                  15

His Gly Arg Gly Val Gly Cys Ala Ala Glu Ala Gly Ala Ala Val Gly
            20                  25                  30

Ala Ser Ala Gly Thr Gly Thr Arg Cys Gly Ala His Asp Gly Glu Val
        35                  40                  45

Pro Ala Glu Ala Ala Arg His His Glu His Ala Ala Pro Gly Pro Gly
    50                  55                  60

Arg Cys Cys Ser Ala Val Val Gln Arg Val Ala Ala Pro Ala Glu Ala
65                  70                  75                  80

Val Trp Ser Val Val Arg Arg Phe Asp Gln Pro Gln Ala Tyr Lys Arg
                85                  90                  95

Phe Val Arg Ser Cys Ala Leu Leu Ala Gly Asp Gly Gly Val Gly Thr
```

```
            100                 105                 110

Leu Arg Glu Val Arg Val Val Ser Gly Leu Pro Ala Ala Ser Ser Arg
        115                 120                 125

Glu Arg Leu Glu Val Leu Asp Asp Glu Ser His Val Leu Ser Phe Arg
    130                 135                 140

Val Val Gly Gly Glu His Arg Leu Gln Asn Tyr Leu Ser Val Thr Thr
145                 150                 155                 160

Val His Pro Ser Pro Ala Ala Pro Asp Ala Ala Thr Val Val Val Glu
                165                 170                 175

Ser Tyr Val Val Asp Val Pro Pro Gly Asn Thr Pro Glu Asp Thr Arg
            180                 185                 190

Val Phe Val Asp Thr Ile Val Lys Cys Asn Leu Gln Ser Leu Ala Thr
        195                 200                 205

Thr Ala Glu Lys Leu Ala Leu Ala Ala Val
    210                 215
```

<210> SEQ ID NO 23
<211> LENGTH: 179
<212> TYPE: PRT
<213> ORGANISM: Physcomitrella patens
<220> FEATURE:
<223> OTHER INFORMATION: moss Physcomitrella patens subspecies patens, ecotype Gransden 2004 predicted protein, locus PHYPADRAFT_222359

<400> SEQUENCE: 23

```
Met Gln Thr Lys Gly Arg Gln Ala Asp Phe Gln Thr Leu Leu Glu Gly
 1               5                  10                  15

Gln Gln Asp Leu Ile Cys Arg Phe His Arg His Glu Leu Gln Pro His
            20                  25                  30

Gln Cys Gly Ser Ile Leu Leu Gln Leu Ile Lys Ala Pro Val Glu Thr
        35                  40                  45

Val Trp Ser Val Ala Arg Ser Phe Asp Lys Pro Gln Val Tyr Lys Arg
    50                  55                  60

Phe Ile Gln Thr Cys Glu Ile Ile Glu Gly Asp Gly Gly Val Gly Ser
65                  70                  75                  80

Ile Arg Glu Val Arg Leu Val Ser Ser Ile Pro Ala Thr Ser Ser Ile
                85                  90                  95

Glu Arg Leu Glu Ile Leu Asp Asp Glu Glu His Ile Ile Ser Phe Arg
            100                 105                 110

Val Leu Gly Gly Gly His Arg Leu Gln Asn Tyr Trp Ser Val Thr Ser
        115                 120                 125

Leu His Ser His Glu Ile Asp Gly Gln Met Gly Thr Leu Val Leu Glu
    130                 135                 140

Ser Tyr Val Val Asp Ile Pro Glu Gly Asn Thr Arg Glu Glu Thr His
145                 150                 155                 160

Met Phe Val Asp Thr Val Val Arg Cys Asn Leu Lys Ala Leu Ala Gln
                165                 170                 175

Val Ser Glu
```

<210> SEQ ID NO 24
<211> LENGTH: 229
<212> TYPE: PRT
<213> ORGANISM: Oryza sativa
<220> FEATURE:
<223> OTHER INFORMATION: rice Indica cultivar group, cultivar 93-11 hypothetical protein OsI_11160

<400> SEQUENCE: 24

```
Met Pro Cys Ile Pro Ala Ser Ser Pro Gly Ile Pro His Gln His Gln
 1               5                  10                  15

His Gln His His Arg Ala Leu Ala Gly Val Gly Met Ala Val Gly Cys
            20                  25                  30

Ala Ala Glu Ala Ala Val Ala Ala Ala Gly Val Ala Gly Thr Arg Cys
        35                  40                  45

Gly Ala His Asp Gly Glu Val Pro Met Glu Val Ala Arg His His Glu
    50                  55                  60

His Ala Glu Pro Gly Ser Gly Arg Cys Cys Ser Ala Val Val Gln His
65                  70                  75                  80

Val Ala Ala Pro Ala Pro Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Val Gly Thr Leu Arg Glu Val Arg Val Val Ser Gly
        115                 120                 125

Leu Pro Ala Ala Ser Ser Arg Glu Arg Leu Glu Ile Leu Asp Asp Glu
    130                 135                 140

Ser His Val Leu Ser Phe Arg Val Val Gly Gly Glu His Arg Leu Lys
145                 150                 155                 160

Asn Tyr Leu Ser Val Thr Thr Val His Pro Ser Pro Ser Ala Pro Thr
                165                 170                 175

Ala Ala Thr Val Val Val Glu Ser Tyr Val Val Asp Val Pro Pro Gly
            180                 185                 190

Asn Thr Pro Glu Asp Thr Arg Val Phe Val Asp Thr Ile Val Lys Cys
        195                 200                 205

Asn Leu Gln Ser Leu Ala Lys Thr Ala Glu Lys Leu Ala Ala Gly Ala
    210                 215                 220

Arg Ala Ala Gly Ser
225
```

<210> SEQ ID NO 25
<211> LENGTH: 229
<212> TYPE: PRT
<213> ORGANISM: Oryza sativa
<220> FEATURE:
<223> OTHER INFORMATION: rice Japonica cultivar group, cultivar Nipponbare (GA3) hypothetical protein Os03g0297600, Bet v I allergen family protein

<400> SEQUENCE: 25

```
Met Pro Cys Ile Pro Ala Ser Ser Pro Gly Ile Pro His Gln His Gln
 1               5                  10                  15

His Gln His His Arg Ala Leu Ala Gly Val Gly Met Ala Val Gly Cys
            20                  25                  30

Ala Ala Glu Ala Ala Val Ala Ala Ala Gly Val Ala Gly Thr Arg Cys
        35                  40                  45

Gly Ala His Asp Gly Glu Val Pro Met Glu Val Ala Arg His His Glu
    50                  55                  60

His Ala Glu Pro Gly Ser Gly Arg Cys Cys Ser Ala Val Val Gln His
65                  70                  75                  80

Val Ala Ala Pro Ala Ala Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110
```

```
Gly Asp Gly Gly Val Gly Thr Leu Arg Glu Val Arg Val Val Ser Gly
        115                 120                 125

Leu Pro Ala Ala Ser Ser Arg Glu Arg Leu Glu Ile Leu Asp Asp Glu
    130                 135                 140

Ser His Val Leu Ser Phe Arg Val Val Gly Gly Glu His Arg Leu Lys
145                 150                 155                 160

Asn Tyr Leu Ser Val Thr Thr Val His Pro Ser Pro Ser Ala Pro Thr
                165                 170                 175

Ala Ala Thr Val Val Val Glu Ser Tyr Val Val Asp Val Pro Pro Gly
            180                 185                 190

Asn Thr Pro Glu Asp Thr Arg Val Phe Val Asp Thr Ile Val Lys Cys
        195                 200                 205

Asn Leu Gln Ser Leu Ala Lys Thr Ala Glu Lys Leu Ala Ala Gly Ala
    210                 215                 220

Arg Ala Ala Gly Ser
225
```

<210> SEQ ID NO 26
<211> LENGTH: 205
<212> TYPE: PRT
<213> ORGANISM: Medicago truncatula
<220> FEATURE:
<223> OTHER INFORMATION: barrel medic unkown protein, clone
      MTYFP_FQ_FR_FS1G-H-19

<400> SEQUENCE: 26

```
Met Pro Ser Pro Val Gln Phe Gln Arg Phe Asp Ser Asn Thr Ala Ile
 1               5                  10                  15

Thr Asn Gly Val Asn Cys Pro Lys Gln Ile Gln Ala Cys Arg Tyr Ala
            20                  25                  30

Leu Ser Ser Leu Lys Pro Thr Val Ser Val Pro Glu Thr Val Val Asp
        35                  40                  45

His His Met His Val Val Gly Gln Asn Gln Cys Tyr Ser Val Val Ile
    50                  55                  60

Gln Thr Ile Asn Ala Ser Val Ser Thr Val Trp Ser Val Val Arg Arg
65                  70                  75                  80

Phe Asp Tyr Pro Gln Gly Tyr Lys His Phe Val Lys Ser Cys Asn Val
                85                  90                  95

Val Ala Ser Gly Asp Gly Ile Arg Val Gly Ala Leu Arg Glu Val Arg
            100                 105                 110

Leu Val Ser Gly Leu Pro Ala Val Ser Ser Thr Glu Arg Leu Asp Ile
        115                 120                 125

Leu Asp Glu Glu Arg His Val Ile Ser Phe Ser Val Val Gly Gly Val
    130                 135                 140

His Arg Cys Arg Asn Tyr Arg Ser Val Thr Thr Leu His Gly Asp Gly
145                 150                 155                 160

Asn Gly Gly Thr Val Val Ile Glu Ser Tyr Val Val Asp Val Pro Gln
                165                 170                 175

Gly Asn Thr Lys Glu Glu Thr Cys Ser Phe Ala Asp Thr Ile Val Arg
            180                 185                 190

Cys Asn Leu Gln Ser Leu Val Gln Ile Ala Glu Lys Leu
        195                 200                 205
```

<210> SEQ ID NO 27
<211> LENGTH: 212
<212> TYPE: PRT

```
<213> ORGANISM: Zea mays
<220> FEATURE:
<223> OTHER INFORMATION: corn (maize) clone 1458362 AT-rich element
      binding factor 3

<400> SEQUENCE: 27

Met Pro Phe Ala Ala Ser Arg Thr Ser Gln Gln Gln His Ser Arg Val
 1               5                   10                  15

Ala Thr Asn Gly Arg Ala Val Ala Val Cys Ala Gly His Ala Gly Val
            20                  25                  30

Pro Asp Glu Val Ala Arg His His Glu His Ala Val Ala Ala Gly Gln
        35                  40                  45

Cys Cys Ala Ala Met Val Gln Ser Ile Ala Ala Pro Val Asp Ala Val
    50                  55                  60

Trp Ser Leu Val Arg Arg Phe Asp Gln Pro Gln Arg Tyr Lys Arg Phe
65                  70                  75                  80

Ile Arg Ser Cys His Leu Val Asp Gly Asp Gly Ala Glu Val Gly Ser
                85                  90                  95

Val Arg Glu Leu Leu Leu Val Ser Gly Leu Pro Ala Glu Ser Ser Arg
            100                 105                 110

Glu Arg Leu Glu Ile Arg Asp Asp Glu Arg Arg Val Ile Ser Phe Arg
        115                 120                 125

Val Leu Gly Gly Asp His Arg Leu Ala Asn Tyr Arg Ser Val Thr Thr
    130                 135                 140

Val His Glu Ala Ala Pro Ser Gln Asp Gly Arg Pro Leu Thr Met Val
145                 150                 155                 160

Val Glu Ser Tyr Val Val Asp Val Pro Pro Gly Asn Thr Val Glu Glu
                165                 170                 175

Thr Arg Ile Phe Val Asp Thr Ile Val Arg Cys Asn Leu Gln Ser Leu
            180                 185                 190

Glu Gly Thr Val Ile Arg Gln Leu Glu Ile Ala Ala Met Pro His Asp
        195                 200                 205

Asp Asn Gln Asn
    210


<210> SEQ ID NO 28
<211> LENGTH: 233
<212> TYPE: PRT
<213> ORGANISM: Zea mays
<220> FEATURE:
<223> OTHER INFORMATION: corn (maize) strain B73, clone ZM_BFb0105018
      unknown protein

<400> SEQUENCE: 28

Met Arg Glu Arg Asn Ser Ser Ile Asp Gln Glu His Gln Arg Gly Ser
 1               5                   10                  15

Ser Ser Arg Ser Thr Met Pro Phe Ala Ala Ser Arg Thr Ser Gln Gln
            20                  25                  30

Gln His Ser Arg Val Ala Thr Asn Gly Arg Ala Val Ala Val Cys Ala
        35                  40                  45

Gly His Ala Gly Val Pro Asp Glu Val Ala Arg His His Glu His Ala
    50                  55                  60

Val Ala Ala Gly Gln Cys Cys Ala Ala Met Val Gln Ser Ile Ala Ala
65                  70                  75                  80

Pro Val Asp Ala Val Trp Ser Leu Val Arg Arg Phe Asp Gln Pro Gln
                85                  90                  95

Arg Tyr Lys Arg Phe Ile Arg Ser Cys His Leu Val Asp Gly Asp Gly
```

```
            100                 105                 110

Ala Glu Val Gly Ser Val Arg Glu Leu Leu Leu Val Ser Gly Leu Pro
        115                 120                 125

Ala Glu Ser Ser Arg Glu Arg Leu Glu Ile Arg Asp Asp Glu Arg Arg
    130                 135                 140

Val Ile Ser Phe Arg Val Leu Gly Gly Asp His Arg Leu Ala Asn Tyr
145                 150                 155                 160

Arg Ser Val Thr Thr Val His Glu Ala Ala Pro Ser Gln Asp Gly Arg
                165                 170                 175

Pro Leu Thr Met Val Val Glu Ser Tyr Val Val Asp Val Pro Pro Gly
            180                 185                 190

Asn Thr Val Glu Glu Thr Arg Ile Phe Val Asp Thr Ile Val Arg Cys
        195                 200                 205

Asn Leu Gln Ser Leu Glu Gly Thr Val Ile Arg Gln Leu Glu Ile Ala
    210                 215                 220

Ala Met Pro His Asp Asp Asn Gln Asn
225                 230


<210> SEQ ID NO 29
<211> LENGTH: 194
<212> TYPE: PRT
<213> ORGANISM: Physcomitrella patens
<220> FEATURE:
<223> OTHER INFORMATION: moss Physcomitrella patens subspecies patens,
      ecotype Gransden 2004 predicted hypothetical
      protein, locus PHYPADRAFT_209242

<400> SEQUENCE: 29

Met Met Gln Glu Lys Gln Gly Arg Pro Asp Phe Gln Phe Leu Leu Glu
 1               5                  10                  15

Gly Gln Gln Asp Leu Ile Cys Arg Phe His Lys His Glu Leu Leu Pro
            20                  25                  30

His Gln Cys Gly Ser Ile Leu Leu Gln Gln Ile Lys Ala Pro Val Gln
        35                  40                  45

Thr Val Trp Leu Ile Val Arg Arg Phe Asp Glu Pro Gln Val Tyr Lys
    50                  55                  60

Arg Phe Ile Gln Arg Cys Asp Ile Val Glu Gly Asp Gly Val Val Gly
65                  70                  75                  80

Ser Ile Arg Glu Val Gln Leu Val Ser Ser Ile Pro Ala Thr Ser Ser
                85                  90                  95

Ile Glu Arg Leu Glu Ile Leu Asp Asp Glu Glu His Ile Ile Ser Phe
            100                 105                 110

Arg Val Leu Gly Gly Gly His Arg Leu Gln Asn Tyr Trp Ser Val Thr
        115                 120                 125

Ser Leu His Arg His Glu Ile Gln Gly Gln Met Gly Thr Leu Val Leu
    130                 135                 140

Glu Ser Tyr Val Val Asp Ile Pro Asp Gly Asn Thr Arg Glu Glu Thr
145                 150                 155                 160

His Thr Phe Val Asp Thr Val Val Arg Cys Asn Leu Lys Ala Leu Ala
                165                 170                 175

Gln Val Ser Glu Gln Lys His Leu Leu Asn Ser Asn Glu Lys Pro Ala
            180                 185                 190

Ala Pro


<210> SEQ ID NO 30
<211> LENGTH: 191
```

<212> TYPE: PRT
<213> ORGANISM: Vitis vinifera
<220> FEATURE:
<223> OTHER INFORMATION: grapevine cultivar PN40024 unnamed protein product, locus GSVIVT00035869001

<400> SEQUENCE: 30

```
Met Lys Val Tyr Ser Pro Ser Gln Ile Leu Ala Glu Arg Gly Pro Arg
 1               5                  10                  15

Ala Gln Ala Met Gly Asn Leu Tyr His Thr His His Leu Leu Pro Asn
            20                  25                  30

Gln Cys Ser Ser Leu Val Val Gln Thr Thr Asp Ala Pro Leu Pro Gln
        35                  40                  45

Val Trp Ser Met Val Arg Arg Phe Asp Arg Pro Gln Ser Tyr Lys Arg
    50                  55                  60

Phe Val Arg Gly Cys Thr Leu Arg Arg Gly Lys Gly Gly Val Gly Ser
65                  70                  75                  80

Val Arg Glu Val Asn Ile Val Ser Gly Leu Pro Ala Glu Ile Ser Leu
                85                  90                  95

Glu Arg Leu Asp Lys Leu Asp Asp Asp Leu His Val Met Arg Phe Thr
            100                 105                 110

Val Ile Gly Gly Asp His Arg Leu Ala Asn Tyr His Ser Thr Leu Thr
        115                 120                 125

Leu His Glu Asp Glu Glu Asp Gly Val Arg Lys Thr Val Val Met Glu
    130                 135                 140

Ser Tyr Val Val Asp Val Pro Gly Gly Asn Ser Ala Gly Glu Thr Cys
145                 150                 155                 160

Tyr Phe Ala Asn Thr Ile Ile Gly Phe Asn Leu Lys Ala Leu Ala Ala
                165                 170                 175

Val Thr Glu Thr Met Ala Leu Lys Ala Asn Ile Pro Ser Gly Phe
            180                 185                 190
```

<210> SEQ ID NO 31
<211> LENGTH: 217
<212> TYPE: PRT
<213> ORGANISM: Physcomitrella patens
<220> FEATURE:
<223> OTHER INFORMATION: moss Physcomitrella patens subspecies patens, ecotype Gransden 2004 predicted hypothetical protein, locus PHYPADRAFT_132509

<400> SEQUENCE: 31

```
Met Gln Gln Val Lys Gly Arg Gln Asp Phe Gln Arg Leu Leu Glu Ala
 1               5                  10                  15

Gln Gln Asp Leu Ile Cys Arg Tyr His Thr His Glu Leu Lys Ala His
            20                  25                  30

Gln Cys Gly Ser Ile Leu Leu Gln Gln Ile Lys Val Pro Leu Pro Ile
        35                  40                  45

Val Trp Ala Ile Val Arg Ser Phe Asp Lys Pro Gln Val Tyr Lys Arg
    50                  55                  60

Phe Ile Gln Thr Cys Lys Ile Thr Glu Gly Asp Gly Gly Val Gly Ser
65                  70                  75                  80

Ile Arg Glu Val His Leu Val Ser Ser Val Pro Ala Thr Cys Ser Ile
                85                  90                  95

Glu Arg Leu Glu Ile Leu Asp Asp Glu Lys His Ile Ile Ser Phe Arg
            100                 105                 110

Val Leu Gly Gly Gly His Arg Leu Gln Asn Tyr Ser Ser Val Ser Ser
        115                 120                 125
```

```
Leu His Glu Leu Glu Val Glu Gly His Pro Cys Thr Leu Val Leu Glu
    130                 135                 140

Ser Tyr Met Val Asp Ile Pro Asp Gly Asn Thr Arg Glu Glu Thr His
145                 150                 155                 160

Met Phe Val Asp Thr Val Val Arg Cys Asn Leu Lys Ser Leu Ala Gln
                165                 170                 175

Ile Ser Glu Gln Gln Tyr Asn Lys Asp Cys Leu Gln Gln Lys Gln His
            180                 185                 190

Asp Gln Gln Gln Met Tyr Gln Gln Arg His Pro Pro Leu Pro Pro Ile
        195                 200                 205

Pro Ile Thr Asp Lys Asn Met Glu Arg
    210                 215


<210> SEQ ID NO 32
<211> LENGTH: 195
<212> TYPE: PRT
<213> ORGANISM: Physcomitrella patens
<220> FEATURE:
<223> OTHER INFORMATION: moss Physcomitrella patens subspecies patens,
      ecotype Gransden 2004 predicted hypothetical
      protein, locus PHYPADRAFT_213389

<400> SEQUENCE: 32

Met Arg Phe Asp Ile Gly His Asn Asp Val Arg Gly Phe Phe Thr Cys
 1               5                  10                  15

Glu Glu Glu His Ala Tyr Ala Leu His Ser Gln Thr Val Glu Leu Asn
            20                  25                  30

Gln Cys Gly Ser Ile Leu Met Gln Gln Ile His Ala Pro Ile Glu Val
        35                  40                  45

Val Trp Ser Ile Val Arg Ser Phe Gly Ser Pro Gln Ile Tyr Lys Lys
    50                  55                  60

Phe Ile Gln Ala Cys Ile Leu Thr Val Gly Asp Gly Gly Val Gly Ser
65                  70                  75                  80

Ile Arg Glu Val Phe Leu Val Ser Gly Val Pro Ala Thr Ser Ser Ile
                85                  90                  95

Glu Arg Leu Glu Ile Leu Asp Asp Glu Lys His Val Phe Ser Phe Arg
            100                 105                 110

Val Leu Lys Gly Gly His Arg Leu Gln Asn Tyr Arg Ser Val Thr Thr
        115                 120                 125

Leu His Glu Gln Glu Val Asn Gly Arg Gln Thr Thr Thr Val Leu Glu
    130                 135                 140

Ser Tyr Val Val Asp Val Pro Asp Gly Asn Thr Arg Glu Glu Thr His
145                 150                 155                 160

Met Phe Ala Asp Thr Val Val Met Cys Asn Leu Lys Ser Leu Ala Gln
                165                 170                 175

Val Ala Glu Trp Arg Ala Met Gln Gly Ile Thr Gln Gln Leu Ser Thr
            180                 185                 190

Ser Ser Leu
        195


<210> SEQ ID NO 33
<211> LENGTH: 172
<212> TYPE: PRT
<213> ORGANISM: Vitis vinifera
<220> FEATURE:
<223> OTHER INFORMATION: grapevine cultivar Pinot Noir, clone ENTAV 115
      hypothetical protein, locus VITISV_004947
```

<400> SEQUENCE: 33

```
Met Gly Asn Leu Tyr His Thr His His Leu Leu Pro Asn Gln Cys Ser
 1               5                  10                  15

Ser Leu Val Val Gln Thr Thr Asp Ala Pro Leu Pro Gln Val Trp Ser
            20                  25                  30

Met Val Arg Arg Phe Asp Arg Pro Gln Ser Tyr Lys Arg Phe Val Arg
        35                  40                  45

Gly Cys Thr Leu Arg Arg Gly Lys Gly Gly Val Gly Ser Val Arg Glu
    50                  55                  60

Val Asn Ile Val Ser Gly Leu Pro Ala Glu Ile Ser Leu Glu Arg Leu
65                  70                  75                  80

Asp Lys Leu Asp Asp Asp Leu His Val Met Arg Phe Thr Val Ile Gly
                85                  90                  95

Gly Asp His Arg Leu Ala Asn Tyr His Ser Thr Leu Thr Leu His Glu
            100                 105                 110

Asp Glu Glu Asp Gly Val Arg Lys Thr Val Val Met Glu Ser Tyr Val
        115                 120                 125

Val Asp Val Pro Gly Gly Asn Ser Ala Gly Glu Thr Cys Tyr Phe Ala
    130                 135                 140

Asn Thr Ile Ile Gly Phe Asn Leu Lys Ala Leu Ala Ala Val Thr Glu
145                 150                 155                 160

Thr Met Ala Leu Lys Ala Asn Ile Pro Ser Gly Phe
                165                 170
```

<210> SEQ ID NO 34
<211> LENGTH: 196
<212> TYPE: PRT
<213> ORGANISM: Picea sitchensis
<220> FEATURE:
<223> OTHER INFORMATION: Sitka spruce cultivar FB3-425, clone WS0281_I24 unknown protein

<400> SEQUENCE: 34

```
Met Glu Asp Leu Ser Ser Trp Arg Glu Gly Arg Ala Met Trp Leu Gly
 1               5                  10                  15

Asn Pro Pro Ser Glu Ser Glu Leu Val Cys Arg His His Arg His Glu
            20                  25                  30

Leu Gln Gly Asn Gln Cys Ser Ser Phe Leu Val Lys His Ile Arg Ala
        35                  40                  45

Pro Val His Leu Val Trp Ser Ile Val Arg Thr Phe Asp Gln Pro Gln
    50                  55                  60

Lys Tyr Lys Pro Phe Val His Ser Cys Ser Val Arg Gly Gly Ile Thr
65                  70                  75                  80

Val Gly Ser Ile Arg Asn Val Asn Val Lys Ser Gly Leu Pro Ala Thr
                85                  90                  95

Ala Ser Glu Glu Arg Leu Glu Ile Leu Asp Asp Asn Glu His Val Phe
            100                 105                 110

Ser Ile Lys Ile Leu Gly Gly Asp His Arg Leu Gln Asn Tyr Ser Ser
        115                 120                 125

Ile Ile Thr Val His Pro Glu Ile Ile Asp Gly Arg Pro Gly Thr Leu
    130                 135                 140

Val Ile Glu Ser Tyr Val Val Asp Val Pro Glu Gly Asn Thr Arg Glu
145                 150                 155                 160

Glu Thr Arg Phe Phe Val Glu Ala Leu Val Lys Cys Asn Leu Lys Ser
                165                 170                 175
```

```
Leu Ala Asp Val Ser Glu Arg Leu Ala Ser Gln His His Thr Glu Leu
            180                 185                 190

Leu Glu Arg Thr
        195


<210> SEQ ID NO 35
<211> LENGTH: 185
<212> TYPE: PRT
<213> ORGANISM: Solanum tuberosum
<220> FEATURE:
<223> OTHER INFORMATION: potato cultivar Kuras, clone 153D02 CAPIP1-like
      protein, similar to Capsicum annuum antimicrobial
      protein (CAPIP1)

<400> SEQUENCE: 35

Met Asn Ala Asn Gly Phe Cys Gly Val Glu Lys Glu Tyr Ile Arg Lys
 1               5                  10                  15

His His Leu His Glu Pro Lys Glu Asn Gln Cys Ser Ser Phe Leu Val
            20                  25                  30

Lys His Ile Arg Ala Pro Val His Leu Val Trp Ser Leu Val Arg Arg
        35                  40                  45

Phe Asp Gln Pro Gln Lys Tyr Lys Pro Phe Ile Ser Arg Cys Ile Val
    50                  55                  60

Gln Gly Asp Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Glu Glu His Ile Leu Ser Val Arg Ile Val Gly Gly Asp His Arg Leu
            100                 105                 110

Arg Asn Tyr Ser Ser Val Ile Ser Val His Pro Glu Val Ile Asp Gly
        115                 120                 125

Arg Pro Gly Thr Val Val Leu Glu Ser Phe Val Val Asp Val Pro Glu
    130                 135                 140

Gly Asn Thr Lys Asp Glu Thr Cys Tyr Phe Val Glu Ala Leu Ile Asn
145                 150                 155                 160

Cys Asn Leu Lys Ser Leu Ala Asp Ile Ser Glu Arg Val Ala Val Gln
                165                 170                 175

Asp Arg Thr Glu Pro Ile Asp Gln Val
            180                 185


<210> SEQ ID NO 36
<211> LENGTH: 190
<212> TYPE: PRT
<213> ORGANISM: Medicago truncatula
<220> FEATURE:
<223> OTHER INFORMATION: barrel medic unkown protein, clone
      MTYFP_FQ_FR_FS1G-E-17

<400> SEQUENCE: 36

Met Asn Asn Gly Cys Glu Gln Gln Gln Tyr Ser Val Ile Glu Thr Gln
 1               5                  10                  15

Tyr Ile Arg Arg His His Lys His Asp Leu Arg Asp Asn Gln Cys Ser
            20                  25                  30

Ser Ala Leu Val Lys His Ile Lys Ala Pro Val His Leu Val Trp Ser
        35                  40                  45

Leu Val Arg Arg Phe Asp Gln Pro Gln Lys Tyr Lys Pro Phe Ile Ser
    50                  55                  60

Arg Cys Ile Met Gln Gly Asp Leu Ser Ile Gly Ser Val Arg Glu Val
65                  70                  75                  80
```

```
Asn Val Lys Ser Gly Leu Pro Ala Thr Thr Ser Thr Glu Arg Leu Glu
                85                  90                  95

Gln Leu Asp Asp Glu Glu His Ile Leu Gly Ile Arg Ile Val Gly Gly
            100                 105                 110

Asp His Arg Leu Arg Asn Tyr Ser Ser Ile Ile Thr Val His Pro Gly
        115                 120                 125

Val Ile Asp Gly Arg Pro Gly Thr Met Val Ile Glu Ser Phe Val Val
    130                 135                 140

Asp Val Pro Glu Gly Asn Thr Lys Asp Glu Thr Cys Tyr Phe Val Glu
145                 150                 155                 160

Ala Leu Ile Arg Tyr Asn Leu Ser Ser Leu Ala Asp Val Ser Glu Arg
                165                 170                 175

Met Ala Val Gln Gly Arg Thr Asp Pro Ile Asn Ile Asn Pro
            180                 185                 190


<210> SEQ ID NO 37
<211> LENGTH: 185
<212> TYPE: PRT
<213> ORGANISM: Vitis vinifera
<220> FEATURE:
<223> OTHER INFORMATION: grapevine cultivar PN40024 unnamed protein
      product, locus GSVIVT00002440001

<400> SEQUENCE: 37

Met Ser Gly Tyr Gly Cys Ile Lys Met Glu Asp Glu Tyr Ile Arg Arg
 1               5                  10                  15

His His Arg His Glu Ile Arg Asp Asn Gln Cys Ser Ser Ser Leu Val
            20                  25                  30

Lys His Ile Lys Ala Pro Val His Leu Val Trp Ser Leu Val Arg Ser
        35                  40                  45

Phe Asp Gln Pro Gln Lys Tyr Lys Pro Phe Val Ser Arg Cys Ile Val
    50                  55                  60

Gln Gly Asp Leu Glu Ile Gly Ser Val Arg Glu Val Asn Val Lys Ser
65                  70                  75                  80

Gly Leu Pro Ala Thr Thr Ser Thr Glu Arg Leu Glu Leu Leu Asp Asp
                85                  90                  95

Glu Glu His Ile Phe Gly Met Arg Ile Val Gly Gly Asp His Arg Leu
            100                 105                 110

Lys Asn Tyr Ser Ser Ile Val Thr Val His Pro Glu Ile Ile Asp Gly
        115                 120                 125

Arg Pro Gly Thr Leu Val Ile Glu Ser Phe Val Val Asp Val Pro Asp
    130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Ile Gln
                165                 170                 175

Asp Arg Thr Glu Pro Ile Asp Arg Met
            180                 185


<210> SEQ ID NO 38
<211> LENGTH: 185
<212> TYPE: PRT
<213> ORGANISM: Vitis vinifera
<220> FEATURE:
<223> OTHER INFORMATION: grapevine cultivar PN40024 unnamed protein
      product, locus GSVIVT00006507001

<400> SEQUENCE: 38
```

```
Met Asn Gly Asn Gly Leu Ser Ser Met Glu Ser Glu Tyr Ile Arg Arg
 1               5                  10                  15

His His Arg His Glu Pro Ala Glu Asn Gln Cys Ser Ser Ala Leu Val
            20                  25                  30

Lys His Ile Lys Ala Pro Val Pro Leu Val Trp Ser Leu Val Arg Arg
        35                  40                  45

Phe Asp Gln Pro Gln Lys Tyr Lys Pro Phe Ile Ser Arg Cys Val Val
    50                  55                  60

Gln Gly Asn Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Asp Glu His Ile Leu Ser Met Arg Ile Ile Gly Gly Asp His Arg Leu
            100                 105                 110

Arg Asn Tyr Ser Ser Ile Ile Ser Leu His Pro Glu Ile Ile Asp Gly
        115                 120                 125

Arg Pro Gly Thr Met Val Ile Glu Ser Tyr Val Val Asp Val Pro Glu
    130                 135                 140

Gly Asn Thr Lys Asp Glu Thr Cys Tyr Phe Val Glu Ala Leu Ile Lys
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Arg Met
            180                 185


<210> SEQ ID NO 39
<211> LENGTH: 208
<212> TYPE: PRT
<213> ORGANISM: Oryza sativa
<220> FEATURE:
<223> OTHER INFORMATION: rice Japonica cultivar group, cultivar
      Nipponbare hypothetical protein OsJ_21703

<400> SEQUENCE: 39

Met Glu Ala His Val Glu Arg Ala Leu Arg Glu Gly Leu Thr Glu Glu
 1               5                  10                  15

Glu Arg Ala Ala Leu Glu Pro Ala Val Met Ala His His Thr Phe Pro
            20                  25                  30

Pro Ser Thr Thr Thr Ala Thr Thr Ala Ala Ala Thr Cys Thr Ser Leu
        35                  40                  45

Val Thr Gln Arg Val Ala Ala Pro Val Arg Ala Val Trp Pro Ile Val
    50                  55                  60

Arg Ser Phe Gly Asn Pro Gln Arg Tyr Lys His Phe Val Arg Thr Cys
65                  70                  75                  80

Ala Leu Ala Ala Gly Asn Gly Pro Ser Phe Gly Ser Val Arg Glu Val
                85                  90                  95

Thr Val Val Ser Gly Pro Ser Arg Leu Pro Pro Gly Thr Glu Arg Leu
            100                 105                 110

Glu Met Leu Asp Asp Asp Arg His Ile Ile Ser Phe Arg Val Val Gly
        115                 120                 125

Gly Gln His Arg Leu Arg Asn Tyr Arg Ser Val Thr Ser Val Thr Glu
    130                 135                 140

Phe Gln Pro Pro Ala Ala Gly Pro Gly Pro Ala Pro Pro Tyr Cys Val
145                 150                 155                 160

Val Val Glu Ser Tyr Val Val Asp Val Pro Asp Gly Asn Thr Ala Glu
```

```
                165                 170                 175

Asp Thr Arg Met Phe Thr Asp Thr Val Val Lys Leu Asn Leu Gln Met
            180                 185                 190

Leu Ala Ala Val Ala Glu Asp Ser Ser Ser Ala Ser Arg Arg Arg Asp
        195                 200                 205


<210> SEQ ID NO 40
<211> LENGTH: 186
<212> TYPE: PRT
<213> ORGANISM: Capsicum annuum
<220> FEATURE:
<223> OTHER INFORMATION: pepper cultivar hanbyul CAPIP1 antimicrobial
      protein

<400> SEQUENCE: 40

Met Met Asn Ala Asn Gly Phe Ser Gly Val Glu Lys Glu Tyr Ile Arg
 1               5                  10                  15

Lys His His Leu His Gln Pro Lys Glu Asn Gln Cys Ser Ser Phe Leu
            20                  25                  30

Val Lys His Ile Arg Ala Pro Val His Leu Val Trp Ser Leu Val Arg
        35                  40                  45

Arg Phe Asp Gln Pro Gln Lys Tyr Lys Pro Phe Val Ser Arg Cys Ile
    50                  55                  60

Ala Gln Gly Asp Leu Glu Ile Gly Ser Leu Arg Glu Val Asp Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Ser Phe Arg Ile Ile Gly Gly Asp His Arg
            100                 105                 110

Leu Arg Asn Tyr Ser Ser Ile Ile Ser Leu His Pro Glu Val Ile Asp
        115                 120                 125

Gly Arg Pro Gly Thr Leu Val Ile Glu Ser Phe Val Val Asp Val Pro
    130                 135                 140

Gln Gly Asn Thr Lys Asp Glu Thr Cys Tyr Phe Val Glu Ala Leu Ile
145                 150                 155                 160

Asn Cys Asn Leu Lys Ser Leu Ala Asp Val Ser Glu Arg Leu Ala Val
                165                 170                 175

Gln Asp Arg Thr Glu Pro Ile Asp Gln Val
            180                 185


<210> SEQ ID NO 41
<211> LENGTH: 186
<212> TYPE: PRT
<213> ORGANISM: Populus trichocarpa
<220> FEATURE:
<223> OTHER INFORMATION: Western balsam poplar (black cottonwood)
      cultivar 383-2499 (Nisqually-1), clone PX0011_H13 unknown
      protein

<400> SEQUENCE: 41

Met Asn Gly Ser Asp Ala Tyr Ser Ala Thr Glu Ala Gln Tyr Val Arg
 1               5                  10                  15

Arg His His Lys His Glu Pro Arg Glu Asn Gln Cys Thr Ser Ala Leu
            20                  25                  30

Val Lys His Ile Lys Ala Pro Ala His Leu Val Trp Ser Leu Val Arg
        35                  40                  45

Arg Phe Asp Gln Pro Gln Arg Tyr Lys Pro Phe Val Ser Arg Cys Val
    50                  55                  60
```

```
Met Asn Gly Glu Leu Gly Ile Gly Ser Val Arg Glu Val Asn Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Gly Val Gln Ile Val Gly Gly Asp His Arg
            100                 105                 110

Leu Lys Asn Tyr Ser Ser Ile Met Thr Val His Pro Glu Phe Ile Asp
        115                 120                 125

Gly Arg Pro Gly Thr Leu Val Ile Glu Ser Phe Ile Val Asp Val Pro
    130                 135                 140

Asp Gly Asn Thr Lys Asp Glu Thr Cys Tyr Phe Val Glu Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
            180                 185


<210> SEQ ID NO 42
<211> LENGTH: 185
<212> TYPE: PRT
<213> ORGANISM: Capsicum annuum
<220> FEATURE:
<223> OTHER INFORMATION: pepper cultivar hanbyul PIP1 (CAPIP1)
      antimicrobial protein

<400> SEQUENCE: 42

Met Asn Ala Asn Gly Phe Ser Gly Val Glu Lys Glu Tyr Ile Arg Lys
 1               5                  10                  15

His His Leu His Gln Pro Lys Glu Asn Gln Cys Ser Ser Phe Leu Val
            20                  25                  30

Lys His Ile Arg Ala Pro Val His Leu Val Trp Ser Leu Val Arg Arg
        35                  40                  45

Phe Asp Gln Pro Gln Lys Tyr Lys Pro Phe Val Ser Arg Cys Ile Ala
    50                  55                  60

Gln Gly Asp Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Glu Glu His Ile Leu Ser Phe Arg Ile Ile Gly Gly Asp His Arg Leu
            100                 105                 110

Arg Asn Tyr Ser Ser Ile Ile Ser Leu His Pro Glu Val Ile Asp Gly
        115                 120                 125

Arg Pro Gly Thr Leu Val Ile Glu Ser Phe Val Val Asp Val Pro Gln
    130                 135                 140

Gly Asn Thr Lys Asp Glu Thr Cys Tyr Phe Val Glu Ala Leu Ile Asn
145                 150                 155                 160

Cys Asn Leu Lys Ser Leu Ala Asp Val Ser Glu Arg Leu Ala Val Gln
                165                 170                 175

Asp Arg Thr Glu Pro Ile Asp Gln Val
            180                 185


<210> SEQ ID NO 43
<211> LENGTH: 186
<212> TYPE: PRT
<213> ORGANISM: Populus trichocarpa x Populus deltoides
<220> FEATURE:
<223> OTHER INFORMATION: Western balsam poplar (black cottonwood) x
      Eastern cottonwood, cultivar H11-11, clone WS0133-I04
```

unknown protein

<400> SEQUENCE: 43

```
Met Asn Gly Ser Asp Ala Tyr Ser Ala Thr Glu Ala Gln Tyr Val Arg
 1               5                  10                  15

Arg His His Lys His Glu Pro Arg Glu Asn Gln Cys Thr Ser Ala Leu
            20                  25                  30

Val Lys His Ile Lys Ala Pro Ala His Leu Val Trp Ser Leu Val Arg
        35                  40                  45

Arg Phe Asp Gln Pro Gln Arg Tyr Lys Pro Phe Val Ser Arg Cys Val
    50                  55                  60

Met Asn Gly Glu Leu Gly Ile Gly Ser Val Arg Glu Val Asn Val Lys
65                  70                  75                  80

Ser Gly Leu Pro Ala Thr Thr Ser Thr Glu Arg Leu Glu Leu Leu Asp
                85                  90                  95

Asp Glu Glu His Ile Leu Gly Val Gln Ile Val Gly Gly Asp His Arg
            100                 105                 110

Leu Lys Asn Tyr Ser Ser Ile Met Thr Val His Pro Glu Phe Ile Asp
        115                 120                 125

Gly Arg Pro Gly Thr Leu Val Ile Glu Ser Phe Ile Val Asp Val Pro
    130                 135                 140

Asp Gly Asn Thr Lys Asp Glu Thr Cys Tyr Phe Val Lys Ala Leu Ile
145                 150                 155                 160

Arg Cys Asn Leu Lys Ser Leu Ala Asp Val Ser Glu Arg Met Ala Val
                165                 170                 175

Gln Asp Arg Val Glu Pro Val Asn Gln Phe
            180                 185
```

<210> SEQ ID NO 44
<211> LENGTH: 188
<212> TYPE: PRT
<213> ORGANISM: Pisum sativum
<220> FEATURE:
<223> OTHER INFORMATION: pea AT-rich element binding factor 3 (ATF3, PsATF), potential transcription factor for PsCHS1

<400> SEQUENCE: 44

```
Met Asn Asn Gly Gly Glu Gln Tyr Ser Ala Ile Glu Thr Gln Tyr Ile
 1               5                  10                  15

Arg Arg Arg His Lys His Asp Leu Arg Asp Asn Gln Cys Ser Ser Ala
            20                  25                  30

Leu Val Lys His Ile Lys Ala Pro Val His Leu Val Trp Ser Leu Val
        35                  40                  45

Arg Arg Phe Asp Gln Pro Gln Lys Tyr Lys Pro Phe Val Ser Arg Cys
    50                  55                  60

Ile Met Gln Gly Asp Leu Gly Ile Gly Ser Val Arg Glu Val Asn Val
65                  70                  75                  80

Lys Ser Gly Leu Pro Ala Thr Thr Ser Thr Glu Arg Leu Glu Gln Leu
                85                  90                  95

Asp Asp Glu Glu His Ile Leu Gly Ile Arg Ile Val Gly Gly Asp His
            100                 105                 110

Arg Leu Arg Asn Tyr Ser Ser Val Ile Thr Val His Pro Glu Val Ile
        115                 120                 125

Asp Gly Arg Pro Gly Thr Met Val Ile Glu Ser Phe Val Val Asp Val
    130                 135                 140

Pro Glu Gly Asn Thr Arg Asp Glu Thr Cys Tyr Phe Val Glu Ala Leu
```

145 150 155 160

Ile Arg Gly Asn Leu Ser Ser Leu Ala Asp Val Ser Glu Arg Met Ala
165 170 175

Val Gln Gly Arg Thr Asp Pro Ile Asn Val Asn Pro
180 185

<210> SEQ ID NO 45
<211> LENGTH: 177
<212> TYPE: PRT
<213> ORGANISM: Vitis vinifera
<220> FEATURE:
<223> OTHER INFORMATION: grapevine cultivar PN40024 unnamed protein product, locus GSVIVT00027009001

<400> SEQUENCE: 45

Met Glu Ala Gln Val Ile Cys Arg His His Ala His Glu Pro Arg Glu
1 5 10 15

Asn Gln Cys Ser Ser Val Leu Val Arg His Val Lys Ala Pro Ala Asn
20 25 30

Leu Val Trp Ser Leu Val Arg Arg Phe Asp Gln Pro Gln Lys Tyr Lys
35 40 45

Pro Phe Val Ser Arg Cys Val Val Gln Gly Asp Leu Arg Ile Gly Ser
50 55 60

Val Arg Glu Val Asn Val Lys Thr Gly Leu Pro Ala Thr Thr Ser Thr
65 70 75 80

Glu Arg Leu Glu Leu Phe Asp Asp Asp Glu His Val Leu Gly Ile Lys
85 90 95

Ile Leu Asp Gly Asp His Arg Leu Arg Asn Tyr Ser Ser Val Ile Thr
100 105 110

Val His Pro Glu Ile Ile Asp Gly Arg Pro Gly Thr Leu Val Ile Glu
115 120 125

Ser Phe Val Val Asp Val Pro Glu Gly Asn Thr Lys Asp Asp Thr Cys
130 135 140

Tyr Phe Val Arg Ala Leu Ile Asn Cys Asn Leu Lys Cys Leu Ala Glu
145 150 155 160

Val Ser Glu Arg Met Ala Met Leu Gly Arg Val Glu Pro Ala Asn Ala
165 170 175

Val

<210> SEQ ID NO 46
<211> LENGTH: 178
<212> TYPE: PRT
<213> ORGANISM: Vitis vinifera
<220> FEATURE:
<223> OTHER INFORMATION: grapevine cultivar Pinot Noir, clone ENTAV 115 hypothetical protein, locus VITISV_004915

<400> SEQUENCE: 46

Met Met Glu Ala Gln Val Ile Cys Arg His His Ala His Glu Pro Arg
1 5 10 15

Glu Asn Gln Cys Ser Ser Val Leu Val Arg His Val Lys Ala Pro Ala
20 25 30

Asn Leu Val Trp Ser Leu Val Arg Arg Phe Asp Gln Pro Gln Lys Tyr
35 40 45

Lys Pro Phe Val Ser Arg Cys Val Val Gln Gly Asp Leu Arg Ile Gly
50 55 60

Ser Val Arg Glu Val Asn Val Lys Thr Gly Leu Pro Ala Thr Thr Ser
65 70 75 80

```
Thr Glu Arg Leu Glu Leu Phe Asp Asp Asp Glu His Val Leu Gly Ile
                85                  90                  95

Lys Ile Leu Asp Gly Asp His Arg Leu Arg Asn Tyr Ser Ser Val Ile
            100                 105                 110

Thr Val His Pro Glu Ile Ile Asp Gly Arg Pro Gly Thr Leu Val Ile
        115                 120                 125

Glu Ser Phe Val Val Asp Val Pro Glu Gly Asn Thr Lys Asp Asp Thr
    130                 135                 140

Cys Tyr Phe Val Arg Ala Leu Ile Asn Cys Asn Leu Lys Cys Leu Ala
145                 150                 155                 160

Glu Val Ser Glu Arg Met Ala Met Leu Gly Arg Val Glu Pro Ala Asn
                165                 170                 175

Ala Val


<210> SEQ ID NO 47
<211> LENGTH: 193
<212> TYPE: PRT
<213> ORGANISM: Arachis hypogaea
<220> FEATURE:
<223> OTHER INFORMATION: peanut pathogenesis-induced protein (PIP,
      AhPIP)
<220> FEATURE:
<221> NAME/KEY: VARIANT
<222> LOCATION: (162)...(162)
<223> OTHER INFORMATION: Xaa = Asp, Asn, Tyr or His

<400> SEQUENCE: 47

Met Met Asn Gly Ser Cys Gly Gly Gly Gly Gly Gly Glu Ala Tyr Gly
 1               5                  10                  15

Ala Ile Glu Ala Gln Tyr Ile Arg Arg His His Arg His Glu Pro Arg
            20                  25                  30

Asp Asn Gln Cys Thr Ser Ala Leu Val Lys His Ile Arg Ala Pro Val
        35                  40                  45

His Leu Val Trp Ser Leu Val Arg Arg Phe Asp Gln Pro Gln Lys Tyr
    50                  55                  60

Lys Pro Phe Val Ser Arg Cys Ile Met Gln Gly Asp Leu Gly Ile Gly
65                  70                  75                  80

Ser Val Arg Glu Val Asn Val Lys Ser Gly Leu Pro Ala Thr Thr Ser
                85                  90                  95

Thr Glu Arg Leu Glu Gln Leu Asp Asp Glu Glu His Ile Leu Gly Ile
            100                 105                 110

Arg Ile Val Gly Gly Asp His Arg Leu Arg Asn Tyr Ser Ser Ile Ile
        115                 120                 125

Thr Val His Pro Glu Val Ile Glu Gly Arg Pro Gly Thr Met Val Ile
    130                 135                 140

Glu Ser Phe Val Val Asp Val Pro Asp Gly Asn Thr Lys Asp Glu Thr
145                 150                 155                 160

Cys Xaa Phe Val Glu Ala Leu Ile Arg Cys Asn Leu Ser Ser Leu Ala
                165                 170                 175

Asp Val Ser Glu Arg Met Ala Val Gln Gly Arg Thr Asp Pro Ile Asn
            180                 185                 190

Gln


<210> SEQ ID NO 48
<211> LENGTH: 217
<212> TYPE: PRT
<213> ORGANISM: Zea mays
```

```
<220> FEATURE:
<223> OTHER INFORMATION: corn (maize), clone 300908 AT-rich element
      binding factor 3

<400> SEQUENCE: 48

Met Val Val Glu Met Asp Gly Gly Val Gly Val Ala Ala Gly Gly Gly
 1               5                  10                  15

Gly Gly Ala Gln Thr Pro Ala Pro Ala Pro Pro Arg Arg Trp Arg Leu
            20                  25                  30

Ala Asp Glu Arg Cys Asp Leu Arg Ala Met Glu Thr Asp Tyr Val Arg
        35                  40                  45

Arg Phe His Arg His Glu Pro Arg Asp His Gln Cys Ser Ser Ala Val
    50                  55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Gly Asp His Arg
    130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
            180                 185                 190

Lys Cys Asn Leu Arg Ser Leu Ala Glu Val Ser Glu Gly Gln Val Ile
        195                 200                 205

Met Asp Gln Thr Glu Pro Leu Asp Arg
    210                 215


<210> SEQ ID NO 49
<211> LENGTH: 217
<212> TYPE: PRT
<213> ORGANISM: Zea mays
<220> FEATURE:
<223> OTHER INFORMATION: corn (maize) strain B73, clone ZM_BFb0036A01
      unknown protein

<400> SEQUENCE: 49

Met Val Val Glu Met Asp Gly Gly Val Gly Val Ala Ala Ala Gly Gly
 1               5                  10                  15

Gly Gly Ala Gln Thr Pro Ala Pro Pro Pro Pro Arg Arg Trp Arg Leu
            20                  25                  30

Ala Asp Glu Arg Cys Asp Leu Arg Ala Met Glu Thr Asp Tyr Val Arg
        35                  40                  45

Arg Phe His Arg His Glu Pro Arg Asp His Gln Cys Ser Ser Ala Val
    50                  55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
            100                 105                 110
```

```
Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Gly Asp His Arg
    130                 135                 140

Leu Gln Asn Tyr Ser Ser Ile Leu Thr Val His Pro Glu Val Ile Asp
145                 150                 155                 160

Gly Arg Pro Gly Thr Leu Val Ile Glu Ser Phe Val Val Asp Val Pro
                165                 170                 175

Asp Gly Asn Thr Lys Asp Glu Thr Cys Tyr Phe Val Glu Ala Leu Leu
                180                 185                 190

Lys Cys Asn Leu Arg Ser Leu Ala Glu Val Ser Glu Gly Gln Val Ile
        195                 200                 205

Met Asp Gln Thr Glu Pro Leu Asp Arg
        210                 215

<210> SEQ ID NO 50
<211> LENGTH: 206
<212> TYPE: PRT
<213> ORGANISM: Oryza sativa
<220> FEATURE:
<223> OTHER INFORMATION: rice Japonica cultivar group, cultivar
      Nipponbare (GA3) conserved hypothetical protein Os06g0528300

<400> SEQUENCE: 50

Met Asn Gly Val Gly Gly Ala Gly Gly Ala Ala Ala Gly Lys Leu Pro
1               5                   10                  15

Met Val Ser His Arg Arg Val Gln Trp Arg Leu Ala Asp Glu Arg Cys
            20                  25                  30

Glu Leu Arg Glu Glu Glu Met Glu Tyr Ile Arg Arg Phe His Arg His
        35                  40                  45

Glu Pro Ser Ser Asn Gln Cys Thr Ser Phe Ala Ala Lys His Ile Lys
    50                  55                  60

Ala Pro Leu His Thr Val Trp Ser Leu Val Arg Arg Phe Asp Gln Pro
65                  70                  75                  80

Gln Leu Phe Lys Pro Phe Val Arg Asn Cys Val Met Arg Glu Asn Ile
                85                  90                  95

Ile Ala Thr Gly Cys Ile Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Asn Phe Ile Gly Gly Asp His Met Leu Lys Asn Tyr
    130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Pro Glu Gly Asn Thr
                165                 170                 175

Lys Asp Asp Ile Ser Tyr Phe Ile Glu Asn Val Leu Arg Cys Asn Leu
            180                 185                 190

Arg Thr Leu Ala Asp Val Ser Glu Glu Arg Leu Ala Asn Pro
        195                 200                 205

<210> SEQ ID NO 51
<211> LENGTH: 206
<212> TYPE: PRT
<213> ORGANISM: Oryza sativa
<220> FEATURE:
<223> OTHER INFORMATION: rice Indica cultivar group, cultivar 93-11
```

hypothetical protein OsI_23215

<400> SEQUENCE: 51

```
Met Asn Gly Ala Gly Gly Ala Gly Gly Ala Ala Ala Gly Lys Leu Pro
 1               5                  10                  15

Met Val Ser His Arg Gln Val Gln Trp Arg Leu Ala Asp Glu Arg Cys
            20                  25                  30

Glu Leu Arg Glu Glu Glu Met Glu Tyr Ile Arg Gln Phe His Arg His
        35                  40                  45

Glu Pro Ser Ser Asn Gln Cys Thr Ser Phe Val Ala Lys His Ile Lys
    50                  55                  60

Ala Pro Leu Gln Thr Val Trp Ser Leu Val Arg Arg Phe Asp Gln Pro
65                  70                  75                  80

Gln Leu Phe Lys Pro Phe Val Arg Lys Cys Val Met Arg Glu Asn Ile
                85                  90                  95

Ile Ala Thr Gly Cys Val Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Lys Phe Ile Gly Gly Asp His Met Leu Lys Asn Tyr
    130                 135                 140

Ser Ser Ile Leu Thr Ile His Ser Glu Val Ile Asp Gly Gln Leu Gly
145                 150                 155                 160

Thr Leu Val Val Glu Ser Phe Val Val Asp Ile Pro Glu Gly Asn Thr
                165                 170                 175

Lys Asp Asp Ile Cys Tyr Phe Ile Glu Asn Ile Leu Arg Cys Asn Leu
            180                 185                 190

Met Thr Leu Ala Asp Val Ser Glu Glu Arg Leu Ala Asn Pro
        195                 200                 205
```

<210> SEQ ID NO 52
<211> LENGTH: 205
<212> TYPE: PRT
<213> ORGANISM: Oryza sativa
<220> FEATURE:
<223> OTHER INFORMATION: rice Japonica cultivar group, cultivar
      Nipponbare hypothetical protein OsJ_06125

<400> SEQUENCE: 52

```
Met Val Glu Val Gly Gly Gly Ala Ala Glu Ala Ala Ala Gly Arg Arg
 1               5                  10                  15

Trp Arg Leu Ala Asp Glu Arg Cys Asp Leu Arg Ala Ala Glu Thr Glu
            20                  25                  30

Tyr Val Arg Arg Phe His Arg His Glu Pro Arg Asp His Gln Cys Ser
        35                  40                  45

Ser Ala Val Ala Lys His Ile Lys Ala Pro Val His Leu Val Trp Ser
    50                  55                  60

Leu Val Arg Arg Phe Asp Gln Pro Gln Leu Phe Lys Pro Phe Val Ser
65                  70                  75                  80

Arg Cys Glu Met Lys Gly Asn Ile Glu Ile Gly Ser Val Arg Glu Val
                85                  90                  95

Asn Val Lys Ser Gly Leu Pro Ala Thr Arg Ser Thr Glu Arg Leu Glu
            100                 105                 110

Leu Leu Asp Asp Asn Glu His Ile Leu Ser Val Arg Phe Val Gly Gly
        115                 120                 125

Asp His Arg Leu Lys Asn Tyr Ser Ser Ile Leu Thr Val His Pro Glu
```

```
    130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
            180                 185                 190

Leu Val Cys Gln Gly Pro Asn Arg Ala Pro Ser Thr Arg
        195                 200                 205


<210> SEQ ID NO 53
<211> LENGTH: 204
<212> TYPE: PRT
<213> ORGANISM: Oryza sativa
<220> FEATURE:
<223> OTHER INFORMATION: rice Japonica cultivar group, cultivar
      Nipponbare (GA3) conserved hypothetical protein Os02g0255500

<400> SEQUENCE: 53

Met Val Glu Val Gly Gly Gly Ala Ala Glu Ala Ala Ala Gly Arg Arg
 1               5                  10                  15

Trp Arg Leu Ala Asp Glu Arg Cys Asp Leu Arg Ala Ala Glu Thr Glu
            20                  25                  30

Tyr Val Arg Arg Phe His Arg His Glu Pro Arg Asp His Gln Cys Ser
        35                  40                  45

Ser Ala Val Ala Lys His Ile Lys Ala Pro Val His Leu Val Trp Ser
    50                  55                  60

Leu Val Arg Arg Phe Asp Gln Pro Gln Leu Phe Lys Pro Phe Val Ser
65                  70                  75                  80

Arg Cys Glu Met Lys Gly Asn Ile Glu Ile Gly Ser Val Arg Glu Val
                85                  90                  95

Asn Val Lys Ser Gly Leu Pro Ala Thr Arg Ser Thr Glu Arg Leu Glu
            100                 105                 110

Leu Leu Asp Asp Asn Glu His Ile Leu Ser Val Arg Phe Val Gly Gly
        115                 120                 125

Asp His Arg Leu Lys Asn Tyr Ser Ser Ile Leu Thr Val His Pro Glu
    130                 135                 140

Val Ile Asp Gly Arg Pro Gly Thr Leu Val Ile Glu Ser Phe Val Val
145                 150                 155                 160

Asp Val Pro Glu Gly Asn Thr Lys Asp Glu Thr Cys Tyr Phe Val Glu
                165                 170                 175

Ala Leu Leu Lys Cys Asn Leu Lys Ser Leu Ala Glu Val Ser Glu Arg
            180                 185                 190

Leu Val Val Lys Asp Gln Thr Glu Pro Leu Asp Arg
        195                 200


<210> SEQ ID NO 54
<211> LENGTH: 199
<212> TYPE: PRT
<213> ORGANISM: Medicago truncatula
<220> FEATURE:
<223> OTHER INFORMATION: barrel medic unkown protein, clone
      MTYFP_FQ_FR_FS1G-G-11

<400> SEQUENCE: 54

Met Glu Lys Met Asn Gly Thr Glu Asn Asn Gly Val Phe Asn Ser Thr
 1               5                  10                  15

Glu Met Glu Tyr Ile Arg Arg His His Asn Gln Gln Pro Gly Glu Asn
```

```
            20                  25                  30

Gln Cys Ser Ser Ala Leu Val Lys His Ile Arg Ala Pro Val Pro Leu
        35                  40                  45

Val Trp Ser Leu Val Arg Arg Phe Asp Gln Pro Gln Lys Tyr Lys Pro
    50                  55                  60

Phe Val Ser Arg Cys Val Val Arg Gly Asn Leu Glu Ile Gly Ser Leu
65                  70                  75                  80

Arg Glu Val Asp Val Lys Ser Gly Leu Pro Ala Thr Thr Ser Thr Glu
                85                  90                  95

Arg Leu Glu Val Leu Asp Asp Asn Glu His Ile Leu Ser Ile Arg Ile
            100                 105                 110

Ile Gly Gly Asp His Arg Leu Arg Asn Tyr Ser Ser Ile Met Ser Leu
        115                 120                 125

His Pro Glu Ile Ile Asp Gly Arg Pro Gly Thr Leu Val Ile Glu Ser
    130                 135                 140

Phe Val Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175

Ser Glu Gly His Ala Val Gln Asp Leu Thr Glu Pro Leu Asp Arg Val
            180                 185                 190

His Glu Leu Leu Ile Ser Gly
        195


<210> SEQ ID NO 55
<211> LENGTH: 199
<212> TYPE: PRT
<213> ORGANISM: Medicago truncatula
<220> FEATURE:
<223> OTHER INFORMATION: barrel medic unkown protein, clone
      MTYF1_F2_F3_F41G-K-4

<400> SEQUENCE: 55

Met Glu Lys Met Asn Gly Thr Glu Asn Asn Gly Val Phe Asn Ser Thr
 1               5                  10                  15

Glu Met Glu Tyr Ile Arg Arg His His Asn Gln Gln Pro Gly Glu Asn
            20                  25                  30

Gln Cys Ser Ser Ala Leu Val Lys His Ile Arg Ala Pro Val Pro Leu
        35                  40                  45

Val Trp Ser Leu Val Arg Arg Phe Asp Gln Pro Gln Lys Tyr Lys Pro
    50                  55                  60

Phe Val Ser Arg Cys Val Val Arg Gly Asn Leu Glu Ile Gly Ser Leu
65                  70                  75                  80

Arg Glu Val Asp Val Lys Ser Gly Leu Pro Ala Thr Thr Ser Thr Glu
                85                  90                  95

Arg Leu Glu Val Leu Asp Asp Asn Glu His Ile Leu Ser Ile Arg Ile
            100                 105                 110

Ile Gly Gly Asp His Arg Leu Arg Asn Tyr Ser Ser Ile Met Ser Leu
        115                 120                 125

His Pro Glu Ile Ile Asp Gly Arg Pro Gly Thr Leu Val Ile Glu Ser
    130                 135                 140

Phe Val Val Asp Val Pro Glu Gly Asn Thr Lys Asp Glu Thr Cys Tyr
145                 150                 155                 160

Phe Val Glu Ala Leu Ile Lys Cys Asn Leu Lys Ser Leu Ser Asp Val
                165                 170                 175
```

```
Ser Glu Gly His Ala Ala Gln Asp Leu Thr Glu Pro Leu Asp Arg Met
            180                 185                 190

His Glu Leu Leu Ile Ser Gly
        195
```

<210> SEQ ID NO 56
<211> LENGTH: 197
<212> TYPE: PRT
<213> ORGANISM: Zea mays
<220> FEATURE:
<223> OTHER INFORMATION: corn (maize), clone 244179 CAPIP1 antimicrobial protein

<400> SEQUENCE: 56

```
Met Val Gly Leu Val Gly Gly Ser Thr Ala Arg Ala Glu His Val Val
 1               5                  10                  15

Ala Asn Ala Gly Gly Glu Ala Glu Tyr Val Arg Arg Met His Arg His
            20                  25                  30

Ala Pro Thr Glu His Gln Cys Thr Ser Thr Leu Val Lys His Ile Lys
        35                  40                  45

Ala Pro Val His Leu Val Trp Gln Leu Val Arg Arg Phe Asp Gln Pro
    50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Glu Ser Pro Thr
            180                 185                 190

Ser Leu Ile Asp Gln
        195
```

<210> SEQ ID NO 57
<211> LENGTH: 197
<212> TYPE: PRT
<213> ORGANISM: Zea mays
<220> FEATURE:
<223> OTHER INFORMATION: corn (maize), clone 1448906 CAPIP1 antimicrobial protein

<400> SEQUENCE: 57

```
Met Val Gly Leu Val Gly Gly Ser Thr Ala Arg Ala Glu His Val Val
 1               5                  10                  15

Ala Asn Ala Gly Gly Glu Ala Glu Tyr Val Arg Arg Met His Arg His
            20                  25                  30

Ala Pro Thr Glu His Gln Cys Thr Ser Thr Leu Val Lys His Ile Lys
        35                  40                  45

Ala Pro Val His Leu Val Trp Glu Leu Val Arg Arg Phe Asp Gln Pro
    50                  55                  60
```

-continued

```
Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Asn Ser Leu Ala Glu Val Ser Glu Gln Leu Ala Val Glu Ser Pro Thr
            180                 185                 190

Ser Leu Ile Asp Gln
        195
```

<210> SEQ ID NO 58
<211> LENGTH: 212
<212> TYPE: PRT
<213> ORGANISM: Zea mays
<220> FEATURE:
<223> OTHER INFORMATION: corn (maize) strain B73, clone ZM_BFc0183D21
unknown protein

<400> SEQUENCE: 58

```
Met Val Met Val Glu Met Asp Gly Gly Val Gly Gly Gly Gly Gly Gly
 1               5                  10                  15

Gly Gln Thr Pro Ala Pro Arg Arg Trp Arg Leu Ala Asp Glu Arg Cys
            20                  25                  30

Asp Leu Arg Ala Met Glu Thr Asp Tyr Val Arg Arg Phe His Arg His
        35                  40                  45

Glu Pro Arg Glu His Gln Cys Ser Ser Ala Val Ala Lys His Ile Lys
    50                  55                  60

Ala Pro Val His Leu Val Trp Ser Leu Val Arg Arg Phe Asp Gln Pro
65                  70                  75                  80

Gln Leu Phe Lys Pro Phe Val Ser Arg Cys Glu Met Lys Gly Asn Ile
                85                  90                  95

Glu Ile Gly Ser Val Arg Glu Val Asn Val Lys Ser Gly Leu Pro Ala
            100                 105                 110

Thr Arg Ser Thr Glu Arg Leu Glu Leu Leu Asp Asp Asn Glu His Ile
        115                 120                 125

Leu Ser Val Arg Phe Val Gly Gly Asp His Arg Leu Gln Asn Tyr Ser
    130                 135                 140

Ser Ile Leu Thr Val His Pro Glu Val Ile Asp Gly Arg Pro Gly Thr
145                 150                 155                 160

Leu Val Ile Glu Ser Phe Val Val Asp Val Pro Asp Gly Asn Thr Lys
                165                 170                 175

Asp Glu Thr Cys Tyr Phe Val Glu Ala Leu Leu Lys Cys Asn Leu Lys
            180                 185                 190

Ser Leu Ala Glu Val Ser Glu Arg Gln Val Val Lys Asp Gln Thr Glu
        195                 200                 205

Pro Leu Asp Arg
    210
```

<210> SEQ ID NO 59
<211> LENGTH: 206
<212> TYPE: PRT
<213> ORGANISM: Oryza sativa
<220> FEATURE:
<223> OTHER INFORMATION: rice Japonica cultivar group, cultivar Nipponbare (GA3) conserved hypothetical protein Os06g0527800

<400> SEQUENCE: 59

```
Met Asn Gly Ala Gly Gly Ala Gly Gly Ala Ala Ala Gly Lys Leu Pro
 1               5                  10                  15

Met Val Ser His Arg Arg Val Gln Cys Arg Leu Ala Asp Lys Arg Cys
            20                  25                  30

Glu Leu Arg Glu Glu Glu Met Glu Tyr Ile Arg Gln Phe His Arg His
        35                  40                  45

Glu Pro Ser Ser Asn Gln Cys Thr Ser Phe Val Ala Lys His Ile Lys
    50                  55                  60

Ala Pro Leu Gln Thr Val Trp Ser Leu Val Arg Arg Phe Asp Gln Pro
65                  70                  75                  80

Gln Leu Phe Lys Pro Phe Val Arg Lys Cys Val Met Arg Glu Asn Ile
                85                  90                  95

Ile Val Thr Gly Cys Val Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Lys Phe Ile Gly Gly Asp His Met Leu Lys Asn Tyr
    130                 135                 140

Ser Ser Ile Leu Thr Ile His Ser Glu Val Ile Asp Gly Gln Leu Gly
145                 150                 155                 160

Thr Leu Val Val Glu Ser Phe Val Val Asp Ile Pro Asp Gly Asn Thr
                165                 170                 175

Lys Asp Asp Ile Cys Tyr Phe Ile Glu Asn Val Leu Arg Cys Asn Leu
            180                 185                 190

Met Thr Leu Ala Asp Val Ser Glu Glu Arg Leu Ala Asn Pro
        195                 200                 205
```

<210> SEQ ID NO 60
<211> LENGTH: 197
<212> TYPE: PRT
<213> ORGANISM: Zea mays
<220> FEATURE:
<223> OTHER INFORMATION: corn (maize) strain B73, clone ZM_BFc0063E17 unknown protein

<400> SEQUENCE: 60

```
Met Val Gly Leu Val Gly Gly Ser Thr Ala Arg Ala Glu His Val Val
 1               5                  10                  15

Ala Asn Ala Gly Gly Glu Thr Glu Tyr Val Arg Arg Leu His Arg His
            20                  25                  30

Ala Pro Ala Glu His Gln Cys Thr Ser Thr Leu Val Lys His Ile Lys
        35                  40                  45

Ala Pro Val His Leu Val Trp Glu Leu Val Arg Ser Phe Asp Gln Pro
    50                  55                  60

Gln Arg Tyr Lys Pro Phe Val Arg Asn Cys Val Val Arg Gly Asp Gln
65                  70                  75                  80

Leu Glu Val Gly Ser Leu Arg Asp Val Asn Val Lys Thr Gly Leu Pro
                85                  90                  95
```

Ala Thr Thr Ser Thr Glu Arg Leu Glu Gln Leu Asp Asp Asp Leu His
            100                 105                 110

Ile Leu Gly Val Lys Phe Val Gly Gly Asp His Arg Leu Gln Asn Tyr
        115                 120                 125

Ser Ser Ile Ile Thr Val His Pro Glu Ser Ile Asp Gly Arg Pro Gly
    130                 135                 140

Thr Leu Val Ile Glu Ser Phe Val Val Asp Val Pro Asp Gly Asn Thr
145                 150                 155                 160

Lys Asp Glu Thr Cys Tyr Phe Val Glu Ala Val Ile Lys Cys Asn Leu
                165                 170                 175

Lys Ser Leu Ala Glu Val Ser Glu Gln Leu Ala Val Glu Ser Pro Thr
            180                 185                 190

Ser Pro Ile Asp Gln
        195

<210> SEQ ID NO 61
<211> LENGTH: 206
<212> TYPE: PRT
<213> ORGANISM: Oryza sativa
<220> FEATURE:
<223> OTHER INFORMATION: rice Indica cultivar group, cultivar 93-11
      hypothetical protein OsI_23218

<400> SEQUENCE: 61

Met Asn Gly Val Gly Gly Ala Gly Gly Ala Ala Ala Gly Lys Leu Pro
1               5                   10                  15

Met Val Ser His Arg Arg Val Gln Trp Arg Leu Ala Asp Glu Arg Cys
            20                  25                  30

Glu Leu Arg Glu Glu Glu Met Glu Tyr Ile Arg Arg Phe His Arg His
        35                  40                  45

Glu Pro Ser Ser Asn Gln Cys Thr Ser Phe Ala Ala Lys His Ile Lys
    50                  55                  60

Ala Pro Leu His Thr Val Trp Ser Leu Val Arg Arg Phe Asp Gln Pro
65                  70                  75                  80

Gln Leu Phe Lys Pro Phe Val Arg Asn Cys Val Met Arg Glu Asn Ile
                85                  90                  95

Ile Ala Thr Gly Cys Ile Arg Glu Val Asn Val Gln Ser Gly Leu Pro
            100                 105                 110

Ala Thr Arg Ser Thr Glu Arg Leu Glu Leu Leu Asp Asp Asn Glu His
        115                 120                 125

Ile Leu Lys Val Lys Phe Ile Gly Gly Asp His Met Leu Lys Asn Tyr
    130                 135                 140

Ser Ser Ile Leu Thr Val His Ser Glu Val Ile Asp Gly Gln Leu Gly
145                 150                 155                 160

Thr Leu Val Val Glu Ser Phe Ile Val Asp Val Leu Glu Gly Asn Thr
                165                 170                 175

Lys Asp Asp Ile Ser Tyr Phe Ile Glu Asn Val Leu Arg Cys Asn Leu
            180                 185                 190

Arg Thr Leu Ala Asp Val Ser Glu Glu Arg Leu Ala Asn Pro
        195                 200                 205

<210> SEQ ID NO 62
<211> LENGTH: 209
<212> TYPE: PRT
<213> ORGANISM: Oryza sativa
<220> FEATURE:
<223> OTHER INFORMATION: rice Japonica cultivar group, cultivar Nipponbare (GA3) conserved hypothetical protein Os05g0213500

<400> SEQUENCE: 62

```
Met Val Gly Leu Val Gly Gly Gly Gly Trp Arg Val Gly Asp Asp Ala
 1               5                  10                  15

Ala Gly Gly Gly Gly Gly Gly Ala Val Ala Ala Gly Ala Ala Ala Ala
            20                  25                  30

Ala Glu Ala Glu His Met Arg Arg Leu His Ser His Ala Pro Gly Glu
        35                  40                  45

His Gln Cys Ser Ser Ala Leu Val Lys His Ile Lys Ala Pro Val His
    50                  55                  60

Leu Val Trp Ser Leu Val Arg Ser Phe Asp Gln Pro Gln Arg Tyr Lys
65                  70                  75                  80

Pro Phe Val Ser Arg Cys Val Val Arg Gly Gly Asp Leu Glu Ile Gly
                85                  90                  95

Ser Val Arg Glu Val Asn Val Lys Thr Gly Leu Pro Ala Thr Thr Ser
            100                 105                 110

Thr Glu Arg Leu Glu Leu Leu Asp Asp Asp Glu His Ile Leu Ser Val
        115                 120                 125

Lys Phe Val Gly Gly Asp His Arg Leu Arg Asn Tyr Ser Ser Ile Val
    130                 135                 140

Thr Val His Pro Glu Ser Ile Asp Gly Arg Pro Gly Thr Leu Val Ile
145                 150                 155                 160

Glu Ser Phe Val Val Asp Val Pro Asp Gly Asn Thr Lys Asp Glu Thr
                165                 170                 175

Cys Tyr Phe Val Glu Ala Val Ile Lys Cys Asn Leu Thr Ser Leu Ala
            180                 185                 190

Glu Val Ser Glu Arg Leu Ala Val Gln Ser Pro Thr Ser Pro Leu Glu
        195                 200                 205

Gln
```

<210> SEQ ID NO 63
<211> LENGTH: 180
<212> TYPE: PRT
<213> ORGANISM: Oryza sativa
<220> FEATURE:
<223> OTHER INFORMATION: rice Japonica cultivar group, cultivar Nipponbare (GA3), clone OSJNBa0052K15 Bet v I allergen-like protein

<400> SEQUENCE: 63

```
Met Val Glu Met Asp Ala Gly Gly Arg Pro Glu Pro Ser Pro Pro Ser
 1               5                  10                  15

Gly Gln Cys Ser Ser Ala Val Thr Met Arg Ile Asn Ala Pro Val His
            20                  25                  30

Leu Val Trp Ser Ile Val Arg Arg Phe Glu Glu Pro His Ile Phe Gln
        35                  40                  45

Pro Phe Val Arg Gly Cys Thr Met Arg Gly Ser Thr Ser Leu Ala Val
    50                  55                  60

Gly Cys Val Arg Glu Val Asp Phe Lys Ser Gly Phe Pro Ala Lys Ser
65                  70                  75                  80

Ser Val Glu Arg Leu Glu Ile Leu Asp Asp Lys Glu His Val Phe Gly
                85                  90                  95

Val Arg Ile Ile Gly Gly Asp His Arg Leu Lys Asn Tyr Ser Ser Val
            100                 105                 110

Leu Thr Ala Lys Pro Glu Val Ile Asp Gly Glu Pro Ala Thr Leu Val
```

```
        115                 120                 125

Ser Glu Ser Phe Val Val Asp Val Pro Glu Gly Asn Thr Ala Asp Glu
    130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
                165                 170                 175

Pro Pro Ala Gln
            180


<210> SEQ ID NO 64
<211> LENGTH: 176
<212> TYPE: PRT
<213> ORGANISM: Vitis vinifera
<220> FEATURE:
<223> OTHER INFORMATION: grapevine cultivar Pinot Noir, clone ENTAV 115
      hypothetical protein, locus VITISV_029498

<400> SEQUENCE: 64

Met Asn Gly Asn Gly Leu Ser Ser Met Glu Ser Glu Tyr Ile Arg Arg
 1               5                  10                  15

His His Arg His Glu Pro Ala Glu Asn Gln Cys Ser Ser Ala Leu Val
            20                  25                  30

Lys His Ile Lys Ala Pro Val Pro Leu Val Trp Ser Leu Val Arg Arg
        35                  40                  45

Phe Asp Gln Pro Gln Lys Tyr Lys Pro Phe Ile Ser Arg Cys Val Val
    50                  55                  60

Gln Gly Asn Leu Glu Ile Gly Ser Leu Arg Glu Val Asp Val Lys Ser
65                  70                  75                  80

Gly Leu Pro Ala Thr Thr Ser Thr Glu Arg Leu Glu Leu Leu Asp Asp
                85                  90                  95

Asp Glu His Ile Leu Ser Met Arg Ile Ile Gly Gly Asp His Arg Leu
            100                 105                 110

Arg Asn Tyr Ser Ser Ile Ile Ser Leu His Pro Glu Ile Ile Asp Gly
        115                 120                 125

Arg Pro Gly Thr Met Val Ile Glu Ser Tyr Val Val Asp Val Pro Glu
    130                 135                 140

Gly Asn Thr Lys Asp Glu Thr Cys Tyr Phe Ser Leu Ala Asp Val Ser
145                 150                 155                 160

Glu Arg Leu Ala Val Ala Gly Thr Val Thr Glu Pro Ile Asp Arg Met
                165                 170                 175


<210> SEQ ID NO 65
<211> LENGTH: 180
<212> TYPE: PRT
<213> ORGANISM: Oryza sativa
<220> FEATURE:
<223> OTHER INFORMATION: rice Indica cultivar group, cultivar 93-11
      hypothetical protein OsI_06615, Bet v I
      allergen-like protein

<400> SEQUENCE: 65

Met Val Glu Met Asp Ala Gly Gly Arg Pro Glu Pro Ser Pro Pro Ser
 1               5                  10                  15

Gly Gln Cys Ser Ser Ala Val Thr Met Arg Ile Asn Ala Pro Val His
            20                  25                  30

Leu Val Trp Ser Ile Val Arg Arg Phe Glu Glu Pro His Ile Phe Gln
        35                  40                  45
```

-continued

```
Pro Phe Val Arg Gly Cys Thr Met Arg Gly Ser Thr Ser Leu Ala Val
    50                  55                  60

Gly Cys Val Arg Glu Val Asp Phe Lys Ser Gly Phe Ser Ala Lys Ser
65                  70                  75                  80

Ser Val Glu Arg Leu Glu Ile Leu Asp Asp Lys Glu His Val Phe Gly
                85                  90                  95

Val Arg Ile Ile Gly Gly Asp His Arg Leu Lys Asn Tyr Ser Ser Val
            100                 105                 110

Leu Thr Ala Lys Pro Glu Val Ile Asp Gly Glu Pro Ala Thr Leu Val
        115                 120                 125

Ser Glu Ser Phe Val Ile Asp Val Pro Glu Gly Asn Thr Ala Asp Glu
    130                 135                 140

Thr Arg His Phe Val Glu Phe Leu Ile Arg Cys Asn Leu Arg Ser Leu
145                 150                 155                 160

Ala Met Val Ser Gln Arg Leu Leu Leu Ala Gln Gly Asp Leu Ala Glu
                165                 170                 175

Pro Pro Ala Gln
            180


<210> SEQ ID NO 66
<211> LENGTH: 215
<212> TYPE: PRT
<213> ORGANISM: Oryza sativa
<220> FEATURE:
<223> OTHER INFORMATION: rice Japonica cultivar group, cultivar
      Nipponbare hypothetical protein OsJ_10498

<400> SEQUENCE: 66

Met Pro Cys Ile Pro Ala Ser Ser Pro Gly Ile Pro His Gln His Gln
 1               5                  10                  15

His Gln His His Arg Ala Leu Ala Gly Val Gly Met Ala Val Gly Cys
            20                  25                  30

Ala Ala Glu Ala Ala Val Ala Ala Ala Gly Val Ala Gly Thr Arg Cys
        35                  40                  45

Gly Ala His Asp Gly Glu Val Pro Met Glu Val Ala Arg His His Glu
    50                  55                  60

His Ala Glu Pro Gly Ser Gly Arg Cys Cys Ser Ala Val Val Gln His
65                  70                  75                  80

Val Ala Ala Pro Ala Ala Ala Val Trp Ser Val Val Arg Arg Phe Asp
                85                  90                  95

Gln Pro Gln Ala Tyr Lys Arg Phe Val Arg Ser Cys Ala Leu Leu Ala
            100                 105                 110

Gly Asp Gly Gly Leu Gly Lys Val Arg Glu Arg Leu Glu Ile Leu Asp
        115                 120                 125

Asp Glu Ser His Val Leu Ser Phe Arg Val Val Gly Gly Glu His Arg
    130                 135                 140

Leu Lys Asn Tyr Leu Ser Val Thr Thr Val His Pro Ser Pro Ser Ala
145                 150                 155                 160

Pro Thr Ala Ala Thr Val Val Val Glu Ser Tyr Val Val Asp Val Pro
                165                 170                 175

Pro Gly Asn Thr Pro Glu Asp Thr Arg Val Phe Val Asp Thr Ile Val
            180                 185                 190

Lys Cys Asn Leu Gln Ser Leu Ala Lys Thr Ala Glu Lys Leu Ala Ala
        195                 200                 205

Gly Ala Arg Ala Ala Gly Ser
    210                 215
```

<210> SEQ ID NO 67
<211> LENGTH: 186
<212> TYPE: PRT
<213> ORGANISM: Rheum australe
<220> FEATURE:
<223> OTHER INFORMATION: Himalayan rhubarb (Rheum emodi) pathogen-induced protein-like protein

<400> SEQUENCE: 67

```
Met Asn Gly Asp Gly Tyr Gly Gly Ser Glu Glu Glu Phe Val Lys Arg
 1               5                  10                  15

Tyr His Glu His Val Leu Ala Asp His Gln Cys Ser Ser Val Leu Val
            20                  25                  30

Glu His Ile Asn Ala Pro Leu His Leu Val Trp Ser Leu Val Arg Ser
        35                  40                  45

Phe Asp Gln Pro Gln Lys Tyr Lys Pro Phe Val Ser Arg Cys Val Val
    50                  55                  60

Gln Gly Gly Asp Leu Glu Ile Gly Ser Val Arg Glu Val Asp Val Lys
65                  70                  75                  80

Ser Gly Leu Pro Ala Thr Thr Ser Met Glu Glu Leu Glu Leu Leu Asp
                85                  90                  95

Asp Lys Glu His Val Leu Arg Val Lys Phe Val Gly Gly Asp His Arg
            100                 105                 110

Leu Lys Asn Tyr Ser Ser Ile Val Ser Leu His Pro Glu Ile Ile Gly
        115                 120                 125

Gly Arg Ser Gly Thr Met Val Ile Glu Ser Phe Ile Val Asp Ile Ala
    130                 135                 140

Asp Gly Asn Thr Lys Glu Glu Thr Cys Tyr Phe Ile Glu Ser Leu Ile
145                 150                 155                 160

Asn Cys Asn Leu Lys Ser Leu Ser Cys Val Ser Glu Arg Leu Ala Val
                165                 170                 175

Glu Asp Ile Ala Glu Arg Ile Ala Gln Met
            180                 185
```

<210> SEQ ID NO 68
<211> LENGTH: 254
<212> TYPE: PRT
<213> ORGANISM: Oryza sativa
<220> FEATURE:
<223> OTHER INFORMATION: rice Japonica cultivar group, cultivar Nipponbare hypothetical protein OsJ_016770

<400> SEQUENCE: 68

```
Met Val Gly Leu Val Gly Gly Gly Gly Trp Arg Val Gly Asp Asp Ala
 1               5                  10                  15

Ala Gly Gly Gly Gly Gly Gly Ala Val Ala Ala Gly Ala Ala Ala Ala
            20                  25                  30

Ala Glu Ala Glu His Met Arg Arg Leu His Ser Gln Gly Pro Arg Arg
        35                  40                  45

Ala Pro Val Gln Leu Arg Ala Arg Gln Ala His Gln Gly Ser Cys Ser
    50                  55                  60

Pro Pro Arg Ile Glu Cys Ala Asn Phe Ala Val Phe Leu Ala Ala Arg
65                  70                  75                  80

Asp Pro Lys Ile Val Trp Ser Leu Val Arg Ser Phe Asp Gln Pro Gln
                85                  90                  95

Arg Tyr Lys Pro Phe Val Ser Arg Cys Val Val Arg Gly Gly Asp Leu
            100                 105                 110
```

```
Glu Ile Gly Ser Val Arg Glu Val Asn Val Lys Thr Gly Leu Pro Ala
        115                 120                 125

Thr Thr Ser Thr Glu Arg Leu Glu Leu Leu Asp Asp Asp Glu His Ile
    130                 135                 140

Leu Ser Val Lys Phe Val Gly Gly Asp His Arg Leu Arg Asn Tyr Ser
145                 150                 155                 160

Ser Ile Val Thr Val His Pro Glu Ser Ile Asp Gly Arg Pro Gly Thr
                165                 170                 175

Leu Val Ile Glu Ser Phe Val Val Asp Val Pro Asp Gly Asn Thr Lys
            180                 185                 190

Asp Glu Thr Cys Tyr Phe Val Glu Ala Val Ile Lys Cys Asn Leu Thr
        195                 200                 205

Ser Leu Ala Glu Met Val Arg Met Ile Ser Leu Val Leu Pro Phe Met
    210                 215                 220

Leu Val Asp Arg Met Ser Gly Ile Thr Cys Glu Ser His Leu Glu Thr
225                 230                 235                 240

Thr Leu Val Arg Cys Gly Glu Tyr Ala Val Leu Ala His Val
                245                 250
```

<210> SEQ ID NO 69
<211> LENGTH: 186
<212> TYPE: PRT
<213> ORGANISM: Oryza sativa
<220> FEATURE:
<223> OTHER INFORMATION: rice Japonica cultivar group, cultivar Nipponbare hypothetical protein OsJ_005784

<400> SEQUENCE: 69

```
Met Glu Pro His Met Glu Arg Ala Leu Arg Glu Ala Val Ala Ser Glu
 1               5                  10                  15

Ala Glu Arg Arg Glu Leu Glu Gly Val Val Arg Ala His His Thr Gly
            20                  25                  30

Trp Asn Ala Pro Leu Ala Ala Val Trp Pro His Arg Ala Arg Val Arg
        35                  40                  45

Pro Thr Arg Ser Gly Thr Ser Thr Ser Ser Ser Arg Ala Ser Ser Pro
    50                  55                  60

Pro Gly Asp Gly Ala Thr Val Gly Ser Val Arg Glu Val Ala Val Val
65                  70                  75                  80

Ser Gly Leu Pro Ala Ser Thr Ser Thr Glu Arg Leu Glu Ile Leu Asp
                85                  90                  95

Asp Asp Arg His Val Leu Ser Phe Arg Val Val Gly Gly Asp His Arg
            100                 105                 110

Leu Arg Asn Tyr Arg Ser Val Thr Ser Val Thr Glu Phe Ser Ser Pro
        115                 120                 125

Ser Ser Pro Pro Arg Pro Tyr Cys Val Val Val Glu Ser Tyr Val Val
    130                 135                 140

Asp Val Pro Glu Gly Asn Thr Glu Glu Asp Thr Arg Met Phe Thr Asp
145                 150                 155                 160

Thr Val Val Lys Leu Asn Leu Gln Lys Leu Ala Ala Val Ala Thr Ser
                165                 170                 175

Ser Ser Pro Pro Ala Ala Gly Asn His His
            180                 185
```

<210> SEQ ID NO 70
<211> LENGTH: 150
<212> TYPE: PRT

<213> ORGANISM: Oryza sativa
<220> FEATURE:
<223> OTHER INFORMATION: rice Japonica cultivar group, cultivar
      Nipponbare hypothetical protein OsJ_005938

<400> SEQUENCE: 70

```
Met Glu Val Val Trp Ser Ile Val Arg Arg Phe Glu Glu Pro His Ile
 1               5                  10                  15

Phe Gln Pro Phe Val Arg Gly Cys Thr Met Arg Gly Ser Thr Ser Leu
            20                  25                  30

Ala Val Gly Cys Val Arg Glu Val Asp Phe Lys Ser Gly Phe Pro Ala
        35                  40                  45

Lys Ser Ser Val Glu Arg Leu Glu Ile Leu Asp Asp Lys Glu His Val
    50                  55                  60

Phe Gly Val Arg Ile Ile Gly Gly Asp His Arg Leu Lys Asn Tyr Ser
65                  70                  75                  80

Ser Val Leu Thr Ala Lys Pro Glu Val Ile Asp Gly Glu Pro Ala Thr
                85                  90                  95

Leu Val Ser Glu Ser Phe Val Val Asp Val Pro Glu Gly Asn Thr Ala
            100                 105                 110

Asp Glu Thr Arg His Phe Val Glu Phe Leu Ile Arg Cys Asn Leu Arg
        115                 120                 125

Ser Leu Ala Met Val Ser Gln Arg Leu Leu Leu Ala Gln Gly Asp Leu
    130                 135                 140

Ala Glu Pro Pro Gly Gln
145                 150
```

<210> SEQ ID NO 71
<211> LENGTH: 206
<212> TYPE: PRT
<213> ORGANISM: Oryza sativa
<220> FEATURE:
<223> OTHER INFORMATION: rice Japonica cultivar group, cultivar
      Nipponbare hypothetical protein OsJ_018129

<400> SEQUENCE: 71

```
Met Pro Tyr Thr Ala Pro Arg Pro Ser Pro Pro Gln His Ser Arg Ile
 1               5                  10                  15

Gly Gly Cys Gly Gly Gly Gly Val Leu Lys Ala Ala Gly Ala Ala Gly
            20                  25                  30

His Ala Ala Ser Cys Val Ala Val Pro Ala Glu Val Ala Arg His His
        35                  40                  45

Glu His Ala Ala Gly Val Gly Gln Cys Cys Ser Ala Val Val Gln Ala
    50                  55                  60

Ile Ala Ala Pro Val Asp Ala Val Trp Arg Thr Ser Thr Ser Ser Gly
65                  70                  75                  80

Ala Ala Ala Ser Trp Thr Ala Thr Ala Thr Ala Gly Pro Leu Pro Val
                85                  90                  95

Gly Ser Val Arg Glu Phe Arg Val Leu Ser Gly Leu Pro Gly Thr Ser
            100                 105                 110

Ser Arg Glu Arg Leu Glu Ile Leu Asp Asp Glu Arg Arg Val Leu Ser
        115                 120                 125

Phe Arg Val Val Gly Gly Glu His Arg Leu Ser Asn Tyr Arg Ser Val
    130                 135                 140

Thr Thr Val His Glu Thr Ala Ala Gly Ala Ala Ala Ala Val Val Val
145                 150                 155                 160

Glu Ser Tyr Val Val Asp Val Pro His Gly Asn Thr Ala Asp Glu Thr
```

```
                165                 170                 175

Arg Met Phe Val Asp Thr Ile Val Arg Cys Asn Leu Gln Ser Leu Ala
            180                 185                 190

Arg Thr Ala Glu Gln Leu Ala Leu Ala Ala Pro Arg Ala Ala
        195                 200                 205


<210> SEQ ID NO 72
<211> LENGTH: 396
<212> TYPE: PRT
<213> ORGANISM: Vitis vinifera
<220> FEATURE:
<223> OTHER INFORMATION: grapevine cultivar Pinot Noir, clone ENTAV 115
      hypothetical protein, locus VITISV_001710
<220> FEATURE:
<221> NAME/KEY: VARIANT
<222> LOCATION: (1)...(395)
<223> OTHER INFORMATION: Xaa = any amino acid

<400> SEQUENCE: 72

Met Pro Ile Ser Ser Leu Pro Phe Ser Leu Tyr Thr Val Thr Pro Asn
 1               5                  10                  15

Pro Leu Lys Leu Ile Thr Thr His Ala His Ala Phe Thr Pro His Thr
            20                  25                  30

His Ile Phe Thr Leu Lys Phe Met Ser His Thr Tyr Cys Pro His Ile
        35                  40                  45

His His Ile Thr Ser Ile His Tyr Thr His Leu Leu Xaa Pro Ile Pro
    50                  55                  60

His Met Pro Leu Gln Pro Pro Leu Pro Pro His Pro Ile Leu Pro Ser
65                  70                  75                  80

Met Pro Ala Phe Gln His Leu Tyr Ser Thr Asn Gln His Leu Gln Val
                85                  90                  95

Ala Leu Phe Ser Ala Arg Gly Pro Asn Ile Arg Asp Phe Asn Phe Gln
            100                 105                 110

Asp Ala Asp Leu Leu Lys Leu Asp Ile Leu Ala Pro Gly Ser Leu Ile
        115                 120                 125

Trp Ala Ala Trp Ser Pro Asn Gly Thr Asp Glu Ala Asn Tyr Val Gly
    130                 135                 140

Glu Gly Ser Pro Thr Val Ala Met Ile Ala Lys Arg Gly Pro Arg His
145                 150                 155                 160

Gly Lys Tyr Met Ala Phe Cys Xaa Met Tyr Arg Asp Asn Val Ala Pro
                165                 170                 175

Lys Gly Val Asn Xaa Ala Val Ala Thr Val Lys Thr Lys Arg Thr Ile
            180                 185                 190

Gln Leu Lys Thr Ser Leu Glu Ile Ala Cys His Tyr Ala Gly Ile Asn
        195                 200                 205

Ile Ser Gly Ile Asn Gly Glu Val Met Pro Gly Gln Trp Glu Tyr Gln
    210                 215                 220

Val Gly Pro Gly Gln Cys Ser Ser Leu Leu Ala Gln Arg Val His Val
225                 230                 235                 240

Pro Leu Ser Ala Val Gly Ser Val Val His Arg Phe Asp Lys Pro Gln
                245                 250                 255

Arg Tyr Gln His Val Ile Lys Ser Cys Arg Ile Glu Asp Gly Phe Glu
            260                 265                 270

Met Arg Met Gly Xaa Leu Arg Asp Val Asn Ile Ile Ser Gly Leu Pro
        275                 280                 285

Thr Ala Thr Asn Thr Gly Arg Leu Asp Met Gln Asp Asp Glu Arg His
    290                 295                 300
```

```
Val Thr Arg Cys Pro His Gln Arg Gln Ser Glu Ser Lys Tyr Thr Glu
305                 310                 315                 320

Asn Asn Asn Ser Asp Ala Ser Ser Ile Lys Ser Pro Ile Asn Gly Pro
                325                 330                 335

Ser Glu His Leu Lys Thr Ala Ala Ser Pro Lys Thr Glu Ser Ile Ile
            340                 345                 350

Val Ile Asp Thr Ser Lys Phe Leu Asn Glu Glu Asp Phe Glu Gly Lys
        355                 360                 365

Asp Glu Thr Ser Ser Ser Asn Gln Val Gln Ile Glu Asp Glu Asn Trp
    370                 375                 380

Glu Thr Arg Phe Pro Asn Thr Asp Ala Gly Ile Trp
385                 390                 395


<210> SEQ ID NO 73
<211> LENGTH: 443
<212> TYPE: PRT
<213> ORGANISM: Vitis vinifera
<220> FEATURE:
<223> OTHER INFORMATION: grapevine cultivar Pinot Noir, clone ENTAV 115
      hypothetical protein, locus VITISV_014403
<220> FEATURE:
<221> NAME/KEY: VARIANT
<222> LOCATION: (1)...(443)
<223> OTHER INFORMATION: Xaa = any amino acid

<400> SEQUENCE: 73

Met Pro Ser Ala Xaa Lys Ser Ser Thr Val Pro Leu Ser Leu Xaa Gln
 1               5                  10                  15

Phe Lys Leu Gly Leu Arg His Gly His Arg Val Ile Pro Trp Gly Asp
            20                  25                  30

Leu Asp Ser Leu Ala Met Leu Gln Arg Gln Leu Asp Val Asp Ile Leu
        35                  40                  45

Val Thr Gly His Thr His Arg Phe Thr Ala Tyr Lys His Glu Gly Gly
    50                  55                  60

Val Val Ile Asn Pro Gly Ser Ala Thr Gly Ala Phe Gly Ser Ile Thr
65                  70                  75                  80

Tyr Asp Val Asn Pro Ser Phe Val Leu Met Asp Ile Asp Gly Leu Arg
                85                  90                  95

Val Val Val Cys Val Tyr Glu Leu Ile Asp Glu Thr Ala Asn Ile Ile
            100                 105                 110

Lys Glu Leu His Ala Arg Lys Ile Ser Phe Gly Thr Lys Ser Met Ile
        115                 120                 125

Xaa Cys Leu Leu Leu Lys Arg Arg Ser Thr Pro Lys Phe Arg Arg Lys
    130                 135                 140

Lys Leu Phe Leu Phe Gln Cys Arg Val Gln Met Thr Leu Thr Leu Thr
145                 150                 155                 160

Asn Leu Ala Val Ser Gly Ile Ala Gln Thr Leu Gln Val Asp Gln Trp
                165                 170                 175

Thr Val Cys Ala Leu Ile Phe Met Thr Arg Arg Asp Ile His Leu Asp
            180                 185                 190

Lys Ala Arg Phe Leu Asp Phe Lys Asp Met Gly Lys Leu Leu Ala Asp
        195                 200                 205

Ala Ser Gly Leu Arg Lys Ala Leu Ser Gly Gly Xaa Val Thr Ala Gly
    210                 215                 220

Met Ala Ile Phe Asp Thr Met Arg His Ile Arg Pro Asp Val Pro Thr
225                 230                 235                 240
```

-continued

```
Val Cys Val Gly Leu Ala Ala Val Ala Met Ile Ala Lys Arg Gly Pro
                245                 250                 255

Arg His Gly Lys Tyr Met Ala Phe Cys Pro Met Tyr Arg Asp Asn Val
            260                 265                 270

Ala Pro Lys Gly Val Asn Val Ala Val Val Thr Val Lys Thr Lys Arg
        275                 280                 285

Thr Ile Gln Leu Lys Thr Ser Leu Glu Ile Ala Cys His Tyr Ala Gly
    290                 295                 300

Ile Asn Ile Ser Gly Ile Asn Gly Glu Val Met Pro Gly Gln Trp Glu
305                 310                 315                 320

Tyr Gln Val Gly Pro Gly Gln Cys Ser Ser Leu Leu Ala Gln Arg Val
                325                 330                 335

His Val Pro Leu Ser Ala Val Gly Ser Val Val His Arg Phe Asp Lys
            340                 345                 350

Pro Gln Arg Tyr Gln His Val Ile Lys Ser Cys Arg Ile Glu Asp Gly
        355                 360                 365

Phe Glu Met Arg Met Gly Arg Leu Arg Asp Val Asn Ile Ile Ser Gly
    370                 375                 380

Leu Pro Thr Ala Thr Asn Thr Gly Arg Leu Asp Met Gln Asp Asp Glu
385                 390                 395                 400

Xaa His Val Thr Arg Cys Pro His Gln Arg Gln Ser Glu Ser Lys Tyr
                405                 410                 415

Thr Glu Asn Asn Asn Ser Asp Ala Ser Ser Val Lys Ser Pro Ile Asn
            420                 425                 430

Gly Pro Ser Glu His Leu Lys Thr Ala Ala Xaa
        435                 440
```

<210> SEQ ID NO 74
<211> LENGTH: 95
<212> TYPE: PRT
<213> ORGANISM: Oryza sativa
<220> FEATURE:
<223> OTHER INFORMATION: rice Indica cultivar group, cultivar Pokkali, clone OSR-385-428-D5 capip1 protein partial sequence

<400> SEQUENCE: 74

```
Glu Ile Gly Ser Val Arg Glu Val Asn Val Lys Thr Gly Leu Pro Ala
 1               5                  10                  15

Thr Thr Ser Thr Glu Arg Leu Glu Leu Leu Asp Asp Asp Glu His Ile
            20                  25                  30

Leu Ser Val Lys Phe Val Gly Gly Asp His Arg Leu Arg Asn Tyr Ser
        35                  40                  45

Ser Ile Val Thr Val His Pro Glu Ser Ile Asp Gly Arg Pro Gly Thr
    50                  55                  60

Leu Val Ile Glu Ser Phe Val Val Asp Val Pro Asp Gly Asn Thr Lys
65                  70                  75                  80

Asp Glu Thr Cys Tyr Phe Val Glu Ala Val Ile Lys Cys Asn Leu
                85                  90                  95
```

<210> SEQ ID NO 75
<211> LENGTH: 191
<212> TYPE: PRT
<213> ORGANISM: Zea mays
<220> FEATURE:
<223> OTHER INFORMATION: corn (maize) strain B73, clone ZM_BFc0034007 unknown protein

<400> SEQUENCE: 75

```
Met Val Val Glu Met Asp Gly Gly Val Gly Val Ala Ala Ala Gly Gly
1               5                   10                  15

Gly Gly Ala Gln Thr Pro Ala Pro Pro Pro Pro Arg Arg Trp Arg Leu
            20                  25                  30

Ala Asp Glu Arg Cys Asp Leu Arg Ala Met Glu Thr Asp Tyr Val Arg
        35                  40                  45

Arg Phe His Arg His Glu Pro Arg Asp His Gln Cys Ser Ser Ala Val
    50                  55                  60

Ala Lys His Ile Lys Ala Pro Val His Leu Val Trp Ser Leu Val Arg
65                  70                  75                  80

Arg Phe Asp Gln Pro Gln Leu Phe Lys Pro Phe Val Ser Arg Cys Glu
                85                  90                  95

Met Lys Gly Asn Ile Glu Ile Gly Ser Val Arg Glu Val Asn Val Lys
            100                 105                 110

Ser Gly Leu Pro Ala Thr Arg Ser Thr Glu Arg Leu Glu Leu Leu Asp
        115                 120                 125

Asp Asp Glu Arg Ile Leu Ser Val Arg Phe Val Gly Gly Asp His Arg
    130                 135                 140

Leu Gln Val Cys Ser Val Leu His Leu Ser Ile Phe Cys Ala Ala His
145                 150                 155                 160

Ala Arg Tyr Phe Ala His His Leu Lys Cys Val Leu Glu Phe Leu Cys
                165                 170                 175

Gln Met His Leu Asp Val Leu Pro Cys Asp Asp Ala Ile Leu Glu
            180                 185                 190


<210> SEQ ID NO 76
<211> LENGTH: 239
<212> TYPE: PRT
<213> ORGANISM: Oryza sativa
<220> FEATURE:
<223> OTHER INFORMATION: rice Japonica cultivar group, cultivar
      Nipponbare hypothetical protein OsJ_020681

<400> SEQUENCE: 76

Met Asn Gly Cys Thr Gly Gly Ala Gly Gly Val Ala Ala Gly Arg Leu
1               5                   10                  15

Pro Ala Val Ser Leu Gln Gln Ala Gln Trp Lys Leu Val Asp Glu Arg
            20                  25                  30

Cys Glu Leu Arg Glu Glu Glu Met Glu Tyr Val Arg Arg Phe His Arg
        35                  40                  45

His Glu Ile Gly Ser Asn Gln Cys Asn Ser Phe Ile Ala Lys His Val
    50                  55                  60

Arg Ala Pro Leu Gln Asn Val Trp Ser Leu Val Arg Arg Phe Asp Gln
65                  70                  75                  80

Pro Gln Ile Tyr Lys Pro Phe Val Arg Lys Cys Val Met Arg Gly Asn
                85                  90                  95

Val Glu Thr Gly Ser Val Arg Glu Ile Ile Val Gln Ser Gly Leu Pro
            100                 105                 110

Ala Thr Arg Ser Ile Glu Arg Leu Glu Phe Leu Asp Asp Asn Glu Tyr
        115                 120                 125

Ile Leu Arg Val Lys Phe Ile Gly Gly Asp His Met Leu Lys Lys Arg
    130                 135                 140

Ile Pro Lys Lys Thr Tyr Ala Ile Ser Ser Arg Thr Cys Ser Asp Ser
145                 150                 155                 160

Ala Ile Ile Ala Val Gly Gln Ser Asn Cys Ala Pro Glu Ile Thr Ala
```

```
                165                 170                 175

Met Asn Gly Gly Val Ser Ile Gln Pro Trp Leu Ile Leu Leu Ala Phe
            180                 185                 190

Phe Ser Ser Pro Ser Asn Gln Thr Asn Pro Asp Ser Leu Arg Asp Met
        195                 200                 205

His Pro Gly Ser Trp Phe Gln Ile Leu Leu Val Leu Ala Met Phe Thr
    210                 215                 220

Cys Ser Lys Gly Ser Val Leu Pro Pro Ser Glu Lys Val Asn Val
225                 230                 235


<210> SEQ ID NO 77
<211> LENGTH: 159
<212> TYPE: PRT
<213> ORGANISM: Arabidopsis sp.
<220> FEATURE:
<223> OTHER INFORMATION: PYR/PYL receptor polypeptide PYL12

<400> SEQUENCE: 77

Met Lys Thr Ser Gln Glu Gln His Val Cys Gly Ser Thr Val Val Gln
 1               5                  10                  15

Thr Ile Asn Ala Pro Leu Pro Leu Val Trp Ser Ile Leu Arg Arg Phe
            20                  25                  30

Asp Asn Pro Lys Thr Phe Lys His Phe Val Lys Thr Cys Lys Leu Arg
        35                  40                  45

Ser Gly Asp Gly Gly Glu Gly Ser Val Arg Glu Val Thr Val Val Ser
    50                  55                  60

Asp Leu Pro Ala Ser Phe Ser Leu Glu Arg Leu Asp Glu Leu Asp Asp
65                  70                  75                  80

Glu Ser His Val Met Val Ile Ser Ile Ile Gly Gly Asp His Arg Leu
                85                  90                  95

Val Asn Tyr Gln Ser Lys Thr Thr Val Phe Val Ala Ala Glu Glu Glu
            100                 105                 110

Lys Thr Val Val Val Glu Ser Tyr Val Val Asp Val Pro Glu Gly Asn
        115                 120                 125

Thr Glu Glu Glu Thr Thr Leu Phe Ala Asp Thr Ile Val Gly Cys Asn
    130                 135                 140

Leu Arg Ser Leu Ala Lys Leu Ser Glu Lys Met Met Glu Leu Thr
145                 150                 155


<210> SEQ ID NO 78
<211> LENGTH: 188
<212> TYPE: PRT
<213> ORGANISM: Arabidopsis sp.
<220> FEATURE:
<223> OTHER INFORMATION: PYR/PYL receptor polypeptide PYL8

<400> SEQUENCE: 78

Met Glu Ala Asn Gly Ile Glu Asn Leu Thr Asn Pro Asn Gln Glu Arg
 1               5                  10                  15

Glu Phe Ile Arg Arg His His Lys His Glu Leu Val Asp Asn Gln Cys
            20                  25                  30

Ser Ser Thr Leu Val Lys His Ile Asn Ala Pro Val His Ile Val Trp
        35                  40                  45

Ser Leu Val Arg Arg Phe Asp Gln Pro Gln Lys Tyr Lys Pro Phe Ile
    50                  55                  60

Ser Arg Cys Val Val Lys Gly Asn Met Glu Ile Gly Thr Val Arg Glu
65                  70                  75                  80
```

```
Val Asp Val Lys Ser Gly Leu Pro Ala Thr Arg Ser Thr Glu Arg Leu
                85                  90                  95

Glu Leu Leu Asp Asp Asn Glu His Ile Leu Ser Ile Arg Ile Val Gly
            100                 105                 110

Gly Asp His Arg Leu Lys Asn Tyr Ser Ser Ile Ile Ser Leu His Pro
        115                 120                 125

Glu Thr Ile Glu Gly Arg Ile Gly Thr Leu Val Ile Glu Ser Phe Val
    130                 135                 140

Val Asp Val Pro Glu Gly Asn Thr Lys Asp Glu Thr Cys Tyr Phe Val
145                 150                 155                 160

Glu Ala Leu Ile Lys Cys Asn Leu Lys Ser Leu Ala Asp Ile Ser Glu
                165                 170                 175

Arg Leu Ala Val Gln Asp Thr Thr Glu Ser Arg Val
            180                 185


<210> SEQ ID NO 79
<211> LENGTH: 211
<212> TYPE: PRT
<213> ORGANISM: Arabidopsis sp.
<220> FEATURE:
<223> OTHER INFORMATION: PYR/PYL receptor polypeptide PYL7

<400> SEQUENCE: 79

Met Glu Met Ile Gly Gly Asp Asp Thr Asp Thr Glu Met Tyr Gly Ala
 1               5                  10                  15

Leu Val Thr Ala Gln Ser Leu Arg Leu Arg His Leu His His Cys Arg
            20                  25                  30

Glu Asn Gln Cys Thr Ser Val Leu Val Lys Tyr Ile Gln Ala Pro Val
        35                  40                  45

His Leu Val Trp Ser Leu Val Arg Arg Phe Asp Gln Pro Gln Lys Tyr
    50                  55                  60

Lys Pro Phe Ile Ser Arg Cys Thr Val Asn Gly Asp Pro Glu Ile Gly
65                  70                  75                  80

Cys Leu Arg Glu Val Asn Val Lys Ser Gly Leu Pro Ala Thr Thr Ser
                85                  90                  95

Thr Glu Arg Leu Glu Gln Leu Asp Asp Glu Glu His Ile Leu Gly Ile
            100                 105                 110

Asn Ile Ile Gly Gly Asp His Arg Leu Lys Asn Tyr Ser Ser Ile Leu
        115                 120                 125

Thr Val His Pro Glu Met Ile Asp Gly Arg Ser Gly Thr Met Val Met
    130                 135                 140

Glu Ser Phe Val Val Asp Val Pro Gln Gly Asn Thr Lys Asp Asp Thr
145                 150                 155                 160

Cys Tyr Phe Val Glu Ser Leu Ile Lys Cys Asn Leu Lys Ser Leu Ala
                165                 170                 175

Cys Val Ser Glu Arg Leu Ala Ala Gln Asp Ile Thr Asn Ser Ile Ala
            180                 185                 190

Thr Phe Cys Asn Ala Ser Asn Gly Tyr Arg Glu Lys Asn His Thr Glu
        195                 200                 205

Thr Asn Leu
    210


<210> SEQ ID NO 80
<211> LENGTH: 187
<212> TYPE: PRT
<213> ORGANISM: Arabidopsis sp.
<220> FEATURE:
```

<223> OTHER INFORMATION: PYR/PYL receptor polypeptide PYL9

<400> SEQUENCE: 80

```
Met Met Asp Gly Val Glu Gly Gly Thr Ala Met Tyr Gly Gly Leu Glu
 1               5                  10                  15

Thr Val Gln Tyr Val Arg Thr His His Gln His Leu Cys Arg Glu Asn
            20                  25                  30

Gln Cys Thr Ser Ala Leu Val Lys His Ile Lys Ala Pro Leu His Leu
        35                  40                  45

Val Trp Ser Leu Val Arg Arg Phe Asp Gln Pro Gln Lys Tyr Lys Pro
    50                  55                  60

Phe Val Ser Arg Cys Thr Val Ile Gly Asp Pro Glu Ile Gly Ser Leu
65                  70                  75                  80

Arg Glu Val Asn Val Lys Ser Gly Leu Pro Ala Thr Thr Ser Thr Glu
                85                  90                  95

Arg Leu Glu Leu Leu Asp Asp Glu Glu His Ile Leu Gly Ile Lys Ile
            100                 105                 110

Ile Gly Gly Asp His Arg Leu Lys Asn Tyr Ser Ser Ile Leu Thr Val
        115                 120                 125

His Pro Glu Ile Ile Glu Gly Arg Ala Gly Thr Met Val Ile Glu Ser
    130                 135                 140

Phe Val Val Asp Val Pro Gln Gly Asn Thr Lys Asp Glu Thr Cys Tyr
145                 150                 155                 160

Phe Val Glu Ala Leu Ile Arg Cys Asn Leu Lys Ser Leu Ala Asp Val
                165                 170                 175

Ser Glu Arg Leu Ala Ser Gln Asp Ile Thr Gln
            180                 185
```

<210> SEQ ID NO 81
<211> LENGTH: 161
<212> TYPE: PRT
<213> ORGANISM: Arabidopsis sp.
<220> FEATURE:
<223> OTHER INFORMATION: PYR/PYL receptor polypeptide PYL11

<400> SEQUENCE: 81

```
Met Glu Thr Ser Gln Lys Tyr His Thr Cys Gly Ser Thr Leu Val Gln
 1               5                  10                  15

Thr Ile Asp Ala Pro Leu Ser Leu Val Trp Ser Ile Leu Arg Arg Phe
            20                  25                  30

Asp Asn Pro Gln Ala Tyr Lys Gln Phe Val Lys Thr Cys Asn Leu Ser
        35                  40                  45

Ser Gly Asp Gly Gly Glu Gly Ser Val Arg Glu Val Thr Val Val Ser
    50                  55                  60

Gly Leu Pro Ala Glu Phe Ser Arg Glu Arg Leu Asp Glu Leu Asp Asp
65                  70                  75                  80

Glu Ser His Val Met Met Ile Ser Ile Ile Gly Gly Asp His Arg Leu
                85                  90                  95

Val Asn Tyr Arg Ser Lys Thr Met Ala Phe Val Ala Ala Asp Thr Glu
            100                 105                 110

Glu Lys Thr Val Val Val Glu Ser Tyr Val Val Asp Val Pro Glu Gly
        115                 120                 125

Asn Ser Glu Glu Glu Thr Thr Ser Phe Ala Asp Thr Ile Val Gly Phe
    130                 135                 140

Asn Leu Lys Ser Leu Ala Lys Leu Ser Glu Arg Val Ala His Leu Lys
145                 150                 155                 160
```

Leu

<210> SEQ ID NO 82
<211> LENGTH: 183
<212> TYPE: PRT
<213> ORGANISM: Arabidopsis sp.
<220> FEATURE:
<223> OTHER INFORMATION: PYR/PYL receptor polypeptide PYL10

<400> SEQUENCE: 82

Met Asn Gly Asp Glu Thr Lys Lys Val Glu Ser Glu Tyr Ile Lys Lys
1               5                   10                  15

His His Arg His Glu Leu Val Glu Ser Gln Cys Ser Ser Thr Leu Val
            20                  25                  30

Lys His Ile Lys Ala Pro Leu His Leu Val Trp Ser Ile Val Arg Arg
        35                  40                  45

Phe Asp Glu Pro Gln Lys Tyr Lys Pro Phe Ile Ser Arg Cys Val Val
    50                  55                  60

Gln Gly Lys Lys Leu Glu Val Gly Ser Val Arg Glu Val Asp Leu Lys
65                  70                  75                  80

Ser Gly Leu Pro Ala Thr Lys Ser Thr Glu Val Leu Glu Ile Leu Asp
                85                  90                  95

Asp Asn Glu His Ile Leu Gly Ile Arg Ile Val Gly Gly Asp His Arg
            100                 105                 110

Leu Lys Asn Tyr Ser Ser Thr Ile Ser Leu His Ser Glu Thr Ile Asp
        115                 120                 125

Gly Lys Thr Gly Thr Leu Ala Ile Glu Ser Phe Val Val Asp Val Pro
    130                 135                 140

Glu Gly Asn Thr Lys Glu Glu Thr Cys Phe Phe Val Glu Ala Leu Ile
145                 150                 155                 160

Gln Cys Asn Leu Asn Ser Leu Ala Asp Val Thr Glu Arg Leu Gln Ala
                165                 170                 175

Glu Ser Met Glu Lys Lys Ile
            180

<210> SEQ ID NO 83
<211> LENGTH: 119
<212> TYPE: PRT
<213> ORGANISM: Arabidopsis sp.
<220> FEATURE:
<223> OTHER INFORMATION: PYR/PYL receptor polypeptide PYL13

<400> SEQUENCE: 83

Met Glu Ser Ser Lys Gln Lys Arg Cys Arg Ser Ser Val Val Glu Thr
1               5                   10                  15

Ile Glu Ala Pro Leu Pro Leu Val Trp Ser Ile Leu Arg Ser Phe Asp
            20                  25                  30

Lys Pro Gln Ala Tyr Gln Arg Phe Val Lys Ser Cys Thr Met Arg Ser
        35                  40                  45

Gly Gly Gly Gly Gly Lys Gly Gly Glu Gly Lys Gly Ser Val Arg Asp
    50                  55                  60

Val Thr Leu Val Ser Gly Phe Pro Ala Asp Phe Ser Thr Glu Arg Leu
65                  70                  75                  80

Glu Glu Leu Asp Asp Glu Ser His Val Met Val Val Ser Ile Ile Gly
                85                  90                  95

Gly Asn His Arg Leu Val Asn Tyr Lys Ser Lys Thr Lys Val Val Ala
            100                 105                 110

Ser Pro Glu Asp Met Ala Lys
115

<210> SEQ ID NO 84
<211> LENGTH: 203
<212> TYPE: PRT
<213> ORGANISM: Arabidopsis sp.
<220> FEATURE:
<223> OTHER INFORMATION: PYR/PYL receptor polypeptide PYL5

<400> SEQUENCE: 84

Met Arg Ser Pro Val Gln Leu Gln His Gly Ser Asp Ala Thr Asn Gly
1 5 10 15

Phe His Thr Leu Gln Pro His Asp Gln Thr Asp Gly Pro Ile Lys Arg
20 25 30

Val Cys Leu Thr Arg Gly Met His Val Pro Glu His Val Ala Met His
35 40 45

His Thr His Asp Val Gly Pro Asp Gln Cys Cys Ser Ser Val Val Gln
50 55 60

Met Ile His Ala Pro Pro Glu Ser Val Trp Ala Leu Val Arg Arg Phe
65 70 75 80

Asp Asn Pro Lys Val Tyr Lys Asn Phe Ile Arg Gln Cys Arg Ile Val
85 90 95

Gln Gly Asp Gly Leu His Val Gly Asp Leu Arg Glu Val Met Val Val
100 105 110

Ser Gly Leu Pro Ala Val Ser Ser Thr Glu Arg Leu Glu Ile Leu Asp
115 120 125

Glu Glu Arg His Val Ile Ser Phe Ser Val Val Gly Gly Asp His Arg
130 135 140

Leu Lys Asn Tyr Arg Ser Val Thr Thr Leu His Ala Ser Asp Asp Glu
145 150 155 160

Gly Thr Val Val Val Glu Ser Tyr Ile Val Asp Val Pro Pro Gly Asn
165 170 175

Thr Glu Glu Glu Thr Leu Ser Phe Val Asp Thr Ile Val Arg Cys Asn
180 185 190

Leu Gln Ser Leu Ala Arg Ser Thr Asn Arg Gln
195 200

<210> SEQ ID NO 85
<211> LENGTH: 207
<212> TYPE: PRT
<213> ORGANISM: Arabidopsis sp.
<220> FEATURE:
<223> OTHER INFORMATION: PYR/PYL receptor polypeptide PYL4

<400> SEQUENCE: 85

Met Leu Ala Val His Arg Pro Ser Ser Ala Val Ser Asp Gly Asp Ser
1 5 10 15

Val Gln Ile Pro Met Met Ile Ala Ser Phe Gln Lys Arg Phe Pro Ser
20 25 30

Leu Ser Arg Asp Ser Thr Ala Ala Arg Phe His Thr His Glu Val Gly
35 40 45

Pro Asn Gln Cys Cys Ser Ala Val Ile Gln Glu Ile Ser Ala Pro Ile
50 55 60

Ser Thr Val Trp Ser Val Val Arg Arg Phe Asp Asn Pro Gln Ala Tyr
65 70 75 80

Lys His Phe Leu Lys Ser Cys Ser Val Ile Gly Gly Asp Gly Asp Asn

-continued

```
                85                  90                  95

Val Gly Ser Leu Arg Gln Val His Val Val Ser Gly Leu Pro Ala Ala
            100                 105                 110

Ser Ser Thr Glu Arg Leu Asp Ile Leu Asp Asp Glu Arg His Val Ile
        115                 120                 125

Ser Phe Ser Val Val Gly Gly Asp His Arg Leu Ser Asn Tyr Arg Ser
    130                 135                 140

Val Thr Thr Leu His Pro Ser Pro Ile Ser Gly Thr Val Val Val Glu
145                 150                 155                 160

Ser Tyr Val Val Asp Val Pro Pro Gly Asn Thr Lys Glu Glu Thr Cys
                165                 170                 175

Asp Phe Val Asp Val Ile Val Arg Cys Asn Leu Gln Ser Leu Ala Lys
            180                 185                 190

Ile Ala Glu Asn Thr Ala Ala Glu Ser Lys Lys Lys Met Ser Leu
        195                 200                 205


<210> SEQ ID NO 86
<211> LENGTH: 215
<212> TYPE: PRT
<213> ORGANISM: Arabidopsis sp.
<220> FEATURE:
<223> OTHER INFORMATION: PYR/PYL receptor polypeptide PYL6

<400> SEQUENCE: 86

Met Pro Thr Ser Ile Gln Phe Gln Arg Ser Ser Thr Ala Ala Glu Ala
 1               5                  10                  15

Ala Asn Ala Thr Val Arg Asn Tyr Pro His His His Gln Lys Gln Val
            20                  25                  30

Gln Lys Val Ser Leu Thr Arg Gly Met Ala Asp Val Pro Glu His Val
        35                  40                  45

Glu Leu Ser His Thr His Val Val Gly Pro Ser Gln Cys Phe Ser Val
    50                  55                  60

Val Val Gln Asp Val Glu Ala Pro Val Ser Thr Val Trp Ser Ile Leu
65                  70                  75                  80

Ser Arg Phe Glu His Pro Gln Ala Tyr Lys His Phe Val Lys Ser Cys
                85                  90                  95

His Val Val Ile Gly Asp Gly Arg Glu Val Gly Ser Val Arg Glu Val
            100                 105                 110

Arg Val Val Ser Gly Leu Pro Ala Ala Phe Ser Leu Glu Arg Leu Glu
        115                 120                 125

Ile Met Asp Asp Asp Arg His Val Ile Ser Phe Ser Val Val Gly Gly
    130                 135                 140

Asp His Arg Leu Met Asn Tyr Lys Ser Val Thr Thr Val His Glu Ser
145                 150                 155                 160

Glu Glu Asp Ser Asp Gly Lys Lys Arg Thr Arg Val Val Glu Ser Tyr
                165                 170                 175

Val Val Asp Val Pro Ala Gly Asn Asp Lys Glu Glu Thr Cys Ser Phe
            180                 185                 190

Ala Asp Thr Ile Val Arg Cys Asn Leu Gln Ser Leu Ala Lys Leu Ala
        195                 200                 205

Glu Asn Thr Ser Lys Phe Ser
    210                 215


<210> SEQ ID NO 87
<211> LENGTH: 190
<212> TYPE: PRT
```

```
<213> ORGANISM: Arabidopsis sp.
<220> FEATURE:
<223> OTHER INFORMATION: PYR/PYL receptor polypeptide PYL2

<400> SEQUENCE: 87

Met Ser Ser Ser Pro Ala Val Lys Gly Leu Thr Asp Glu Glu Gln Lys
 1               5                  10                  15

Thr Leu Glu Pro Val Ile Lys Thr Tyr His Gln Phe Glu Pro Asp Pro
            20                  25                  30

Thr Thr Cys Thr Ser Leu Ile Thr Gln Arg Ile His Ala Pro Ala Ser
        35                  40                  45

Val Val Trp Pro Leu Ile Arg Arg Phe Asp Asn Pro Glu Arg Tyr Lys
    50                  55                  60

His Phe Val Lys Arg Cys Arg Leu Ile Ser Gly Asp Gly Asp Val Gly
65                  70                  75                  80

Ser Val Arg Glu Val Thr Val Ile Ser Gly Leu Pro Ala Ser Thr Ser
                85                  90                  95

Thr Glu Arg Leu Glu Phe Val Asp Asp Asp His Arg Val Leu Ser Phe
            100                 105                 110

Arg Val Val Gly Gly Glu His Arg Leu Lys Asn Tyr Lys Ser Val Thr
        115                 120                 125

Ser Val Asn Glu Phe Leu Asn Gln Asp Ser Gly Lys Val Tyr Thr Val
    130                 135                 140

Val Leu Glu Ser Tyr Thr Val Asp Ile Pro Glu Gly Asn Thr Glu Glu
145                 150                 155                 160

Asp Thr Lys Met Phe Val Asp Thr Val Val Lys Leu Asn Leu Gln Lys
                165                 170                 175

Leu Gly Val Ala Ala Thr Ser Ala Pro Met His Asp Asp Glu
            180                 185                 190


<210> SEQ ID NO 88
<211> LENGTH: 209
<212> TYPE: PRT
<213> ORGANISM: Arabidopsis sp.
<220> FEATURE:
<223> OTHER INFORMATION: PYR/PYL receptor polypeptide PYL3

<400> SEQUENCE: 88

Met Asn Leu Ala Pro Ile His Asp Pro Ser Ser Ser Ser Thr Thr Thr
 1               5                  10                  15

Thr Ser Ser Ser Thr Pro Tyr Gly Leu Thr Lys Asp Glu Phe Ser Thr
            20                  25                  30

Leu Asp Ser Ile Ile Arg Thr His His Thr Phe Pro Arg Ser Pro Asn
        35                  40                  45

Thr Cys Thr Ser Leu Ile Ala His Arg Val Asp Ala Pro Ala His Ala
    50                  55                  60

Ile Trp Arg Phe Val Arg Asp Phe Ala Asn Pro Asn Lys Tyr Lys His
65                  70                  75                  80

Phe Ile Lys Ser Cys Thr Ile Arg Val Asn Gly Asn Gly Ile Lys Glu
                85                  90                  95

Ile Lys Val Gly Thr Ile Arg Glu Val Ser Val Val Ser Gly Leu Pro
            100                 105                 110

Ala Ser Thr Ser Val Glu Ile Leu Glu Val Leu Asp Glu Glu Lys Arg
        115                 120                 125

Ile Leu Ser Phe Arg Val Leu Gly Gly Glu His Arg Leu Asn Asn Tyr
    130                 135                 140
```

```
Arg Ser Val Thr Ser Val Asn Glu Phe Val Val Leu Glu Lys Asp Lys
145                 150                 155                 160

Lys Lys Arg Val Tyr Ser Val Val Leu Glu Ser Tyr Ile Val Asp Ile
                165                 170                 175

Pro Gln Gly Asn Thr Glu Glu Asp Thr Arg Met Phe Val Asp Thr Val
            180                 185                 190

Val Lys Ser Asn Leu Gln Asn Leu Ala Val Ile Ser Thr Ala Ser Pro
        195                 200                 205

Thr


<210> SEQ ID NO 89
<211> LENGTH: 191
<212> TYPE: PRT
<213> ORGANISM: Arabidopsis sp.
<220> FEATURE:
<223> OTHER INFORMATION: PYR/PYL receptor polypeptide PYR1

<400> SEQUENCE: 89

Met Pro Ser Glu Leu Thr Pro Glu Glu Arg Ser Glu Leu Lys Asn Ser
 1               5                  10                  15

Ile Ala Glu Phe His Thr Tyr Gln Leu Asp Pro Gly Ser Cys Ser Ser
            20                  25                  30

Leu His Ala Gln Arg Ile His Ala Pro Pro Glu Leu Val Trp Ser Ile
        35                  40                  45

Val Arg Arg Phe Asp Lys Pro Gln Thr Tyr Lys His Phe Ile Lys Ser
    50                  55                  60

Cys Ser Val Glu Gln Asn Phe Glu Met Arg Val Gly Cys Thr Arg Asp
65                  70                  75                  80

Val Ile Val Ile Ser Gly Leu Pro Ala Asn Thr Ser Thr Glu Arg Leu
                85                  90                  95

Asp Ile Leu Asp Asp Glu Arg Arg Val Thr Gly Phe Ser Ile Ile Gly
            100                 105                 110

Gly Glu His Arg Leu Thr Asn Tyr Lys Ser Val Thr Thr Val His Arg
        115                 120                 125

Phe Glu Lys Glu Asn Arg Ile Trp Thr Val Val Leu Glu Ser Tyr Val
    130                 135                 140

Val Asp Met Pro Glu Gly Asn Ser Glu Asp Asp Thr Arg Met Phe Ala
145                 150                 155                 160

Asp Thr Val Val Lys Leu Asn Leu Gln Lys Leu Ala Thr Val Ala Glu
                165                 170                 175

Ala Met Ala Arg Asn Ser Gly Asp Gly Ser Gly Ser Gln Val Thr
            180                 185                 190


<210> SEQ ID NO 90
<211> LENGTH: 166
<212> TYPE: PRT
<213> ORGANISM: Arabidopsis sp.
<220> FEATURE:
<223> OTHER INFORMATION: PYR/PYL receptor polypeptide PYL1

<400> SEQUENCE: 90

Met Ala Asn Ser Glu Ser Ser Ser Ser Pro Val Asn Glu Glu Glu Asn
 1               5                  10                  15

Ser Gln Arg Ile Ser Thr Leu His His Gln Thr Met Pro Ser Asp Leu
            20                  25                  30

Thr Gln Asp Glu Phe Thr Gln Leu Ser Gln Ser Ile Ala Glu Phe His
        35                  40                  45
```

-continued

```
Thr Tyr Arg Asp Val Asn Val Ile Ser Gly Leu Pro Ala Asn Thr Ser
    50                  55                  60

Arg Glu Arg Leu Asp Leu Leu Asp Asp Asp Arg Arg Val Thr Gly Phe
65                  70                  75                  80

Ser Ile Thr Gly Gly Glu His Arg Leu Arg Asn Tyr Lys Ser Val Thr
                85                  90                  95

Thr Val His Arg Phe Glu Lys Glu Glu Glu Glu Glu Arg Ile Trp Thr
            100                 105                 110

Val Val Leu Glu Ser Tyr Val Val Asp Val Pro Glu Gly Asn Ser Glu
        115                 120                 125

Glu Asp Thr Arg Leu Phe Ala Asp Thr Val Ile Arg Leu Asn Leu Gln
    130                 135                 140

Lys Leu Ala Ser Ile Thr Glu Ala Met Asn Arg Asn Asn Asn Asn Asn
145                 150                 155                 160

Asn Ser Ser Gln Val Arg
                165
```

<210> SEQ ID NO 91
<211> LENGTH: 50
<212> TYPE: PRT
<213> ORGANISM: Artificial Sequence
<220> FEATURE:
<223> OTHER INFORMATION: synthetic PYR/PYL receptor polypeptide consensus sequence
<220> FEATURE:
<221> NAME/KEY: VARIANT
<222> LOCATION: (1)...(50)
<223> OTHER INFORMATION: Xaa = any amino acid

<400> SEQUENCE: 91

```
Gly Xaa Xaa Arg Xaa Val Xaa Xaa Xaa Ser Gly Xaa Pro Ala Xaa Xaa
 1               5                  10                  15

Ser Xaa Glu Xaa Leu Xaa Xaa Xaa Asp Xaa Xaa Xaa Xaa Xaa Xaa Xaa
            20                  25                  30

Xaa Xaa Xaa Xaa Gly Gly Xaa His Arg Leu Xaa Asn Tyr Lys Ser Xaa
        35                  40                  45

Xaa Xaa
    50
```

<210> SEQ ID NO 92
<211> LENGTH: 41
<212> TYPE: PRT
<213> ORGANISM: Artificial Sequence
<220> FEATURE:
<223> OTHER INFORMATION: synthetic PYR/PYL receptor polypeptide consensus sequence
<220> FEATURE:
<221> NAME/KEY: VARIANT
<222> LOCATION: (1)...(41)
<223> OTHER INFORMATION: Xaa = any amino acid

<400> SEQUENCE: 92

```
Xaa Xaa Xaa Xaa Xaa Xaa Xaa Xaa Xaa Glu Ser Xaa Xaa Val Asp Xaa
 1               5                  10                  15

Pro Xaa Gly Asn Xaa Xaa Xaa Xaa Thr Xaa Xaa Phe Xaa Xaa Xaa Xaa
            20                  25                  30

Xaa Xaa Xaa Asn Leu Xaa Xaa Leu Xaa
        35                  40
```

<210> SEQ ID NO 93
<211> LENGTH: 36
<212> TYPE: PRT

<213> ORGANISM: Artificial Sequence
<220> FEATURE:
<223> OTHER INFORMATION: synthetic PYR/PYL receptor polypeptide consensus sequence
<220> FEATURE:
<221> NAME/KEY: VARIANT
<222> LOCATION: (1)...(36)
<223> OTHER INFORMATION: Xaa = any amino acid

<400> SEQUENCE: 93

```
Cys Xaa Ser Xaa Xaa Xaa Xaa Xaa Xaa Xaa Ala Pro Xaa Xaa Xaa Xaa
 1               5                  10                  15

Trp Xaa Xaa Xaa Xaa Xaa Phe Xaa Xaa Pro Xaa Xaa Xaa Xaa Xaa Phe
            20                  25                  30

Xaa Xaa Xaa Cys
        35
```

<210> SEQ ID NO 94
<211> LENGTH: 25
<212> TYPE: PRT
<213> ORGANISM: Artificial Sequence
<220> FEATURE:
<223> OTHER INFORMATION: synthetic PYR/PYL receptor polypeptide consensus sequence
<220> FEATURE:
<221> NAME/KEY: VARIANT
<222> LOCATION: (1)...(25)
<223> OTHER INFORMATION: Xaa = any amino acid

<400> SEQUENCE: 94

```
Gly Xaa Xaa Arg Xaa Val Xaa Xaa Xaa Ser Xaa Xaa Pro Ala Xaa Xaa
 1               5                  10                  15

Ser Xaa Glu Xaa Leu Xaa Xaa Xaa Asp
            20                  25
```

<210> SEQ ID NO 95
<211> LENGTH: 11
<212> TYPE: PRT
<213> ORGANISM: Artificial Sequence
<220> FEATURE:
<223> OTHER INFORMATION: synthetic PYR/PYL receptor polypeptide consensus sequence
<220> FEATURE:
<221> NAME/KEY: VARIANT
<222> LOCATION: (1)...(11)
<223> OTHER INFORMATION: Xaa = any amino acid

<400> SEQUENCE: 95

```
Gly Gly Xaa His Arg Leu Xaa Asn Tyr Xaa Ser
 1               5                  10
```

<210> SEQ ID NO 96
<211> LENGTH: 36
<212> TYPE: PRT
<213> ORGANISM: Artificial Sequence
<220> FEATURE:
<223> OTHER INFORMATION: synthetic PYR/PYL receptor polypeptide PYR1 to PYL12 consensus sequence
<220> FEATURE:
<221> NAME/KEY: VARIANT
<222> LOCATION: (1)...(36)
<223> OTHER INFORMATION: Xaa = any amino acid

<400> SEQUENCE: 96

```
Cys Xaa Ser Xaa Xaa Xaa Xaa Xaa Xaa Xaa Ala Pro Xaa Xaa Xaa Xaa
 1               5                  10                  15

Trp Xaa Xaa Xaa Xaa Xaa Phe Xaa Xaa Pro Xaa Xaa Xaa Lys Xaa Phe
            20                  25                  30
```

```
Xaa Xaa Xaa Cys
        35


<210> SEQ ID NO 97
<211> LENGTH: 25
<212> TYPE: PRT
<213> ORGANISM: Artificial Sequence
<220> FEATURE:
<223> OTHER INFORMATION: synthetic PYR/PYL receptor polypeptide PYR1 to
      PYL12 consensus sequence
<220> FEATURE:
<221> NAME/KEY: VARIANT
<222> LOCATION: (1)...(25)
<223> OTHER INFORMATION: Xaa = any amino acid

<400> SEQUENCE: 97

Gly Xaa Xaa Arg Xaa Val Xaa Xaa Xaa Ser Xaa Leu Pro Ala Xaa Xaa
 1               5                  10                  15

Ser Xaa Glu Xaa Leu Xaa Xaa Xaa Asp
            20                  25


<210> SEQ ID NO 98
<211> LENGTH: 11
<212> TYPE: PRT
<213> ORGANISM: Artificial Sequence
<220> FEATURE:
<223> OTHER INFORMATION: synthetic PYR/PYL receptor polypeptide PYR1 to
      PYL12 consensus sequence
<220> FEATURE:
<221> NAME/KEY: VARIANT
<222> LOCATION: (1)...(11)
<223> OTHER INFORMATION: Xaa = any amino acid

<400> SEQUENCE: 98

Gly Gly Xaa His Arg Leu Xaa Asn Tyr Xaa Ser
 1               5                  10


<210> SEQ ID NO 99
<211> LENGTH: 31
<212> TYPE: PRT
<213> ORGANISM: Artificial Sequence
<220> FEATURE:
<223> OTHER INFORMATION: synthetic PYR/PYL receptor polypeptide PYR1 to
      PYL12 consensus sequence
<220> FEATURE:
<221> NAME/KEY: VARIANT
<222> LOCATION: (1)...(31)
<223> OTHER INFORMATION: Xaa = any amino acid

<400> SEQUENCE: 99

Glu Ser Xaa Xaa Val Asp Xaa Pro Xaa Gly Asn Xaa Xaa Xaa Xaa Thr
 1               5                  10                  15

Xaa Xaa Phe Xaa Xaa Xaa Xaa Xaa Xaa Xaa Asn Leu Xaa Xaa Leu
            20                  25                  30


<210> SEQ ID NO 100
<211> LENGTH: 45
<212> TYPE: PRT
<213> ORGANISM: Artificial Sequence
<220> FEATURE:
<223> OTHER INFORMATION: synthetic PYR/PYL receptor polypeptide PYR1 to
      PYL6 consensus sequence
<220> FEATURE:
<221> NAME/KEY: VARIANT
<222> LOCATION: (1)...(45)
<223> OTHER INFORMATION: Xaa = any amino acid

<400> SEQUENCE: 100
```

```
His Xaa Xaa Xaa Xaa Xaa Xaa Xaa Xaa Cys Xaa Ser Xaa Xaa Xaa Xaa
 1               5                  10                  15

Xaa Xaa Xaa Ala Pro Xaa Xaa Xaa Xaa Trp Xaa Xaa Xaa Xaa Xaa Phe
            20                  25                  30

Xaa Xaa Pro Xaa Xaa Tyr Lys Xaa Phe Xaa Xaa Xaa Cys
        35                  40                  45


<210> SEQ ID NO 101
<211> LENGTH: 48
<212> TYPE: PRT
<213> ORGANISM: Artificial Sequence
<220> FEATURE:
<223> OTHER INFORMATION: synthetic PYR/PYL receptor polypeptide PYR1 to
      PYL6 consensus sequence
<220> FEATURE:
<221> NAME/KEY: VARIANT
<222> LOCATION: (1)...(48)
<223> OTHER INFORMATION: Xaa = any amino acid

<400> SEQUENCE: 101

Val Gly Arg Xaa Val Xaa Val Xaa Ser Gly Leu Pro Ala Xaa Xaa Ser
 1               5                  10                  15

Xaa Glu Xaa Leu Xaa Xaa Xaa Asp Xaa Xaa Xaa Xaa Xaa Xaa Xaa Phe
            20                  25                  30

Xaa Xaa Xaa Gly Gly Xaa His Arg Leu Xaa Asn Tyr Xaa Ser Val Thr
        35                  40                  45


<210> SEQ ID NO 102
<211> LENGTH: 33
<212> TYPE: PRT
<213> ORGANISM: Artificial Sequence
<220> FEATURE:
<223> OTHER INFORMATION: synthetic PYR/PYL receptor polypeptide PYR1 to
      PYL6 consensus sequence
<220> FEATURE:
<221> NAME/KEY: VARIANT
<222> LOCATION: (1)...(33)
<223> OTHER INFORMATION: Xaa = any amino acid

<400> SEQUENCE: 102

Val Xaa Glu Ser Tyr Xaa Val Asp Xaa Pro Xaa Gly Asn Xaa Xaa Xaa
 1               5                  10                  15

Xaa Thr Xaa Xaa Phe Xaa Asp Xaa Xaa Xaa Xaa Xaa Asn Leu Gln Xaa
            20                  25                  30

Leu


<210> SEQ ID NO 103
<211> LENGTH: 50
<212> TYPE: PRT
<213> ORGANISM: Artificial Sequence
<220> FEATURE:
<223> OTHER INFORMATION: synthetic PYR/PYL receptor polypeptide PYL7 to
      PYL10 consensus sequence
<220> FEATURE:
<221> NAME/KEY: VARIANT
<222> LOCATION: (1)...(50)
<223> OTHER INFORMATION: Xaa = any amino acid

<400> SEQUENCE: 103

His Xaa His Xaa Xaa Xaa Xaa Xaa Gln Cys Xaa Ser Xaa Leu Val Lys
 1               5                  10                  15

Xaa Ile Xaa Ala Pro Xaa His Xaa Val Trp Ser Xaa Val Arg Arg Phe
            20                  25                  30

Asp Xaa Pro Gln Lys Tyr Lys Pro Phe Xaa Ser Arg Cys Xaa Val Xaa
        35                  40                  45
```

```
Gly Xaa
    50


<210> SEQ ID NO 104
<211> LENGTH: 65
<212> TYPE: PRT
<213> ORGANISM: Artificial Sequence
<220> FEATURE:
<223> OTHER INFORMATION: synthetic PYR/PYL receptor polypeptide PYL7 to
      PYL10 consensus sequence
<220> FEATURE:
<221> NAME/KEY: VARIANT
<222> LOCATION: (1)...(65)
<223> OTHER INFORMATION: Xaa = any amino acid

<400> SEQUENCE: 104

Glu Xaa Gly Xaa Xaa Arg Glu Val Xaa Xaa Lys Ser Gly Leu Pro Ala
 1               5                  10                  15

Thr Xaa Ser Thr Glu Xaa Leu Glu Xaa Leu Asp Asp Xaa Glu His Ile
            20                  25                  30

Leu Xaa Ile Xaa Ile Xaa Gly Gly Asp His Arg Leu Lys Asn Tyr Ser
        35                  40                  45

Ser Xaa Xaa Xaa Xaa His Xaa Glu Xaa Ile Xaa Gly Xaa Xaa Gly Thr
    50                  55                  60

Xaa
65


<210> SEQ ID NO 105
<211> LENGTH: 40
<212> TYPE: PRT
<213> ORGANISM: Artificial Sequence
<220> FEATURE:
<223> OTHER INFORMATION: synthetic PYR/PYL receptor polypeptide PYL7 to
      PYL10 consensus sequence
<220> FEATURE:
<221> NAME/KEY: VARIANT
<222> LOCATION: (1)...(40)
<223> OTHER INFORMATION: Xaa = any amino acid

<400> SEQUENCE: 105

Xaa Xaa Glu Ser Phe Val Val Asp Val Pro Xaa Gly Asn Thr Lys Xaa
 1               5                  10                  15

Xaa Thr Cys Xaa Phe Val Glu Xaa Leu Ile Xaa Cys Asn Leu Xaa Ser
            20                  25                  30

Leu Ala Xaa Xaa Xaa Glu Arg Leu
        35                  40


<210> SEQ ID NO 106
<211> LENGTH: 44
<212> TYPE: PRT
<213> ORGANISM: Artificial Sequence
<220> FEATURE:
<223> OTHER INFORMATION: synthetic PYR/PYL receptor polypeptide PYL11 to
      PYL13 consensus sequence
<220> FEATURE:
<221> NAME/KEY: VARIANT
<222> LOCATION: (1)...(44)
<223> OTHER INFORMATION: Xaa = any amino acid

<400> SEQUENCE: 106

Cys Xaa Ser Xaa Xaa Val Xaa Thr Ile Xaa Ala Pro Leu Xaa Leu Val
 1               5                  10                  15

Trp Ser Ile Leu Arg Xaa Phe Asp Xaa Pro Xaa Xaa Xaa Xaa Xaa Phe
            20                  25                  30
```

```
Val Lys Xaa Cys Xaa Xaa Xaa Ser Gly Xaa Gly Gly
        35                  40


<210> SEQ ID NO 107
<211> LENGTH: 49
<212> TYPE: PRT
<213> ORGANISM: Artificial Sequence
<220> FEATURE:
<223> OTHER INFORMATION: synthetic PYR/PYL receptor polypeptide PYL11 to
      PYL13 consensus sequence
<220> FEATURE:
<221> NAME/KEY: VARIANT
<222> LOCATION: (1)...(49)
<223> OTHER INFORMATION: Xaa = any amino acid

<400> SEQUENCE: 107

Gly Ser Val Arg Xaa Val Thr Xaa Val Ser Xaa Xaa Pro Ala Xaa Phe
 1               5                  10                  15

Ser Xaa Glu Arg Leu Xaa Glu Leu Asp Asp Glu Ser His Val Met Xaa
            20                  25                  30

Xaa Ser Ile Ile Gly Gly Xaa His Arg Leu Val Asn Tyr Xaa Ser Lys
        35                  40                  45

Thr


<210> SEQ ID NO 108
<211> LENGTH: 188
<212> TYPE: PRT
<213> ORGANISM: Zea mays
<220> FEATURE:
<223> OTHER INFORMATION: corn (maize) PYR/PYL receptor polypeptide

<400> SEQUENCE: 108

Met Glu Pro His Met Glu Ser Ala Leu Arg Gln Gly Leu Ser Glu Ala
 1               5                  10                  15

Glu Gln Arg Glu Leu Glu Gly Val Val Arg Ala His His Thr Phe Pro
            20                  25                  30

Gly Arg Ala Pro Gly Thr Cys Thr Ser Leu Val Thr Gln Arg Val Asp
        35                  40                  45

Ala Pro Leu Ala Ala Val Trp Pro Ile Val Arg Gly Phe Gly Ser Pro
    50                  55                  60

Gln Arg Tyr Lys His Phe Ile Lys Ser Cys Asp Leu Lys Ala Gly Asp
65                  70                  75                  80

Gly Ala Thr Val Gly Ser Val Arg Glu Val Thr Val Val Ser Gly Leu
                85                  90                  95

Pro Ala Ser Thr Ser Thr Glu Arg Leu Glu Ile Leu Asp Asp His Arg
            100                 105                 110

His Ile Leu Ser Phe Arg Val Val Gly Gly Asp His Arg Leu Arg Asn
        115                 120                 125

Tyr Arg Ser Val Thr Ser Val Thr Glu Phe Gln Pro Gly Pro Tyr Cys
    130                 135                 140

Val Val Leu Glu Ser Tyr Val Val Asp Val Pro Asp Gly Asn Thr Glu
145                 150                 155                 160

Glu Asp Thr Arg Met Phe Thr Asp Thr Val Val Lys Leu Asn Leu Gln
                165                 170                 175

Lys Leu Ala Ala Ile Ala Thr Ser Ser Ser Ala Asn
            180                 185


<210> SEQ ID NO 109
<211> LENGTH: 205
<212> TYPE: PRT
```

<213> ORGANISM: Zea mays
<220> FEATURE:
<223> OTHER INFORMATION: corn (maize) PYR/PYL receptor polypeptide

<400> SEQUENCE: 109

```
Met Asp Gln Gln Gly Ala Gly Gly Asp Val Glu Val Pro Ala Gly Leu
 1               5                  10                  15

Gly Leu Thr Ala Ala Glu Tyr Glu Gln Leu Arg Pro Thr Val Asp Ala
            20                  25                  30

His His Arg Tyr Ala Val Gly Glu Gly Gln Cys Ser Ser Leu Leu Ala
        35                  40                  45

Gln Arg Ile His Ala Pro Pro Ala Ala Val Trp Ala Ile Val Arg Arg
    50                  55                  60

Phe Asp Cys Pro Gln Val Tyr Lys His Phe Ile Arg Ser Cys Ala Val
65                  70                  75                  80

Arg Pro Asp Pro Asp Ala Gly Asp Ala Leu Arg Pro Gly Arg Leu Arg
                85                  90                  95

Glu Val Cys Val Ile Ser Gly Leu Pro Ala Ser Thr Ser Thr Glu Arg
            100                 105                 110

Leu Asp His Leu Asp Asp Ala Ala Arg Val Phe Gly Phe Ser Ile Thr
        115                 120                 125

Gly Gly Glu His Arg Leu Arg Asn Tyr Arg Ser Val Thr Thr Val Ser
    130                 135                 140

Glu Leu Ala Gly Pro Gly Ile Cys Thr Val Val Leu Glu Ser Tyr Ala
145                 150                 155                 160

Val Asp Val Pro Asp Gly Asn Thr Glu Asp Asp Thr Arg Leu Phe Ala
                165                 170                 175

Asp Thr Val Ile Arg Leu Asn Leu Gln Lys Leu Lys Ser Val Ala Glu
            180                 185                 190

Ala Ser Thr Ser Ser Ser Ala Pro Pro Pro Pro Ser Glu
        195                 200                 205
```

<210> SEQ ID NO 110
<211> LENGTH: 220
<212> TYPE: PRT
<213> ORGANISM: Zea mays
<220> FEATURE:
<223> OTHER INFORMATION: corn (maize) PYR/PYL receptor polypeptide

<400> SEQUENCE: 110

```
Met Pro Cys Ile Gln Ala Ser Ser Pro Gly Gly Met Pro His Gln His
 1               5                  10                  15

Gly Arg Gly Arg Val Leu Gly Gly Gly Val Gly Cys Ala Ala Glu Val
            20                  25                  30

Ala Ala Ala Val Ala Ala Ser Ala Gly Gly Met Arg Cys Gly Ala His
        35                  40                  45

Asp Gly Glu Val Pro Ala Glu Ala Ala Arg His His Glu His Ala Ala
    50                  55                  60

Ala Gly Pro Gly Arg Cys Cys Ser Ala Val Val Gln His Val Ala Ala
65                  70                  75                  80

Pro Ala Ala Ala Val Trp Ser Val Val Arg Arg Phe Asp Gln Pro Gln
                85                  90                  95

Val Tyr Lys Arg Phe Val Arg Ser Cys Ala Leu Leu Ala Gly Asp Gly
            100                 105                 110

Gly Val Gly Thr Leu Arg Glu Val Arg Val Val Ser Gly Leu Pro Ala
        115                 120                 125
```

```
Ala Ser Ser Arg Glu Arg Leu Glu Val Leu Asp Asp Glu Ser His Val
    130                 135                 140

Leu Ser Phe Arg Val Val Gly Gly Glu His Arg Leu Arg Asn Tyr Leu
145                 150                 155                 160

Ser Val Thr Thr Val His Pro Ser Pro Ala Ala Pro Asp Ala Ala Thr
                165                 170                 175

Val Val Val Glu Ser Tyr Val Val Asp Val Pro Pro Gly Asn Thr Pro
            180                 185                 190

Glu Asp Thr Arg Val Phe Val Asp Thr Ile Val Lys Cys Asn Leu Gln
        195                 200                 205

Ser Leu Ala Thr Thr Ala Glu Lys Leu Ala Ala Val
    210                 215                 220


<210> SEQ ID NO 111
<211> LENGTH: 221
<212> TYPE: PRT
<213> ORGANISM: Glycine max
<220> FEATURE:
<223> OTHER INFORMATION: soybean PYR/PYL receptor polypeptide

<400> SEQUENCE: 111

Met Glu Lys Ala Glu Ser Ser Ala Ser Thr Ser Glu Pro Asp Ser Asp
 1               5                  10                  15

Glu Asn His His Arg His Pro Thr Asn His His Ile Asn Pro Pro Ser
            20                  25                  30

Gly Leu Thr Pro Leu Glu Phe Ala Ser Leu Ile Pro Ser Val Ala Glu
        35                  40                  45

His His Ser Tyr Leu Val Gly Ser Gly Gln Cys Ser Ser Leu Leu Ala
    50                  55                  60

Gln Arg Val Gln Ala Pro Pro Asp Ala Val Trp Ser Val Val Arg Arg
65                  70                  75                  80

Phe Asp Lys Pro Gln Thr Tyr Lys His Phe Ile Lys Ser Cys Ala Val
                85                  90                  95

Lys Glu Pro Phe His Met Ala Val Gly Val Thr Arg Asp Val Asn Val
            100                 105                 110

Ile Ser Gly Leu Pro Ala Ala Thr Ser Thr Glu Arg Leu Asp Leu Leu
        115                 120                 125

Asp Asp Ile Arg Cys Val Thr Gly Phe Ser Ile Ile Gly Gly Glu His
    130                 135                 140

Arg Leu Arg Asn Tyr Arg Ser Val Thr Thr Val His Ser Phe Glu Asp
145                 150                 155                 160

Asp Ala Asp Asp Gly Lys Ile Tyr Thr Val Val Leu Glu Ser Tyr Val
                165                 170                 175

Val Asp Val Pro Asp Gly Asn Thr Glu Glu Asp Thr Arg Leu Phe Ala
            180                 185                 190

Asp Thr Val Val Lys Leu Asn Leu Gln Lys Leu Ala Ser Val Thr Glu
        195                 200                 205

Gly Thr Asn Arg Asp Gly Asp Gly Lys Ser His Ser Arg
    210                 215                 220


<210> SEQ ID NO 112
<211> LENGTH: 214
<212> TYPE: PRT
<213> ORGANISM: Glycine max
<220> FEATURE:
<223> OTHER INFORMATION: soybean PYR/PYL receptor polypeptide

<400> SEQUENCE: 112
```

```
Met Glu Lys Thr His Ser Ser Ser Ala Glu Glu Gln Asp Pro Thr Arg
 1               5                  10                  15

Arg His Leu Asp Pro Pro Pro Gly Leu Thr Ala Glu Glu Phe Glu Asp
            20                  25                  30

Leu Lys Pro Ser Val Leu Glu His His Thr Tyr Ser Val Thr Pro Thr
        35                  40                  45

Arg Gln Ser Ser Ser Leu Leu Ala Gln Arg Ile His Ala Pro Pro His
    50                  55                  60

Ala Val Trp Ser Val Val Arg Cys Phe Asp Asn Pro Gln Ala Tyr Lys
65                  70                  75                  80

His Phe Ile Lys Ser Cys His Val Lys Glu Gly Phe Gln Leu Ala Val
                85                  90                  95

Gly Ser Thr Arg Asp Val His Val Ile Ser Gly Leu Pro Ala Ala Thr
            100                 105                 110

Ser Thr Glu Arg Leu Asp Leu Leu Asp Asp Asp Arg His Val Ile Gly
        115                 120                 125

Phe Thr Ile Val Gly Gly Asp His Arg Leu Arg Asn Tyr Arg Ser Val
    130                 135                 140

Thr Ser Val His Gly Phe Glu Cys Asp Gly Lys Ile Trp Thr Val Val
145                 150                 155                 160

Leu Glu Ser Tyr Val Val Asp Val Pro Glu Gly Asn Thr Glu Glu Asp
                165                 170                 175

Thr Arg Leu Phe Ala Asp Thr Val Val Lys Leu Asn Leu Gln Lys Leu
            180                 185                 190

Ala Ser Val Ser Glu Gly Met Cys Gly Asp Gly Asp Gly Asp Gly Asp
        195                 200                 205

Gly Lys Gly Asn Lys Ser
    210


<210> SEQ ID NO 113
<211> LENGTH: 216
<212> TYPE: PRT
<213> ORGANISM: Glycine max
<220> FEATURE:
<223> OTHER INFORMATION: soybean PYR/PYL receptor polypeptide

<400> SEQUENCE: 113

Met Leu Gln Asn Ser Ser Met Ser Ser Leu Leu Leu His Arg Ile Asn
 1               5                  10                  15

Gly Gly Gly Gly Ala Thr Thr Ala Thr Asn Cys His Asp Thr Val Phe
            20                  25                  30

Met Thr Val Pro Asp Gly Val Ala Arg Tyr His Thr His Ala Val Ala
        35                  40                  45

Pro Asn Gln Cys Cys Ser Ser Val Ala Gln Glu Ile Gly Ala Ser Val
    50                  55                  60

Ala Thr Val Trp Ser Val Leu Arg Arg Phe Asp Asn Pro Gln Ala Tyr
65                  70                  75                  80

Lys His Phe Val Lys Ser Cys His Val Ile Gly Gly Asp Gly Asp Val
                85                  90                  95

Gly Thr Leu Arg Glu Val His Val Ile Ser Gly Leu Pro Ala Ala Arg
            100                 105                 110

Ser Thr Glu Arg Leu Glu Ile Leu Asp Asp Glu Arg His Val Ile Ser
        115                 120                 125

Phe Ser Val Val Gly Gly Asp His Arg Leu Ala Asn Tyr Arg Ser Val
    130                 135                 140
```

Thr Thr Leu His Pro Thr Ala Ser Ser Ala Ser Gly Gly Cys Ser Gly
145 150 155 160

Thr Val Val Val Glu Ser Tyr Val Val Asp Val Pro Pro Gly Asn Thr
165 170 175

Arg Glu Asp Thr Arg Val Phe Val Asp Thr Ile Val Lys Cys Asn Leu
180 185 190

Gln Ser Leu Ala Gln Thr Ala Glu Asn Leu Thr Leu Arg Lys Asn Asn
195 200 205

Asn Asn Asp Tyr Lys Cys Cys Ser
210 215

<210> SEQ ID NO 114
<211> LENGTH: 208
<212> TYPE: PRT
<213> ORGANISM: Glycine max
<220> FEATURE:
<223> OTHER INFORMATION: soybean PYR/PYL receptor polypeptide

<400> SEQUENCE: 114

Met Thr Ser Leu Gln Phe His Arg Phe Asn Pro Ala Thr Asp Thr Ser
1 5 10 15

Thr Ala Ile Ala Asn Gly Val Asn Cys Pro Lys Pro Pro Ser Thr Leu
20 25 30

Arg Leu Leu Ala Lys Val Ser Leu Ser Val Pro Glu Thr Val Ala Arg
35 40 45

His His Ala His Pro Val Gly Pro Asn Gln Cys Cys Ser Val Val Ile
50 55 60

Gln Ala Ile Asp Ala Pro Val Ser Ala Val Trp Pro Val Val Arg Arg
65 70 75 80

Phe Asp Asn Pro Gln Ala Tyr Lys His Phe Val Lys Ser Cys His Val
85 90 95

Val Ala Ala Ala Gly Gly Gly Glu Asp Gly Ile Arg Val Gly Ala Leu
100 105 110

Arg Glu Val Arg Val Val Ser Gly Leu Pro Ala Val Ser Ser Thr Glu
115 120 125

Arg Leu Glu Ile Leu Asp Asp Glu Arg His Val Met Ser Phe Ser Val
130 135 140

Val Gly Gly Asp His Arg Leu Arg Asn Tyr Arg Ser Val Thr Thr Leu
145 150 155 160

His Gly Asp Gly Asn Gly Gly Thr Val Val Ile Glu Ser Tyr Val Val
165 170 175

Asp Val Pro Pro Gly Asn Thr Lys Glu Glu Thr Cys Val Phe Val Asp
180 185 190

Thr Ile Val Arg Cys Asn Leu Gln Ser Leu Ala Gln Ile Ala Glu Thr
195 200 205

<210> SEQ ID NO 115
<211> LENGTH: 176
<212> TYPE: PRT
<213> ORGANISM: Glycine max
<220> FEATURE:
<223> OTHER INFORMATION: soybean PYR/PYL receptor polypeptide

<400> SEQUENCE: 115

Ala Tyr Pro Val Leu Gly Leu Thr Pro Glu Glu Phe Ser Glu Leu Glu
1 5 10 15

Ser Ile Ile Asn Thr His His Lys Phe Glu Pro Ser Pro Glu Ile Cys

```
            20                  25                  30

Ser Ser Ile Ile Ala Gln Arg Ile Asp Ala Pro Ala His Thr Val Trp
        35                  40                  45

Pro Leu Val Arg Ser Phe Glu Asn Pro Gln Lys Tyr Lys His Phe Val
    50                  55                  60

Lys Ser Cys Asn Met Arg Ser Gly Asp Gly Gly Val Gly Ser Ile Arg
65                  70                  75                  80

Glu Val Thr Val Val Ser Gly Leu Pro Ala Ser Thr Ser Thr Glu Arg
                85                  90                  95

Leu Glu Ile Leu Asp Asp Asp Lys His Leu Leu Ser Phe Arg Val Val
            100                 105                 110

Gly Gly Glu His Arg Leu His Asn Tyr Arg Ser Val Thr Ser Val Asn
        115                 120                 125

Glu Phe Lys Asn Pro Asp Asn Gly Lys Val Tyr Thr Ile Val Leu Glu
    130                 135                 140

Ser Tyr Val Val Asp Ile Pro Glu Gly Asn Thr Gly Val Asp Thr Lys
145                 150                 155                 160

Met Phe Val Asp Thr Val Val Lys Leu Asn Leu Gln Lys Leu Gly Glu
                165                 170                 175


<210> SEQ ID NO 116
<211> LENGTH: 172
<212> TYPE: PRT
<213> ORGANISM: Glycine max
<220> FEATURE:
<223> OTHER INFORMATION: soybean PYR/PYL receptor polypeptide

<400> SEQUENCE: 116

Glu Phe Thr Glu Leu Glu Ser Thr Ile Asn Thr His His Lys Phe Glu
 1               5                  10                  15

Ala Ser Pro Glu Ile Cys Ser Ser Ile Ile Ala Gln Arg Ile Asp Ala
            20                  25                  30

Pro Ala His Thr Val Trp Pro Leu Val Arg Ser Phe Glu Asn Pro Gln
        35                  40                  45

Lys Tyr Lys His Phe Val Lys Ser Cys Asn Met Arg Ser Gly Asp Gly
    50                  55                  60

Gly Val Gly Ser Ile Arg Glu Val Thr Val Val Ser Gly Leu Pro Ala
65                  70                  75                  80

Ser Thr Ser Thr Glu Arg Leu Glu Ile Leu Asp Asp Asp Asn His Leu
                85                  90                  95

Leu Ser Phe Arg Val Val Gly Gly Glu His Arg Leu His Asn Tyr Arg
            100                 105                 110

Ser Val Thr Ser Val Asn Glu Phe Lys Arg Pro Asp Asn Gly Lys Val
        115                 120                 125

Tyr Thr Ile Val Leu Glu Ser Tyr Val Val Asp Ile Pro Glu Gly Asn
    130                 135                 140

Thr Gly Val Asp Thr Lys Met Phe Val Asp Thr Val Val Lys Leu Asn
145                 150                 155                 160

Leu Gln Lys Leu Gly Glu Val Ala Met Ala Thr Asn
                165                 170


<210> SEQ ID NO 117
<211> LENGTH: 191
<212> TYPE: PRT
<213> ORGANISM: Glycine max
<220> FEATURE:
<223> OTHER INFORMATION: soybean PYR/PYL receptor polypeptide
```

<400> SEQUENCE: 117

Met Thr Glu Leu Ser Ser Arg Glu Val Glu Tyr Ile Arg Arg His His
1 5 10 15

Ser Lys Ala Ala Glu Asp Asn Gln Cys Ala Ser Ala Leu Val Lys His
20 25 30

Ile Arg Ala Pro Leu Pro Leu Val Trp Ser Leu Val Arg Arg Phe Asp
35 40 45

Glu Pro Gln Lys Tyr Lys Pro Phe Val Ser Arg Cys Val Val Arg Gly
50 55 60

Asn Leu Glu Ile Gly Ser Leu Arg Glu Val Asp Val Lys Ser Gly Leu
65 70 75 80

Pro Ala Thr Thr Ser Thr Glu Arg Leu Glu Ile Leu Asp Asp Asn His
85 90 95

His Ile Leu Ser Val Arg Ile Ile Gly Gly Asp His Arg Leu Arg Asn
100 105 110

Tyr Ser Ser Ile Met Ser Leu His Pro Glu Ile Val Asp Gly Arg Pro
115 120 125

Gly Thr Leu Val Ile Glu Ser Phe Val Val Asp Ile Pro Glu Gly Asn
130 135 140

Thr Lys Asp Glu Thr Cys Tyr Phe Val Glu Ala Leu Ile Lys Cys Asn
145 150 155 160

Leu Lys Ser Leu Ala Asp Val Ser Glu Gly Leu Thr Leu Gln Asp His
165 170 175

Thr Glu Pro Ile Asp Arg Lys Tyr Glu Leu Leu Ile Thr Arg Gly
180 185 190

<210> SEQ ID NO 118
<211> LENGTH: 185
<212> TYPE: PRT
<213> ORGANISM: Glycine max
<220> FEATURE:
<223> OTHER INFORMATION: soybean PYR/PYL receptor polypeptide

<400> SEQUENCE: 118

Met Asn Gly Gly Glu Ser Tyr Gly Ala Ile Glu Thr Gln Tyr Ile Arg
1 5 10 15

Arg His His Lys His Glu Pro Arg Glu Asn Gln Cys Thr Ser Ala Leu
20 25 30

Val Lys His Ile Arg Ala Pro Val His Leu Val Trp Ser Leu Val Arg
35 40 45

Arg Phe Asp Gln Pro Gln Lys Tyr Lys Pro Phe Val Ser Arg Cys Ile
50 55 60

Met Gln Gly Asp Leu Gly Ile Gly Ser Val Arg Glu Val Asn Val Lys
65 70 75 80

Ser Gly Leu Pro Ala Thr Thr Ser Thr Glu Arg Leu Glu Gln Leu Asp
85 90 95

Asp Glu Glu His Ile Leu Gly Ile Arg Ile Val Gly Gly Asp His Arg
100 105 110

Leu Arg Asn Tyr Ser Ser Ile Ile Thr Val His Pro Glu Val Ile Asp
115 120 125

Gly Arg Pro Gly Thr Met Val Ile Glu Ser Phe Val Val Asp Val Pro
130 135 140

Asp Gly Asn Thr Arg Asp Glu Thr Cys Tyr Phe Val Glu Ala Leu Ile
145 150 155 160

```
Arg Cys Asn Leu Ser Ser Leu Ala Asp Val Ser Glu Arg Met Ala Val
                165                 170                 175

Gln Gly Arg Thr Asn Pro Ile Asn His
            180                 185


<210> SEQ ID NO 119
<211> LENGTH: 178
<212> TYPE: PRT
<213> ORGANISM: Glycine max
<220> FEATURE:
<223> OTHER INFORMATION: soybean PYR/PYL receptor polypeptide

<400> SEQUENCE: 119

Met Ser Pro Asn Asn Pro Ser Thr Ile Val Ser Asp Ala Val Ala Arg
 1               5                  10                  15

His His Thr His Val Val Ser Pro His Gln Cys Cys Ser Ala Val Val
            20                  25                  30

Gln Glu Ile Ala Ala Pro Val Ser Thr Val Trp Ser Val Val Arg Arg
        35                  40                  45

Phe Asp Asn Pro Gln Ala Tyr Lys His Phe Val Lys Ser Cys His Val
    50                  55                  60

Ile Leu Gly Asp Gly Asp Val Gly Thr Leu Arg Glu Val Arg Val Ile
65                  70                  75                  80

Ser Gly Leu Pro Ala Ala Val Ser Thr Glu Arg Leu Asp Val Leu Asp
                85                  90                  95

Asp Glu Arg His Val Ile Gly Phe Ser Met Val Gly Gly Asp His Arg
            100                 105                 110

Leu Ser Asn Tyr Arg Ser Val Thr Ile Leu His Pro Arg Ser Ala Thr
        115                 120                 125

Asp Thr Val Val Val Glu Ser Tyr Val Val Asp Val Pro Ala Gly Asn
    130                 135                 140

Thr Thr Glu Asp Thr Arg Val Phe Val Asp Thr Ile Leu Arg Cys Asn
145                 150                 155                 160

Leu Gln Ser Leu Ala Lys Phe Ala Glu Asn Leu Thr Asn Lys Leu His
                165                 170                 175

Gln Arg


<210> SEQ ID NO 120
<211> LENGTH: 246
<212> TYPE: PRT
<213> ORGANISM: Glycine max
<220> FEATURE:
<223> OTHER INFORMATION: soybean PYR/PYL receptor polypeptide

<400> SEQUENCE: 120

Met Ser Arg Ser His Asn Lys Arg Lys Pro Phe Ser Phe Ile Phe Lys
 1               5                  10                  15

Ile Thr Leu Leu Glu Leu Leu Ser Ser Leu Leu Ser Ser Ser Leu Arg
            20                  25                  30

Phe Ala Met Asp Lys Thr His Ser Gly Glu Glu Gln Asp Pro Asn Pro
        35                  40                  45

Thr His Pro Thr Arg Asn His Leu Asp Pro Pro Pro Gly Leu Thr Pro
    50                  55                  60

Glu Glu Phe Glu Asp Leu Lys Pro Ser Val Leu Glu His His Thr Tyr
65                  70                  75                  80

Ser Val Thr Pro Thr Arg Gln Cys Ser Ser Leu Leu Ala Gln Arg Ile
                85                  90                  95
```

-continued

```
His Ala Pro Pro His Thr Val Trp Thr Val Val Arg Cys Phe Asp Asn
            100                 105                 110

Pro Gln Ala Tyr Lys His Phe Ile Lys Ser Cys His Val Lys Glu Gly
        115                 120                 125

Phe Gln Leu Ala Val Gly Ser Thr Arg Asp Val His Val Ile Ser Gly
    130                 135                 140

Leu Pro Ala Ala Thr Ser Thr Glu Arg Leu Asp Leu Leu Asp Asp Asp
145                 150                 155                 160

Arg His Val Ile Gly Phe Thr Ile Val Gly Gly Asp His Arg Leu Arg
                165                 170                 175

Asn Tyr Arg Ser Val Thr Ser Val His Gly Phe Glu Arg Asp Gly Lys
            180                 185                 190

Ile Trp Thr Val Val Leu Glu Ser Tyr Val Val Asp Val Pro Glu Gly
        195                 200                 205

Asn Thr Glu Glu Asp Thr Arg Leu Phe Ala Asp Thr Val Val Lys Leu
    210                 215                 220

Asn Leu Gln Lys Leu Ala Ser Val Thr Glu Gly Met Cys Gly Asp Ser
225                 230                 235                 240

Asp Gly Lys Gly Asn Asn
                245


<210> SEQ ID NO 121
<211> LENGTH: 223
<212> TYPE: PRT
<213> ORGANISM: Glycine max
<220> FEATURE:
<223> OTHER INFORMATION: soybean PYR/PYL receptor polypeptide

<400> SEQUENCE: 121

Met Glu Lys Ala Glu Ser Ser Ala Ser Thr Ser Glu Pro Asp Ser Asp
 1               5                  10                  15

Asp Asn His His Arg His Pro Thr Asn His His Leu Asn Pro Pro Ser
            20                  25                  30

Gly Leu Thr Pro Leu Glu Phe Ala Ser Leu Val Pro Ser Val Ala Glu
        35                  40                  45

His His Ser Tyr Leu Val Gly Pro Gly Gln Cys Ser Ser Leu Leu Ala
    50                  55                  60

Gln Arg Val His Ala Pro Pro Asp Ala Val Trp Ser Phe Val Arg Arg
65                  70                  75                  80

Phe Asp Lys Pro Gln Thr Tyr Lys His Phe Ile Lys Ser Cys Ala Val
                85                  90                  95

Lys Glu Pro Phe His Met Ala Val Gly Val Thr Arg Asp Val Asn Val
            100                 105                 110

Ile Ser Gly Leu Pro Ala Ala Thr Ser Thr Glu Arg Leu Asp Phe Leu
        115                 120                 125

Asp Asp Val Arg Arg Val Thr Gly Phe Ser Ile Ile Gly Gly Glu His
    130                 135                 140

Arg Leu Arg Asn Tyr Arg Ser Val Thr Thr Val His Ser Phe Asp Asp
145                 150                 155                 160

Asp Asn Ala Ser Ala Asp Gly Lys Ile Tyr Thr Val Val Leu Glu Ser
                165                 170                 175

Tyr Val Val Asp Val Pro Asp Gly Asn Thr Glu Glu Asp Thr Arg Leu
            180                 185                 190

Phe Ala Asp Thr Val Val Lys Leu Asn Leu Gln Lys Leu Ala Ser Val
        195                 200                 205
```

```
Thr Glu Gly Thr Asn Gly Asp Gly Asp Gly Lys Pro His Ser Arg
    210                 215                 220


<210> SEQ ID NO 122
<211> LENGTH: 229
<212> TYPE: PRT
<213> ORGANISM: Glycine max
<220> FEATURE:
<223> OTHER INFORMATION: soybean PYR/PYL receptor polypeptide

<400> SEQUENCE: 122

Met Pro Ser Ser Leu His Phe Asp Arg Phe Asn Pro Ile Thr His Ala
 1               5                  10                  15

Ala Thr Thr Val Ala Ile Ala Asn Gly Val Asn Cys Pro Lys Gln Pro
            20                  25                  30

Gln Ala Pro Pro Ser Ser Thr Ala Ala Arg Arg Leu Val Val Pro Ser
        35                  40                  45

Leu Ser Ser Gly Arg Gly Ile Ala Ala Pro Asp Thr Val Ala Leu His
    50                  55                  60

His Ala His Val Val Asp Pro Asn Gln Cys Cys Ser Ile Val Thr Gln
65                  70                  75                  80

His Ile Asn Ala Pro Val Ser Ala Val Trp Ala Val Val Arg Arg Phe
                85                  90                  95

Asp Asn Pro Gln Gly Tyr Lys Asn Phe Val Arg Ser Cys His Val Ile
            100                 105                 110

Thr Gly Asp Gly Ile Arg Val Gly Ala Val Arg Glu Val Arg Val Val
        115                 120                 125

Ser Gly Leu Pro Ala Glu Thr Ser Thr Glu Arg Leu Glu Ile Leu Asp
    130                 135                 140

Asp Glu Arg His Val Ile Ser Phe Ser Met Val Gly Gly Asp His Arg
145                 150                 155                 160

Leu Arg Asn Tyr Gln Ser Val Thr Thr Leu His Ala Asn Gly Asn Gly
                165                 170                 175

Thr Leu Val Ile Glu Ser Tyr Val Val Asp Val Pro Gln Gly Asn Thr
            180                 185                 190

Lys Glu Glu Thr Cys Val Phe Val Asp Thr Ile Val Arg Cys Asn Leu
        195                 200                 205

Gln Ser Leu Ala Gln Ile Ala Glu Asn Arg Thr Asn Asn Cys Glu His
    210                 215                 220

Thr Ala Gln His Cys
225


<210> SEQ ID NO 123
<211> LENGTH: 191
<212> TYPE: PRT
<213> ORGANISM: Glycine max
<220> FEATURE:
<223> OTHER INFORMATION: soybean PYR/PYL receptor polypeptide

<400> SEQUENCE: 123

Met Asn Gly Ile Gly Asn Asp Gly Gly Gly Gly Leu Ser Asn Val Glu
 1               5                  10                  15

Met Glu Tyr Ile Arg Arg His His Arg His Glu Pro Gly Glu Asn Gln
            20                  25                  30

Cys Gly Ser Ala Leu Val Lys His Ile Arg Ala Pro Val Pro Gln Val
        35                  40                  45

Trp Ser Leu Val Arg Arg Phe Asp Gln Pro Gln Lys Tyr Lys Pro Phe
    50                  55                  60
```

Val Ser Arg Cys Val Val Arg Gly Asn Leu Glu Ile Gly Ser Leu Arg
65 70 75 80

Glu Val Asp Val Lys Ser Gly Leu Pro Ala Thr Thr Ser Thr Glu Arg
85 90 95

Leu Glu Leu Leu Asp Asp Asn Glu His Leu Leu Ser Ile Arg Ile Ile
100 105 110

Gly Gly Asp His Arg Leu Arg Asn Tyr Ser Ser Ile Met Ser Leu His
115 120 125

Pro Glu Ile Ile Asp Gly Arg Pro Gly Thr Leu Val Ile Glu Ser Phe
130 135 140

Val Val Asp Val Pro Glu Gly Asn Thr Lys Asp Glu Thr Cys Tyr Phe
145 150 155 160

Val Glu Ala Leu Ile Lys Cys Asn Leu Lys Ser Leu Ala Asp Val Ser
165 170 175

Glu Gly Ile Ala Val Gln Asp Arg Thr Glu Pro Ile Asp Arg Ile
180 185 190

<210> SEQ ID NO 124
<211> LENGTH: 169
<212> TYPE: PRT
<213> ORGANISM: Glycine max
<220> FEATURE:
<223> OTHER INFORMATION: soybean PYR/PYL receptor polypeptide

<400> SEQUENCE: 124

Met Val Ala Arg His His Ala His Ala Val Gly Pro Asn Gln Cys Cys
1 5 10 15

Ser Phe Val Ile Gln Ala Ile Asp Ala Pro Val Ser Ala Val Trp Pro
20 25 30

Val Val Arg Arg Phe Asp Asn Pro Gln Ala Tyr Lys His Phe Val Lys
35 40 45

Ser Cys His Val Val Ala Ala Gly Gly Ala Gly Gly Asp Gly Gly Ile
50 55 60

His Val Gly Ala Leu Arg Glu Val Arg Val Val Ser Gly Leu Pro Ala
65 70 75 80

Val Ser Ser Thr Glu Arg Leu Glu Ile Leu Asp Asp Glu Arg His Val
85 90 95

Met Ser Phe Ser Val Val Gly Gly Asp His Arg Leu Arg Asn Tyr Arg
100 105 110

Ser Val Thr Thr Leu His Gly Asp Gly Ser Asn Gly Gly Thr Val Val
115 120 125

Ile Glu Ser Tyr Val Val Asp Ile Pro Ala Gly Asn Thr Lys Glu Glu
130 135 140

Thr Cys Val Phe Val Asp Thr Ile Val Arg Cys Asn Leu Gln Ser Leu
145 150 155 160

Ala Gln Met Ala Glu Asn Met Gly Ser
165

<210> SEQ ID NO 125
<211> LENGTH: 210
<212> TYPE: PRT
<213> ORGANISM: Glycine max
<220> FEATURE:
<223> OTHER INFORMATION: soybean PYR/PYL receptor polypeptide

<400> SEQUENCE: 125

Met Thr Ile Leu Pro His Ser Asn Asn Lys Ser Ser Asn His Lys Phe

```
 1               5                  10                  15

Ile Ala His Gln Asn Tyr Met Ala Ser Glu Thr His His His Val Gln
            20                  25                  30

Gly Leu Thr Pro Glu Glu Leu Thr Lys Leu Glu Pro Ile Ile Lys Lys
        35                  40                  45

Tyr His Leu Phe Glu Gln Ser Pro Asn Thr Cys Phe Ser Ile Ile Thr
    50                  55                  60

Tyr Arg Ile Glu Ala Pro Ala Lys Ala Val Trp Pro Phe Val Arg Ser
65                  70                  75                  80

Phe Asp Asn Pro Gln Lys Tyr Lys His Phe Ile Lys Gly Cys Asn Met
                85                  90                  95

Arg Gly Asp Gly Gly Val Gly Ser Ile Arg Glu Val Thr Val Val Ser
            100                 105                 110

Gly Leu Pro Ala Ser Thr Ser Thr Glu Arg Leu Glu Ile Leu Asp Asp
        115                 120                 125

Asp Lys His Val Leu Ser Phe Arg Val Val Gly Gly Glu His Arg Leu
    130                 135                 140

Lys Asn Tyr Arg Ser Val Thr Ser Val Asn Glu Phe Asn Lys Glu Gly
145                 150                 155                 160

Lys Val Tyr Thr Ile Val Leu Glu Ser Tyr Ile Val Asp Ile Pro Glu
                165                 170                 175

Gly Asn Thr Glu Glu Asp Thr Lys Met Phe Val Asp Thr Val Val Lys
            180                 185                 190

Leu Asn Leu Gln Lys Leu Gly Val Val Ala Met Ala Ser Ser Met His
        195                 200                 205

Gly Gln
    210


<210> SEQ ID NO 126
<211> LENGTH: 193
<212> TYPE: PRT
<213> ORGANISM: Glycine max
<220> FEATURE:
<223> OTHER INFORMATION: soybean PYR/PYL receptor polypeptide

<400> SEQUENCE: 126

Met Asn Arg Ile Gly Asn Gly Gly Gly Gly Gly Gly Gly Leu Ser Asn
 1               5                  10                  15

Val Glu Met Glu Tyr Ile Arg Arg His His Arg His Glu Pro Gly Glu
            20                  25                  30

Asn Gln Cys Gly Ser Ala Leu Val Lys His Ile Arg Ala Pro Val Pro
        35                  40                  45

Gln Val Trp Ser Leu Val Arg Arg Phe Asp Gln Pro Gln Lys Tyr Lys
    50                  55                  60

Pro Phe Ile Ser Arg Cys Val Val Arg Gly Asn Leu Glu Ile Gly Ser
65                  70                  75                  80

Leu Arg Glu Val Asp Val Lys Ser Gly Leu Pro Ala Thr Thr Ser Thr
                85                  90                  95

Glu Arg Leu Glu Leu Leu Asp Asp Asn Glu His Ile Leu Ser Ile Arg
            100                 105                 110

Ile Ile Gly Gly Asp His Arg Leu Arg Asn Tyr Ser Ser Ile Met Ser
        115                 120                 125

Leu His Pro Glu Ile Ile Asp Gly Arg Pro Gly Thr Leu Val Ile Glu
    130                 135                 140

Ser Phe Val Val Asp Val Pro Glu Gly Asn Thr Lys Asp Glu Thr Cys
```

145 150 155 160

Tyr Phe Val Glu Ala Leu Ile Lys Cys Asn Leu Lys Ser Leu Ala Asp
165 170 175

Val Ser Glu Gly Leu Ala Val Gln Asp Cys Thr Glu Pro Ile Asp Arg
180 185 190

Ile

<210> SEQ ID NO 127
<211> LENGTH: 188
<212> TYPE: PRT
<213> ORGANISM: Glycine max
<220> FEATURE:
<223> OTHER INFORMATION: soybean PYR/PYL receptor polypeptide

<400> SEQUENCE: 127

Met Ala Ser Glu Thr His His His Val Gln Gly Leu Thr Pro Glu Glu
1 5 10 15

Leu Thr Gln Leu Glu Pro Ile Ile Lys Lys Tyr His Leu Phe Glu Ala
20 25 30

Ser Ser Asn Lys Cys Phe Ser Ile Ile Thr His Arg Ile Glu Ala Pro
35 40 45

Ala Ser Ser Val Trp Pro Leu Val Arg Asn Phe Asp Asn Pro Gln Lys
50 55 60

Tyr Lys His Phe Ile Lys Gly Cys Asn Met Lys Gly Asp Gly Ser Val
65 70 75 80

Gly Ser Ile Arg Glu Val Thr Val Val Ser Gly Leu Pro Ala Ser Thr
85 90 95

Ser Thr Glu Arg Leu Glu Ile Leu Asp Asp Asp Lys His Val Leu Ser
100 105 110

Phe Arg Val Val Gly Gly Glu His Arg Leu Gln Asn Tyr Arg Ser Val
115 120 125

Thr Ser Val Asn Glu Phe His Lys Glu Gly Lys Val Tyr Thr Ile Val
130 135 140

Leu Glu Ser Tyr Ile Val Asp Ile Pro Glu Gly Asn Thr Glu Glu Asp
145 150 155 160

Thr Lys Met Phe Val Asp Thr Val Val Lys Leu Asn Leu Gln Lys Leu
165 170 175

Gly Val Val Ala Met Ala Ser Ser Met Asn Gly Arg
180 185

<210> SEQ ID NO 128
<211> LENGTH: 177
<212> TYPE: PRT
<213> ORGANISM: Glycine max
<220> FEATURE:
<223> OTHER INFORMATION: soybean PYR/PYL receptor polypeptide

<400> SEQUENCE: 128

Met Leu Pro Asn Asn Pro Ser Thr Ile Val Pro Asp Ala Val Ala Arg
1 5 10 15

His His Thr His Val Val Ser Pro Gln Gln Cys Cys Ser Ala Val Val
20 25 30

Gln Glu Ile Ala Ala Pro Val Ser Thr Val Trp Ser Val Val Arg Arg
35 40 45

Phe Asp Asn Pro Gln Ala Tyr Lys His Phe Val Lys Ser Cys His Val
50 55 60

Ile Leu Gly Asp Gly Asp Val Gly Thr Leu Arg Glu Val His Val Ile 65 70 75 80

Ser Gly Leu Pro Ala Ala Val Ser Thr Glu Arg Leu Asp Val Leu Asp
85 90 95

Asp Glu Arg His Val Ile Gly Phe Ser Met Val Gly Gly Asp His Arg
100 105 110

Leu Phe Asn Tyr Arg Ser Val Thr Thr Leu His Pro Arg Ser Ala Ala
115 120 125

Gly Thr Val Val Val Glu Ser Tyr Val Val Asp Val Pro Pro Gly Asn
130 135 140

Thr Thr Glu Asp Thr Arg Val Phe Val Asp Thr Ile Leu Arg Cys Asn
145 150 155 160

Leu Gln Ser Leu Ala Lys Phe Ala Glu Asn Leu Thr Lys Leu His Gln
165 170 175

Arg

<210> SEQ ID NO 129
<211> LENGTH: 185
<212> TYPE: PRT
<213> ORGANISM: Glycine max
<220> FEATURE:
<223> OTHER INFORMATION: soybean PYR/PYL receptor polypeptide

<400> SEQUENCE: 129

Met Asn Gly Gly Glu Ser Tyr Gly Ala Ile Glu Thr Gln Tyr Ile Arg
1 5 10 15

Arg His His Lys His Glu Pro Arg Glu Asn Gln Cys Thr Ser Ala Leu
20 25 30

Val Lys His Ile Arg Ala Pro Val His Leu Val Trp Ser Leu Val Arg
35 40 45

Arg Phe Asp Gln Pro Gln Lys Tyr Lys Pro Phe Val Ser Arg Cys Ile
50 55 60

Met Gln Gly Asp Leu Gly Ile Gly Ser Val Arg Glu Val Asn Val Lys
65 70 75 80

Ser Gly Leu Pro Ala Thr Thr Ser Thr Glu Arg Leu Glu Gln Leu Asp
85 90 95

Asp Glu Glu His Ile Leu Gly Ile Arg Ile Val Gly Gly Asp His Arg
100 105 110

Leu Arg Asn Tyr Ser Ser Ile Ile Thr Val His Pro Glu Val Ile Asp
115 120 125

Gly Arg Pro Gly Thr Met Val Ile Glu Ser Phe Val Val Asp Val Pro
130 135 140

Asp Gly Asn Thr Arg Asp Glu Thr Cys Tyr Phe Val Glu Ala Leu Ile
145 150 155 160

Arg Cys Asn Leu Ser Ser Leu Ala Asp Val Ser Glu Arg Met Ala Val
165 170 175

Gln Gly Arg Thr Asn Pro Ile Asn His
180 185

<210> SEQ ID NO 130
<211> LENGTH: 191
<212> TYPE: PRT
<213> ORGANISM: Glycine max
<220> FEATURE:
<223> OTHER INFORMATION: soybean PYR/PYL receptor polypeptide

<400> SEQUENCE: 130

Met Gly Ile Thr Ile Gly Ile Gln Cys Leu Glu Ile Glu Glu Ile Ser

-continued

```
1               5                   10                  15

Ile Cys Asp Gly Met Phe Cys Tyr Leu Val Asp Phe Val Asp Val Lys
            20                  25                  30

Glu Lys Met Asn Tyr Cys Leu Met Trp Phe Gly Tyr Phe Pro Ser Gln
        35                  40                  45

Val Trp Ser Leu Val Arg Arg Phe Asp Gln Pro Gln Lys Tyr Lys Pro
    50                  55                  60

Phe Val Ser Arg Cys Ile Met Gln Gly Asp Leu Gly Ile Gly Ser Val
65                  70                  75                  80

Arg Glu Val Asn Val Lys Ser Gly Leu Pro Ala Thr Thr Ser Thr Glu
                85                  90                  95

Arg Leu Glu Gln Leu Asp Asp Glu Glu His Ile Leu Gly Ile Arg Ile
            100                 105                 110

Val Gly Gly Asp His Arg Leu Arg Asn Tyr Ser Ser Ile Ile Thr Val
        115                 120                 125

His Pro Glu Val Ile Asp Gly Arg Pro Ser Thr Met Val Ile Glu Ser
    130                 135                 140

Phe Val Val Asp Val Pro Asp Gly Asn Thr Arg Asp Glu Thr Cys Tyr
145                 150                 155                 160

Phe Val Glu Ala Leu Ile Arg Cys Asn Leu Ser Ser Leu Ala Asp Val
                165                 170                 175

Ser Glu Arg Met Ala Val Gln Gly Arg Thr Asp Pro Ile Asn His
            180                 185                 190


<210> SEQ ID NO 131
<211> LENGTH: 185
<212> TYPE: PRT
<213> ORGANISM: Glycine max
<220> FEATURE:
<223> OTHER INFORMATION: soybean PYR/PYL receptor polypeptide

<400> SEQUENCE: 131

Met Asn Gly Gly Glu Ser Tyr Gly Ala Ile Glu Thr Gln Tyr Ile Arg
1               5                   10                  15

Arg His His Lys His Glu Pro Arg Glu Asn Gln Cys Thr Ser Ala Leu
            20                  25                  30

Val Lys His Ile Arg Ala Pro Val His Leu Val Trp Ser Leu Val Arg
        35                  40                  45

Arg Phe Asp Gln Pro Gln Lys Tyr Lys Pro Phe Val Ser Arg Cys Ile
    50                  55                  60

Met Gln Gly Asp Leu Gly Ile Gly Ser Val Arg Glu Val Asn Val Lys
65                  70                  75                  80

Ser Gly Leu Pro Ala Thr Thr Ser Thr Glu Arg Leu Glu Gln Leu Asp
                85                  90                  95

Asp Glu Glu His Ile Leu Gly Ile Arg Ile Val Gly Gly Asp His Arg
            100                 105                 110

Leu Arg Asn Tyr Ser Ser Ile Ile Thr Val His Pro Glu Val Ile Asp
        115                 120                 125

Gly Arg Pro Ser Thr Met Val Ile Glu Ser Phe Val Val Asp Val Pro
    130                 135                 140

Asp Gly Asn Thr Arg Asp Glu Thr Cys Tyr Phe Val Glu Ala Leu Ile
145                 150                 155                 160

Arg Cys Asn Leu Ser Ser Leu Ala Asp Val Ser Glu Arg Met Ala Val
                165                 170                 175

Gln Gly Arg Thr Asp Pro Ile Asn His
```

```
            180                 185


<210> SEQ ID NO 132
<211> LENGTH: 204
<212> TYPE: PRT
<213> ORGANISM: Sorghum bicolor
<220> FEATURE:
<223> OTHER INFORMATION: sorghum PYR/PYL receptor polypeptide

<400> SEQUENCE: 132

Met Glu Thr His Val Glu Arg Ala Leu Arg Ala Thr Leu Thr Glu Ala
 1               5                  10                  15

Glu Val Arg Ala Leu Glu Pro Ala Val Arg Glu His His Thr Phe Pro
            20                  25                  30

Ala Gly Arg Val Ala Ala Gly Thr Thr Thr Pro Thr Pro Thr Thr Cys
        35                  40                  45

Thr Ser Leu Val Ala Gln Arg Val Ser Ala Pro Val Arg Ala Val Trp
    50                  55                  60

Pro Ile Val Arg Ser Phe Gly Asn Pro Gln Arg Tyr Lys His Phe Val
65                  70                  75                  80

Arg Thr Cys Ala Leu Ala Ala Gly Asp Gly Ala Ser Val Gly Ser Val
                85                  90                  95

Arg Glu Val Thr Val Val Ser Gly Leu Pro Ala Ser Ser Ser Thr Glu
            100                 105                 110

Arg Leu Glu Val Leu Asp Asp Asp Arg His Ile Leu Ser Phe Arg Val
        115                 120                 125

Val Gly Gly Asp His Arg Leu Arg Asn Tyr Arg Ser Val Thr Ser Val
    130                 135                 140

Thr Glu Phe Gln Pro Gly Pro Tyr Cys Val Val Glu Ser Tyr Ala
145                 150                 155                 160

Val Asp Val Pro Glu Gly Asn Thr Ala Glu Asp Thr Arg Met Phe Thr
                165                 170                 175

Asp Thr Val Val Arg Leu Asn Leu Gln Lys Leu Ala Ala Val Ala Glu
            180                 185                 190

Glu Ser Ala Ala Ala Ala Ala Ala Gly Asn Arg Arg
        195                 200


<210> SEQ ID NO 133
<211> LENGTH: 204
<212> TYPE: PRT
<213> ORGANISM: Sorghum bicolor
<220> FEATURE:
<223> OTHER INFORMATION: sorghum PYR/PYL receptor polypeptide

<400> SEQUENCE: 133

Met Glu Pro His Met Glu Thr Ala Leu Arg Gln Gly Gly Leu Ser Glu
 1               5                  10                  15

Leu Glu Gln Arg Glu Leu Glu Pro Val Val Arg Ala His His Thr Phe
            20                  25                  30

Pro Gly Arg Ser Pro Gly Thr Thr Cys Thr Ser Leu Val Thr Gln Arg
        35                  40                  45

Val Asp Ala Pro Leu Ser Ala Val Trp Pro Ile Val Arg Gly Phe Ala
    50                  55                  60

Ala Pro Gln Arg Tyr Lys His Phe Ile Lys Ser Cys Asp Leu Arg Ser
65                  70                  75                  80

Gly Asp Gly Ala Thr Val Gly Ser Val Arg Glu Val Thr Val Val Ser
                85                  90                  95
```

```
Gly Leu Pro Ala Ser Thr Ser Thr Glu Arg Leu Glu Ile Leu Asp Asp
            100                 105                 110

Asp Arg His Ile Leu Ser Phe Arg Val Val Gly Gly Asp His Arg Leu
        115                 120                 125

Arg Asn Tyr Arg Ser Val Thr Ser Val Thr Glu Phe His His His His
    130                 135                 140

Gln Ala Ala Ala Gly Arg Pro Tyr Cys Val Val Val Glu Ser Tyr Val
145                 150                 155                 160

Val Asp Val Pro Glu Gly Asn Thr Glu Glu Asp Thr Arg Met Phe Thr
                165                 170                 175

Asp Thr Val Val Lys Leu Asn Leu Gln Lys Leu Ala Ala Ile Ala Thr
            180                 185                 190

Ser Ser Ala Ala Ala Ala Ala Ser Asn Ser Ser Thr
        195                 200


<210> SEQ ID NO 134
<211> LENGTH: 258
<212> TYPE: PRT
<213> ORGANISM: Sorghum bicolor
<220> FEATURE:
<223> OTHER INFORMATION: sorghum PYR/PYL receptor polypeptide

<400> SEQUENCE: 134

Met Val Glu Ser Pro Asn Pro Asn Ser Pro Ser Arg Pro Leu Cys Ile
 1               5                  10                  15

Lys Tyr Thr Arg Ala Pro Ala Arg His Phe Ser Pro Pro Leu Pro Phe
            20                  25                  30

Ser Ser Leu Ile Ile Ser Ala Asn Pro Ile Glu Pro Lys Ala Met Asp
        35                  40                  45

Lys Gln Gly Ala Gly Gly Asp Val Glu Val Pro Ala Gly Leu Gly Leu
    50                  55                  60

Thr Ala Ala Glu Tyr Glu Gln Leu Arg Ser Thr Val Asp Ala His His
65                  70                  75                  80

Arg Tyr Ala Val Gly Glu Gly Gln Cys Ser Ser Leu Leu Ala Gln Arg
                85                  90                  95

Ile Gln Ala Pro Pro Ala Ala Val Trp Ala Ile Val Arg Arg Phe Asp
            100                 105                 110

Cys Pro Gln Val Tyr Lys His Phe Ile Arg Ser Cys Ala Leu Arg Pro
        115                 120                 125

Asp Pro Glu Ala Gly Asp Ala Leu Arg Pro Gly Arg Leu Arg Glu Val
    130                 135                 140

Ser Val Ile Ser Gly Leu Pro Ala Ser Thr Ser Thr Glu Arg Leu Asp
145                 150                 155                 160

Leu Leu Asp Asp Ala Ala Arg Val Phe Gly Phe Ser Ile Thr Gly Gly
                165                 170                 175

Glu His Arg Leu Arg Asn Tyr Arg Ser Val Thr Thr Val Ser Glu Leu
            180                 185                 190

Ala Asp Pro Gly Ile Cys Thr Val Val Leu Glu Ser Tyr Val Val Asp
        195                 200                 205

Val Pro Asp Gly Asn Thr Glu Asp Asp Thr Arg Leu Phe Ala Asp Thr
    210                 215                 220

Val Ile Arg Leu Asn Leu Gln Lys Leu Lys Ser Val Ala Glu Ala Asn
225                 230                 235                 240

Ala Ala Ala Ala Ala Ser Phe Val Ser Val Val Pro Pro Pro Glu Pro
                245                 250                 255
```

Glu Glu

<210> SEQ ID NO 135
<211> LENGTH: 222
<212> TYPE: PRT
<213> ORGANISM: Sorghum bicolor
<220> FEATURE:
<223> OTHER INFORMATION: sorghum PYR/PYL receptor polypeptide

<400> SEQUENCE: 135

```
Met Pro Cys Leu Gln Ala Ser Ser Ser Pro Gly Ser Met Pro His Gln
 1               5                  10                  15

His His Gly Arg Val Leu Ala Gly Val Gly Cys Ala Ala Glu Val Ala
            20                  25                  30

Ala Ala Ala Val Ala Ala Thr Ser Pro Ala Ala Gly Met Arg Cys Gly
        35                  40                  45

Ala His Asp Gly Glu Val Pro Ala Glu Ala Ala Arg His His Glu His
    50                  55                  60

Ala Ala Pro Gly Pro Gly Arg Cys Cys Ser Ala Val Val Gln His Val
65                  70                  75                  80

Ala Ala Pro Ala Ser Ala Val Trp Ser Val Val Arg Arg Phe Asp Gln
                85                  90                  95

Pro Gln Ala Tyr Lys Arg Phe Val Arg Ser Cys Ala Leu Leu Ala Gly
            100                 105                 110

Asp Gly Gly Val Gly Thr Leu Arg Glu Val Arg Val Val Ser Gly Leu
        115                 120                 125

Pro Ala Ala Ser Ser Arg Glu Arg Leu Glu Val Leu Asp Asp Glu Ser
    130                 135                 140

His Val Leu Ser Phe Arg Val Val Gly Gly Glu His Arg Leu Gln Asn
145                 150                 155                 160

Tyr Leu Ser Val Thr Thr Val His Pro Ser Pro Ala Ala Pro Asp Ala
                165                 170                 175

Ala Thr Val Val Val Glu Ser Tyr Val Val Asp Val Pro Pro Gly Asn
            180                 185                 190

Thr Pro Glu Asp Thr Arg Val Phe Val Asp Thr Ile Val Lys Cys Asn
        195                 200                 205

Leu Gln Ser Leu Ala Thr Thr Ala Glu Lys Leu Ala Ala Val
    210                 215                 220
```

<210> SEQ ID NO 136
<211> LENGTH: 211
<212> TYPE: PRT
<213> ORGANISM: Sorghum bicolor
<220> FEATURE:
<223> OTHER INFORMATION: sorghum PYR/PYL receptor polypeptide

<400> SEQUENCE: 136

```
Met Val Glu Met Asp Gly Gly Val Gly Val Val Gly Gly Gly Gln Gln
 1               5                  10                  15

Thr Pro Ala Pro Arg Arg Trp Arg Leu Ala Asp Glu Leu Arg Cys Asp
            20                  25                  30

Leu Arg Ala Met Glu Thr Asp Tyr Val Arg Arg Phe His Arg His Glu
        35                  40                  45

Pro Arg Asp His Gln Cys Ser Ser Ala Val Ala Lys His Ile Lys Ala
    50                  55                  60

Pro Val His Leu Val Trp Ser Leu Val Arg Arg Phe Asp Gln Pro Gln
65                  70                  75                  80
```

Leu Phe Lys Pro Phe Val Ser Arg Cys Glu Met Lys Gly Asn Ile Glu
85 90 95

Ile Gly Ser Val Arg Glu Val Asn Val Lys Ser Gly Leu Pro Ala Thr
100 105 110

Arg Ser Thr Glu Arg Leu Glu Leu Leu Asp Asp Asn Glu His Ile Leu
115 120 125

Ser Val Lys Phe Val Gly Gly Asp His Arg Leu Gln Asn Tyr Ser Ser
130 135 140

Ile Leu Thr Val His Pro Glu Val Ile Asp Gly Arg Pro Gly Thr Leu
145 150 155 160

Val Ile Glu Ser Phe Val Val Asp Val Pro Asp Gly Asn Thr Lys Asp
165 170 175

Glu Thr Cys Tyr Phe Val Glu Ala Leu Leu Lys Cys Asn Leu Lys Ser
180 185 190

Leu Ala Glu Val Ser Glu Arg Gln Val Ile Lys Asp Gln Thr Glu Pro
195 200 205

Leu Asp Arg
210

<210> SEQ ID NO 137
<211> LENGTH: 216
<212> TYPE: PRT
<213> ORGANISM: Sorghum bicolor
<220> FEATURE:
<223> OTHER INFORMATION: sorghum PYR/PYL receptor polypeptide

<400> SEQUENCE: 137

Met Pro Tyr Thr Ala Pro Arg Pro Ser Pro Gln Gln His Ser Arg Val
1 5 10 15

Thr Gly Gly Gly Ala Lys Ala Ala Ile Val Ala Ala Ser His Gly Ala
20 25 30

Ser Cys Ala Ala Val Pro Ala Glu Val Ala Arg His His Glu His Ala
35 40 45

Ala Arg Ala Gly Gln Cys Cys Ser Ala Val Val Gln Ala Ile Ala Ala
50 55 60

Pro Val Gly Ala Val Trp Ser Val Val Arg Arg Phe Asp Arg Pro Gln
65 70 75 80

Ala Tyr Lys His Phe Ile Arg Ser Cys Arg Leu Val Asp Asp Gly Gly
85 90 95

Gly Gly Ala Gly Ala Gly Ala Gly Ala Thr Val Ala Val Gly Ser Val
100 105 110

Arg Glu Val Arg Val Val Ser Gly Leu Pro Ala Thr Ser Ser Arg Glu
115 120 125

Arg Leu Glu Ile Leu Asp Asp Glu Arg Arg Val Leu Ser Phe Arg Val
130 135 140

Val Gly Gly Glu His Arg Leu Ala Asn Tyr Arg Ser Val Thr Thr Val
145 150 155 160

His Glu Ala Glu Ala Gly Ala Gly Gly Thr Val Val Val Glu Ser Tyr
165 170 175

Val Val Asp Val Pro Pro Gly Asn Thr Ala Asp Glu Thr Arg Val Phe
180 185 190

Val Asp Thr Ile Val Arg Cys Asn Leu Gln Ser Leu Ala Arg Thr Ala
195 200 205

Glu Arg Leu Ala Leu Ala Leu Ala
210 215

<210> SEQ ID NO 138
<211> LENGTH: 24
<212> TYPE: PRT
<213> ORGANISM: Artificial Sequence
<220> FEATURE:
<223> OTHER INFORMATION: synthetic PYR/PYL receptor polypeptide consensus sequence
<220> FEATURE:
<221> NAME/KEY: VARIANT
<222> LOCATION: (1)...(24)
<223> OTHER INFORMATION: Xaa = any amino acid

<400> SEQUENCE: 138

```
Glu Xaa Leu Xaa Xaa Xaa Asp Xaa Xaa Xaa Xaa Xaa Xaa Xaa Xaa Xaa
 1               5                  10                  15

Xaa Xaa Gly Gly Xaa His Xaa Leu
            20
```

<210> SEQ ID NO 139
<211> LENGTH: 50
<212> TYPE: PRT
<213> ORGANISM: Artificial Sequence
<220> FEATURE:
<223> OTHER INFORMATION: synthetic PYR/PYL receptor polypeptide PYR1 to PYL6 consensus sequence
<220> FEATURE:
<221> NAME/KEY: VARIANT
<222> LOCATION: (1)...(50)
<223> OTHER INFORMATION: Xaa = any amino acid

<400> SEQUENCE: 139

```
Val Gly Xaa Xaa Arg Xaa Val Xaa Val Xaa Ser Gly Leu Pro Ala Xaa
 1               5                  10                  15

Xaa Ser Xaa Glu Xaa Leu Xaa Xaa Xaa Asp Xaa Xaa Xaa Xaa Xaa Xaa
            20                  25                  30

Xaa Phe Xaa Xaa Xaa Gly Gly Xaa His Arg Leu Xaa Asn Tyr Xaa Ser
        35                  40                  45

Val Thr
    50
```

<210> SEQ ID NO 140
<211> LENGTH: 105
<212> TYPE: PRT
<213> ORGANISM: Artificial Sequence
<220> FEATURE:
<223> OTHER INFORMATION: synthetic PYR/PYL receptor polypeptide PYL7 to PYL10 consensus sequence
<220> FEATURE:
<221> NAME/KEY: VARIANT
<222> LOCATION: (1)...(105)
<223> OTHER INFORMATION: Xaa = any amino acid

<400> SEQUENCE: 140

```
Glu Xaa Gly Xaa Xaa Arg Glu Val Xaa Xaa Lys Ser Gly Leu Pro Ala
 1               5                  10                  15

Thr Xaa Ser Thr Glu Xaa Leu Glu Xaa Leu Asp Asp Xaa Glu His Ile
            20                  25                  30

Leu Xaa Ile Xaa Ile Xaa Gly Gly Asp His Arg Leu Lys Asn Tyr Ser
        35                  40                  45

Ser Xaa Xaa Xaa Xaa His Xaa Glu Xaa Ile Xaa Gly Xaa Xaa Gly Thr
    50                  55                  60

Xaa Xaa Xaa Glu Ser Phe Val Val Asp Val Pro Xaa Gly Asn Thr Lys
65                  70                  75                  80

Xaa Xaa Thr Cys Xaa Phe Val Glu Xaa Leu Ile Xaa Cys Asn Leu Xaa
```

-continued

```
              85                  90                  95

Ser Leu Ala Xaa Xaa Xaa Glu Arg Leu
            100                 105


<210> SEQ ID NO 141
<211> LENGTH: 6
<212> TYPE: PRT
<213> ORGANISM: Artificial Sequence
<220> FEATURE:
<223> OTHER INFORMATION: synthetic 6xHis tag, poly-His tag

<400> SEQUENCE: 141

His His His His His His
 1               5
```